(12) United States Patent
Roden et al.

(10) Patent No.: US 9,149,517 B2
(45) Date of Patent: Oct. 6, 2015

(54) MULTITYPE HPV PEPTIDE COMPOSITIONS AND METHODS FOR TREATMENT OR PREVENTION OF HUMAN PAPILLOMAVIRUS INFECTION

(75) Inventors: Richard Roden, Severna Park, MD (US); Subhashini Jagu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 690 days.

(21) Appl. No.: 12/740,815

(22) PCT Filed: Nov. 3, 2008

(86) PCT No.: PCT/US2008/082290
§ 371 (c)(1),
(2), (4) Date: Jul. 22, 2010

(87) PCT Pub. No.: WO2009/059325
PCT Pub. Date: May 7, 2009

(65) Prior Publication Data
US 2010/0297144 A1    Nov. 25, 2010

Related U.S. Application Data

(60) Provisional application No. 61/001,630, filed on Nov. 2, 2007, provisional application No. 61/001,629, filed on Nov. 2, 2007.

(51) Int. Cl.
| | |
|---|---|
| *A61K 39/42* | (2006.01) |
| *C07K 14/025* | (2006.01) |
| *C07H 21/04* | (2006.01) |
| *C07K 16/08* | (2006.01) |
| *A61K 39/12* | (2006.01) |
| *C07K 14/005* | (2006.01) |
| *C12N 7/00* | (2006.01) |
| *A61K 39/00* | (2006.01) |

(52) U.S. Cl.
CPC .............. *A61K 39/12* (2013.01); *C07K 14/005* (2013.01); *C12N 7/00* (2013.01); *A61K 39/42* (2013.01); *A61K 2039/55505* (2013.01); *A61K 2039/55561* (2013.01); *A61K 2039/55566* (2013.01); *A61K 2039/55577* (2013.01); *A61K 2039/58* (2013.01); *A61K 2039/645* (2013.01); *A61K 2039/70* (2013.01); *C12N 2710/20022* (2013.01); *C12N 2710/20034* (2013.01)

(58) Field of Classification Search
CPC .............................. A61K 39/00; C07K 14/00
See application file for complete search history.

(56) References Cited

U.S. PATENT DOCUMENTS

| | | | |
|---|---|---|---|
| 5,618,536 A | * | 4/1997 | Lowy et al. ............ 424/192.1 |
| 2005/0159386 A1 | | 7/2005 | Kieny et al. |
| 2007/0037151 A1 | | 2/2007 | Babe et al. |
| 2007/0099199 A1 | | 5/2007 | Lu et al. |

FOREIGN PATENT DOCUMENTS

| | | | |
|---|---|---|---|
| WO | WO 2006/083984 A1 | * | 8/2006 |
| WO | WO-2006083984 A1 | | 8/2006 |
| WO | WO-2007095320 A2 | | 8/2007 |
| WO | WO-2009059325 A2 | | 5/2009 |

OTHER PUBLICATIONS

Roden et al. (Virology, 2000, vol. 270, p. 254-257).*
Chinese Office Action issued in Chinese Application No. 200880120046 dated Mar. 20, 2012.
International Preliminary Report on Patentability and Written Opinion, dated May 14, 2010, issued in parent International Application No. PCT/US2008/082290.
Gambhira et al. "Protection of Rabbits against Challenge with Rabbit Papillomaviruses by Immunization with the N Terminus of Human Papillomavirus Type 16 Minor Capsid Antigen L2"; *Journal of Virology*, Nov. 2007, p. 11585-11592.
Campo et al. "A Peptide Encoding a B-Cell Epitope from the N-Terminus of the Capsid Protein L2 of Bovine Papillomavirus-4 Prevents Disease"; *Virology* 234, 261-266 (1997) Article No. VY978649.
PCT/US2008/082290 International Search Report issued Apr. 22, 2009.
Australian Patent App. No. 2008318320; Examination Report issued Mar. 1, 2013.
European Patent App. No. 08844778.4; Extended Search Report issued Aug. 29, 2012.
Mexican Patent App. No. MX/a/2010/004850; Office Action issued Sep. 3, 2012.
Eurasian Patent App. No. 201000735; Office Action issued Apr. 23, 2012.
Eurasian Patent App. No. 201000735; Office Action issued Feb. 26, 2013.
Office Action issued in Malaysian Patent Application No. PI 2010002013 dated Sep. 15, 2014.
European Communication issued in European Application No. 08 844 788.4-1403 dated Jan. 20, 2015.
Canadian Office Action issued in Application No. 2,704,455 dated Jan. 20, 2015.
European Office Action issued in Application No. 08 844 778.4-1403 dated Jan. 20, 2015.

* cited by examiner

*Primary Examiner* — Agnieszka Boesen
(74) *Attorney, Agent, or Firm* — Venable LLP; Stefan J. Kirchanski; Miguel A. Lopez

(57) ABSTRACT

Embodiments of the invention are directed to methods and compositions of multitype HPV polypeptides.

33 Claims, 4 Drawing Sheets

SEQUENCE LISTING

<160> NUMBER OF SEQ ID NOS: 129

<210> SEQ ID NO 1
<211> LENGTH: 473
<212> TYPE: PRT
<213> ORGANISM: Human papillomavirus type 16

```
<400> SEQUENCE: 1

Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Asp Gln Ile Leu Gln Tyr
        35                  40                  45

Gly Ser Met Gly Val Phe Phe Gly Gly Leu Gly Ile Gly Thr Gly Ser
50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Pro Val Pro Ser Ile Pro Pro
        115                 120                 125

Asp Val Ser Gly Phe Ser Ile Thr Thr Ser Thr Asp Thr Thr Pro Ala
130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
210                 215                 220

Leu Gly Leu Tyr Ser Arg Thr Thr Gln Gln Val Lys Val Val Asp Pro
225                 230                 235                 240

Ala Phe Val Thr Ala Pro Thr Lys Leu Ile Thr Tyr Asp Asn Pro Ala
                245                 250                 255

Tyr Glu Gly Ile Asp Val Asp Asn Thr Phe Tyr Phe Pro Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
290                 295                 300

Arg Ile Gly Asn Lys Gln Thr Leu Arg Thr Arg Ser Gly Lys Ser Ile
305                 310                 315                 320

Gly Ala Lys Val His Tyr Tyr Tyr Asp Leu Ser Thr Ile Asn Pro Ala
                325                 330                 335

Glu Glu Ile Glu Leu Gln Thr Ile Thr Pro Ser Thr Tyr Thr Thr Thr
            340                 345                 350

Ser His Ala Ala Ser Pro Thr Ser Ile Asn Asn Gly Leu Tyr Asp Ile
        355                 360                 365

Tyr Ala Asp Asp Phe Ile Thr Asp Thr Val Thr Thr Pro Val Pro Ala
370                 375                 380

Ile Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415
```

```
Pro Ile Asn Thr Thr Asp Gln Thr Pro Ser Leu Ile Pro Ile Val Pro
            420                 425                 430

Gly Ser Pro Gln Tyr Thr Ile Ile Ala Asp Gly Gly Asp Phe Tyr Leu
            435                 440                 445

His Pro Ser Tyr Tyr Met Leu Arg Lys Arg Arg Lys Arg Leu Pro Tyr
    450                 455                 460

Phe Phe Ser Asp Val Ser Leu Ala Ala
465                 470

<210> SEQ ID NO 2
<211> LENGTH: 462
<212> TYPE: PRT
<213> ORGANISM: Human papillomavirus type 18

<400> SEQUENCE: 2

Met Val Ser His Arg Ala Ala Arg Arg Lys Arg Ala Ser Val Thr Asp
1               5                   10                  15

Leu Tyr Lys Thr Cys Lys Gln Ser Gly Thr Cys Pro Ser Asp Val Val
            20                  25                  30

Asn Lys Val Glu Gly Thr Thr Leu Ala Asp Lys Ile Leu Gln Trp Ser
        35                  40                  45

Ser Leu Gly Ile Phe Leu Gly Gly Leu Gly Ile Gly Thr Gly Ser Gly
    50                  55                  60

Thr Gly Gly Arg Thr Gly Tyr Ile Pro Leu Gly Gly Arg Ser Asn Thr
65                  70                  75                  80

Val Val Asp Val Gly Pro Thr Arg Pro Pro Val Val Ile Glu Pro Val
                85                  90                  95

Gly Pro Thr Asp Pro Ser Ile Val Thr Leu Ile Glu Asp Ser Ser Val
            100                 105                 110

Val Thr Ser Gly Ala Pro Arg Pro Thr Phe Thr Gly Thr Ser Gly Phe
        115                 120                 125

Asp Ile Thr Ser Ala Gly Thr Thr Thr Pro Ala Val Leu Asp Ile Thr
    130                 135                 140

Pro Ser Ser Thr Ser Val Ser Ile Ser Thr Thr Asn Phe Thr Asn Pro
145                 150                 155                 160

Ala Phe Ser Asp Pro Ser Ile Ile Glu Val Pro Gln Thr Gly Glu Val
                165                 170                 175

Ser Gly Asn Val Phe Val Gly Thr Pro Thr Ser Gly Thr His Gly Tyr
            180                 185                 190

Glu Glu Ile Pro Leu Gln Thr Phe Ala Ser Ser Gly Thr Gly Glu Glu
        195                 200                 205

Pro Ile Ser Ser Thr Pro Leu Pro Thr Val Arg Arg Val Thr Gly Pro
    210                 215                 220

Arg Leu Tyr Ser Arg Ala Tyr Gln Gln Val Ser Val Ala Asn Pro Glu
225                 230                 235                 240

Phe Leu Thr Arg Pro Ser Ser Leu Ile Thr Tyr Asp Asn Pro Ala Phe
                245                 250                 255

Glu Pro Met Asp Thr Thr Leu Thr Phe Glu Pro Arg Ser Asn Val Pro
            260                 265                 270

Asp Ser Asp Phe Met Asp Ile Arg Leu His Arg Pro Ala Ser Thr
        275                 280                 285

Ser Arg Arg Gly Thr Val Arg Phe Ser Arg Leu Gly Gln Arg Ala Thr
    290                 295                 300

Met Phe Thr Arg Ser Gly Thr Gln Ile Gly Ala Arg Val His Phe Tyr
```

```
                305                 310                 315                 320

His Asp Ile Ser Pro Ile Ala Pro Ser Pro Glu Tyr Ile Glu Leu Gln
                    325                 330                 335

Pro Leu Val Ser Ala Thr Glu Asp Asn Gly Leu Phe Asp Ile Tyr Ala
                340                 345                 350

Asp Asp Ile Asp Pro Ala Leu Pro Val Pro Ser Arg Pro Thr Thr Ser
            355                 360                 365

Ser Ala Val Ser Thr Tyr Ser Pro Thr Ile Ser Ala Ser Ser Tyr
        370                 375                 380

Ser Asn Val Thr Val Pro Leu Thr Ser Ser Trp Asp Val Pro Val Tyr
385                 390                 395                 400

Thr Gly Pro Asp Ile Thr Leu Pro Ser Thr Thr Ser Val Trp Pro Ile
                    405                 410                 415

Val Ser Pro Thr Asp Pro Ala Ser Thr Gln Tyr Ile Gly Ile His Gly
                420                 425                 430

Thr His Tyr Tyr Leu Trp Pro Leu Tyr Tyr Phe Ile Pro Lys Lys Arg
            435                 440                 445

Lys Arg Val Pro Tyr Phe Phe Ala Asp Gly Phe Val Ala Ala
        450                 455                 460

<210> SEQ ID NO 3
<211> LENGTH: 463
<212> TYPE: PRT
<213> ORGANISM: Human papillomavirus type 45

<400> SEQUENCE: 3

Met Val Ser His Arg Ala Ala Arg Arg Lys Arg Ala Ser Ala Thr Asp
1               5                   10                  15

Leu Tyr Lys Thr Cys Lys Gln Ser Gly Thr Cys Pro Pro Asp Val Ile
                20                  25                  30

Asn Lys Val Glu Gly Thr Thr Leu Ala Asp Arg Ile Leu Gln Trp Ser
            35                  40                  45

Ser Leu Gly Ile Phe Leu Gly Gly Leu Gly Ile Gly Thr Gly Ser Gly
        50                  55                  60

Ser Gly Gly Arg Thr Gly Tyr Val Pro Leu Gly Gly Arg Ser Asn Thr
65                  70                  75                  80

Val Val Asp Val Gly Pro Thr Arg Pro Pro Val Val Ile Asp Pro Val
                85                  90                  95

Gly Pro Thr Asp Pro Ser Ile Val Thr Leu Val Glu Glu Ser Ser Val
            100                 105                 110

Val Ser Ser Gly Ala Pro Val Pro Thr Phe Thr Gly Thr Ser Gly Phe
        115                 120                 125

Glu Ile Thr Ser Ser Gly Thr Thr Thr Pro Ala Val Leu Asp Ile Thr
    130                 135                 140

Pro Thr Val Asp Ser Val Ser Ile Ser Ser Thr Ser Phe Thr Asn Pro
145                 150                 155                 160

Ala Phe Ser Asp Pro Ser Ile Ile Glu Val Pro Gln Thr Gly Glu Val
                165                 170                 175

Ser Gly Asn Ile Phe Val Gly Thr Pro Thr Ser Gly Ser His Gly Tyr
            180                 185                 190

Glu Glu Ile Pro Leu Gln Thr Phe Ala Ser Ser Gly Ser Gly Thr Glu
        195                 200                 205

Pro Ile Ser Ser Thr Pro Leu Pro Thr Val Arg Arg Val Ala Gly Pro
    210                 215                 220
```

-continued

Arg Leu Tyr Ser Arg Ala Asn Gln Gln Val Arg Val Ser Thr Ser Gln
225                 230                 235                 240

Phe Leu Thr Arg Pro Ser Ser Leu Val Thr Phe Asp Asn Pro Ala Tyr
            245                 250                 255

Glu Pro Leu Asp Thr Thr Leu Ser Phe Glu Pro Thr Ser Asn Val Pro
            260                 265                 270

Asp Ser Asp Phe Met Asp Ile Ile Arg Leu His Arg Pro Ala Leu Ser
            275                 280                 285

Ser Arg Arg Gly Thr Val Arg Phe Ser Arg Leu Gly Gln Arg Ala Thr
            290                 295                 300

Met Phe Thr Arg Ser Gly Lys Gln Ile Gly Gly Arg Val His Phe Tyr
305                 310                 315                 320

His Asp Ile Ser Pro Ile Ala Ala Thr Glu Glu Ile Glu Leu Gln Pro
            325                 330                 335

Leu Leu Ser Ala Thr Asp Asp Ser Asp Leu Phe Asp Val Tyr Ala Asp
            340                 345                 350

Phe Pro Pro Ala Ser Thr Thr Pro Ser Thr Ile Asn Lys Ser Phe
            355                 360                 365

Thr Tyr Pro Lys Tyr Ser Leu Thr Met Pro Ser Thr Ala Ala Ser Ser
370                 375                 380

Tyr Ser Asn Val Thr Val Pro Leu Thr Ser Ala Trp Asp Val Pro Ile
385                 390                 395                 400

Tyr Thr Gly Pro Asp Ile Ile Leu Pro Ser His Thr Pro Met Trp Pro
            405                 410                 415

Ser Thr Ser Pro Thr Asn Ala Ala Thr Ser Thr Tyr Ile Gly Ile His
            420                 425                 430

Gly Thr Gln Tyr Tyr Leu Trp Pro Trp Tyr Tyr Phe Pro Lys Lys
            435                 440                 445

Arg Lys Arg Ile Pro Tyr Phe Phe Ala Asp Gly Phe Val Ala Ala
450                 455                 460

<210> SEQ ID NO 4
<211> LENGTH: 507
<212> TYPE: PRT
<213> ORGANISM: Human papillomavirus type 1a

<400> SEQUENCE: 4

Met Tyr Arg Leu Arg Arg Lys Arg Ala Ala Pro Lys Asp Ile Tyr Pro
1               5                   10                  15

Ser Cys Lys Ile Ser Asn Thr Cys Pro Pro Asp Ile Gln Asn Lys Ile
            20                  25                  30

Glu His Thr Thr Ile Ala Asp Lys Ile Leu Gln Tyr Gly Ser Leu Gly
            35                  40                  45

Val Phe Leu Gly Gly Leu Gly Ile Gly Thr Ala Arg Gly Ser Gly Gly
        50                  55                  60

Arg Ile Gly Tyr Thr Pro Leu Gly Glu Gly Gly Gly Val Arg Val Ala
65                  70                  75                  80

Thr Arg Pro Thr Pro Val Arg Pro Thr Ile Pro Val Glu Thr Val Gly
            85                  90                  95

Pro Ser Glu Ile Phe Pro Ile Asp Val Val Asp Pro Thr Gly Pro Ala
            100                 105                 110

Val Ile Pro Leu Gln Asp Leu Gly Arg Asp Phe Pro Ile Pro Thr Val
        115                 120                 125

Gln Val Ile Ala Glu Ile His Pro Ile Ser Asp Ile Pro Asn Ile Val
        130                 135                 140

```
Ala Ser Ser Thr Asn Glu Gly Glu Ser Ala Ile Leu Asp Val Leu Arg
145                 150                 155                 160

Gly Asn Ala Thr Ile Arg Thr Val Ser Arg Thr Gln Tyr Asn Asn Pro
            165                 170                 175

Ser Phe Thr Val Ala Ser Thr Ser Asn Ile Ser Ala Gly Glu Ala Ser
            180                 185                 190

Thr Ser Asp Ile Val Phe Val Ser Asn Gly Ser Gly Asp Arg Val Val
            195                 200                 205

Gly Glu Asp Ile Pro Leu Val Glu Leu Asn Leu Gly Leu Glu Thr Asp
210                 215                 220

Thr Ser Ser Val Val Gln Glu Thr Ala Phe Ser Ser Thr Pro Ile
225                 230                 235                 240

Ala Glu Arg Pro Ser Phe Arg Pro Ser Arg Phe Tyr Asn Arg Arg Leu
            245                 250                 255

Tyr Glu Gln Val Gln Val Gln Asp Pro Arg Phe Val Glu Gln Pro Gln
            260                 265                 270

Ser Met Val Thr Phe Asp Asn Pro Ala Phe Glu Pro Glu Leu Asp Glu
            275                 280                 285

Val Ser Ile Ile Phe Gln Arg Asp Leu Asp Ala Leu Ala Gln Thr Pro
290                 295                 300

Val Pro Glu Phe Arg Asp Val Val Tyr Leu Ser Lys Pro Thr Phe Ser
305                 310                 315                 320

Arg Glu Pro Gly Gly Arg Leu Arg Val Ser Arg Leu Gly Lys Ser Ser
            325                 330                 335

Thr Ile Arg Thr Arg Leu Gly Thr Ala Ile Gly Ala Arg Thr His Phe
            340                 345                 350

Phe Tyr Asp Leu Ser Ser Ile Ala Pro Glu Asp Ser Ile Glu Leu Leu
            355                 360                 365

Pro Leu Gly Glu His Ser Gln Thr Thr Val Ile Ser Ser Asn Leu Gly
370                 375                 380

Asp Thr Ala Phe Ile Gln Gly Glu Thr Ala Glu Asp Leu Glu Val
385                 390                 395                 400

Ile Ser Leu Glu Thr Pro Gln Leu Tyr Ser Glu Glu Leu Leu Asp
                405                 410                 415

Thr Asn Glu Ser Val Gly Glu Asn Leu Gln Leu Thr Ile Thr Asn Ser
            420                 425                 430

Glu Gly Glu Val Ser Ile Leu Asp Leu Thr Gln Ser Arg Val Arg Pro
            435                 440                 445

Pro Phe Gly Thr Glu Asp Thr Ser Leu His Val Tyr Tyr Pro Asn Ser
            450                 455                 460

Ser Lys Gly Thr Pro Ile Ile Asn Pro Glu Glu Ser Phe Thr Pro Leu
465                 470                 475                 480

Val Ile Ile Ala Leu Asn Asn Ser Thr Gly Asp Phe Glu Leu His Pro
                485                 490                 495

Ser Leu Arg Lys Arg Arg Lys Arg Ala Tyr Val
            500                 505
```

<210> SEQ ID NO 5
<211> LENGTH: 468
<212> TYPE: PRT
<213> ORGANISM: Human papillomavirus type 2

<400> SEQUENCE: 5

Met Ser Ile Arg Ala Lys Arg Arg Lys Arg Ala Ser Pro Thr Asp Leu

```
  1               5                  10                 15
Tyr Arg Thr Cys Lys Gln Ala Gly Thr Cys Pro Pro Asp Ile Ile Pro
             20                 25                 30

Arg Val Glu Gln Asn Thr Leu Ala Asp Lys Leu Leu Lys Trp Gly Ser
             35                 40                 45

Leu Gly Val Phe Phe Gly Leu Gly Ile Gly Thr Gly Ser Gly Thr
 50                 55                 60

Gly Gly Arg Thr Gly Tyr Ile Pro Val Gly Ser Arg Pro Thr Thr Val
 65                 70                 75                 80

Val Asp Ile Gly Pro Thr Pro Arg Pro Pro Val Ile Ile Glu Pro Val
                 85                 90                 95

Gly Ala Ser Glu Pro Ser Ile Val Thr Leu Val Glu Asp Ser Ser Ile
                100                105                110

Ile Asn Ala Gly Ala Ser His Pro Thr Phe Thr Gly Thr Gly Gly Phe
                115                120                125

Glu Val Thr Thr Ser Thr Val Thr Asp Pro Ala Val Leu Asp Ile Thr
                130                135                140

Pro Ser Gly Thr Ser Val Gln Val Ser Ser Ser Phe Leu Asn Pro
145                150                155                160

Leu Tyr Thr Glu Pro Ala Ile Val Glu Ala Pro Gln Thr Gly Glu Val
                165                170                175

Ser Gly His Val Leu Val Ser Thr Ala Thr Ser Gly Ser His Gly Tyr
                180                185                190

Glu Glu Ile Pro Met Gln Thr Phe Ala Thr Ser Gly Gly Ser Gly Thr
                195                200                205

Glu Pro Ile Ser Ser Thr Pro Leu Pro Gly Val Arg Arg Val Ala Gly
                210                215                220

Pro Arg Leu Tyr Ser Arg Ala Asn Gln Gln Val Gln Val Arg Asp Pro
225                230                235                240

Ala Phe Leu Ala Arg Pro Ala Asp Leu Val Thr Phe Asp Asn Pro Val
                245                250                255

Tyr Asp Pro Glu Glu Thr Ile Ile Phe Gln His Pro Asp Leu His Glu
                260                265                270

Pro Pro Asp Pro Asp Phe Leu Asp Ile Val Ala Leu His Arg Pro Ala
                275                280                285

Leu Thr Ser Arg Arg Gly Thr Val Arg Phe Ser Arg Leu Gly Arg Arg
                290                295                300

Ala Thr Leu Arg Thr Arg Ser Gly Lys Gln Ile Gly Ala Arg Val His
305                310                315                320

Phe Tyr His Asp Ile Ser Pro Ile Gly Thr Glu Glu Leu Glu Met Glu
                325                330                335

Pro Leu Leu Pro Pro Ala Ser Thr Asp Asn Thr Asp Met Leu Tyr Asp
                340                345                350

Val Tyr Ala Asp Ser Asp Val Leu Gln Pro Leu Leu Asp Glu Leu Pro
                355                360                365

Ala Ala Pro Arg Gly Ser Leu Ser Leu Ala Asp Thr Ala Val Ser Ala
                370                375                380

Thr Ser Ala Ser Thr Leu Arg Gly Ser Thr Thr Val Pro Leu Ser Ser
385                390                395                400

Gly Ile Asp Val Pro Val Tyr Thr Gly Pro Asp Ile Glu Pro Pro Asn
                405                410                415

Val Pro Gly Met Gly Pro Leu Ile Pro Val Ala Pro Ser Leu Pro Ser
                420                425                430
```

```
Ser Val Tyr Ile Phe Gly Gly Asp Tyr Tyr Leu Met Pro Ser Tyr Val
        435                 440                 445
Leu Trp Pro Lys Arg Arg Lys Arg Val His Tyr Phe Phe Ala Asp Gly
450                 455                 460
Phe Val Ala Ala
465

<210> SEQ ID NO 6
<211> LENGTH: 473
<212> TYPE: PRT
<213> ORGANISM: Human papillomavirus type 3

<400> SEQUENCE: 6

Met Val Ala His Arg Ala Arg Arg Lys Arg Ala Ser Ala Thr Gln
1               5                   10                  15

Leu Tyr Arg Thr Cys Lys Ala Ala Gly Thr Cys Pro Pro Asp Val Ile
            20                  25                  30

Pro Lys Val Glu Gly Thr Thr Leu Ala Asp Arg Ile Leu Gln Trp Gly
        35                  40                  45

Ser Leu Gly Val Tyr Leu Gly Gly Leu Gly Ile Gly Thr Gly Ser Gly
    50                  55                  60

Thr Gly Gly Arg Thr Gly Tyr Ala Pro Ile Ser Thr Arg Pro Gly Thr
65                  70                  75                  80

Val Val Asp Val Ser Val Pro Ala Lys Pro Pro Val Val Ile Glu Pro
                85                  90                  95

Val Gly Pro Ser Asp Pro Ser Ile Val Asn Leu Leu Glu Asp Ser Ser
            100                 105                 110

Ile Ile Asn Ser Gly Ser Thr Ile Pro Thr Phe Thr Gly Thr Asp Gly
        115                 120                 125

Phe Glu Val Ile Ser Ser Ala Thr Thr Thr Pro Ala Val Leu Asp Ile
    130                 135                 140

Thr Pro Ala Ser Asp Asn Val Val Val Ser Ser Thr Asn Phe Ser Asn
145                 150                 155                 160

Pro Ala Phe Thr Glu Pro Ser Leu Leu Glu Val Pro Gln Asn Gly Glu
                165                 170                 175

Val Ser Gly His Ile Leu Ile Ser Thr Pro Thr Ser Gly Thr His Gly
            180                 185                 190

Tyr Glu Glu Ile Pro Met Glu Thr Phe Ala Ser Pro Gly Thr Gly Thr
        195                 200                 205

Glu Pro Ile Ser Ser Thr Pro Val Pro Gly Val Ser Arg Ile Ala Gly
    210                 215                 220

Pro Arg Leu Tyr Ser Lys Ala Val Thr Gln Val Lys Val Thr Asp Pro
225                 230                 235                 240

Ala Phe Leu Thr Arg Pro Arg Ser Leu Met Thr Phe Asp Asn Pro Val
                245                 250                 255

Phe Glu Pro Glu Asp Glu Thr Ile Ile Phe Glu Arg Pro Tyr Ser Pro
            260                 265                 270

Ser Gln Val Pro Asp Ser Asp Phe Leu Asp Ile Leu Arg Leu His Arg
        275                 280                 285

Pro Ala Leu Thr Ser Arg Arg Gly Thr Val Arg Tyr Ser Arg Val Gly
    290                 295                 300

Gln Lys Leu Ser Met Arg Thr Arg Ser Gly Lys Gly Leu Gly Ala Arg
305                 310                 315                 320

Val His Tyr Tyr Gln Asp Leu Ser Pro Ile Gly Pro Thr Glu Asp Ile
```

-continued

```
                    325                 330                 335
Glu Met Glu Pro Leu Ile Ala Pro Ala Ser Ala Ser Ala Tyr Asp Ser
                340                 345                 350
Leu Tyr Asp Val Tyr Ala Asp Val Asp Ala Asp Ile Gly Phe Thr
                355                 360                 365
Ser Gly Gly Arg Ser Asp Thr Leu Ser Arg Gly Arg Ala Thr Val Ser
            370                 375                 380
Pro Leu Ser Ser Thr Leu Ser Thr Lys Tyr Gly Asn Val Thr Ile Pro
385                 390                 395                 400
Phe Val Ser Pro Val Asp Val Pro Leu Gln Pro Gly Pro Asp Ile Leu
                405                 410                 415
Leu Pro Ala Ser Ala Gln Trp Pro Phe Val Pro Leu Ser Pro Val Asp
                420                 425                 430
Thr Thr His Tyr Val Tyr Ile Asp Gly Gly Asp Phe Tyr Leu Trp Pro
                435                 440                 445
Val Thr Phe Phe Leu Pro Arg Arg Arg Arg Lys Arg Val Ser Tyr
            450                 455                 460
Phe Leu Ala Asp Gly Thr Val Ala Leu
465                 470

<210> SEQ ID NO 7
<211> LENGTH: 521
<212> TYPE: PRT
<213> ORGANISM: Human papillomavirus type 4

<400> SEQUENCE: 7

Met Gln Ser Leu Ser Arg Arg Lys Arg Asp Ser Val Pro Asn Leu Tyr
1               5                   10                  15
Ala Lys Cys Gln Leu Ser Gly Asn Cys Leu Pro Asp Val Lys Asn Lys
                20                  25                  30
Val Glu Ala Asp Thr Leu Ala Asp Arg Leu Leu Arg Trp Leu Gly Ser
            35                  40                  45
Val Ile Tyr Leu Gly Gly Leu Gly Ile Gly Thr Gly Arg Gly Ser Gly
        50                  55                  60
Gly Ser Thr Gly Tyr Asn Pro Ile Gly Ala Pro Ser Arg Val Thr Pro
65                  70                  75                  80
Ser Gly Thr Leu Val Arg Pro Thr Val Pro Val Glu Ser Leu Gly Pro
                85                  90                  95
Ser Glu Ile Ile Pro Ile Asp Ala Ile Asp Pro Thr Thr Ser Ser Val
                100                 105                 110
Val Pro Leu Glu Asp Leu Thr Ile Pro Asp Val Thr Val Asp Ser Gly
            115                 120                 125
Asp Thr Arg Gly Ile Gly Glu Thr Thr Leu Gln Pro Ala Gln Val Asp
        130                 135                 140
Ile Ser Thr Ser His Asp Pro Ile Ser Asp Val Thr Gly Ala Ser Ser
145                 150                 155                 160
His Pro Thr Ile Ile Ser Gly Glu Asp Asn Ala Ile Ala Val Leu Asp
                165                 170                 175
Val Ser Pro Ile Glu Pro Pro Thr Lys Arg Ile Ala Leu Ala Thr Arg
                180                 185                 190
Gly Ala Ser Ala Thr Pro His Val Ser Val Ile Ser Gly Thr Thr Glu
            195                 200                 205
Phe Gly Gln Ser Ser Asp Leu Asn Val Phe Val Asn Ala Thr Phe Ser
        210                 215                 220
```

```
Gly Asp Ser Ile Gly Tyr Thr Glu Glu Ile Pro Leu Glu Pro Leu Asn
225                 230                 235                 240

Pro Phe Gln Glu Phe Glu Ile Glu Ser Pro Pro Lys Thr Ser Thr Pro
            245                 250                 255

Arg Asp Val Leu Asn Arg Ala Ile Gly Arg Ala Arg Asp Leu Tyr Asn
            260                 265                 270

Arg Arg Val Gln Gln Ile Pro Thr Arg Asn Pro Ala Leu Leu Thr Gln
        275                 280                 285

Pro Ser Arg Ala Ile Val Phe Gly Phe Glu Asn Pro Ala Phe Asp Ala
    290                 295                 300

Asp Ile Thr Gln Thr Phe Glu Arg Asp Leu Glu Gln Val Ala Ala Ala
305                 310                 315                 320

Pro Asp Ala Asp Phe Ala Asp Ile Val Thr Ile Gly Arg Pro Arg Phe
                325                 330                 335

Ser Glu Thr Asp Ala Gly Gln Ile Arg Val Ser Arg Leu Gly Arg Arg
            340                 345                 350

Gly Thr Ile Lys Thr Arg Ser Gly Val Gln Ile Gly Gln Ala Val His
        355                 360                 365

Phe Tyr Tyr Asp Leu Ser Thr Ile Asp Thr Ala Asp Ala Ile Glu Leu
    370                 375                 380

Ser Thr Leu Gly Gln His Ser Gly Glu Gln Ser Ile Val Asp Ala Met
385                 390                 395                 400

Ile Glu Ser Ser Leu Ile Asp Pro Phe Glu Met Pro Asp Pro Thr Phe
                405                 410                 415

Thr Glu Gln Gln Leu Leu Asp Pro Leu Thr Glu Ala Phe Ser Gln
            420                 425                 430

Ser His Leu Val Leu Thr Ser Ser Arg Arg Gly Thr Ser Phe Thr Ile
    435                 440                 445

Pro Thr Ile Pro Pro Gly Leu Gly Leu Arg Ile Tyr Val Asp Asp Val
    450                 455                 460

Gly Ser Asp Leu Phe Val Ser Tyr Pro Glu Ser Arg Val Ile Pro Ala
465                 470                 475                 480

Gly Gly Leu Pro Thr Glu Pro Phe Val Pro Leu Glu Pro Ala Leu Leu
                485                 490                 495

Ser Asp Ile Phe Ser Thr Asp Phe Val Tyr Arg Pro Ser Leu Tyr Arg
            500                 505                 510

Lys Lys Arg Lys Arg Leu Glu Met Phe
        515                 520

<210> SEQ ID NO 8
<211> LENGTH: 518
<212> TYPE: PRT
<213> ORGANISM: Human papillomavirus type 5

<400> SEQUENCE: 8

Met Ala Arg Ala Lys Arg Val Lys Arg Asp Ser Val Thr His Ile Tyr
1               5                   10                  15

Gln Thr Cys Lys Gln Ala Gly Thr Cys Pro Pro Asp Val Ile Asn Lys
            20                  25                  30

Val Glu Gln Thr Thr Val Ala Asp Asn Ile Leu Lys Tyr Gly Ser Ala
        35                  40                  45

Gly Val Phe Phe Gly Gly Leu Gly Ile Ser Thr Gly Arg Gly Thr Gly
    50                  55                  60

Gly Ala Thr Gly Tyr Val Pro Leu Gly Glu Gly Pro Gly Val Arg Val
65                  70                  75                  80
```

```
Gly Gly Thr Pro Thr Val Val Arg Pro Ser Leu Val Pro Glu Thr Ile
                85                  90                  95

Gly Pro Val Asp Ile Leu Pro Ile Asp Thr Val Asn Pro Val Glu Pro
                100                 105                 110

Thr Ala Ser Ser Val Val Pro Leu Thr Glu Ser Thr Gly Ala Asp Leu
            115                 120                 125

Leu Pro Gly Glu Val Glu Thr Ile Ala Glu Ile His Pro Val Pro Glu
130                 135                 140

Gly Pro Ser Val Asp Thr Pro Val Val Thr Thr Ser Thr Gly Ser Ser
145                 150                 155                 160

Ala Val Leu Glu Val Ala Pro Glu Pro Ile Pro Pro Thr Arg Val Arg
                165                 170                 175

Val Ser Arg Thr Gln Tyr His Asn Pro Ser Phe Gln Ile Ile Thr Glu
            180                 185                 190

Ser Thr Pro Ala Gln Gly Glu Ser Ser Leu Ala Asp His Val Leu Val
        195                 200                 205

Thr Ser Gly Ser Gly Gly Gln Arg Ile Gly Gly Asp Ile Thr Asp Ile
    210                 215                 220

Ile Glu Leu Glu Glu Ile Pro Ser Arg Tyr Thr Phe Glu Ile Glu Glu
225                 230                 235                 240

Pro Thr Pro Pro Arg Arg Ser Ser Thr Pro Leu Pro Arg Asn Gln Ser
                245                 250                 255

Val Gly Arg Arg Arg Gly Phe Ser Leu Thr Asn Arg Arg Leu Val Gln
            260                 265                 270

Gln Val Gln Val Asp Asn Pro Leu Phe Leu Thr Gln Pro Ser Lys Leu
        275                 280                 285

Val Arg Phe Ala Phe Asp Asn Pro Val Phe Glu Glu Val Thr Asn
    290                 295                 300

Ile Phe Glu Asn Asp Leu Asp Val Phe Glu Glu Pro Pro Asp Arg Asp
305                 310                 315                 320

Phe Leu Asp Val Arg Glu Leu Gly Arg Pro Gln Tyr Ser Thr Thr Pro
                325                 330                 335

Ala Gly Tyr Val Arg Val Ser Arg Leu Gly Thr Arg Ala Thr Ile Arg
            340                 345                 350

Thr Arg Ser Gly Ala Gln Ile Gly Ser Gln Val His Phe Tyr Arg Asp
        355                 360                 365

Leu Ser Ser Ile Asn Thr Glu Asp Pro Ile Glu Leu Gln Leu Leu Gly
    370                 375                 380

Gln His Ser Gly Asp Ala Thr Ile Val Gln Gly Pro Val Glu Ser Thr
385                 390                 395                 400

Phe Ile Asp Met Asp Ile Ser Glu Asn Pro Leu Ser Glu Ser Ile Glu
                405                 410                 415

Ala Tyr Ser His Asp Leu Leu Leu Asp Glu Thr Val Glu Asp Phe Ser
            420                 425                 430

Gly Ser Gln Leu Val Ile Gly Asn Arg Arg Ser Thr Asn Ser Tyr Thr
        435                 440                 445

Val Pro Arg Phe Glu Thr Thr Arg Asn Gly Ser Tyr Tyr Thr Gln Asp
    450                 455                 460

Thr Lys Gly Tyr Tyr Val Ala Tyr Pro Glu Ser Arg Asn Asn Ala Glu
465                 470                 475                 480

Ile Ile Tyr Pro Thr Pro Asp Ile Pro Val Val Ile Ile His Pro His
                485                 490                 495
```

```
Asp Ser Thr Gly Asp Phe Tyr Leu His Pro Ser Leu Arg Arg Lys
                500                 505                 510

Arg Lys Arg Lys Tyr Leu
        515
```

<210> SEQ ID NO 9
<211> LENGTH: 459
<212> TYPE: PRT
<213> ORGANISM: Human papillomavirus type 6

<400> SEQUENCE: 9

```
Met Ala His Ser Arg Ala Arg Arg Lys Arg Ala Ser Ala Thr Gln
1               5                   10                  15

Leu Tyr Gln Thr Cys Lys Leu Thr Gly Thr Cys Pro Pro Asp Val Ile
                20                  25                  30

Pro Lys Val Glu His Asn Thr Ile Ala Asp Gln Ile Leu Lys Trp Gly
            35                  40                  45

Ser Leu Gly Val Phe Phe Gly Gly Leu Gly Ile Gly Thr Gly Ser Gly
50                  55                  60

Thr Gly Gly Arg Thr Gly Tyr Val Pro Leu Gly Thr Ser Ala Lys Pro
65                  70                  75                  80

Ser Ile Thr Ser Gly Pro Met Ala Arg Pro Pro Val Val Val Glu Pro
                85                  90                  95

Val Ala Pro Ser Asp Pro Ser Ile Val Ser Leu Ile Glu Glu Ser Ala
            100                 105                 110

Ile Ile Asn Ala Gly Ala Pro Glu Ile Val Pro Pro Ala His Gly Gly
        115                 120                 125

Phe Thr Ile Thr Ser Ser Glu Thr Thr Thr Pro Ala Ile Leu Asp Val
130                 135                 140

Ser Val Thr Ser His Thr Thr Thr Ser Ile Phe Arg Asn Pro Val Phe
145                 150                 155                 160

Thr Glu Pro Ser Val Thr Gln Pro Gln Pro Pro Val Glu Ala Asn Gly
                165                 170                 175

His Ile Leu Ile Ser Ala Pro Thr Ile Thr Ser His Pro Ile Glu Glu
            180                 185                 190

Ile Pro Leu Asp Thr Phe Val Ile Ser Ser Ser Asp Ser Gly Pro Thr
        195                 200                 205

Ser Ser Thr Pro Val Pro Gly Thr Ala Pro Arg Pro Arg Val Gly Leu
210                 215                 220

Tyr Ser Arg Ala Leu His Gln Val Gln Val Thr Asp Pro Ala Phe Leu
225                 230                 235                 240

Ser Thr Pro Gln Arg Leu Ile Thr Tyr Asp Asn Pro Val Tyr Glu Gly
                245                 250                 255

Glu Asp Val Ser Val Gln Phe Ser His Asp Ser Ile His Asn Ala Pro
            260                 265                 270

Asp Glu Ala Phe Met Asp Ile Ile Arg Leu His Arg Pro Ala Ile Ala
        275                 280                 285

Ser Arg Arg Gly Leu Val Arg Tyr Ser Arg Ile Gly Gln Arg Gly Ser
290                 295                 300

Met His Thr Arg Ser Gly Lys His Ile Gly Ala Arg Ile His Tyr Phe
305                 310                 315                 320

Tyr Asp Ile Ser Pro Ile Ala Gln Ala Glu Glu Ile Glu Met His
                325                 330                 335

Pro Leu Val Ala Ala Gln Glu Asp Thr Phe Asp Ile Tyr Ala Glu Ser
            340                 345                 350
```

```
Phe Glu Pro Asp Ile Asn Pro Thr Gln His Pro Val Thr Asn Ile Ser
            355                 360                 365

Asp Thr Tyr Leu Thr Ser Thr Pro Asn Thr Val Thr Gln Pro Trp Gly
    370                 375                 380

Asn Thr Thr Val Pro Leu Ser Ile Pro Asn Asp Leu Phe Leu Gln Ser
385                 390                 395                 400

Gly Pro Asp Ile Thr Phe Pro Thr Ala Pro Met Gly Thr Pro Phe Ser
                405                 410                 415

Pro Val Thr Pro Ala Leu Pro Thr Gly Pro Val Phe Ile Thr Gly Ser
                420                 425                 430

Gly Phe Tyr Leu His Pro Ala Trp Tyr Phe Ala Arg Lys Arg Arg Lys
            435                 440                 445

Arg Ile Pro Leu Phe Phe Ser Asp Val Ala Ala
            450                 455
```

<210> SEQ ID NO 10
<211> LENGTH: 456
<212> TYPE: PRT
<213> ORGANISM: Human papillomavirus type 7

<400> SEQUENCE: 10

```
Met Val Ser Ser Arg Pro Arg Arg Lys Arg Ala Ser Ala Thr Gln
1               5                   10                  15

Leu Tyr Gln Thr Cys Lys Ala Ala Gly Thr Cys Pro Pro Asp Val Val
                20                  25                  30

Asn Lys Val Glu Gln Thr Thr Val Ala Asp Gln Ile Leu Lys Trp Gly
            35                  40                  45

Ser Met Gly Val Phe Phe Gly Gly Leu Gly Ile Gly Ser Gly Ser Gly
        50                  55                  60

Ser Gly Gly Arg Ala Gly Tyr Val Pro Leu Ser Thr Gly Ser Arg Ala
65                  70                  75                  80

Ile Pro Pro Lys Ser Leu Ala Pro Asp Val Ile Ala Arg Pro Pro Val
                85                  90                  95

Val Val Asp Thr Val Ala Pro Thr Asp Pro Ser Ile Val Ser Leu Ile
                100                 105                 110

Glu Glu Ser Ser Ile Ile Gln Ser Gly Ala Pro Ser Pro Val Ile Pro
            115                 120                 125

Thr Glu Gly Gly Phe Ser Ile Thr Ser Ser Gly Thr Asp Val Pro Ala
        130                 135                 140

Ile Leu Asp Ile Ser Ser Thr Asn Thr Val His Val Thr Ser Thr Thr
145                 150                 155                 160

His His Asn Pro Ile Phe Thr Asp Pro Ser Val Val Gln Pro Ile Pro
                165                 170                 175

Pro Val Glu Ala Ser Gly Arg Ile Ile Val Ser His Ser Ser Ile Thr
                180                 185                 190

Thr Gly Ala Ala Glu Glu Ile Pro Met Asp Thr Phe Val His Ser
            195                 200                 205

Asp Pro Leu Ser Ser Thr Pro Val Pro Gly Val Ser Ala Arg Pro Lys
        210                 215                 220

Val Gly Leu Tyr Ser Lys Ala Leu Gln Gln Val Glu Ile Val Asp Pro
225                 230                 235                 240

Thr Phe Met Ser Thr Pro Gln Arg Leu Ile Thr Tyr Asp Asn Pro Val
                245                 250                 255

Phe Asp Asn Ile Glu Asp Thr Leu His Phe Glu Gln Pro Ser Ile His
```

```
                 260                 265                 270
Asn Ala Pro Asp Pro Ala Phe Met Asp Ile Ile Thr Leu His Arg Pro
            275                 280                 285
Ala Leu Thr Ser Arg Arg Gly Val Val Arg Phe Ser Arg Val Gly Gln
        290                 295                 300
Arg Gly Thr Met Tyr Thr Arg Arg Gly Thr Arg Ile Gly Gly Arg Val
305                 310                 315                 320
His Phe Phe Lys Asp Ile Ser Pro Ile Ala Ser Ser Glu Glu Ile Glu
                325                 330                 335
Leu His Pro Leu Val Ala Ser Pro Asn Asn Ser Asp Leu Phe Asp Val
            340                 345                 350
Tyr Ala Asp Ile Asp Asp Ile Asp Glu Asn Ile Leu Tyr Ser Thr Ile
        355                 360                 365
Asp Asn Asn Thr Pro Thr Ser Thr Tyr Ser Leu Tyr Pro Gly Asn Ser
    370                 375                 380
Thr Arg Ile Ala Asn Thr Ser Ile Pro Leu Ala Thr Ile Pro Asp Thr
385                 390                 395                 400
Phe Leu Thr Ser Gly Pro Asp Ile Val Phe Pro Ser Val Pro Ala Gly
                405                 410                 415
Thr Pro Tyr Leu Pro Val Ser Pro Ser Ile Pro Ala Ile Ser Val Leu
            420                 425                 430
Ile Arg Gly Thr Asp Tyr Tyr Leu Asn Pro Ala Tyr Tyr Phe Arg Lys
        435                 440                 445
Arg Arg Lys Arg Ile Leu Ala Tyr
    450                 455

<210> SEQ ID NO 11
<211> LENGTH: 518
<212> TYPE: PRT
<213> ORGANISM: Human papillomavirus type 8

<400> SEQUENCE: 11

Met Ala Arg Ala Arg Arg Val Lys Arg Asp Ser Val Thr His Ile Tyr
1               5                   10                  15
Gln Thr Cys Lys Gln Ala Gly Thr Cys Pro Pro Asp Val Ile Asn Lys
            20                  25                  30
Val Glu Gln Thr Thr Val Ala Asp Asn Ile Leu Lys Tyr Gly Ser Ala
        35                  40                  45
Gly Val Phe Phe Gly Gly Leu Gly Ile Gly Thr Gly Arg Gly Thr Gly
    50                  55                  60
Gly Val Thr Gly Tyr Thr Pro Leu Ser Glu Gly Pro Gly Ile Arg Val
65                  70                  75                  80
Gly Asn Thr Pro Thr Val Val Arg Pro Ser Leu Val Pro Glu Ala Val
                85                  90                  95
Gly Pro Met Asp Ile Leu Pro Ile Asp Thr Ile Asp Pro Val Glu Pro
            100                 105                 110
Ser Val Ser Ser Val Val Pro Leu Thr Glu Ser Ser Gly Ala Asp Leu
        115                 120                 125
Leu Pro Gly Glu Val Glu Thr Ile Ala Glu Ile His Pro Val Pro Glu
    130                 135                 140
Gly Pro Thr Ile Asp Ser Pro Val Val Thr Thr Ser Lys Gly Ser Ser
145                 150                 155                 160
Ala Ile Leu Glu Val Ala Pro Glu Pro Thr Pro Pro Thr Arg Val Arg
                165                 170                 175
```

```
Val Ser Arg Thr Gln Tyr His Asn Pro Ser Phe Gln Ile Ile Thr Asp
            180                 185                 190

Ser Thr Pro Thr Gln Gly Glu Ser Ser Leu Ala Asp His Ile Leu Val
            195                 200                 205

Thr Ser Gly Ser Gly Gln Thr Ile Gly Ser Asp Ile Thr Asp Val
        210                 215                 220

Ile Glu Leu Gln Glu Phe Pro Ser Arg Tyr Ser Phe Glu Ile Asp Glu
225                 230                 235                 240

Pro Thr Pro Pro Arg Gln Ser Ser Thr Pro Ile Glu Arg Pro Gln Val
            245                 250                 255

Val Gly Arg Arg Arg Gly Ile Ser Leu Thr Asn Arg Arg Leu Ile Gln
            260                 265                 270

Gln Val Ala Val Glu Asp Pro Leu Phe Leu Ser Lys Pro Ser Lys Leu
        275                 280                 285

Val Arg Phe Ser Phe Asp Asn Pro Val Phe Glu Glu Glu Val Thr Asn
            290                 295                 300

Ile Phe Glu Gln Asp Val Asp Met Val Glu Glu Pro Pro Asp Arg Asp
305                 310                 315                 320

Phe Leu Asp Val Arg Gln Leu Gly Arg Pro Gln Tyr Ser Thr Thr Pro
            325                 330                 335

Ala Gly Tyr Val Arg Val Ser Arg Leu Gly Thr Arg Gly Thr Ile Arg
            340                 345                 350

Thr Arg Ser Gly Ala Gln Ile Gly Ser Gln Val His Phe Tyr Arg Asp
            355                 360                 365

Leu Ser Ser Ile Asn Thr Glu Asp Pro Ile Glu Leu Gln Leu Leu Gly
370                 375                 380

Gln His Ser Gly Asp Ser Thr Ile Val Gln Gly Pro Val Glu Ser Thr
385                 390                 395                 400

Phe Val Asn Val Asp Ile Ser Glu Asn Pro Leu Ser Glu Ser Ile Gln
            405                 410                 415

Ala Phe Ser Asp Asp Leu Leu Leu Asp Glu Thr Val Glu Asp Phe Ser
            420                 425                 430

Gly Ser Gln Leu Val Ile Gly Asn Arg Arg Ser Thr Thr Ser Tyr Thr
            435                 440                 445

Val Pro Arg Phe Glu Thr Thr Arg Ser Gly Ser Tyr Tyr Val Gln Asp
450                 455                 460

Thr Lys Gly Tyr Tyr Val Ala Tyr Pro Glu Ser Arg Asn Asn Glu Glu
465                 470                 475                 480

Ile Ile Tyr Pro Thr Pro Asp Leu Pro Val Val Ile Ile His Thr His
            485                 490                 495

Asp Asn Ser Gly Asp Phe Phe Leu His Pro Ser Leu Arg Arg Arg Lys
            500                 505                 510

Arg Lys Arg Lys Tyr Leu
            515

<210> SEQ ID NO 12
<211> LENGTH: 533
<212> TYPE: PRT
<213> ORGANISM: Human papillomavirus type 9

<400> SEQUENCE: 12

Met Val Arg Ala Lys Arg Thr Lys Arg Ala Ser Val Thr Asp Ile Tyr
1               5                   10                  15

Arg Gly Cys Lys Ala Ala Gly Thr Cys Pro Pro Asp Val Ile Asn Lys
            20                  25                  30
```

```
Val Glu His Thr Thr Ile Ala Asp Lys Ile Leu Gln Tyr Gly Ser Ala
         35                  40                  45

Gly Val Phe Phe Gly Gly Leu Gly Ile Ser Thr Gly Arg Gly Thr Gly
 50                  55                  60

Gly Ala Thr Gly Tyr Val Pro Leu Gly Glu Gly Pro Gly Val Arg Val
 65                  70                  75                  80

Gly Gly Thr Pro Thr Ile Val Arg Pro Gly Val Ile Pro Glu Ile Ile
                 85                  90                  95

Gly Pro Thr Asp Leu Ile Pro Leu Asp Thr Val Arg Pro Ile Asp Pro
                100                 105                 110

Thr Ala Pro Ser Ile Val Thr Gly Thr Asp Ser Thr Val Asp Leu Leu
                115                 120                 125

Pro Gly Glu Ile Glu Ser Ile Ala Glu Ile His Pro Val Pro Val Asp
                130                 135                 140

Asn Ala Val Val Asp Thr Pro Val Val Thr Glu Gly Arg Arg Gly Ser
145                 150                 155                 160

Ser Ala Ile Leu Glu Val Ala Asp Pro Ser Pro Met Arg Thr Arg
                165                 170                 175

Val Ala Arg Thr Gln Tyr His Asn Pro Ala Phe Gln Ile Ile Ser Glu
                180                 185                 190

Ser Thr Pro Met Ser Gly Glu Ser Leu Ala Asp His Ile Ile Val
                195                 200                 205

Phe Glu Gly Ser Gly Gly Gln Leu Val Gly Gly Pro Arg Glu Ser Tyr
                210                 215                 220

Thr Ala Ser Ser Glu Asn Ile Glu Leu Gln Glu Phe Pro Ser Arg Tyr
225                 230                 235                 240

Ser Phe Glu Ile Asp Glu Gly Thr Pro Pro Arg Thr Ser Thr Pro Val
                245                 250                 255

Gln Arg Ala Val Gln Ser Leu Ser Ser Leu Arg Arg Ala Leu Tyr Asn
                260                 265                 270

Arg Arg Leu Thr Glu Gln Val Ala Val Thr Asp Pro Leu Phe Leu Ser
                275                 280                 285

Arg Pro Ser Arg Leu Val Gln Phe Gln Phe Asp Asn Pro Ala Phe Glu
                290                 295                 300

Asp Glu Val Thr Gln Ile Phe Glu Arg Asp Leu Ser Thr Val Glu Glu
305                 310                 315                 320

Pro Pro Asp Arg Gln Phe Leu Asp Val Gln Arg Leu Ser Arg Pro Leu
                325                 330                 335

Tyr Thr Glu Thr Pro Gln Gly Tyr Val Arg Val Ser Arg Leu Gly Arg
                340                 345                 350

Arg Ala Thr Ile Arg Thr Arg Ser Gly Ala Gln Val Gly Ala Gln Val
                355                 360                 365

His Phe Tyr Arg Asp Leu Ser Thr Ile Asn Thr Glu Glu Pro Ile Glu
                370                 375                 380

Met Gln Leu Leu Gly Glu His Ser Gly Asp Ser Thr Ile Val Gln Gly
385                 390                 395                 400

Pro Val Glu Ser Ser Ile Val Asp Val Asn Ile Asp Glu Pro Asp Gly
                405                 410                 415

Leu Glu Val Gly Arg Gln Glu Thr Pro Ser Val Glu Asp Val Asp Phe
                420                 425                 430

Asn Ser Glu Asp Leu Leu Leu Asp Glu Gly Val Glu Asp Phe Ser Gly
                435                 440                 445
```

```
Ser Gln Leu Val Val Gly Thr Arg Arg Ser Thr Asn Thr Leu Thr Val
450                 455                 460

Pro Arg Phe Glu Thr Pro Arg Asp Thr Ser Phe Tyr Ile Gln Asp Ile
465                 470                 475                 480

Gln Gly Tyr Thr Val Ser Tyr Pro Glu Ser Arg Gln Thr Thr Asp Ile
                485                 490                 495

Ile Phe Pro His Pro Asp Thr Pro Thr Val Val Ile His Ile Asn Asp
                500                 505                 510

Thr Ser Gly Asp Tyr Tyr Leu His Pro Ser Leu Gln Arg Lys Lys Arg
                515                 520                 525

Lys Arg Lys Tyr Leu
        530

<210> SEQ ID NO 13
<211> LENGTH: 470
<212> TYPE: PRT
<213> ORGANISM: Human papillomavirus type 10

<400> SEQUENCE: 13

Met Val Ala Gln Arg Ala Arg Arg Lys Arg Ala Ser Ala Thr Gln
1               5                   10                  15

Leu Tyr Arg Thr Cys Lys Ala Ser Gly Thr Cys Pro Pro Asp Val Ile
                20                  25                  30

Pro Lys Val Glu Gly Thr Thr Leu Ala Asp Arg Ile Leu Gln Trp Gly
            35                  40                  45

Ser Leu Gly Val Tyr Leu Gly Gly Leu Gly Ile Gly Thr Gly Ser Gly
    50                  55                  60

Thr Gly Gly Arg Thr Gly Tyr Val Pro Ile Ser Thr Arg Pro Gly Thr
65                  70                  75                  80

Val Val Asp Val Ser Val Pro Ala Arg Pro Pro Val Val Ile Glu Pro
                85                  90                  95

Val Gly Pro Ser Asp Pro Ser Ile Val Asn Leu Leu Glu Asp Ser Ser
            100                 105                 110

Ile Ile Asn Ser Gly Ser Thr Ile Pro Thr Phe Ser Gly Thr Ser Gly
        115                 120                 125

Phe Glu Val Thr Ser Ser Ala Thr Thr Thr Pro Ala Val Leu Asp Ile
130                 135                 140

Thr Pro Ala Ser Glu Asn Val Val Ile Ser Ser Thr Asn Phe Thr Asn
145                 150                 155                 160

Pro Ala Phe Thr Glu Pro Ser Leu Val Glu Val Pro Gln Ser Gly Glu
                165                 170                 175

Val Ser Gly His Ile Leu Ile Ser Thr Pro Thr Ala Gly Thr His Gly
            180                 185                 190

Tyr Glu Glu Ile Pro Met Asp Thr Phe Ala Ser Ser Gly Thr Gly Thr
        195                 200                 205

Glu Pro Ile Ser Ser Thr Pro Val Pro Gly Val Ser Arg Ile Ala Gly
210                 215                 220

Pro Arg Leu Tyr Ser Arg Ala Asn Thr Gln Val Lys Val Ser Asp Pro
225                 230                 235                 240

Ala Phe Leu Ser Arg Pro Ser Ser Leu Leu Thr Phe Asp Asn Pro Val
                245                 250                 255

Phe Glu Pro Glu Asp Glu Thr Ile Ile Phe Glu Arg Pro Tyr Ser Pro
            260                 265                 270

Ser Arg Val Pro Asp Pro Asp Phe Leu Asp Ile Val Arg Leu His Arg
        275                 280                 285
```

Pro Ala Leu Thr Ser Arg Arg Gly Thr Val Arg Phe Ser Arg Leu Gly
                290                 295                 300

Gln Lys Phe Ser Met Arg Thr Arg Ser Gly Lys Gly Ile Gly Ala Arg
305                 310                 315                 320

Val His Tyr Tyr Gln Asp Leu Ser Pro Ile Ala Pro Ile Glu Asp Ile
                325                 330                 335

Glu Met Glu Pro Leu Leu Ala Pro Ala Ala Ser Asp Thr Ile Tyr Asp
                340                 345                 350

Ile Phe Ala Asp Val Asp Gly Asp Val Ala Phe Thr Glu Gly Tyr
                355                 360                 365

Arg Ser Thr Thr Gln Ser Arg Gly Tyr Asn Thr Thr Ser Pro Leu Ser
    370                 375                 380

Ser Thr Leu Ser Thr Lys Tyr Gly Asn Val Thr Ile Pro Phe Val Ser
385                 390                 395                 400

Pro Val Asp Val Thr Leu His Thr Gly Pro Asp Ile Val Leu Pro Thr
                405                 410                 415

Ser Ala Gln Trp Pro Tyr Val Pro Leu Ser Pro Ala Asp Thr Thr His
                420                 425                 430

Tyr Val Tyr Ile Asp Gly Gly Asp Phe Tyr Leu Trp Pro Val Thr Phe
                435                 440                 445

His Phe Ser Arg His Arg Arg Lys Arg Val Ser Tyr Phe Phe Ala
    450                 455                 460

Asp Gly Thr Leu Ala Leu
465                 470

<210> SEQ ID NO 14
<211> LENGTH: 455
<212> TYPE: PRT
<213> ORGANISM: Human papillomavirus type 11

<400> SEQUENCE: 14

Met Lys Pro Arg Ala Arg Arg Lys Arg Ala Ser Ala Thr Gln Leu
1               5                   10                  15

Tyr Gln Thr Cys Lys Ala Thr Gly Thr Cys Pro Pro Asp Val Ile Pro
                20                  25                  30

Lys Val Glu His Thr Thr Ile Ala Asp Gln Ile Leu Lys Trp Gly Ser
                35                  40                  45

Leu Gly Val Phe Phe Gly Gly Leu Gly Ile Gly Thr Gly Ala Gly Ser
    50                  55                  60

Gly Gly Arg Ala Gly Tyr Ile Pro Leu Gly Ser Ser Pro Lys Pro Ala
65                  70                  75                  80

Ile Thr Gly Gly Pro Ala Ala Arg Pro Pro Val Leu Val Glu Pro Val
                85                  90                  95

Ala Pro Ser Asp Pro Ser Ile Val Ser Leu Ile Glu Glu Ser Ala Ile
                100                 105                 110

Ile Asn Ala Gly Ala Pro Glu Val Val Pro Pro Thr Gln Gly Gly Phe
    115                 120                 125

Thr Ile Thr Ser Ser Glu Ser Thr Thr Pro Ala Ile Leu Asp Val Ser
130                 135                 140

Val Thr Asn His Thr Thr Thr Ser Val Phe Gln Asn Pro Leu Phe Thr
145                 150                 155                 160

Glu Pro Ser Val Ile Gln Pro Gln Pro Pro Val Glu Ala Asn Gly His
                165                 170                 175

Ile Leu Ile Ser Ala Pro Thr Ile Thr Ser Gln His Val Glu Asp Ile

```
            180                 185                 190
Pro Leu Asp Thr Phe Val Val Ser Ser Asp Ser Gly Pro Thr Ser
            195                 200                 205

Ser Thr Pro Leu Pro Arg Ala Phe Pro Arg Pro Arg Val Gly Leu Tyr
    210                 215                 220

Ser Arg Ala Leu Gln Gln Val Gln Val Arg Asp Pro Ala Phe Leu Ser
225                 230                 235                 240

Thr Pro Gln Arg Leu Val Thr Tyr Asp Asn Pro Val Tyr Glu Gly Glu
                245                 250                 255

Asp Val Ser Leu Gln Phe Thr His Glu Ser Ile His Asn Ala Pro Asp
            260                 265                 270

Glu Ala Phe Met Asp Ile Ile Arg Leu His Arg Pro Ala Ile Thr Ser
        275                 280                 285

Arg Arg Gly Leu Val Arg Phe Ser Arg Ile Gly Gln Arg Gly Ser Met
    290                 295                 300

Tyr Thr Arg Ser Gly Gln His Ile Gly Ala Arg Ile His Tyr Phe Gln
305                 310                 315                 320

Asp Ile Ser Pro Val Thr Gln Ala Ala Glu Glu Ile Glu Leu His Pro
                325                 330                 335

Leu Val Ala Ala Glu Asn Asp Thr Phe Asp Ile Tyr Ala Glu Pro Phe
            340                 345                 350

Asp Pro Ile Pro Asp Pro Val Gln His Ser Val Thr Gln Ser Tyr Leu
        355                 360                 365

Thr Ser Thr Pro Asn Thr Leu Ser Gln Ser Trp Gly Asn Thr Thr Val
    370                 375                 380

Pro Leu Ser Ile Pro Ser Asp Trp Phe Val Gln Ser Gly Pro Asp Ile
385                 390                 395                 400

Thr Phe Pro Thr Ala Ser Met Gly Thr Pro Phe Ser Pro Val Thr Pro
                405                 410                 415

Ala Leu Pro Thr Gly Pro Val Phe Ile Thr Gly Ser Asp Phe Tyr Leu
            420                 425                 430

His Pro Thr Trp Tyr Phe Ala Arg Arg Arg Arg Lys Arg Ile Pro Leu
        435                 440                 445

Phe Phe Thr Asp Val Ala Ala
    450                 455

<210> SEQ ID NO 15
<211> LENGTH: 518
<212> TYPE: PRT
<213> ORGANISM: Human papillomavirus type 12

<400> SEQUENCE: 15

Met Ala Arg Ala Lys Arg Val Lys Arg Asp Ser Val Thr His Ile Tyr
1               5                   10                  15

Gln Thr Cys Lys Gln Ala Gly Thr Cys Pro Pro Asp Val Leu Asn Lys
            20                  25                  30

Val Glu Gln Thr Thr Val Ala Asp Asn Ile Leu Lys Tyr Gly Ser Gly
        35                  40                  45

Gly Val Phe Phe Gly Gly Leu Gly Ile Gly Thr Gly Arg Gly Thr Gly
    50                  55                  60

Gly Val Thr Gly Tyr Arg Pro Leu Pro Glu Gly Pro Gly Ile Arg Val
65                  70                  75                  80

Gly Gly Thr Pro Thr Val Val Arg Pro Ser Leu Val Pro Glu Ser Val
                85                  90                  95
```

```
Gly Pro Ala Asp Ile Leu Pro Ile Asp Thr Ile Asp Pro Val Glu Pro
            100                 105                 110

Thr Ala Ser Ser Val Val Pro Leu Thr Glu Ser Ser Ala Thr Asp Leu
        115                 120                 125

Leu Pro Gly Glu Val Glu Thr Ile Ala Glu Ile Asn Pro Val Ser Glu
    130                 135                 140

Gly Pro Thr Ile Asp Ser Pro Val Val Thr Thr Ser Arg Gly Ser Ser
145                 150                 155                 160

Ala Ile Leu Glu Val Ala Pro Asp Pro Ile Pro Pro Thr Arg Val Arg
                165                 170                 175

Val Ala Arg Thr Gln Tyr His Asn Pro Ala Phe Gln Ile Ile Thr Glu
            180                 185                 190

Ser Thr Pro Ala Gln Gly Glu Thr Ser Leu Ala Asp His Ile Leu Val
        195                 200                 205

Thr Ser Gly Ser Gly Gly Gln Thr Ile Gly Ser Asp Ile Thr Asp Ile
    210                 215                 220

Ile Glu Leu Gln Glu Ile Pro Ser Arg Tyr Ser Phe Glu Ile Glu Glu
225                 230                 235                 240

Pro Thr Pro Pro Arg Gln Ser Ser Thr Pro Leu Gln Arg Thr Gln Thr
                245                 250                 255

Thr Gly Arg Arg Arg Gly Val Ser Leu Thr Asn Arg Arg Leu Val Gln
            260                 265                 270

Gln Val Gln Val Asp Asn Pro Leu Phe Ile Asp Lys Pro Ser Lys Leu
        275                 280                 285

Val Arg Phe Ser Phe Asp Asn Pro Val Phe Glu Glu Asp Ile Thr Asn
    290                 295                 300

Ile Phe Glu Gln Asp Leu Glu Thr Phe Glu Glu Pro Pro Asp Arg Asp
305                 310                 315                 320

Phe Leu Asp Ile Lys Lys Leu Ser Arg Pro Gln Tyr Ser Thr Thr Pro
                325                 330                 335

Ala Gly Tyr Val Arg Val Ser Arg Leu Gly Thr Arg Gly Thr Ile Arg
            340                 345                 350

Thr Arg Ser Gly Ala Gln Ile Gly Ser Gln Val His Phe Tyr Arg Asp
        355                 360                 365

Leu Ser Ser Ile Asp Ser Glu Asp Pro Ile Glu Leu Gln Leu Leu Gly
    370                 375                 380

Gln His Ser Gly Asp Ala Thr Ile Val Gln Gly Thr Val Glu Ser Thr
385                 390                 395                 400

Phe Val Asp Met Asp Ile Ala Glu Asp Pro Leu Ser Glu Ser Ile Glu
                405                 410                 415

Ala His Ser Asp Asp Leu Leu Leu Asp Glu Ala Val Glu Asp Phe Ser
            420                 425                 430

Gly Ser Gln Leu Val Ile Gly Asn Arg Arg Ser Thr Thr Ser Tyr Thr
        435                 440                 445

Val Pro Arg Phe Glu Thr Thr Arg Ser Ser Tyr Tyr Val Gln Asp
    450                 455                 460

Thr Gln Gly Tyr Tyr Val Ala Tyr Pro Glu His Arg Asn Thr Ala Glu
465                 470                 475                 480

Ile Ile Tyr Pro Thr Pro Asp Ile Pro Val Val Ile His Thr His
                485                 490                 495

Asp Asn Ser Gly Asp Phe Tyr Leu His Pro Ser Leu Arg Arg Arg Lys
            500                 505                 510

Arg Lys Arg Lys Tyr Leu
```

515

<210> SEQ ID NO 16
<211> LENGTH: 463
<212> TYPE: PRT
<213> ORGANISM: Human papillomavirus type 13

<400> SEQUENCE: 16

```
Met Ala His Ser Arg Ala Arg Arg Lys Arg Ala Ser Ala Thr Gln
1               5                   10                  15

Leu Tyr Gln Thr Cys Lys Ala Ser Gly Thr Cys Pro Pro Asp Val Ile
                20                  25                  30

Pro Lys Val Glu Gln Asn Thr Leu Ala Asp Lys Ile Leu Lys Trp Gly
            35                  40                  45

Ser Leu Gly Val Phe Phe Gly Gly Leu Gly Ile Gly Thr Gly Ser Gly
        50                  55                  60

Thr Gly Gly Arg Thr Gly Tyr Val Pro Val Gly Ser Thr Pro Arg Pro
65                  70                  75                  80

Ala Ile Ser Thr Gly Pro Thr Ala Arg Pro Pro Ile Val Val Asp Thr
                85                  90                  95

Val Gly Pro Thr Asp Pro Ser Ile Val Ser Leu Val Glu Glu Ser Ala
            100                 105                 110

Ile Ile Asn Ser Gly Val Pro Asp Pro Leu Pro Pro Val His Gly Gly
        115                 120                 125

Phe Glu Ile Thr Thr Ser Gln Ser Ala Thr Pro Ala Ile Leu Asp Val
130                 135                 140

Ser Val Thr Thr Gln Asn Thr Thr Ser Thr Ser Ile Phe Arg Asn Pro
145                 150                 155                 160

Val Phe Ser Glu Pro Ser Ile Thr Gln Ser Gln Pro Ser Ile Glu Ser
                165                 170                 175

Gly Ala His Val Phe Ile Ser Pro Ser Thr Ile Ser Pro His Ser Thr
            180                 185                 190

Glu Asp Ile Pro Leu Asp Thr Phe Ile Val Ser Ser Ser Asp Ser Asn
        195                 200                 205

Pro Ala Ser Ser Thr Pro Val Pro Ala Thr Val Ala Arg Pro Arg Leu
    210                 215                 220

Gly Leu Tyr Ser Arg Ala Leu His Gln Val Gln Val Thr Asp Pro Ala
225                 230                 235                 240

Phe Leu Ser Ser Pro Gln Arg Leu Ile Thr Phe Asp Asn Pro Thr Tyr
                245                 250                 255

Glu Gly Glu Asp Ile Ser Leu Gln Phe Ala His Asn Thr Ile His Glu
            260                 265                 270

Pro Pro Asp Glu Ala Phe Met Asp Ile Ile Arg Leu His Arg Pro Ala
        275                 280                 285

Ile Thr Ser Arg Arg Gly Leu Val Arg Phe Ser Arg Ile Gly Gln Arg
    290                 295                 300

Gly Ser Met Tyr Thr Arg Ser Gly Lys His Ile Gly Gly Arg Val His
305                 310                 315                 320

Phe Phe Lys Asp Ile Ser Pro Ile Ser Ala Ala Glu Glu Ile Glu
                325                 330                 335

Leu His Pro Leu Val Ala Ala Ala Gln Asp His Ser Gly Leu Phe Asp
            340                 345                 350

Ile Tyr Ala Glu Pro Asp Pro Asp Pro Val Ala Val Asn Thr Ser Gly
        355                 360                 365
```

```
Ser Leu Ser Ser Ala Ser Thr Pro Phe Ala Gln Ser Ser Leu Ser Ser
    370                 375                 380

Ala Pro Trp Gly Asn Thr Thr Val Pro Leu Ser Leu Pro Gly Asp Ile
385                 390                 395                 400

Phe Ile Gln Pro Gly Pro Asp Ile Thr Phe Pro Thr Ala Pro Thr Val
                405                 410                 415

Thr Pro Tyr Asn Pro Val Thr Pro Ala Leu Pro Thr Gly Pro Val Phe
            420                 425                 430

Ile Thr Ala Ser Gly Phe Tyr Leu Tyr Pro Thr Trp Tyr Phe Thr Arg
        435                 440                 445

Lys Arg Arg Lys Arg Val Ser Leu Phe Phe Thr Asp Val Ala Ala
    450                 455                 460

<210> SEQ ID NO 17
<211> LENGTH: 519
<212> TYPE: PRT
<213> ORGANISM: Human papillomavirus type 14

<400> SEQUENCE: 17

Met Ala Arg Ala Arg Arg Val Lys Arg Asp Ser Ala Thr Asn Ile Tyr
1               5                   10                  15

Arg Thr Cys Lys Gln Ala Gly Thr Cys Pro Pro Asp Val Ile Asn Lys
                20                  25                  30

Val Glu Ser Thr Thr Ile Ala Asp Lys Ile Leu Gln Tyr Gly Ser Ala
            35                  40                  45

Gly Val Phe Phe Gly Gly Leu Gly Ile Ser Thr Gly Lys Gly Thr Gly
        50                  55                  60

Gly Thr Thr Gly Tyr Val Pro Leu Gly Glu Gly Pro Ala Val Arg Val
65                  70                  75                  80

Gly Gly Ala Pro Thr Ile Ile Arg Pro Ala Leu Val Pro Asp Thr Ile
                85                  90                  95

Gly Pro Ser Asp Ile Ile Pro Val Asp Thr Leu Asp Pro Val Glu Pro
            100                 105                 110

Thr Thr Ser Ser Ile Val Pro Leu Thr Asp Ser Thr Gly Pro Asp Leu
        115                 120                 125

Leu Pro Gly Glu Val Glu Thr Ile Ala Glu Val His Pro Gly Pro Ser
    130                 135                 140

Arg Pro Pro Thr Asp Thr Pro Val Thr Thr Ser Thr Gly Gly Ser Ser
145                 150                 155                 160

Ala Ile Leu Glu Val Ala Pro Glu Pro Thr Pro Pro Ser Arg Val Arg
                165                 170                 175

Val Thr Arg Thr Gln Tyr His Asn Pro Ser Phe Gln Val Ile Thr Glu
            180                 185                 190

Ser Thr Pro Thr Thr Gly Glu Ser Ser Leu Ala Asp Asn Ile Leu Val
        195                 200                 205

Thr Ser Gly Ser Gly Gly Gln Thr Ile Gly Gly Ala Thr Pro Glu Leu
    210                 215                 220

Ile Glu Leu Gln Glu Leu Pro Ser Arg Tyr Ser Phe Glu Ile Glu Glu
225                 230                 235                 240

Pro Thr Pro Pro Arg Arg Thr Ser Thr Pro Leu Gln Arg Ile Gln Thr
                245                 250                 255

Ala Ile Arg Arg Arg Gly Gly Leu Thr Asn Arg Arg Leu Val Gln Gln
            260                 265                 270

Val Ser Val Glu Asn Pro Leu Phe Leu Thr Arg Pro Ser Arg Leu Val
        275                 280                 285
```

Gln Phe Gln Phe Asp Asn Pro Ala Phe Glu Glu Val Thr Gln Ile
            290                 295                 300

Phe Glu Gln Asp Ile Glu Asp Phe Asn Glu Pro Pro Arg Asp Phe
305                 310                 315                 320

Leu Asp Val Gln Arg Leu Gly Arg Pro Gln Tyr Ser Glu Thr Pro Ala
                325                 330                 335

Gly Tyr Leu Arg Val Ser Arg Leu Gly Gln Arg Arg Thr Ile Arg Thr
            340                 345                 350

Arg Ser Gly Ala Gln Ile Gly Ser Gln Val His Phe Tyr Arg Asp Leu
        355                 360                 365

Ser Ser Ile Asn Thr Glu Asp Pro Ile Glu Leu Gln Leu Leu Gly Gln
    370                 375                 380

His Ser Gly Asp Ala Thr Ile Val Gln Gly Pro Val Glu Ser Thr Phe
385                 390                 395                 400

Val Asp Ile Asn Val Asp Glu Asn Pro Leu Ser Glu Asp Phe Ser Ala
                405                 410                 415

His Ser Asp Asp Leu Leu Leu Asp Glu Ala Asn Glu Asp Phe Ser Gly
            420                 425                 430

Ser Gln Leu Val Val Gly Asn Arg Arg Ser Thr Ser Ser Tyr Thr Val
        435                 440                 445

Pro Arg Phe Glu Thr Thr Arg Ser Gly Ser Tyr Tyr Ala Gln Asp Thr
    450                 455                 460

Lys Gly Tyr Tyr Val Ala Tyr Pro Glu Asp Arg Asp Ile Ser Met Asp
465                 470                 475                 480

Ile Ile Tyr Pro Thr Pro Glu Leu Pro Val Val Ile Ile His Thr Tyr
                485                 490                 495

Asp Thr Ser Gly Asp Phe Tyr Leu His Pro Ser Leu His Lys Arg Leu
            500                 505                 510

Lys Arg Lys Arg Lys Tyr Leu
        515

<210> SEQ ID NO 18
<211> LENGTH: 533
<212> TYPE: PRT
<213> ORGANISM: Human papillomavirus type 15

<400> SEQUENCE: 18

Met Ala Arg Ala Arg Arg Val Lys Arg Ala Ser Val Thr Asp Ile Tyr
1               5                   10                  15

Arg Gly Cys Lys Gln Ala Gly Thr Cys Pro Pro Asp Val Leu Asn Lys
            20                  25                  30

Val Glu Gln Thr Thr Ile Ala Asp Lys Ile Leu Lys Tyr Gly Ser Ala
        35                  40                  45

Ala Val Phe Phe Gly Gly Leu Gly Ile Gly Thr Gly Arg Gly Ser Gly
    50                  55                  60

Gly Ala Thr Gly Tyr Val Pro Leu Gly Glu Gly Pro Gly Val Arg Val
65                  70                  75                  80

Gly Gly Thr Pro Thr Ile Val Arg Pro Gly Val Thr Pro Glu Leu Ile
                85                  90                  95

Gly Pro Ala Asp Val Ile Pro Ile Asp Thr Val Thr Pro Ile Asp Pro
            100                 105                 110

Ala Ala Pro Ser Ile Val Thr Ile Thr Asp Ser Ser Ala Val Asp Leu
        115                 120                 125

Leu Pro Glu Leu Glu Thr Ile Ala Glu Ile His Pro Val Pro Thr Asp

```
            130                 135                 140
Asn Val Asp Ile Asp Thr Pro Val Val Thr Gly Gly Arg Asp Ser Ser
145                 150                 155                 160

Ala Ile Leu Glu Val Ala Asp Pro Ser Pro Val Arg Thr Arg Val
                165                 170                 175

Ser Arg Thr Gln Tyr His Asn Pro Ser Phe Gln Ile Ile Thr Glu Ser
                180                 185                 190

Thr Pro Leu Ser Gly Glu Ser Ala Leu Ala Asp His Val Ile Val Phe
                195                 200                 205

Glu Gly Ser Gly Gly Gln Asn Ile Gly Gly Ser Arg Ser Ala Ala Leu
                210                 215                 220

Asp Ala Ala Gln Glu Ser Phe Glu Met Gln Thr Trp Pro Ser Arg Tyr
225                 230                 235                 240

Ser Phe Glu Ile Gln Glu Gly Thr Pro Pro Arg Ser Ser Thr Pro Val
                245                 250                 255

Gln Arg Ala Val Gln Ser Leu Ser Ser Leu Arg Arg Ala Leu Tyr Asn
                260                 265                 270

Arg Arg Leu Thr Glu Gln Val Ala Val Thr Asp Pro Leu Phe Leu Gly
                275                 280                 285

Arg Pro Ser Arg Leu Val Gln Phe Gln Phe Asp Asn Pro Thr Phe Glu
                290                 295                 300

Glu Glu Val Thr Gln Thr Phe Glu Arg Asp Val Glu Ala Phe Glu Glu
305                 310                 315                 320

Pro Pro Asp Arg Gln Phe Leu Asp Val Val Arg Leu Gly Arg Pro Thr
                325                 330                 335

Tyr Ser Glu Thr Pro Gln Gly Tyr Val Arg Val Ser Arg Leu Gly Arg
                340                 345                 350

Arg Ala Thr Ile Arg Thr Arg Ser Gly Ala Gln Val Gly Ala Gln Val
                355                 360                 365

His Phe Tyr Arg Asp Leu Ser Thr Ile Asp Ser Glu Ala Leu Glu Met
                370                 375                 380

Gln Leu Leu Gly Glu His Ser Gly Asp Ser Thr Ile Val Gln Ala Pro
385                 390                 395                 400

Met Glu Ser Ser Phe Ile Asp Ile Asn Ile Asp Glu Pro Asp Ser Leu
                405                 410                 415

His Val Gly Leu Gln Asp Ser Thr Glu Ala Asp Ile Asp Tyr Asn
                420                 425                 430

Ser Ala Asp Leu Leu Leu Glu Asp Asn Ile Glu Asp Phe Ser Gly Ser
                435                 440                 445

His Leu Val Phe Gly Asn Thr Arg Arg Ser Thr Thr Thr Tyr Thr Val
                450                 455                 460

Pro Arg Phe Glu Ser Pro Arg Asn Thr Gly Phe Tyr Ile Gln Asp Val
465                 470                 475                 480

His Gly Tyr Asn Val Ala Tyr Pro Glu Ser Arg Asp Thr Thr Glu Ile
                485                 490                 495

Ile Leu Pro Gln Ser Asp Thr Pro Thr Val Val Ile Asn Phe Glu Glu
                500                 505                 510

Ala Gly Gly Asp Tyr Tyr Leu His Pro Ser Leu Lys Thr Arg Lys Arg
                515                 520                 525

Lys Arg Lys Tyr Leu
530

<210> SEQ ID NO 19
```

<211> LENGTH: 524
<212> TYPE: PRT
<213> ORGANISM: Human papillomavirus type 17

<400> SEQUENCE: 19

```
Met Ala Arg Ser Arg Ile Lys Arg Ala Ser Val Thr Asp Ile Tyr
1               5                   10                  15

Arg Gly Cys Lys Gln Ala Gly Thr Cys Pro Pro Asp Val Ile Asn Lys
                20                  25                  30

Val Glu Gln Thr Thr Ile Ala Asp Lys Ile Leu Lys Tyr Gly Ser Ser
            35                  40                  45

Gly Val Phe Phe Gly Gly Leu Gly Ile Ser Thr Gly Arg Gly Thr Gly
        50                  55                  60

Gly Ala Thr Gly Tyr Phe Pro Leu Gly Glu Gly Pro Gly Val Arg Val
65                  70                  75                  80

Gly Gly Ala Pro Thr Ile Val Arg Pro Gly Val Ile Pro Glu Leu Ile
                85                  90                  95

Gly Pro Ala Asp Val Ile Pro Ile Asp Thr Val Thr Pro Ile Asp Pro
            100                 105                 110

Ala Ala Pro Ser Ile Val Thr Ile Thr Asp Ser Ser Ala Val Asp Leu
        115                 120                 125

Leu Pro Thr Glu Leu Glu Thr Ile Ala Glu Ile His Pro Val Pro Thr
130                 135                 140

Asp Asn Leu Asp Ile Asp Thr Pro Val Val Ser Gly Gly Arg Asp Ser
145                 150                 155                 160

Ser Ala Val Leu Glu Val Ala Asp Pro Ser Pro Pro Val Arg Thr Arg
                165                 170                 175

Val Ser Arg Thr Gln Tyr His Asn Pro Ser Phe Gln Val Ile Thr Glu
            180                 185                 190

Ser Thr Pro Leu Ser Gly Glu Ser Ala Met Ala Asp His Val Leu Val
        195                 200                 205

Phe Glu Gly Phe Gly Gly Gln Asn Ile Gly Gly Ser Arg Asn Ala Ala
210                 215                 220

Ile Asp Thr Ala Gln Glu Ser Phe Glu Met Gln Ser Trp Pro Ser Arg
225                 230                 235                 240

Tyr Ser Phe Glu Leu Glu Glu Gly Thr Pro Pro Arg Thr Ser Thr Pro
                245                 250                 255

Val Gln Arg Ala Val Glu Ser Leu Ser Ser Leu Arg Arg Ala Leu Tyr
            260                 265                 270

Asn Arg Arg Leu Thr Glu Gln Val Ala Val Thr Asp Pro Leu Phe Leu
        275                 280                 285

Ser Arg Pro Ser Arg Leu Val Gln Phe Gln Phe Asp Asn Pro Ala Phe
290                 295                 300

Glu Glu Glu Val Thr Gln Leu Phe Glu Arg Asp Ile Glu Ala Val Glu
305                 310                 315                 320

Glu Pro Pro Asp Arg Gln Phe Leu Asp Val Val Arg Leu Gly Arg Pro
                325                 330                 335

Thr Tyr Ser Glu Thr Pro Gln Gly Tyr Leu Arg Val Ser Arg Leu Gly
            340                 345                 350

Arg Arg Ala Ser Ile Arg Thr Arg Ser Gly Ala Gln Val Gly Ala Gln
        355                 360                 365

Val His Phe Tyr Arg Asp Val Ser Thr Ile Asp Ser Asp Ala Leu Glu
370                 375                 380

Met Gln Leu Leu Gly Glu His Ser Gly Asp Thr Thr Ile Val Gln Gly
```

```
                385                 390                 395                 400
Pro Val Glu Ser Ser Phe Val Asp Ile Asn Ile Asp Glu Pro Gly Pro
                405                 410                 415

Leu Asn Val Gly Ile Gln Glu Ser Pro Leu Ala Asp Thr Ile Glu Glu
                420                 425                 430

Asp Phe Asn Ser Ala Asp Leu Leu Glu Asp Ala Val Asp Asp Phe
            435                 440                 445

Ser Gly Ser Gln Leu Val Phe Gly Asn Pro Arg Arg Ser Thr Thr Ser
            450                 455                 460

Val Thr Val Pro Arg Phe Glu Thr Pro Arg Asp Thr Gly Phe Tyr Ile
465                 470                 475                 480

His Asp Thr Gln Gly Tyr Thr Val Ala Tyr Pro Glu Ser Arg Asp Thr
                485                 490                 495

Thr Glu Ile Ile Leu Pro His Asp Thr Pro Thr Val Val Ile Lys
                500                 505                 510

Phe Ala Glu Ala Gly Gly Arg Phe Leu Phe Thr Pro
            515                 520

<210> SEQ ID NO 20
<211> LENGTH: 520
<212> TYPE: PRT
<213> ORGANISM: Human papillomavirus type 19

<400> SEQUENCE: 20

Met Ala Arg Ala Arg Thr Lys Arg Asp Ser Ala Thr Asn Ile Tyr
1               5                   10                  15

Arg Thr Cys Lys Gln Ala Gly Thr Cys Pro Pro Asp Val Ile Asn Lys
                20                  25                  30

Val Glu Gln Thr Thr Ile Ala Asp Lys Ile Leu Gln Tyr Gly Ser Ala
            35                  40                  45

Gly Val Phe Phe Gly Gly Leu Gly Ile Ser Thr Gly Lys Gly Thr Gly
        50                  55                  60

Gly Ala Thr Gly Tyr Val Pro Leu Gly Glu Gly Pro Val Arg Val Gly
65              70                  75                  80

Gly Thr Ala Thr Val Ile Arg Pro Ser Leu Val Pro Asp Thr Ile Gly
                85                  90                  95

Pro Ser Asp Ile Ile Pro Val Asp Thr Leu Asn Pro Val Glu Pro Thr
            100                 105                 110

Thr Ser Ser Ile Val Pro Leu Thr Glu Ala Ser Gly Ser Asp Leu Leu
        115                 120                 125

Pro Gly Glu Val Glu Thr Ile Ala Glu Val His Pro Thr Pro Ser Ile
    130                 135                 140

Pro Ser Thr Asp Thr Pro Val Thr Thr Thr Ser Ser Gly Ala Ser Ala
145             150                 155                 160

Val Leu Glu Val Ala Pro Glu Pro Val Pro Pro Ser Arg Val Arg Val
                165                 170                 175

Thr Arg Thr Gln Tyr His Asn Pro Ser Phe Gln Ile Leu Thr Glu Ser
            180                 185                 190

Thr Pro Thr Gln Gly Glu Ser Ser Leu Ala Asp His Ile Leu Val Thr
        195                 200                 205

Ser Gly Ser Gly Gly Gln Thr Ile Gly Ser Ser Gly Ser Asp Leu Ile
    210                 215                 220

Glu Leu Gln Glu Phe Pro Thr Arg Tyr Ser Phe Glu Ile Glu Glu Pro
225             230                 235                 240
```

```
Thr Pro Pro Arg Gln Ser Ser Thr Pro Ile Gln Arg Leu Arg Thr Ala
            245                 250                 255

Phe Arg Arg Arg Gly Gly Leu Thr Asn Arg Arg Leu Val Gln Gln Val
        260                 265                 270

Ala Val Asp Asp Pro Ile Phe Leu Thr Gln Pro Ser Arg Leu Val Ser
        275                 280                 285

Phe Gln Phe Asp Asn Pro Ala Phe Glu Glu Val Thr Gln Ile Phe
        290                 295                 300

Glu Gln Asp Leu Asp Asn Phe Arg Glu Pro Asn Arg Asp Phe Leu
305                 310                 315                 320

Asp Val Gln Thr Leu Gly Arg Pro Gln Tyr Ser Glu Thr Pro Ser Gly
            325                 330                 335

Tyr Ile Arg Val Ser Arg Leu Gly Gln Arg Thr Ile Arg Thr Arg
        340                 345                 350

Ser Gly Ala Gln Ile Gly Ser Gln Val His Phe Tyr Arg Asp Leu Ser
            355                 360                 365

Thr Ile Asp Ser Glu Asp Pro Ile Glu Leu Gln Leu Leu Gly Gln His
370                 375                 380

Ser Gly Asp Ala Ser Ile Val Gln Gly Asn Thr Glu Ser Thr Phe Ile
385                 390                 395                 400

Asn Ile Asn Ile Asp Glu Asn Pro Leu Ala Glu Asp Tyr Ser Ile Thr
                405                 410                 415

Ala Asn Ser Glu Asp Leu Leu Leu Asp Glu Ala Gln Glu Asp Phe Ser
            420                 425                 430

Gly Ser Gln Leu Val Val Gly Gly Arg Arg Ser Thr Ser Thr Tyr Thr
        435                 440                 445

Val Pro Gln Phe Glu Thr Thr Arg Ser Gly Ser Tyr Tyr Thr Gln Asp
450                 455                 460

Thr Lys Gly Tyr Tyr Val Ala Tyr Pro Glu Asp Arg Ser Thr Ser Lys
465                 470                 475                 480

Asp Ile Ile Tyr Pro Met Pro Asp Leu Pro Val Val Ile Ile His Thr
                485                 490                 495

Tyr Asp Thr Ser Gly Asp Phe Tyr Leu His Pro Ser Leu Arg Lys Arg
            500                 505                 510

Phe Lys Arg Lys Arg Lys Tyr Leu
        515                 520

<210> SEQ ID NO 21
<211> LENGTH: 518
<212> TYPE: PRT
<213> ORGANISM: Human papillomavirus type 20

<400> SEQUENCE: 21

Met Ala Arg Ala Lys Arg Val Lys Arg Asp Ser Ala Thr Asn Ile Tyr
1               5                   10                  15

Arg Thr Cys Lys Gln Ala Gly Thr Cys Pro Pro Asp Val Ile Asn Lys
            20                  25                  30

Val Glu Ser Thr Thr Ile Ala Asp Lys Ile Leu Gln Tyr Gly Ser Ala
        35                  40                  45

Gly Val Phe Phe Gly Gly Leu Gly Ile Ser Thr Gly Lys Gly Thr Gly
    50                  55                  60

Gly Thr Thr Gly Tyr Val Pro Leu Gly Glu Gly Pro Ser Val Arg Val
65                  70                  75                  80

Gly Gly Thr Pro Thr Val Ile Arg Pro Ala Leu Val Pro Asp Thr Ile
                85                  90                  95
```

```
Gly Pro Ser Asp Ile Ile Pro Val Asp Thr Leu Asn Pro Val Glu Pro
            100                 105                 110

Ser Thr Ser Ser Ile Val Pro Leu Thr Glu Ser Thr Gly Pro Asp Leu
        115                 120                 125

Leu Pro Gly Glu Val Glu Thr Ile Ala Glu Ile His Pro Gly Pro Ser
    130                 135                 140

Arg Pro Thr Asp Thr Pro Val Thr Ser Thr Ser Gly Ser Ser
145                 150                 155                 160

Ala Val Leu Glu Val Ala Pro Glu Pro Thr Pro Ala Arg Val Arg
                165                 170                 175

Val Ser Arg Thr Gln Tyr His Asn Pro Ser Phe Gln Ile Ile Thr Glu
        180                 185                 190

Ser Thr Pro Thr Leu Gly Glu Ser Ser Leu Ala Asp His Ile Val Val
        195                 200                 205

Thr Ser Gly Ser Gly Gly Gln Ala Ile Gly Gly Met Thr Pro Glu Leu
    210                 215                 220

Ile Glu Leu Gln Asp Phe Pro Ser Arg Tyr Ser Phe Glu Ile Glu Glu
225                 230                 235                 240

Pro Thr Pro Pro Arg Arg Thr Ser Thr Pro Met Gln Arg Leu Gln Asn
                245                 250                 255

Val Phe Arg Arg Arg Gly Gly Leu Thr Asn Arg Arg Leu Val Gln Gln
        260                 265                 270

Val Pro Val Asp Asn Pro Leu Phe Leu Thr Gln Pro Ser Arg Leu Val
        275                 280                 285

Arg Phe Gln Phe Asp Asn Pro Val Phe Glu Glu Val Thr Gln Ile
        290                 295                 300

Phe Glu Gln Asp Leu Asp Thr Phe Asn Glu Pro Pro Asp Arg Asp Phe
305                 310                 315                 320

Leu Asp Val Gln Ser Leu Gly Arg Pro Gln Tyr Ser Glu Thr Pro Ala
                325                 330                 335

Gly Tyr Val Arg Val Ser Arg Ala Gly Gln Arg Arg Thr Ile Arg Thr
        340                 345                 350

Arg Ser Gly Ala Gln Ile Gly Ser Gln Val His Phe Tyr Arg Asp Leu
        355                 360                 365

Ser Ser Ile Asp Thr Glu Asp Pro Ile Glu Leu Gln Leu Leu Gly Gln
    370                 375                 380

His Ser Gly Asp Ala Thr Ile Val Gln Gly Pro Val Glu Ser Thr Phe
385                 390                 395                 400

Val Asp Ile Asn Val Asp Glu Asn Pro Leu Ser Glu Ile Ser Ala Tyr
                405                 410                 415

Ser Asp Asp Leu Leu Leu Asp Glu Ala Asn Glu Asp Phe Ser Gly Ser
        420                 425                 430

Gln Leu Val Val Gly Gly Arg Arg Ser Thr Ser Thr Tyr Thr Val Pro
    435                 440                 445

His Phe Glu Thr Thr Arg Ser Ser Ser Tyr Tyr Val Gln Asp Thr Lys
        450                 455                 460

Gly Tyr Tyr Val Ala Tyr Pro Glu Asp Arg Asp Val Ser Lys Asp Ile
465                 470                 475                 480

Ile Tyr Pro Asn Pro Asp Leu Pro Val Val Ile Ile His Thr Tyr Asp
                485                 490                 495

Thr Ser Gly Asp Phe Tyr Leu His Pro Ser Leu Thr Lys Arg Leu Lys
        500                 505                 510
```

Arg Lys Arg Lys Tyr Leu
        515

<210> SEQ ID NO 22
<211> LENGTH: 520
<212> TYPE: PRT
<213> ORGANISM: Human papillomavirus type 21

<400> SEQUENCE: 22

Met Ala Arg Ala Lys Arg Val Lys Arg Asp Ser Ala Thr Asn Ile Tyr
1               5                   10                  15

Arg Thr Cys Lys Gln Ala Gly Thr Cys Pro Pro Asp Val Ile Asn Lys
            20                  25                  30

Val Glu Ser Thr Thr Ile Ala Asp Lys Ile Leu Gln Tyr Gly Ser Ala
        35                  40                  45

Gly Val Phe Phe Gly Gly Leu Gly Ile Ser Thr Gly Lys Gly Thr Gly
    50                  55                  60

Gly Thr Thr Gly Tyr Val Pro Leu Gly Glu Gly Pro Ala Val Arg Val
65                  70                  75                  80

Gly Asn Ala Pro Thr Val Ile Arg Pro Ala Leu Val Pro Asp Thr Ile
                85                  90                  95

Gly Pro Ser Asp Ile Ile Pro Val Asp Thr Leu Asn Pro Val Glu Pro
            100                 105                 110

Thr Thr Ser Ser Ile Val Pro Leu Thr Asp Ser Thr Gly Pro Asp Leu
        115                 120                 125

Leu Pro Gly Glu Val Glu Thr Ile Ala Glu Ile His Pro Gly Pro Thr
    130                 135                 140

Arg Pro Pro Pro Asp Thr Ala Val Thr Thr Ser Thr Asn Gly Ser Ser
145                 150                 155                 160

Ala Val Leu Glu Val Ala Pro Glu Pro Thr Pro Pro Ser Arg Val Arg
                165                 170                 175

Val Thr Arg Thr Gln Tyr His Asn Pro Ser Phe Gln Val Ile Thr Glu
            180                 185                 190

Ser Thr Pro Thr Thr Gly Glu Ser Ser Leu Ala Asp His Ile Leu Val
        195                 200                 205

Thr Ser Gly Thr Gly Gly Gln Thr Ile Gly Gly Ser Thr Pro Glu Leu
    210                 215                 220

Ile Glu Leu Gln Asp Phe Pro Ser Arg Tyr Ser Phe Glu Ile Glu Glu
225                 230                 235                 240

Pro Thr Pro Pro Arg Arg Thr Ser Thr Pro Ile Gln Arg Ile Gln Asn
                245                 250                 255

Ile Ile Arg Arg Arg Gly Gly Leu Thr Asn Arg Arg Leu Val Gln
            260                 265                 270

Gln Val Asn Val Glu Asn Pro Leu Phe Val Ser Arg Pro Ser Arg Leu
        275                 280                 285

Val Gln Phe Gln Phe Asp Asn Pro Ala Phe Glu Glu Val Thr Gln
    290                 295                 300

Ile Phe Glu Gln Asp Ile Asp Thr Phe Asn Glu Pro Pro Asp Arg Asp
305                 310                 315                 320

Phe Leu Asp Ile Lys Thr Leu Gly Arg Pro Gln Tyr Ser Glu Thr Pro
                325                 330                 335

Ala Gly Tyr Val Arg Val Ser Arg Leu Gly Lys Arg Gly Thr Ile Arg
            340                 345                 350

Thr Arg Ser Gly Thr Gln Ile Gly Ser Gln Val His Phe Tyr Arg Asp
        355                 360                 365

```
Leu Ser Thr Ile Asn Thr Glu Asp Pro Ile Glu Leu Gln Leu Leu Gly
    370                 375                 380

Glu His Ser Gly Asp Ala Thr Ile Val Gln Gly Pro Val Glu Ser Thr
385                 390                 395                 400

Phe Ile Asp Ile Asn Val Asp Glu Asn Pro Leu Ser Glu Asp Phe Ser
                405                 410                 415

Ala His Ser Asp Asp Leu Leu Leu Asp Glu Ala Asn Glu Asp Phe Ser
                420                 425                 430

Gly Ser Gln Leu Val Val Gly Arg Arg Ser Thr Ser Ser Tyr Thr
                435                 440                 445

Val Pro Arg Phe Glu Thr Thr Arg Ser Gly Ser Tyr Tyr Val Gln Asp
    450                 455                 460

Thr Lys Gly Tyr Tyr Val Ala Tyr Pro Glu Asp Arg Asp Thr Ser Thr
465                 470                 475                 480

Asp Ile Ile Tyr Pro Thr Pro Asp Leu Pro Val Val Ile Ile His Thr
                485                 490                 495

Phe Asp Thr Ser Gly Asp Phe Tyr Leu His Pro Ser Leu Ser Arg Lys
                500                 505                 510

Phe Lys Arg Arg Arg Lys Tyr Leu
                515                 520

<210> SEQ ID NO 23
<211> LENGTH: 524
<212> TYPE: PRT
<213> ORGANISM: Human papillomavirus type 22

<400> SEQUENCE: 23

Met Ala Arg Ala Arg Arg Thr Lys Arg Ala Ser Val Thr Asp Ile Tyr
1               5                   10                  15

Lys Gly Cys Lys Ala Ser Gly Thr Cys Pro Pro Asp Val Ile Asn Lys
                20                  25                  30

Val Glu Gln Asn Thr Leu Ala Asp Lys Ile Leu Lys Tyr Gly Ser Val
                35                  40                  45

Gly Val Phe Phe Gly Gly Leu Gly Ile Ser Thr Gly Lys Gly Thr Gly
            50                  55                  60

Gly Pro Thr Gly Tyr Ile Pro Leu Gly Gln Gly Pro Gly Val Arg Val
65              70                  75                  80

Gly Ala Thr Pro Thr Val Arg Pro Gly Val Ile Pro Glu Ile Ile
                85                  90                  95

Gly Pro Thr Glu Leu Ile Pro Val Asp Ser Val Thr Pro Ile Asp Pro
                100                 105                 110

Ala Ala Pro Ser Ile Val Thr Leu Thr Asp Ser Ser Ala Gly Ala Asp
                115                 120                 125

Leu Leu Pro Gly Glu Val Glu Thr Ile Ala Glu Val His Pro Val Pro
    130                 135                 140

Ile Asp Asn Val Glu Leu Asp Thr Pro Leu Val Ser Gly Asp Arg His
145                 150                 155                 160

Ala Ile Leu Glu Val Thr Asp Ala Asn Pro Pro Phe Arg Arg Thr Val
                165                 170                 175

Thr Arg Thr Gln Tyr His Asn Pro Ala Phe Glu Ile Ile Ser Glu Ser
                180                 185                 190

Thr Pro Leu Ile Gly Glu Ser Thr Pro Ser Asp His Val Phe Val Phe
                195                 200                 205

Glu Gly Ser Gly Gly Val Gln Val Gly Asp Ala Asn Glu Ser Ile Glu
```

```
                210                 215                 220

Leu Asp Thr Phe Pro Ser Arg Tyr Ser Phe Asp Ile Glu Glu Pro Thr
225                 230                 235                 240

Pro Pro Arg Arg Val Ser Thr Pro Ile Glu Arg Ile Ser Gln Glu Phe
                245                 250                 255

Arg Thr Leu Arg Arg Ala Leu Tyr Asn Arg Arg Leu Thr Glu Gln Val
                260                 265                 270

Gln Val Arg Asp Pro Leu Phe Ile Arg Ser Pro Ser Arg Leu Val Arg
            275                 280                 285

Phe Gln Phe Asp Asn Pro Val Phe Asp Glu Val Thr Gln Ile Phe
        290                 295                 300

Glu Arg Asp Val Ala Ala Val Glu Glu Pro Pro Asp Arg Asp Phe Leu
305                 310                 315                 320

Asp Ile Glu Arg Leu Gly Arg Pro Ile Leu Thr Glu Thr Ala Glu Gly
                325                 330                 335

Arg Val Arg Val Ser Arg Leu Gly Gln Arg Ala Ser Leu Ser Thr Arg
                340                 345                 350

Ser Gly Ala Arg Val Gly Ala Arg Val His Phe Phe Thr Asp Ile Ser
            355                 360                 365

Thr Ile Asn Ala Glu Glu Pro Ile Glu Leu Glu Leu Leu Gly Glu His
    370                 375                 380

Ser Gly Asp Ser Ser Val Val Gln Glu Pro Phe Glu Ser Thr Ile Leu
385                 390                 395                 400

Asp Val Asn Ile Asp Asn Ile Pro Glu Ser Leu Asp Thr Asn Ile Ala
                405                 410                 415

Glu Thr Ser Val Asp Tyr Asp Ser Ala Asp Leu Leu Leu Asp Asn Gly
                420                 425                 430

Val Glu Asp Phe Ser Arg Ser Gln Leu Val Ile Gly Pro Ser Asp Arg
            435                 440                 445

Ser Leu Pro Ser Ile Thr Val Pro Gln Phe Glu Ser Pro Arg Glu Thr
    450                 455                 460

Ile Val Tyr Ile Gln Asp Ile Glu Gly Asn Thr Val Val Tyr Pro Lys
465                 470                 475                 480

Tyr Glu Glu Arg Pro Thr Ile Ile Leu Pro Thr Pro Ser Gly Pro Ala
                485                 490                 495

Ile Ile Gln Ser Pro Thr His Ser Ser Phe Asp Tyr Tyr Leu His Pro
            500                 505                 510

Ser Leu Arg Arg Lys Arg Lys Arg Lys Tyr Leu
    515                 520

<210> SEQ ID NO 24
<211> LENGTH: 519
<212> TYPE: PRT
<213> ORGANISM: Human papillomavirus type 23

<400> SEQUENCE: 24

Met Val Arg Ala Gln Arg Thr Lys Arg Ala Ser Val Thr Asp Ile Tyr
1                 5                  10                  15

Lys Gly Cys Lys Ala Ser Gly Thr Cys Pro Pro Asp Val Leu Asn Lys
                20                  25                  30

Val Glu Gln Asn Thr Leu Ala Asp Lys Ile Leu Lys Tyr Gly Ser Val
            35                  40                  45

Gly Val Phe Phe Gly Gly Leu Gly Ile Gly Thr Gly Lys Gly Thr Gly
        50                  55                  60
```

```
Gly Ala Thr Gly Tyr Val Pro Leu Arg Pro Gly Val Arg Val Gly Gly
 65                  70                  75                  80

Thr Pro Thr Val Val Arg Pro Ala Val Ile Pro Glu Ile Ile Gly Pro
                 85                  90                  95

Thr Glu Leu Ile Pro Val Asp Ser Ile Ala Pro Ile Asp Pro Glu Ala
            100                 105                 110

Pro Ser Ile Val Ser Leu Thr Asp Ser Gly Ala Ala Asp Leu Phe
        115                 120                 125

Pro Ser Glu Ala Glu Thr Ile Ala Glu Val His Pro Thr Pro Val Asp
    130                 135                 140

Ile Gly Ile Asp Thr Pro Ile Val Ala Gly Arg Asp Ala Ile Leu
145                 150                 155                 160

Glu Val Val Asp Thr Asn Pro Pro Thr Arg Phe Ser Val Thr Arg Thr
                165                 170                 175

Gln Tyr Asp Asn Pro Ser Phe Gln Ile Ile Ser Glu Ser Thr Pro Ile
            180                 185                 190

Thr Gly Glu Ala Ser Leu Ala Asp His Val Phe Val Phe Glu Gly Ser
        195                 200                 205

Gly Gly Gln His Val Gly Ala Val Thr Glu Glu Ile Glu Leu Asp Thr
    210                 215                 220

Tyr Pro Ser Arg Tyr Ser Phe Glu Ile Glu Glu Ala Thr Pro Pro Arg
225                 230                 235                 240

Arg Thr Ser Thr Pro Ile Glu Arg Ile Ser Gln Glu Phe Arg Asn Leu
                245                 250                 255

Arg Arg Ala Leu Tyr Asn Arg Arg Leu Thr Glu Gln Val Gln Val Lys
            260                 265                 270

Asn Pro Leu Phe Leu Thr Thr Pro Ser Lys Leu Val Arg Phe Gln Phe
        275                 280                 285

Asp Asn Pro Val Phe Asp Glu Glu Val Thr Gln Ile Phe Glu Arg Asp
    290                 295                 300

Val Ala Glu Val Glu Glu Pro Pro Asp Arg Asp Phe Leu Asp Ile Asp
305                 310                 315                 320

Arg Leu Gly Arg Pro Leu Leu Thr Glu Ser Thr Glu Gly Arg Ile Arg
                325                 330                 335

Leu Ser Arg Leu Gly Gln Arg Ala Ser Ile Gln Thr Arg Ser Gly Thr
            340                 345                 350

Arg Val Gly Ser Arg Val His Phe Tyr Thr Asp Leu Ser Thr Ile Asn
        355                 360                 365

Thr Glu Glu Pro Ile Glu Leu Glu Leu Leu Gly Glu His Ser Gly Asp
    370                 375                 380

Ala Ser Val Ile Glu Glu Pro Leu Gln Ser Thr Val Ile Asp Met Asn
385                 390                 395                 400

Leu Asp Asp Val Glu Ala Ile Gln Asp Thr Ile Asp Thr Ala Asp Asp
                405                 410                 415

Tyr Asn Ser Ala Asp Leu Leu Leu Asp Asn Ala Ile Glu Glu Phe Asn
            420                 425                 430

Asn Ser Gln Leu Val Phe Gly Thr Ser Asp Arg Ser Ser Ser Ala Tyr
        435                 440                 445

Ser Ile Pro Arg Phe Glu Ser Pro Arg Glu Thr Ile Val Tyr Val Gln
        450                 455                 460

Asp Ile Glu Gly Asn Gln Val Ile Tyr Pro Gly Pro Thr Glu Arg Pro
465                 470                 475                 480

Thr Ile Ile Phe Pro Leu Pro Ser Ala Pro Ala Val Val Ile His Thr
```

```
                    485                 490                 495
Leu Asp Lys Ser Phe Asp Tyr Tyr Leu His Pro Ser Leu Arg Lys Lys
                500                 505                 510
Arg Arg Lys Arg Lys Tyr Leu
        515

<210> SEQ ID NO 25
<211> LENGTH: 523
<212> TYPE: PRT
<213> ORGANISM: Human papillomavirus type 24

<400> SEQUENCE: 25

Met Val Arg Ala Lys Arg Thr Lys Arg Asp Ser Ala Thr Asn Ile Tyr
1               5                   10                  15
Arg Thr Cys Lys Gln Ala Gly Thr Cys Pro Pro Asp Val Ile Asn Lys
            20                  25                  30
Val Glu Gln Ser Thr Ile Ala Asp Asn Ile Leu Lys Tyr Gly Ser Ala
        35                  40                  45
Gly Val Phe Phe Gly Gly Leu Gly Ile Ser Thr Gly Arg Gly Thr Gly
    50                  55                  60
Gly Thr Thr Gly Tyr Val Pro Leu Gly Glu Gly Thr Gly Val Arg Val
65                  70                  75                  80
Gly Ser Thr Pro Thr Val Val Arg Pro Ala Leu Val Pro Glu Val Ile
                85                  90                  95
Gly Pro Ala Asp Leu Leu Pro Val Asp Thr Ile Ala Pro Val Asp Pro
            100                 105                 110
Ala Ser Ser Ser Ile Val Pro Leu Thr Glu Ser Ser Gly Val Asp Leu
        115                 120                 125
Leu Pro Gly Glu Ile Glu Thr Ile Ala Glu Val His Pro Ile Pro Asp
    130                 135                 140
Val Pro Thr Phe Asp Thr Pro Val Val Thr Thr Ser Lys Gly Ser Ser
145                 150                 155                 160
Ala Ile Leu Glu Val Ala Pro Glu Pro Thr Pro Pro Thr Arg Val Arg
                165                 170                 175
Val Ser Arg Thr Gln Tyr His Asn Pro Ala Phe His Ile Ile Thr Glu
            180                 185                 190
Ser Thr Pro Ser Gln Gly Glu Ser Ser Leu Ser Asp Glu Ile Ile Val
        195                 200                 205
Ala Ser Gly Ala Gly Gly Gln Ser Val Gly Val Ser Glu Asn Ile Glu
    210                 215                 220
Leu Gln Asp Leu Ser Asn Arg Tyr Ser Phe Glu Ile Glu Thr Pro Thr
225                 230                 235                 240
Pro Pro Arg Arg Ser Ser Thr Pro Leu Gln Arg Ala Thr Gln Ala Phe
                245                 250                 255
Arg Gln Arg Ser Leu Thr Asn Arg Arg Leu Leu Gln Gln Val Pro Val
            260                 265                 270
Glu Asp Pro Leu Phe Leu Thr Gln Pro Ser Lys Leu Val Arg Phe Ala
        275                 280                 285
Phe Glu Asn Pro Ala Phe Glu Glu Val Thr Gln Val Phe Glu Gln
    290                 295                 300
Asp Leu Ala Gly Phe Val Glu Pro Pro Asn Arg Asp Phe Leu Asp Ile
305                 310                 315                 320
Ala Glu Leu Gly Arg Pro Arg Phe Ser Glu Thr Arg Glu Gly Tyr Val
                325                 330                 335
```

Arg Leu Ser Arg Leu Gly Arg Ala Thr Ile Arg Thr Arg Ala Gly
            340                 345                 350

Thr Gln Ile Gly Ala Gln Val His Phe Tyr Lys Asp Leu Ser Ser Ile
        355                 360                 365

Asn Thr Glu Ala Pro Ile Glu Leu Asp Leu Leu Gly Gln His Ser Gly
    370                 375                 380

Asp Ala Thr Ile Val His Gly Thr Val Glu Ser Thr Phe Ile Asp Thr
385                 390                 395                 400

Asn Ile Glu Glu Asn Pro Leu Ala Glu Gln Met Glu Leu Glu Ile Asp
            405                 410                 415

Thr Tyr Pro Glu Ala His Ser Phe Asp Ala Leu Leu Asp Glu Ala Thr
        420                 425                 430

Asp Asp Phe Ser Gly Ser Gln Leu Val Ile Gly Asn Arg Arg Ser Thr
    435                 440                 445

Thr Ser Tyr Thr Val Pro Arg Phe Glu Ser Pro Arg Asn Ser Ser Tyr
450                 455                 460

Tyr Val Gln Asp Leu Gln Gly Tyr Tyr Val Ala Tyr Pro Glu Ser Arg
465                 470                 475                 480

Asp Lys Ile Glu Leu Ile Tyr Pro Ser Pro Thr Leu Pro Ala Val Val
            485                 490                 495

Ile His Thr Glu Asp Ser Ser Gly Asp Phe Tyr Leu His Pro Ser Leu
        500                 505                 510

Leu Gln Arg Arg Arg Arg Lys Arg Lys Tyr Leu
    515                 520

<210> SEQ ID NO 26
<211> LENGTH: 520
<212> TYPE: PRT
<213> ORGANISM: Human papillomavirus type 25

<400> SEQUENCE: 26

Met Ala Arg Ala Arg Arg Val Lys Arg Asp Ser Ala Thr Asn Ile Tyr
1               5                   10                  15

Arg Thr Cys Lys Gln Ala Gly Thr Cys Pro Pro Asp Val Leu Asn Lys
            20                  25                  30

Val Glu Asn Thr Thr Ile Ala Asp Lys Ile Leu Gln Tyr Gly Ser Ala
        35                  40                  45

Gly Val Phe Phe Gly Gly Leu Gly Ile Ser Thr Gly Lys Gly Thr Gly
    50                  55                  60

Gly Thr Thr Gly Tyr Val Pro Leu Gly Glu Gly Pro Ile Arg Val Gly
65                  70                  75                  80

Gly Thr Pro Thr Val Ile Arg Pro Ser Leu Val Pro Asp Thr Ile Gly
            85                  90                  95

Pro Ser Asp Ile Ile Pro Val Asp Thr Leu Asn Pro Val Glu Pro Thr
        100                 105                 110

Ser Ser Ser Ile Val Pro Leu Thr Glu Ser Ser Gly Pro Asp Leu Leu
    115                 120                 125

Pro Gly Glu Val Glu Thr Ile Ala Glu Ile His Pro Gly Pro Val Val
130                 135                 140

Pro Ser Thr Asp Thr Pro Val Thr Thr Ser Arg Gly Ala Ser Ala
145                 150                 155                 160

Val Leu Glu Val Ala Pro Glu Pro Thr Pro Pro Ser Arg Val Arg Val
            165                 170                 175

Ser Gly Thr Gln Tyr His Asn Pro Ser Phe Gln Val Ile Thr Glu Ser
        180                 185                 190

Thr Pro Ala Gln Gly Glu Ser Ser Leu Ala Asp His Ile Leu Val Thr
            195                 200                 205

Ser Gly Ser Gly Gly Gln Thr Ile Gly Gly Thr Ala Ser Asp Leu Ile
    210                 215                 220

Glu Leu Gln Glu Phe Pro Thr Arg Tyr Ser Phe Glu Ile Asp Glu Pro
225                 230                 235                 240

Thr Pro Pro Arg Gln Ser Ser Thr Pro Leu Gln Arg Ile Arg Thr Ala
            245                 250                 255

Leu Arg Arg Arg Gly Gly Leu Thr Asn Arg Arg Leu Val Gln Gln Val
        260                 265                 270

Pro Val Glu Asp Pro Leu Phe Leu Ser Gln Pro Ser Arg Leu Val Arg
    275                 280                 285

Phe Gln Phe Asp Asn Pro Val Phe Glu Asp Glu Val Thr Gln Ile Phe
    290                 295                 300

Glu Gln Asp Leu Asn Asp Phe Gln Glu Pro Pro Asp Arg Asp Phe Leu
305                 310                 315                 320

Asp Ile Arg Ser Leu Gly Arg Pro Gln Tyr Ser Glu Thr Pro Ala Gly
            325                 330                 335

Tyr Val Arg Val Ser Arg Leu Gly Gln Arg Arg Thr Ile Arg Thr Arg
        340                 345                 350

Ser Gly Ala Gln Ile Gly Ser Gln Val His Phe Tyr Arg Asp Leu Ser
    355                 360                 365

Ser Ile Asn Thr Glu Asp Pro Ile Glu Leu Gln Leu Leu Gly Gln His
    370                 375                 380

Ser Gly Asp Ala Thr Ile Val Gln Gly Leu Thr Glu Ser Thr Phe Val
385                 390                 395                 400

Asp Val Asn Val Asp Glu Asn Pro Leu Ala Glu Asp Phe Ser Ile Ser
            405                 410                 415

Ala His Ser Asp Asp Leu Leu Leu Asp Glu Ala Asn Glu Asp Phe Ser
        420                 425                 430

Gly Ser Gln Leu Val Val Gly Gly Arg Arg Ser Thr Ser Thr Tyr Thr
    435                 440                 445

Val Pro Arg Val Glu Thr Thr Arg Ser Ala Ser Tyr Tyr Thr Gln Asp
    450                 455                 460

Ile Gln Gly Tyr Tyr Val Ser Tyr Pro Glu Asp Arg Asp Thr Ser Lys
465                 470                 475                 480

Asp Ile Ile Tyr Pro Met Pro Asp Leu Pro Val Val Ile Ile His Thr
            485                 490                 495

Tyr Asp Thr Ser Gly Asp Phe Tyr Leu His Pro Ser Leu Thr Thr Arg
        500                 505                 510

Arg Arg Arg Lys Arg Lys Tyr Leu
    515                 520

<210> SEQ ID NO 27
<211> LENGTH: 472
<212> TYPE: PRT
<213> ORGANISM: Human papillomavirus type 26

<400> SEQUENCE: 27

Met Val Ala Val Arg Ala Pro Arg Arg Lys Arg Ala Ser Ala Thr Asp
1               5                   10                  15

Leu Tyr Lys Thr Cys Lys Ala Ala Gly Thr Cys Pro Pro Asp Val Ile
            20                  25                  30

Pro Lys Ile Glu Gly Ser Thr Leu Ala Asp Lys Ile Leu Gln Trp Ser

```
              35                  40                  45
Gly Leu Gly Ile Phe Leu Gly Leu Gly Ile Gly Thr Gly Thr Gly
 50                  55                  60

Ser Gly Gly Arg Thr Gly Tyr Ile Pro Leu Gly Gly Gly Arg Pro
 65                  70                  75                  80

Ser Val Val Asp Ile Gly Pro Thr Arg Pro Pro Ile Ile Ile Glu Pro
                 85                  90                  95

Val Gly Pro Thr Glu Pro Ser Ile Val Thr Leu Val Glu Glu Ser Ser
            100                 105                 110

Ile Ile Gln Ser Gly Ala Pro Ile Pro Thr Phe Ser Gly Gly Asn Gly
            115                 120                 125

Phe Glu Leu Thr Thr Ser Ser Ala Thr Thr Pro Ala Val Leu Asp Ile
130                 135                 140

Thr Pro Ser Ala Gly Thr Val His Val Thr Ser Thr Asn Ile Gln Asn
145                 150                 155                 160

Pro Leu Tyr Ile Glu Pro Pro Ile Asp Ile Pro Gln Ala Gly Glu Ala
                165                 170                 175

Ser Gly His Ile Phe Thr Thr Ser Thr Ala Gly Thr His Ser Tyr
            180                 185                 190

Glu Glu Ile Pro Met Glu Val Phe Ala Ser Thr Asn Gly Thr Gly Leu
            195                 200                 205

Glu Pro Ile Ser Ser Thr Pro Ile Pro Gly Ile Gln Arg Val Ser Ala
210                 215                 220

Pro Arg Leu Tyr Ser Lys Ala Tyr Gln Gln Val Lys Val Thr Asp Pro
225                 230                 235                 240

Asn Phe Ile Gly Asn Pro Ser Thr Phe Val Thr Phe Asp Asn Pro Ala
                245                 250                 255

Tyr Glu Pro Ile Asp Glu Thr Leu Thr Tyr Ala Ser Ser Ser Thr Val
            260                 265                 270

Ala Pro Asp Pro Asp Phe Leu Asp Ile Ile Ala Leu His Arg Pro Ala
            275                 280                 285

Leu Thr Ser Arg Lys Gly Thr Val Arg Tyr Ser Arg Leu Gly Gln Lys
290                 295                 300

Ala Thr Met Lys Thr Arg Ser Gly Lys Gln Ile Gly Ala Thr Val His
305                 310                 315                 320

Tyr Tyr His Asp Ile Ser Pro Ile Gln Ser Phe Ala Glu His Glu Glu
                325                 330                 335

Ile Glu Leu Gln Pro Leu His Thr Ser Thr His Ser Ser Ala Pro Leu
            340                 345                 350

Phe Asp Ile Tyr Ala Asp Pro Asp Thr Val Pro Ser Ile His Thr Pro
            355                 360                 365

Arg Met Ser Tyr Ser Pro Thr Thr Leu Pro Val Pro Arg Tyr Ala Ser
370                 375                 380

Asn Val Phe Ser Ser Ile Asn Thr Ser Thr Asn Val Thr Val Pro
385                 390                 395                 400

Leu Ser Thr Ser Phe Glu Leu Pro Val Tyr Ser Gly Ser Asp Ile Tyr
                405                 410                 415

Thr Pro Thr Ser Ser Pro Thr Trp Pro Ser Leu Pro Pro Pro Thr
            420                 425                 430

Thr Asn Leu Pro Ala Ile Val Val His Gly Asp Asn Tyr Tyr Leu Trp
            435                 440                 445

Pro Tyr Ile Tyr Leu Ile His Lys Arg Arg Lys Arg Met Pro Tyr Phe
450                 455                 460
```

```
Phe Ser Asp Gly Phe Val Ala Tyr
465                 470
```

<210> SEQ ID NO 28
<211> LENGTH: 464
<212> TYPE: PRT
<213> ORGANISM: Human papillomavirus type 27

<400> SEQUENCE: 28

```
Met Pro Arg Ala Lys Arg Lys Arg Ala Ser Pro Thr Asp Leu Tyr
1               5                   10                  15

Arg Thr Cys Lys Gln Ala Gly Thr Cys Pro Pro Asp Ile Ile Pro Arg
            20                  25                  30

Leu Glu Gln Asn Thr Leu Ala Asp Lys Ile Leu Lys Trp Gly Ser Leu
            35                  40                  45

Gly Val Phe Phe Gly Gly Leu Gly Ile Gly Thr Gly Ser Gly Thr Gly
        50                  55                  60

Gly Arg Thr Gly Tyr Ile Pro Val Gly Thr Arg Pro Thr Thr Val Val
65                  70                  75                  80

Asp Ile Gly Val Ala Pro Lys Pro Pro Val Val Ile Glu Pro Val Gly
                85                  90                  95

Ala Ser Glu Pro Ser Ile Val Thr Leu Val Glu Asp Ser Ser Ile Ile
                100                 105                 110

Asn Ala Gly Ala Ser His Pro Thr Phe Thr Gly Thr Gly Gly Phe Glu
            115                 120                 125

Val Thr Thr Ser Thr Val Thr Asp Pro Ala Val Leu Asp Ile Thr Pro
        130                 135                 140

Ser Gly Thr Ser Val Gln Val Ser Ser Ser Phe Leu Asn Pro Leu
145                 150                 155                 160

Tyr Thr Glu Pro Ala Ile Val Glu Ala Pro Gln Thr Gly Glu Val Ser
                165                 170                 175

Gly His Val Leu Val Ser Thr Ala Thr Ser Gly Ser His Gly Tyr Glu
            180                 185                 190

Glu Ile Pro Met Gln Thr Phe Ala Thr Ser Gly Gly Ser Gly Gln Glu
        195                 200                 205

Pro Ile Ser Ser Thr Pro Leu Pro Gly Val Arg Arg Val Ala Gly Pro
210                 215                 220

Arg Leu Tyr Ser Arg Ala Asn Gln Gln Val Gln Val Arg Asp Pro Ala
225                 230                 235                 240

Phe Leu Glu Arg Pro Ala Asp Leu Val Thr Phe Asp Asn Pro Val Tyr
                245                 250                 255

Asp Pro Glu Glu Thr Ile Ile Phe Gln His Pro Asp Phe His Glu Pro
            260                 265                 270

Pro Asp Pro Asp Phe Leu Asp Ile Val Ala Leu His Arg Pro Ala Leu
        275                 280                 285

Thr Ser Arg Gln Gly Thr Val Arg Phe Ser Arg Leu Gly Arg Arg Ala
    290                 295                 300

Thr Leu Arg Thr Arg Ser Gly Lys Gln Ile Gly Ala Arg Val His Phe
305                 310                 315                 320

Tyr His Asp Ile Ser Pro Val Val Pro Asp Glu Leu Glu Met Glu Pro
                325                 330                 335

Leu Leu Pro Pro Ala Ser Thr Val Gly Ser Asp Val Leu Tyr Asp Val
            340                 345                 350

Tyr Ala Asp Pro Asp Val Leu Gln Pro Leu Asp Asp Tyr Tyr Pro Ala
```

```
            355                 360                 365
Pro Arg Gly Ser Leu Ala Asn Thr Thr Val Ser Ala Ser Ser Ala Ser
            370                 375                 380

Thr Leu Arg Gly Ser Thr Thr Ala Pro Leu Ser Gly Gly Val Asp Val
385                 390                 395                 400

Pro Val Tyr Thr Gly Pro Asp Ile Glu Pro Val Val Pro Gly Leu
                405                 410                 415

Gly Pro Leu Ile Pro Val Ala Pro Ser Leu Pro Ser Val Tyr Ile
            420                 425                 430

Phe Gly Gly Asp Tyr Tyr Leu Leu Pro Ser Tyr Ile Leu Trp Pro Lys
            435                 440                 445

Arg Arg Lys Arg Val Asn Tyr Phe Phe Ala Asp Gly Phe Val Ala Ala
            450                 455                 460

<210> SEQ ID NO 29
<211> LENGTH: 473
<212> TYPE: PRT
<213> ORGANISM: Human papillomavirus type 28

<400> SEQUENCE: 29

Met Val Ala His Arg Ala Arg Arg Lys Arg Ala Ser Ala Thr Gln
1               5                   10                  15

Leu Tyr Arg Thr Cys Lys Ala Ala Gly Thr Cys Pro Pro Asp Val Ile
                20                  25                  30

Pro Lys Val Glu Gly Thr Thr Leu Ala Asp Arg Ile Leu Gln Trp Gly
            35                  40                  45

Gly Leu Gly Ile Tyr Leu Gly Leu Gly Ile Gly Thr Gly Ser Gly
            50                  55                  60

Thr Gly Gly Arg Thr Gly Tyr Val Pro Leu Ser Thr Arg Pro Gly Thr
65                  70                  75                  80

Val Val Asp Val Ser Val Pro Ala Arg Pro Pro Val Val Ile Glu Pro
                85                  90                  95

Val Gly Pro Ser Asp Pro Ser Ile Val Asn Leu Leu Glu Asp Ser Ser
            100                 105                 110

Ile Ile Asn Ser Gly Ser Thr Val Pro Thr Phe Ser Gly Thr Gly Gly
        115                 120                 125

Phe Glu Val Thr Ser Ser Ala Thr Thr Thr Pro Ala Val Leu Asp Ile
130                 135                 140

Thr Pro Ala Thr Asp Asn Val Val Ile Ser Ser Ser Asn Phe Thr Asn
145                 150                 155                 160

Pro Ala Phe Thr Glu Pro Ser Leu Leu Glu Val Pro Gln Asn Gly Glu
                165                 170                 175

Val Ser Gly His Ile Leu Val Ser Thr Pro Thr Ala Gly Thr His Ser
            180                 185                 190

Tyr Glu Glu Ile Pro Met Glu Thr Phe Ala Ser Pro Gly Thr Gly Asn
        195                 200                 205

Glu Pro Ile Ser Ser Thr Pro Val Pro Gly Val Ser Arg Ile Ala Gly
210                 215                 220

Pro Arg Leu Tyr Ala Lys Ala Val Thr Gln Val Lys Val Thr Asp Pro
225                 230                 235                 240

Ala Phe Leu Ser Arg Pro Thr Ser Leu Val Thr Phe Asp Asn Pro Ala
                245                 250                 255

Phe Glu Pro Gly Asp Glu Thr Ile Ile Phe Glu Arg Pro Tyr Pro Pro
            260                 265                 270
```

```
Ser Gln Val Pro Asp Pro Asp Phe Met Asp Ile Ile Arg Leu His Arg
        275                 280                 285

Pro Ala Leu Thr Ser Arg Arg Gly Thr Val Arg Phe Ser Arg Leu Gly
    290                 295                 300

Thr Lys Leu Ser Met His Thr Arg Ser Gly Lys Gly Ile Gly Ala Arg
305                 310                 315                 320

Val His Tyr Tyr Gln Asp Leu Ser Pro Ile Gly Pro Thr Glu Asp Ile
                325                 330                 335

Glu Met Glu Pro Leu Leu Ala Pro Ala Glu Asn Ala Ala Gly Asp Ser
                340                 345                 350

Ile Tyr Asp Val Phe Ala Asp Val Glu Asp Ala Asp Ile Ala Phe Thr
                355                 360                 365

Gly Arg Ser Arg Ser Ala Thr Ser Ser Arg Gly Tyr Thr Thr Val Ser
370                 375                 380

Pro Leu Ser Ser Thr Leu Thr Thr Lys Tyr Gly Asn Val Thr Ile Pro
385                 390                 395                 400

Phe Val Ser Pro Val Asp Val His Leu His Pro Gly Pro Asp Ile Ile
                405                 410                 415

Thr Pro Ala Ser Thr Gln Trp Pro Phe Val Pro Leu Val Pro Ala Asp
                420                 425                 430

Thr Thr His Tyr Val Tyr Ile Asp Gly Gly Asp Phe Tyr Leu Trp Pro
            435                 440                 445

Val Thr Leu Phe Val Pro Arg Arg Arg Arg Lys Arg Leu Ser Tyr
            450                 455                 460

Phe Leu Ala Asp Gly Thr Val Ala Leu
465                 470

<210> SEQ ID NO 30
<211> LENGTH: 473
<212> TYPE: PRT
<213> ORGANISM: Human papillomavirus type 29

<400> SEQUENCE: 30

Met Val Ala His Arg Ala Arg Arg Arg Lys Arg Ala Ser Ala Thr Glu
1               5                   10                  15

Leu Tyr Lys Thr Cys Lys Val Ala Gly Thr Cys Pro Pro Asp Val Ile
                20                  25                  30

Pro Lys Val Glu Gly Thr Thr Leu Ala Asp Arg Ile Leu Gln Trp Gly
                35                  40                  45

Ser Leu Gly Val Tyr Leu Gly Gly Leu Gly Ile Gly Thr Gly Ser Gly
            50                  55                  60

Thr Gly Gly Arg Thr Gly Tyr Val Pro Val Gly Thr Arg Pro Gly Thr
65                  70                  75                  80

Val Val Asp Val Ser Ile Pro Thr Arg Pro Pro Val Val Ile Glu Pro
                85                  90                  95

Val Gly Pro Ser Asp Pro Ser Ile Val Thr Leu Leu Glu Glu Ser Ser
                100                 105                 110

Val Ile Asn Ser Gly Ala Thr Ile Pro Thr Phe Thr Gly Thr Ser Gly
            115                 120                 125

Phe Glu Ile Thr Ser Ser Ala Thr Thr Thr Pro Ala Val Leu Asp Ile
            130                 135                 140

Thr Pro Ala Gly Asp Asn Val Val Ile Thr Ser Thr Asn Phe Asn Asn
145                 150                 155                 160

Pro Leu Phe Thr Glu Pro Ser Leu Leu Glu Ile Pro Gln Thr Gly Glu
                165                 170                 175
```

```
Thr Ser Gly Arg Val Leu Val Gly Thr Pro Thr Ser Gly Val His Gly
            180                 185                 190

Tyr Glu Glu Ile Pro Met Asp Thr Phe Ala Thr Ser Gly Thr Gly Leu
            195                 200                 205

Glu Pro Ile Ser Ser Thr Pro Val Pro Gly Val Ser Arg Val Ala Gly
210                 215                 220

Pro Arg Leu Tyr Gly Lys Ala Leu Thr Gln Val Arg Val Ser Asp Pro
225                 230                 235                 240

Ala Phe Leu Thr Gln Pro Ser Ser Phe Val Thr Phe Asp Asn Pro Val
                245                 250                 255

Tyr Asp Pro Glu Asp Glu Thr Ile Ile Phe Glu Arg Pro Ser Pro Gly
            260                 265                 270

Thr Arg Val Pro Asp Pro Asp Phe Met Asp Ile Val Lys Leu His Arg
            275                 280                 285

Pro Ala Leu Thr Ser Arg Arg Gly Thr Val Arg Phe Ser Arg Val Gly
            290                 295                 300

Gln Lys Phe Ser Met Arg Thr Arg Ser Gly Thr Asn Ile Gly Ala Arg
305                 310                 315                 320

Val His Tyr Tyr His Asp Leu Ser Pro Ile Leu Pro Thr Glu Asp Ile
                325                 330                 335

Glu Leu Glu Pro Leu Leu Pro Pro Ala Asp Pro Thr Ala Glu Glu Ser
            340                 345                 350

Leu Tyr Asp Ile Tyr Ala Asp Val Asp Glu Ala Asp Met Ala Phe Thr
            355                 360                 365

Gly Gly Gly Arg Gly Ala Thr Thr Tyr Gly Gly Arg Ile Thr Pro Ser
370                 375                 380

Val Phe Ser Ser Thr Leu Ser Thr Arg Tyr Gly Asn Val Thr Ile Pro
385                 390                 395                 400

Phe Val Ser Pro Val Asp Val Pro Leu His Thr Gly Pro Asp Ile Ile
                405                 410                 415

Leu Pro Ser Ser Ala Gln Trp Pro Phe Val Pro Val Ala Pro Ala Asp
            420                 425                 430

Thr Thr His Tyr Val Tyr Ile Asp Gly Gly Asp Tyr Phe Leu Trp Pro
            435                 440                 445

Val Thr Phe Pro Val Ser Arg Lys Arg Arg Lys Arg Leu Ser Tyr
450                 455                 460

Phe Leu Ala Asp Gly Phe Val Ala Leu
465                 470
```

<210> SEQ ID NO 31
<211> LENGTH: 463
<212> TYPE: PRT
<213> ORGANISM: Human papillomavirus type 30

<400> SEQUENCE: 31

```
Met Val Ala His Arg Ala Arg Arg Lys Arg Ala Ser Ala Thr Gln
1               5                   10                  15

Leu Tyr Gln Thr Cys Lys Gln Ala Gly Thr Cys Pro Ser Asp Val Ile
            20                  25                  30

Asn Lys Ile Glu His Thr Thr Leu Ala Asp Lys Ile Leu Gln Trp Gly
            35                  40                  45

Ser Leu Phe Thr Phe Phe Gly Asn Leu Gly Ile Gly Thr Gly Ala Gly
        50                  55                  60

Ser Gly Gly Arg Ala Gly Tyr Val Pro Leu Gly Thr Arg Pro Thr Thr
```

```
            65                  70                  75                  80
Val Val Asp Ala Ser Pro Ala Arg Pro Ile Val Glu Ser Val
                    85                  90                  95
Gly Pro Thr Asp Pro Ser Ile Val Thr Leu Val Glu Glu Ser Ser Val
                    100                 105                 110
Val Asn Ala Gly Ala Ser Phe Pro Asn Phe Thr Gly Thr Ala Gly Phe
                    115                 120                 125
Glu Val Thr Ser Ser Thr Thr Thr Pro Ala Val Leu Asp Ile Thr
            130                 135                 140
Pro Thr Thr Gly Ser Val His Val Ser Ser Thr His Phe Thr Asn Pro
145                 150                 155                 160
Ser Phe Val Glu Pro Val Ile Glu Val Pro Gln Thr Gly Glu Val
                    165                 170                 175
Ser Gly His Ile Leu Val Ser Thr Pro Thr Ser Gly Val His Ser Tyr
                    180                 185                 190
Glu Glu Ile Pro Met Gln Thr Phe Ala Val His Gly Thr Gly Thr Glu
            195                 200                 205
Pro Ile Ser Ser Thr Pro Ile Pro Gly Leu Arg Arg Ile Ala Ala Pro
210                 215                 220
Arg Leu Tyr Gln Arg Ala Phe Gln Gln Val Lys Val Thr Asp Pro Thr
225                 230                 235                 240
Phe Leu Thr Lys Pro Glu Thr Leu Ile Thr Val Asp Asn Pro Val Phe
                    245                 250                 255
Glu Asp Ala Asp Thr Thr Leu Thr Phe Ser Pro Ser Gly Val Ala Pro
                    260                 265                 270
Asp Pro Asp Phe Leu Asp Ile Val Ala Leu His Arg Pro Ala Phe Thr
            275                 280                 285
Thr Arg Arg Gly Gly Val Arg Phe Ser Arg Leu Gly Thr Lys Ala Thr
            290                 295                 300
Met Arg Thr Arg Ser Gly Lys Gln Ile Gly Ala Arg Val His Tyr Tyr
305                 310                 315                 320
Tyr Asp Val Ser Pro Ile Ala His Thr Glu Glu Ile Glu Met Gln Pro
                    325                 330                 335
Leu Leu Ser Ala Asn Asn Ser Phe Asp Gly Leu Tyr Asp Ile Tyr Ala
                    340                 345                 350
Asn Leu Asp Asp Glu Ala Pro Val Ser Ser His Leu Ser Ile Ala Thr
            355                 360                 365
Pro Ser Arg Leu Pro Thr Asn Thr Val Pro Leu Ser Phe Ser Ser Gln
            370                 375                 380
Thr Thr Asn Val Thr Ile Pro Leu Gly Lys Tyr Trp Asp Val Pro Ile
385                 390                 395                 400
Tyr Ser Gly Pro Asp Ile Val Leu Pro Thr Gly Pro Thr Thr Trp Pro
                    405                 410                 415
Tyr Ala Pro Gln Ala Pro Phe Asp Thr Thr His Asp Val Val Ile His
                    420                 425                 430
Gly Ser Thr Phe Ala Leu Trp Pro Val Tyr Phe Leu Arg Arg Arg Arg
                    435                 440                 445
Arg Lys His Val Pro Tyr Phe Leu Ala Asp Gly Val Ala Ala
            450                 455                 460

<210> SEQ ID NO 32
<211> LENGTH: 466
<212> TYPE: PRT
<213> ORGANISM: Human papillomavirus type 31
```

<400> SEQUENCE: 32

```
Met Arg Ser Lys Arg Ser Thr Lys Arg Thr Lys Arg Ala Ser Ala Thr
1               5                   10                  15

Gln Leu Tyr Gln Thr Cys Lys Ala Ala Gly Thr Cys Pro Ser Asp Val
            20                  25                  30

Ile Pro Lys Ile Glu His Thr Thr Ile Ala Asp Gln Ile Leu Arg Tyr
        35                  40                  45

Gly Ser Met Gly Val Phe Phe Gly Gly Leu Gly Ile Gly Ser Gly Ser
    50                  55                  60

Gly Thr Gly Gly Arg Thr Gly Tyr Val Pro Leu Ser Thr Arg Pro Ser
65              70                  75                  80

Thr Val Ser Glu Ala Ser Ile Pro Ile Arg Pro Pro Val Ser Ile Asp
                85                  90                  95

Pro Val Gly Pro Leu Asp Pro Ser Ile Val Ser Leu Val Glu Glu Ser
                100                 105                 110

Gly Ile Val Asp Val Gly Ala Pro Ala Pro Ile Pro His Pro Pro Thr
            115                 120                 125

Thr Ser Gly Phe Asp Ile Ala Thr Thr Ala Asp Thr Thr Pro Ala Ile
    130                 135                 140

Leu Asp Val Thr Ser Val Ser Thr His Glu Asn Pro Thr Phe Thr Asp
145                 150                 155                 160

Pro Ser Val Leu Gln Pro Pro Thr Pro Ala Glu Thr Ser Gly His Leu
                165                 170                 175

Leu Leu Ser Ser Ser Ser Ile Ser Thr His Asn Tyr Glu Glu Ile Pro
            180                 185                 190

Met Asp Thr Phe Ile Val Ser Thr Asn Asn Glu Asn Ile Thr Ser Ser
        195                 200                 205

Thr Pro Ile Pro Gly Val Arg Arg Pro Ala Arg Leu Gly Leu Tyr Ser
    210                 215                 220

Lys Ala Thr Gln Gln Val Lys Val Ile Asp Pro Thr Phe Leu Ser Ala
225                 230                 235                 240

Pro Lys Gln Leu Ile Thr Tyr Glu Asn Pro Ala Tyr Glu Thr Val Asn
                245                 250                 255

Ala Glu Glu Ser Leu Tyr Phe Ser Asn Thr Ser His Asn Ile Ala Pro
            260                 265                 270

Asp Pro Asp Phe Leu Asp Ile Ile Ala Leu His Arg Pro Ala Leu Thr
        275                 280                 285

Ser Arg Arg Asn Thr Val Arg Tyr Ser Arg Leu Gly Asn Lys Gln Thr
    290                 295                 300

Leu Arg Thr Arg Ser Gly Ala Thr Ile Gly Ala Arg Val His Tyr Tyr
305                 310                 315                 320

Tyr Asp Ile Ser Ser Ile Asn Pro Ala Gly Glu Ser Ile Glu Met Gln
                325                 330                 335

Pro Leu Gly Ala Ser Ala Thr Thr Ser Thr Leu Asn Asp Gly Leu
            340                 345                 350

Tyr Asp Ile Tyr Ala Asp Thr Asp Phe Thr Val Asp Thr Pro Ala Thr
        355                 360                 365

His Asn Val Ser Pro Ser Thr Ala Val Gln Ser Thr Ser Ala Val Ser
    370                 375                 380

Ala Tyr Val Pro Thr Asn Thr Thr Val Pro Leu Ser Thr Gly Phe Asp
385                 390                 395                 400

Ile Pro Ile Phe Ser Gly Pro Asp Val Pro Ile Glu His Ala Pro Thr
```

```
            405                 410                 415
Gln Val Phe Pro Phe Pro Leu Ala Pro Thr Thr Pro Gln Val Ser Ile
            420                 425                 430

Phe Val Asp Gly Gly Asp Phe Tyr Leu His Pro Ser Tyr Tyr Met Leu
            435                 440                 445

Lys Arg Arg Lys Arg Val Ser Tyr Phe Phe Thr Asp Val Ser Val
    450                 455                 460

Ala Ala
465

<210> SEQ ID NO 33
<211> LENGTH: 476
<212> TYPE: PRT
<213> ORGANISM: Human papillomavirus type 32

<400> SEQUENCE: 33

Met Pro Pro His Arg Ser Arg Arg Lys Arg Ala Ser Ala Thr Gln
1               5                   10                  15

Leu Tyr Gln Thr Cys Lys Ala Ser Gly Thr Cys Pro Pro Asp Val Ile
                20                  25                  30

Pro Lys Ile Glu Gly Arg Thr Trp Ala Asp Gln Ile Leu Lys Trp Gly
            35                  40                  45

Ser Thr Gly Val Phe Phe Gly Gly Leu Gly Ile Gly Thr Gly Ala Gly
50                  55                  60

Ser Gly Gly Arg Thr Gly Tyr Val Pro Ile Gly Thr Arg Pro Pro Val
65                  70                  75                  80

Val Ala Glu Pro Gly Pro Ala Ile Arg Pro Pro Val Val Val Asp Thr
                85                  90                  95

Ile Gly Pro Thr Asp Pro Ser Val Ile Ser Leu Leu Glu Glu Ser Ala
            100                 105                 110

Val Ile Asp Ser Ser Ile Pro Val Pro Thr Asp Thr Ser His Gly Gly
        115                 120                 125

Phe Asn Ile Thr Ser Ser Ala Ser Gly Pro Ser Ser Thr Pro Ala Val
130                 135                 140

Leu Asp Ile Ser Pro Pro Thr Asn Thr Ile Arg Val Ala Ser Thr Thr
145                 150                 155                 160

Ser His Asn Pro Val Tyr Ser Asp Pro Phe Thr Leu Arg Pro Ser Leu
                165                 170                 175

Pro Val Glu Gly Asn Gly Arg Leu Leu Thr Ser His Pro Thr Ile Ala
            180                 185                 190

Pro His Ser Tyr Glu Glu Ile Pro Met Asp Thr Phe Val Val Ser Thr
        195                 200                 205

Asp Thr Ser Asn Thr Val Thr Ser Thr Pro Ile Pro Gly Pro Arg Pro
210                 215                 220

Thr Met Arg Leu Gly Leu Tyr Thr Arg Val Thr Gln Gln Arg Pro Val
225                 230                 235                 240

Ala Thr Thr Thr Phe Leu Thr Ser Pro Glu Arg Leu Val Thr Tyr Asp
                245                 250                 255

Asn Pro Ala Tyr Glu Gly Pro Ala Glu Gly Thr Leu Glu Phe Glu His
            260                 265                 270

Pro Thr Ile His Glu Ala Pro Asp Ser Asp Phe Met Asp Ile Ile Ala
        275                 280                 285

Leu His Arg Pro Val Leu Ser Ala Arg Gln Gly Thr Val Arg Val Ser
290                 295                 300
```

```
Arg Ile Gly Gln Arg Ala Ser Leu Gln Thr Arg Ser Gly Ala Arg Ile
305                 310                 315                 320

Gly Ser Arg Val His Phe Phe His Asp Ile Ser Pro Ile Thr Arg Pro
            325                 330                 335

Ser Glu Ala Ile Glu Leu Gln Pro Leu Gly Ser Ser Ser Thr Ala Val
            340                 345                 350

Ser Thr Thr Ala Ser Ser Ala Ile Asn Asp Gly Leu Phe Asp Val Tyr
            355                 360                 365

Val Asp Pro Asp Ile Pro Ser His Ala Leu Pro Pro Leu Arg Ser
370                 375                 380

Pro Thr His Val Ser Thr Val Ser Leu Thr Ser Leu Gly Ser Val Pro
385                 390                 395                 400

Ala Gln Thr Ala Asn Thr Thr Val Pro Leu Ser Leu Pro Thr Asn Ile
            405                 410                 415

Asn Val Gly Pro Asp Leu Ser Pro Pro Glu Ser Pro Pro Phe Ile Ser
            420                 425                 430

Thr Arg Pro Val Ser Pro Ser Phe Asp Ser Val Met Val Leu Gly Trp
            435                 440                 445

Asp Phe Ile Leu His Pro Ser Tyr Met Trp Arg Lys Arg Arg Lys Pro
450                 455                 460

Val Pro Tyr Phe Phe Ala Asp Val Arg Val Ala Ala
465                 470                 475

<210> SEQ ID NO 34
<211> LENGTH: 467
<212> TYPE: PRT
<213> ORGANISM: Human papillomavirus type 33

<400> SEQUENCE: 34

Met Arg His Lys Arg Ser Thr Arg Lys Arg Ala Ser Ala Thr Gln
1               5                   10                  15

Leu Tyr Gln Thr Cys Lys Ala Thr Gly Thr Cys Pro Pro Asp Val Ile
                20                  25                  30

Pro Lys Val Glu Gly Ser Thr Ile Ala Asp Gln Ile Leu Lys Tyr Gly
            35                  40                  45

Ser Leu Gly Val Phe Phe Gly Gly Leu Gly Ile Gly Thr Gly Ser Gly
50                  55                  60

Ser Gly Gly Arg Thr Gly Tyr Val Pro Ile Gly Thr Asp Pro Pro Thr
65                  70                  75                  80

Ala Ala Ile Pro Leu Gln Pro Ile Arg Pro Pro Val Thr Val Asp Thr
                85                  90                  95

Val Gly Pro Leu Asp Ser Ser Ile Val Ser Leu Ile Glu Glu Thr Ser
            100                 105                 110

Phe Ile Glu Ala Gly Ala Pro Ala Pro Ser Ile Pro Thr Pro Ser Gly
            115                 120                 125

Phe Asp Val Thr Thr Ser Ala Asp Thr Thr Pro Ala Ile Ile Asn Val
            130                 135                 140

Ser Ser Val Gly Glu Ser Ser Ile Gln Thr Ile Ser Thr His Leu Asn
145                 150                 155                 160

Pro Thr Phe Thr Glu Pro Ser Val Leu His Pro Pro Ala Pro Ala Glu
                165                 170                 175

Ala Ser Gly His Phe Ile Phe Ser Ser Pro Thr Val Ser Thr Gln Ser
            180                 185                 190

Tyr Glu Asn Ile Pro Met Asp Thr Phe Val Val Ser Thr Asp Ser Ser
            195                 200                 205
```

```
Asn Val Thr Ser Ser Thr Pro Ile Pro Gly Ser Arg Pro Val Ala Arg
        210                 215                 220

Leu Gly Leu Tyr Ser Arg Asn Thr Gln Gln Val Lys Val Val Asp Pro
225                 230                 235                 240

Ala Phe Leu Thr Ser Pro His Lys Leu Ile Thr Tyr Asp Asn Pro Ala
                245                 250                 255

Phe Glu Ser Phe Asp Pro Glu Asp Thr Leu Gln Phe Gln His Ser Asp
                260                 265                 270

Ile Ser Pro Ala Pro Asp Pro Asp Phe Leu Asp Ile Ile Ala Leu His
            275                 280                 285

Arg Pro Ala Ile Thr Ser Arg Arg His Thr Val Arg Phe Ser Arg Val
        290                 295                 300

Gly Gln Lys Ala Thr Leu Lys Thr Arg Ser Gly Lys Gln Ile Gly Ala
305                 310                 315                 320

Arg Ile His Tyr Tyr Gln Asp Leu Ser Pro Ile Val Pro Leu Asp His
                325                 330                 335

Thr Val Pro Asn Glu Gln Tyr Glu Leu Gln Pro Leu His Asp Thr Ser
                340                 345                 350

Thr Ser Ser Tyr Ser Ile Asn Asp Gly Leu Tyr Asp Val Tyr Ala Asp
            355                 360                 365

Asp Val Asp Asn Val His Thr Pro Met Gln His Ser Tyr Ser Thr Phe
            370                 375                 380

Ala Thr Thr Arg Thr Ser Asn Val Ser Ile Pro Leu Asn Thr Gly Phe
385                 390                 395                 400

Asp Thr Pro Val Met Ser Gly Pro Asp Ile Pro Ser Pro Leu Phe Pro
                405                 410                 415

Thr Ser Ser Pro Phe Val Pro Ile Ser Pro Phe Phe Pro Phe Asp Thr
                420                 425                 430

Ile Val Val Asp Gly Ala Asp Phe Val Leu His Pro Ser Tyr Phe Ile
            435                 440                 445

Leu Arg Arg Arg Arg Lys Arg Phe Pro Tyr Phe Phe Thr Asp Val Arg
        450                 455                 460

Val Ala Ala
465

<210> SEQ ID NO 35
<211> LENGTH: 472
<212> TYPE: PRT
<213> ORGANISM: Human papillomavirus type 34

<400> SEQUENCE: 35

Met Arg Arg Lys Arg Asp Thr His Ile Arg Arg Lys Arg Ala Ser Ala
1               5                   10                  15

Thr Gln Leu Tyr Lys Thr Cys Lys Gln Ser Gly Thr Cys Pro Pro Asp
                20                  25                  30

Ile Ile Pro Lys Val Glu Gly Asn Thr Leu Ala Asp Gln Ile Leu Lys
            35                  40                  45

Tyr Gly Ser Ile Gly Val Phe Phe Gly Gly Leu Gly Ile Gly Ser Gly
        50                  55                  60

Ser Gly Thr Gly Gly Arg Thr Gly Tyr Val Pro Leu Pro Thr Thr Thr
65                  70                  75                  80

Pro Ser Arg Pro Val Glu Ile Pro Leu Gln Pro Thr Arg Pro Pro Val
                85                  90                  95

Ile Thr Ser Val Gly Ala Ser Asp Ser Ser Ile Val Ser Leu Val Glu
```

```
                  100                 105                 110
Glu Ser Ser Phe Ile Glu Ala Gly Val Pro Gly Pro Thr Ser Ile Val
            115                 120                 125
Pro Ser Ser Gly Phe Asn Val Thr Thr Ser Val Asp Ser Thr Pro
            130                 135                 140
Ala Ile Ile Asp Val Ala Thr Ile Ser Asp Thr Thr Gln Val Ser Val
145                 150                 155                 160
Ser Thr Phe Asn Asn Pro Thr Phe Thr Asp Pro Ser Val Leu Gln Pro
                165                 170                 175
Pro Pro Pro Leu Glu Ala Ser Gly Arg Leu Leu Phe Ser Asn Asp Thr
            180                 185                 190
Val Thr Thr His Ser Tyr Glu Asn Ile Pro Leu Asp Thr Phe Val Val
            195                 200                 205
Thr Thr Asp Asn Asn Ser Ile Val Ser Ser Thr Pro Ile Pro Gly Arg
210                 215                 220
His Pro Pro Ala Arg Leu Gly Leu Tyr Gly Arg Ala Ile Gln Gln Val
225                 230                 235                 240
Lys Val Val Asp Pro Ala Phe Val Thr Thr Pro Thr Arg Leu Val Thr
                245                 250                 255
Tyr Asp Asn Pro Ala Phe Glu Gly Leu Gln Asp Thr Thr Leu Glu Phe
            260                 265                 270
Gln His Ser Asp Leu His Asn Ala Pro Asp Ser Asp Phe Leu Asp Ile
            275                 280                 285
Val Lys Leu His Arg Pro Ala Leu Thr Ala Arg Lys Thr Gly Ile Arg
            290                 295                 300
Val Ser Arg Leu Gly Gln Arg Ala Thr Met Phe Thr Arg Ser Gly Lys
305                 310                 315                 320
Arg Ile Gly Gly Arg Val His Phe Tyr His Asp Leu Ser Pro Ile Pro
                325                 330                 335
Thr Glu Asn Ile Glu Leu Gln Pro Leu Leu Pro Ser Ala Ser Ala Thr
            340                 345                 350
Val Thr Asp Ala Asn Gly Ile Asn Asp Gly Leu Tyr Asp Val Leu Leu
            355                 360                 365
Asp Asn Asn Val Asp Ile Thr Glu Val Glu Thr Pro Thr Gly Thr Asn
370                 375                 380
Thr Gln Ser Val Phe Ala Ser Glu Ile Ser Thr Thr Ala Asn Thr
385                 390                 395                 400
Thr Ile Pro Leu Asn Ala Gly Leu Asp Thr His Pro Gly Pro Asp Ile
                405                 410                 415
Ala Leu Pro Val Pro Thr Ala Glu Thr Ile Phe Thr Pro Thr Val Pro
            420                 425                 430
Val Gln Pro Ser Gly Pro Ile Tyr Ile Tyr Gly Ser Asp Phe Ile Leu
            435                 440                 445
His Pro Ser Leu Tyr Val Ile Pro Arg Lys Arg Lys Arg Leu Ser Tyr
            450                 455                 460
Phe Phe Ala Asp Val Ala Thr Tyr
465                 470

<210> SEQ ID NO 36
<211> LENGTH: 469
<212> TYPE: PRT
<213> ORGANISM: Human papillomavirus type 35

<400> SEQUENCE: 36
```

```
Met Arg His Lys Arg Ser Thr Lys Arg Val Lys Arg Ala Ser Ala Thr
1               5                   10                  15

Gln Leu Tyr Arg Thr Cys Lys Ala Ala Gly Thr Cys Pro Pro Asp Val
            20                  25                  30

Ile Pro Lys Val Glu Gly Asn Thr Val Ala Asp Gln Ile Leu Lys Tyr
            35                  40                  45

Gly Ser Met Ala Val Phe Phe Gly Gly Leu Gly Ile Gly Ser Gly Ser
50                      55                  60

Gly Thr Gly Gly Arg Ser Gly Tyr Val Pro Leu Gly Thr Thr Pro Pro
65                  70                  75                  80

Thr Ala Ala Thr Asn Ile Pro Ile Arg Pro Pro Val Thr Val Glu Ser
                85                  90                  95

Ile Pro Leu Asp Thr Ile Gly Pro Leu Asp Ser Ser Ile Val Ser Leu
            100                 105                 110

Val Glu Glu Thr Ser Phe Ile Glu Ser Gly Ala Pro Val Val Thr Pro
            115                 120                 125

Arg Val Pro Pro Thr Thr Gly Phe Thr Ile Thr Ser Thr Asp Thr
130                     135                 140

Thr Pro Ala Ile Leu Asp Val Thr Ser Ile Ser Thr His Asp Asn Pro
145                 150                 155                 160

Thr Phe Thr Asp Pro Ser Val Leu His Pro Pro Thr Pro Ala Glu Thr
                165                 170                 175

Ser Gly His Phe Val Leu Ser Ser Ser Ile Ser Thr His Asn Tyr
                180                 185                 190

Glu Glu Ile Pro Met Asp Thr Phe Ile Val Ser Thr Asp Ser Asn Asn
            195                 200                 205

Ile Thr Asn Ser Thr Pro Ile Pro Gly Ser Arg Pro Thr Thr Arg Leu
            210                 215                 220

Gly Leu Tyr Ser Lys Gly Thr Gln Gln Val Lys Val Val Asp Pro Ala
225                 230                 235                 240

Phe Met Thr Ser Pro Ala Lys Leu Ile Thr Tyr Asp Asn Pro Ala Tyr
                245                 250                 255

Glu Gly Leu Asn Pro Asp Thr Thr Leu Gln Phe Glu His Glu Asp Ile
                260                 265                 270

Ser Leu Ala Pro Asp Pro Asp Phe Met Asp Ile Ile Ala Leu His Arg
275                 280                 285

Pro Ala Leu Thr Ser Arg Lys Gly Thr Ile Arg Tyr Ser Arg Val Gly
            290                 295                 300

Asn Lys Arg Thr Met His Thr Arg Ser Gly Lys Ala Ile Gly Ala Arg
305                 310                 315                 320

Val His Tyr Tyr Gln Asp Leu Ser Ser Ile Thr Glu Asp Ile Glu Leu
                325                 330                 335

Gln Pro Leu Gln His Val Pro Ser Ser Leu Pro His Thr Thr Val Ser
            340                 345                 350

Thr Ser Leu Asn Asp Gly Met Phe Asp Ile Tyr Ala Pro Ile Asp Thr
            355                 360                 365

Glu Glu Asp Ile Ile Phe Ser Ala Ser Ser Asn Asn Thr Leu Tyr Thr
            370                 375                 380

Thr Ser Asn Thr Ala Tyr Val Pro Ser Asn Thr Thr Ile Pro Leu Ser
385                 390                 395                 400

Ser Gly Tyr Asp Ile Pro Ile Thr Ala Gly Pro Asp Ile Val Phe Asn
                405                 410                 415

Ser Asn Thr Ile Thr Asn Ser Val Leu Pro Val Pro Thr Gly Pro Ile
```

```
            420             425             430
Tyr Ser Ile Ile Ala Asp Gly Gly Asp Phe Tyr Leu His Pro Ser Tyr
                435                 440                 445

Tyr Leu Leu Lys Arg Arg Arg Lys Ala Ile Pro Tyr Phe Phe Ala Asp
    450                 455                 460

Val Ser Val Ala Val
465

<210> SEQ ID NO 37
<211> LENGTH: 518
<212> TYPE: PRT
<213> ORGANISM: Human papillomavirus type 36

<400> SEQUENCE: 37

Met Ala Arg Ala Lys Arg Val Lys Arg Asp Ser Val Thr His Ile Tyr
1               5                   10                  15

Gln Thr Cys Lys Gln Ala Gly Thr Cys Pro Pro Asp Val Val Asn Lys
            20                  25                  30

Val Glu Gln Thr Thr Val Ala Asp Asn Ile Leu Lys Tyr Gly Ser Ala
        35                  40                  45

Gly Val Phe Phe Gly Gly Leu Gly Ile Gly Ser Gly Arg Gly Thr Gly
    50                  55                  60

Gly Ala Thr Gly Tyr Val Pro Leu Ser Glu Gly Pro Gly Ile Arg Val
65                  70                  75                  80

Gly Gly Thr Pro Thr Val Val Arg Pro Ser Leu Val Pro Glu Ala Ile
                85                  90                  95

Gly Pro Val Asp Ile Leu Pro Ile Asp Thr Ile Asp Pro Val Glu Pro
            100                 105                 110

Thr Ala Ser Ser Val Val Pro Leu Thr Glu Ser Thr Gly Pro Asp Leu
        115                 120                 125

Leu Pro Gly Glu Val Glu Thr Ile Ala Glu Ile His Pro Val Ala Glu
    130                 135                 140

Gly Pro Ser Val Asp Thr Pro Val Val Thr Thr Ser Thr Gly Ser Ser
145                 150                 155                 160

Ala Val Leu Glu Val Ala Pro Glu Pro Ile Pro Pro Thr Arg Val Arg
                165                 170                 175

Ile Ser Arg Thr Gln Tyr His Asn Pro Ser Phe Gln Ile Ile Thr Glu
            180                 185                 190

Ser Thr Pro Ala Gln Gly Glu Ser Ser Leu Ala Asp His Ile Leu Val
        195                 200                 205

Thr Ser Gly Ser Gly Gly Gln Arg Ile Gly Ala Asp Ile Thr Asp Glu
    210                 215                 220

Ile Glu Leu Gln Glu Leu Pro Ser Arg Tyr Thr Phe Glu Asn Glu Glu
225                 230                 235                 240

Pro Thr Pro Pro Arg Arg Ser Ser Thr Pro Leu Gln Ala Thr Arg Ala
                245                 250                 255

Ala Gly Arg Arg Arg Gly Val Ser Leu Thr Asn Arg Arg Leu Val Gln
            260                 265                 270

Gln Val Pro Val Glu Asn Pro Leu Phe Leu Thr Gln Pro Ser Arg Leu
        275                 280                 285

Val Arg Phe Ala Phe Glu Asn Pro Ala Phe Glu Glu Val Thr Asn
    290                 295                 300

Ile Phe Glu His Asp Val Asp Ala Phe Glu Glu Pro Pro Asp Arg Asp
305                 310                 315                 320
```

```
Phe Leu Asp Val Gln Arg Leu Gly Arg Pro Gln Tyr Ser Thr Thr Pro
            325                 330                 335

Ala Gly Tyr Val Arg Val Ser Arg Leu Gly Thr Arg Ala Thr Ile Arg
        340                 345                 350

Thr Arg Ser Gly Ala Gln Ile Gly Ser Gln Val His Phe Tyr Arg Asp
    355                 360                 365

Leu Ser Ser Ile Asn Thr Glu Asp Pro Ile Glu Leu Gln Leu Leu Gly
370                 375                 380

Gln His Ser Gly Asp Ala Ser Ile Val Gln Gly Pro Val Glu Ser Thr
385                 390                 395                 400

Phe Ile Asp Val Asn Val Ser Glu Asn Pro Leu Ser Glu Ser Val Glu
            405                 410                 415

Ala Phe Ser Asp Asp Leu Leu Leu Asp Glu Ala Val Glu Asp Phe Ser
        420                 425                 430

Gly Ser Gln Leu Val Ile Gly Asn Arg Arg Ser Thr Thr Ser Tyr Thr
    435                 440                 445

Val Pro Arg Phe Glu Thr Thr Arg Ser Gly Ser Tyr Tyr Val Gln Asp
450                 455                 460

Ser Lys Gly Tyr Tyr Val Ala Tyr Pro Glu Ser Arg Asn Asn Ala Glu
465                 470                 475                 480

Ile Ile Tyr Pro Thr Pro Asp Ile Pro Val Val Ile His Thr His
            485                 490                 495

Asp Asn Thr Gly Asp Phe Tyr Leu His Pro Ser Leu Arg Trp Arg Lys
        500                 505                 510

Arg Lys Arg Lys Tyr Leu
        515

<210> SEQ ID NO 38
<211> LENGTH: 534
<212> TYPE: PRT
<213> ORGANISM: Human papillomavirus type 37

<400> SEQUENCE: 38

Met Ala Arg Ala Arg Arg Thr Lys Arg Ala Ser Val Thr Asp Ile Tyr
1               5                   10                  15

Arg Gly Cys Lys Gln Ala Gly Thr Cys Pro Pro Asp Val Ile Asn Lys
            20                  25                  30

Val Glu Gln Thr Thr Ile Ala Asp Lys Ile Leu Lys Tyr Gly Gly Ala
        35                  40                  45

Gly Val Phe Phe Gly Gly Leu Gly Ile Ser Thr Gly Arg Gly Thr Gly
    50                  55                  60

Gly Ala Thr Gly Tyr Val Pro Leu Gly Glu Gly Pro Gly Val Arg Val
65                  70                  75                  80

Gly Gly Ala Pro Thr Ile Val Arg Pro Gly Val Ile Pro Glu Leu Ile
            85                  90                  95

Gly Pro Ala Asp Val Ile Pro Ile Asp Thr Val Thr Pro Ile Asp Pro
        100                 105                 110

Ala Ala Pro Ser Ile Val Thr Ile Thr Asp Ser Ser Ala Val Asp Leu
    115                 120                 125

Leu Pro Asn Glu Ile Glu Thr Ile Ala Glu Val His Pro Val Pro Thr
130                 135                 140

Asp Asn Leu Asp Ile Asp Thr Pro Val Val Thr Gly Gly Arg Asp Ser
145                 150                 155                 160

Ser Ala Val Leu Glu Val Ala Asp Pro Ser Pro Pro Val Arg Thr Arg
            165                 170                 175
```

Val Ser Arg Thr Gln Tyr His Asn Pro Ser Phe Gln Ile Ile Thr Glu
              180                 185                 190

Ser Thr Pro Leu Ala Gly Glu Ser Ala Leu Ala Asp His Val Ile Val
              195                 200                 205

Phe Glu Gly Thr Gly Gly Gln Asn Ile Gly Gly Ser Arg Asn Ala Thr
210                 215                 220

Ile Glu Thr Ala Gln Glu Ser Phe Glu Met Gln Ser Trp Pro Ser Arg
225                 230                 235                 240

Tyr Ser Phe Glu Ile Glu Glu Gly Thr Pro Pro Arg Ser Ser Thr Pro
              245                 250                 255

Val Gln Arg Ala Val Gln Ser Leu Ser Ser Leu Arg Arg Ala Leu Tyr
              260                 265                 270

Asn Arg Arg Leu Thr Glu Gln Val Ala Val Thr Asp Pro Leu Phe Leu
              275                 280                 285

Ser Arg Pro Ser Gln Leu Val Gln Phe Gln Phe Asp Asn Pro Ala Phe
              290                 295                 300

Glu Glu Glu Val Thr Gln Ile Phe Glu Arg Asp Leu Glu Ala Val Glu
305                 310                 315                 320

Glu Pro Pro Asp Arg Gln Phe Leu Asp Val Ile Arg Leu Gly Arg Pro
              325                 330                 335

Thr Val Ala Glu Thr Pro Gln Ala Tyr Leu Arg Val Ser Arg Leu Gly
              340                 345                 350

Arg Arg Ala Thr Ile Arg Thr Arg Ser Gly Ala Gln Val Gly Ala Gln
              355                 360                 365

Val His Phe Tyr Arg Asp Leu Ser Thr Ile Asp Ser Asp Ala Leu Glu
              370                 375                 380

Met Gln Leu Leu Gly Glu His Ser Gly Asp Thr Thr Ile Val Gln Gly
385                 390                 395                 400

Pro Val Glu Ser Ser Phe Val Asp Ile Asn Ile Asp Glu Pro Gly Pro
              405                 410                 415

Leu Asn Ile Gly Gln Gln Glu Ser Thr Met Ala Asp Asp Thr Asp Phe
              420                 425                 430

Asn Ser Ala Asp Leu Leu Leu Glu Asp Ala Val Glu Asp Phe Ser Gly
              435                 440                 445

Ser Gln Leu Val Phe Gly Thr Ser Arg Arg Ser Thr Asn Ser Ile Thr
              450                 455                 460

Ile Pro Arg Phe Glu Thr Pro Arg Asp Thr Gly Phe Tyr Ile Gln Asp
465                 470                 475                 480

Ile Gln Gly Tyr Asn Val Ala Tyr Pro Glu Ser Arg Asp Thr Thr Gln
              485                 490                 495

Val Ile Leu Pro Gln Pro Glu Thr Pro Thr Val Val Ile Arg Phe Gly
              500                 505                 510

Glu Ala Gly Thr Asp Tyr Tyr Leu His Pro Ser Leu Lys Lys Lys Lys
              515                 520                 525

Arg Lys Arg Lys Tyr Leu
    530

<210> SEQ ID NO 39
<211> LENGTH: 527
<212> TYPE: PRT
<213> ORGANISM: Human papillomavirus type 38

<400> SEQUENCE: 39

Met Val Arg Ala Arg Arg Thr Lys Arg Ala Ser Val Thr Asp Ile Tyr

-continued

```
1               5                   10                  15
Arg Gly Cys Lys Ala Ser Asn Thr Cys Pro Asp Val Ile Asn Lys
            20                  25                  30
Val Glu Gln Ser Thr Ile Ala Asp Lys Ile Leu Lys Tyr Gly Ser Ala
            35                  40                  45
Ala Val Phe Phe Gly Gly Leu Gly Ile Ser Thr Gly Arg Gly Thr Gly
            50                  55                  60
Gly Ala Thr Gly Tyr Val Pro Leu Gly Gln Gly Pro Gly Val Arg Val
65                  70                  75                  80
Gly Gly Ala Pro Thr Val Val Arg Pro Gly Val Ile Pro Glu Val Ile
                    85                  90                  95
Gly Pro Thr Glu Leu Ile Pro Ile Asp Ser Val Thr Pro Ile Asp Pro
                100                 105                 110
Thr Ala Pro Ser Ile Val Ser Leu Thr Asp Ser Ser Ala Val Asp Leu
                115                 120                 125
Leu Pro Gly Glu Val Glu Thr Ile Ala Glu Val His Pro Gly Pro Ile
130                 135                 140
Asp Pro Ile Glu Ile Asp Thr Pro Val Val Ser Gly Gly Arg Asn Thr
145                 150                 155                 160
Asn Ala Ile Leu Glu Val Ala Asp Pro His Pro Pro Thr Arg Ala Thr
                165                 170                 175
Val Ser Arg Thr Gln Tyr Asn Asn Pro Ala Phe Gln Ile Ile Ser Glu
                180                 185                 190
Val Ile Pro Thr Ser Gly Glu Ser Ser Leu Ala Asp His Val Leu Val
                195                 200                 205
Ser Glu Gly Ser Gly Gly Gln Gln Ile Gly Gly Thr Arg Thr Ala Glu
                210                 215                 220
Glu Ile Glu Leu Gln Pro Leu Leu Ser Arg Tyr Ser Phe Glu Ile Glu
225                 230                 235                 240
Glu Pro Thr Pro Pro Arg Arg Thr Ser Thr Pro Leu Gln Arg Ala Arg
                245                 250                 255
Gln Gln Phe Ser Ser Leu Arg Arg Ala Leu Tyr Asn Arg Arg Leu Thr
                260                 265                 270
Glu Gln Val Gly Val Thr Asp Pro Leu Phe Phe Thr Ser Pro Ser Lys
                275                 280                 285
Leu Val Arg Phe Gln Phe Asp Asn Pro Val Phe Asp Glu Gln Val Thr
                290                 295                 300
Gln Ile Phe Glu Gln Asp Ile Ala Asp Phe Glu Glu Pro Pro Asp Arg
305                 310                 315                 320
Gln Phe Leu Asp Val Val Lys Leu Gly Arg Pro Thr Leu Thr Glu Ser
                325                 330                 335
Ala Glu Gly Tyr Val Arg Val Ser Arg Leu Gly Arg Arg Gly Thr Ile
                340                 345                 350
Arg Thr Arg Ser Gly Thr Gln Ile Gly Ser Gln Val His Phe Tyr Arg
                355                 360                 365
Asp Leu Ser Thr Ile Asn Thr Glu Glu Pro Leu Glu Met Gln Leu Leu
                370                 375                 380
Gly Glu His Ser Gly Asp Ala Ser Ile Val Gln Gly Pro Val Glu Ser
385                 390                 395                 400
Thr Leu Val Asp Val Asn Val Thr Glu Val Pro Glu Gly Val Leu Thr
                405                 410                 415
Glu Thr Ser Met Asp Pro Asp Thr Phe Asn Ser Glu Asp Leu Leu Leu
                420                 425                 430
```

```
Asp Asp Ala Ile Glu Asp Phe Ser Gly Ser Gln Leu Val Val Gly Thr
            435                 440                 445

Pro Arg Arg Ser Thr Thr Ser Ile Thr Val Pro Arg Phe Gln Thr Pro
        450                 455                 460

Gln Asn Pro Thr Ile Tyr Tyr Gln Asp Ile Gln Gly Tyr His Val Ser
465                 470                 475                 480

Tyr Pro Glu Ser Arg Glu Arg Pro Ala Ile Ile Tyr Pro Thr Pro Asp
                485                 490                 495

Ile Pro Thr Val Val Ile His Val Ala Asp Ser Ser Gly Asp Phe Tyr
            500                 505                 510

Leu His Pro Ser Leu Arg Trp Arg Arg Arg Lys Arg Lys Tyr Leu
        515                 520                 525

<210> SEQ ID NO 40
<211> LENGTH: 470
<212> TYPE: PRT
<213> ORGANISM: Human papillomavirus type 39

<400> SEQUENCE: 40

Met Val Ser His Arg Ala Ala Arg Arg Lys Arg Ala Ser Ala Thr Asp
1               5                   10                  15

Leu Tyr Arg Thr Cys Lys Gln Ser Gly Thr Cys Pro Pro Asp Val Val
            20                  25                  30

Asp Lys Val Glu Gly Thr Thr Leu Ala Asp Lys Ile Leu Gln Trp Thr
        35                  40                  45

Ser Leu Gly Ile Phe Leu Gly Gly Leu Gly Ile Gly Thr Gly Thr Gly
    50                  55                  60

Thr Gly Gly Arg Thr Gly Tyr Ile Pro Leu Gly Gly Arg Pro Asn Thr
65                  70                  75                  80

Val Val Asp Val Ser Pro Ala Arg Pro Pro Val Val Ile Glu Pro Val
                85                  90                  95

Gly Pro Ser Glu Pro Ser Ile Val Gln Leu Val Glu Asp Ser Ser Val
            100                 105                 110

Ile Thr Ser Gly Thr Pro Val Pro Thr Phe Thr Gly Thr Ser Gly Phe
        115                 120                 125

Glu Ile Thr Ser Ser Ser Thr Thr Thr Pro Ala Val Leu Asp Ile Thr
    130                 135                 140

Pro Ser Ser Gly Ser Val Gln Ile Thr Ser Thr Ser Tyr Thr Asn Pro
145                 150                 155                 160

Ala Phe Thr Asp Pro Ser Leu Ile Glu Val Pro Gln Thr Gly Glu Thr
                165                 170                 175

Ser Gly Asn Ile Phe Val Ser Thr Pro Thr Ser Gly Thr His Gly Tyr
            180                 185                 190

Glu Glu Ile Pro Met Glu Val Phe Ala Thr His Gly Thr Gly Thr Glu
        195                 200                 205

Pro Ile Ser Ser Thr Pro Thr Pro Gly Ile Ser Arg Val Ala Gly Pro
    210                 215                 220

Arg Leu Tyr Ser Arg Ala His Gln Gln Val Arg Val Ser Asn Phe Asp
225                 230                 235                 240

Phe Val Thr His Pro Ser Ser Phe Val Thr Phe Asp Asn Pro Ala Phe
                245                 250                 255

Glu Pro Val Asp Thr Thr Leu Thr Tyr Glu Ala Ala Asp Ile Ala Pro
            260                 265                 270

Asp Pro Asp Phe Leu Asp Ile Val Arg Leu His Arg Pro Ala Leu Thr
```

```
                275                 280                 285
Ser Arg Lys Gly Thr Val Arg Phe Ser Arg Leu Gly Lys Lys Ala Thr
290                 295                 300

Met Val Thr Arg Arg Gly Thr Gln Ile Gly Ala Gln Val His Tyr Tyr
305                 310                 315                 320

His Asp Ile Ser Ser Ile Ala Pro Ala Glu Ser Ile Glu Leu Gln Pro
            325                 330                 335

Leu Val His Ala Glu Pro Ser Asp Ala Ser Asp Ala Leu Phe Asp Ile
                340                 345                 350

Tyr Ala Asp Val Asp Asn Asn Thr Tyr Leu Asp Thr Ala Phe Asn Asn
            355                 360                 365

Thr Arg Asp Ser Gly Thr Thr Tyr Asn Thr Gly Ser Leu Pro Ser Val
        370                 375                 380

Ala Ser Ser Ala Ser Thr Lys Tyr Ala Asn Thr Thr Ile Pro Phe Ser
385                 390                 395                 400

Thr Ser Trp Asn Met Pro Val Asn Thr Gly Pro Asp Ile Ala Leu Pro
                405                 410                 415

Ser Thr Thr Pro Gln Leu Pro Leu Val Pro Ser Gly Pro Ile Asp Thr
            420                 425                 430

Thr Tyr Ala Ile Thr Ile Gln Gly Ser Asn Tyr Tyr Leu Leu Pro Leu
                435                 440                 445

Leu Tyr Phe Phe Leu Lys Lys Arg Lys Arg Ile Pro Tyr Phe Phe Ser
        450                 455                 460

Asp Gly Tyr Val Ala Val
465                 470

<210> SEQ ID NO 41
<211> LENGTH: 467
<212> TYPE: PRT
<213> ORGANISM: Human papillomavirus type 40

<400> SEQUENCE: 41

Met Val Ser Ser Arg Pro Arg Arg Lys Arg Ala Ser Ala Thr Gln
1               5                   10                  15

Leu Tyr Gln Thr Cys Lys Ala Ala Gly Thr Cys Pro Pro Asp Val Val
                20                  25                  30

His Lys Val Glu Gln Thr Thr Val Ala Asp Gln Ile Leu Lys Trp Gly
            35                  40                  45

Ser Met Gly Val Phe Phe Gly Gly Leu Gly Ile Gly Ser Gly Ser Gly
50                  55                  60

Thr Gly Gly Arg Ala Gly Tyr Val Pro Leu Ser Thr Gly Ser Arg Ala
65                  70                  75                  80

Val Pro Pro Lys Ser Leu Val Pro Asp Val Val Ala Arg Pro Pro Val
                85                  90                  95

Val Val Asp Thr Val Ala Pro Ser Asp Pro Ser Ile Val Ser Leu Ile
            100                 105                 110

Glu Glu Ser Ser Ile Ile Gln Ser Gly Ala Pro Ser Leu Thr Ile Pro
        115                 120                 125

Thr Glu Gly Gly Phe Ser Val Thr Ser Ser Gly Thr Asp Val Pro Ala
    130                 135                 140

Ile Leu Asp Val Ser Ser Thr Asn Thr Val His Val Thr Ala Thr Thr
145                 150                 155                 160

His His Asn Pro Val Phe Thr Asp Pro Ser Val Val Gln Pro Ile Pro
                165                 170                 175
```

Pro Val Glu Ala Gly Gly Arg Leu Ile Val Ser His Ser Thr Ile Thr
            180                 185                 190

Thr Ser Ala Ala Glu Glu Ile Pro Leu Asp Thr Phe Val Val His Ser
        195                 200                 205

Asp Pro Leu Ser Ser Thr Pro Val Pro Gly Thr Ser Gly Arg Pro Arg
    210                 215                 220

Leu Gly Leu Tyr Ser Lys Ala Leu Gln Gln Val Glu Ile Val Asp Pro
225                 230                 235                 240

Ala Phe Leu Ser Thr Pro Gln Arg Leu Ile Thr Tyr Asp Asn Pro Val
                245                 250                 255

Phe Glu Asn Val Asp Asp Thr Leu Gln Phe Glu Gln Pro Ser Ile His
            260                 265                 270

Asp Ala Pro Asp Pro Ala Phe Met Asp Ile Ile Thr Leu His Arg Pro
        275                 280                 285

Ala Leu Thr Ser Arg Arg Gly Val Ile Arg Phe Ser Arg Val Gly Gln
    290                 295                 300

Arg Gly Thr Met Tyr Thr Arg Arg Gly Thr Arg Ile Gly Gly Arg Val
305                 310                 315                 320

His Phe Phe Arg Asp Ile Ser Pro Ile Gly Ala Ala Asp Asp Ile Glu
                325                 330                 335

Leu His Pro Leu Val Ala Ser Ala Pro His Thr Leu Glu Thr Pro His
            340                 345                 350

Thr Leu Glu Thr Pro Leu Asp Thr Thr Asp Ala Leu Phe Asp Val Tyr
        355                 360                 365

Ala Asp Met Asp Thr Ile Asp Asp Ala Ala Tyr Ala Thr Phe Ser
    370                 375                 380

Leu His Pro Ala Asp Ser Thr Arg Ile Ser Asn Thr Ser Ile Pro Leu
385                 390                 395                 400

Ala Thr Val Ser Asp Thr Leu Leu Thr Ser Gly Pro Asp Ile Val Phe
                405                 410                 415

Pro Ser Ile Pro Ala Gly Thr Pro Tyr Leu Pro Val Ser Pro Ser Ile
            420                 425                 430

Pro Ala Ile Ser Val Leu Ile His Gly Thr Asp Tyr Tyr Leu His Pro
        435                 440                 445

Ala Tyr Tyr Leu Arg Lys Arg Arg Lys Arg Ile Leu Ala His Gln Tyr
    450                 455                 460

Val Ala Thr
465

<210> SEQ ID NO 42
<211> LENGTH: 554
<212> TYPE: PRT
<213> ORGANISM: Human papillomavirus type 41

<400> SEQUENCE: 42

Met Leu Ala Arg Gln Arg Val Lys Arg Ala Asn Pro Glu Gln Leu Tyr
1               5                   10                  15

Lys Thr Cys Lys Ala Thr Gly Gly Asp Cys Pro Pro Asp Val Ile Lys
            20                  25                  30

Arg Tyr Glu Gln Thr Thr Pro Ala Asp Ser Ile Leu Lys Tyr Gly Ser
        35                  40                  45

Val Gly Val Phe Phe Gly Gly Leu Gly Ile Gly Thr Gly Arg Gly Gly
    50                  55                  60

Gly Gly Thr Val Leu Gly Ala Gly Ala Val Gly Gly Arg Pro Ser Ile
65                  70                  75                  80

```
Ser Ser Gly Ala Ile Gly Pro Arg Asp Ile Leu Pro Ile Glu Ser Gly
                85                  90                  95

Gly Pro Ser Leu Ala Glu Glu Ile Pro Leu Leu Pro Met Ala Pro Arg
            100                 105                 110

Val Pro Arg Pro Thr Asp Pro Phe Arg Pro Ser Val Leu Glu Glu Pro
        115                 120                 125

Phe Ile Ile Arg Pro Pro Glu Arg Pro Asn Ile Leu His Glu Gln Arg
130                 135                 140

Phe Pro Thr Asp Ala Ala Pro Phe Asp Asn Gly Asn Thr Glu Ile Thr
145                 150                 155                 160

Thr Ile Pro Ser Gln Tyr Asp Val Ser Gly Gly Val Asp Ile Gln
                165                 170                 175

Ile Ile Glu Leu Pro Ser Val Asn Asp Pro Gly Pro Ser Val Val Thr
            180                 185                 190

Arg Thr Gln Tyr Asn Asn Pro Thr Phe Glu Val Glu Val Ser Thr Asp
        195                 200                 205

Ile Ser Gly Glu Thr Ser Ser Thr Asp Asn Ile Ile Val Gly Ala Glu
    210                 215                 220

Ser Gly Gly Thr Ser Val Gly Asp Asn Ala Glu Leu Ile Pro Leu Leu
225                 230                 235                 240

Asp Ile Ser Arg Gly Asp Thr Ile Asp Thr Thr Ile Leu Ala Pro Gly
                245                 250                 255

Glu Glu Glu Thr Ala Phe Val Thr Ser Thr Pro Glu Arg Val Pro Ile
            260                 265                 270

Gln Glu Arg Leu Pro Ile Arg Pro Tyr Gly Arg Gln Tyr Gln Gln Val
        275                 280                 285

Arg Val Thr Asp Pro Glu Phe Leu Asp Ser Ala Ala Val Leu Val Ser
290                 295                 300

Leu Glu Asn Pro Val Phe Asp Ala Asp Ile Thr Leu Thr Phe Glu Asp
305                 310                 315                 320

Asp Leu Gln Gln Ala Leu Arg Ser Asp Thr Asp Leu Arg Asp Val Arg
                325                 330                 335

Arg Leu Ser Arg Pro Tyr Tyr Gln Arg Arg Thr Thr Gly Leu Arg Val
            340                 345                 350

Ser Arg Leu Gly Gln Arg Arg Gly Thr Ile Ser Thr Arg Ser Gly Val
        355                 360                 365

Gln Val Gly Ser Ala Ala His Phe Phe Gln Asp Ile Ser Pro Ile Gly
    370                 375                 380

Gln Ala Ile Glu Pro Ile Asp Ala Ile Glu Leu Asp Val Leu Gly Glu
385                 390                 395                 400

Gln Ser Gly Glu Gly Thr Ile Val Arg Gly Asp Pro Thr Pro Ser Ile
                405                 410                 415

Glu Gln Asp Ile Gly Leu Thr Ala Leu Gly Asp Asn Ile Glu Asn Glu
            420                 425                 430

Leu Gln Glu Ile Asp Leu Leu Thr Ala Asp Gly Glu Asp Gln Glu
        435                 440                 445

Gly Arg Asp Leu Gln Leu Val Phe Ser Thr Gly Asn Asp Glu Val Val
450                 455                 460

Asp Ile Met Thr Ile Pro Ile Arg Ala Gly Gly Asp Arg Pro Ser
                465                 470                 475                 480

Val Phe Ile Phe Ser Asp Asp Gly Thr His Ile Val Tyr Pro Thr Ser
                485                 490                 495
```

```
Thr Thr Ala Thr Thr Pro Leu Val Pro Ala Gln Pro Ser Asp Val Pro
            500                 505                 510

Tyr Ile Val Val Asp Leu Tyr Ser Gly Ser Met Asp Tyr Asp Ile His
            515                 520                 525

Pro Ser Leu Leu Arg Arg Lys Arg Lys Lys Arg Lys Arg Val Tyr Phe
            530                 535                 540

Ser Asp Gly Arg Val Ala Ser Arg Pro Lys
545                 550

<210> SEQ ID NO 43
<211> LENGTH: 477
<212> TYPE: PRT
<213> ORGANISM: Human papillomavirus type 42

<400> SEQUENCE: 43

Met Pro Pro Gln Arg Ser Arg Arg Arg Lys Arg Ala Ser Ala Thr Gln
1               5                   10                  15

Leu Tyr Gln Thr Cys Lys Ala Ser Gly Thr Cys Pro Pro Asp Val Ile
            20                  25                  30

Pro Lys Val Glu Gly Thr Thr Leu Ala Asp Lys Ile Leu Gln Trp Gly
            35                  40                  45

Ser Leu Gly Val Phe Phe Gly Gly Leu Gly Ile Gly Thr Gly Ala Gly
    50                  55                  60

Thr Gly Gly Arg Thr Gly Tyr Val Pro Leu Gly Thr Arg Pro Pro Val
65                  70                  75                  80

Ile Ala Glu Pro Gly Pro Ala Val Arg Pro Pro Ile Ala Val Asp Thr
            85                  90                  95

Val Gly Pro Ser Asp Pro Ser Ile Val Ser Leu Leu Glu Glu Ser Ser
            100                 105                 110

Val Ile Asp Ala Gly Ile Thr Val Pro Asp Ile Thr Ser His Gly Gly
            115                 120                 125

Phe Asn Ile Thr Thr Ser Thr Gly Gly Pro Ala Ser Thr Pro Ala Ile
    130                 135                 140

Leu Asp Ile Ser Pro Pro Thr Asn Thr Ile Arg Val Thr Thr Thr Thr
145                 150                 155                 160

Ser Thr Asn Pro Leu Tyr Ile Asp Pro Phe Thr Leu Gln Pro Pro Leu
            165                 170                 175

Pro Ala Glu Val Asn Gly Arg Leu Leu Ile Ser Thr Pro Thr Ile Thr
            180                 185                 190

Pro His Ser Tyr Glu Glu Ile Pro Met Asp Thr Phe Val Val Ser Thr
            195                 200                 205

Asp Thr Thr Asn Thr Phe Thr Ser Thr Pro Ile Pro Gly Pro Arg Ser
    210                 215                 220

Ser Ala Arg Leu Gly Leu Tyr Ser Arg Ala Thr Gln Gln Arg Pro Val
225                 230                 235                 240

Thr Thr Ser Ala Phe Leu Thr Ser Pro Ala Arg Leu Val Thr Tyr Asp
            245                 250                 255

Asn Pro Ala Tyr Glu Gly Leu Thr Glu Asp Thr Leu Val Phe Glu His
            260                 265                 270

Pro Ser Ile His Thr Ala Pro Asp Pro Asp Phe Met Asp Ile Val Ala
            275                 280                 285

Leu His Arg Pro Met Leu Ser Ser Lys Gln Gly Ser Val Arg Val Ser
    290                 295                 300

Arg Ile Gly Gln Arg Leu Ser Met Gln Thr Arg Arg Gly Thr Arg Phe
305                 310                 315                 320
```

```
Gly Ser Arg Val His Phe Phe His Asp Leu Ser Pro Ile Thr His Ser
                325                 330                 335

Ser Glu Thr Ile Glu Leu Gln Pro Leu Ser Ala Ser Val Ser Ala
            340                 345                 350

Ala Ser Asn Ile Asn Asp Gly Leu Phe Asp Ile Tyr Val Asp Thr Ser
            355                 360                 365

Asp Val Asn Val Thr Asn Thr Thr Ser Ser Ile Pro Met His Gly Phe
370                 375                 380

Ala Thr Pro Arg Leu Ser Thr Thr Ser Phe Pro Thr Leu Pro Ser Met
385                 390                 395                 400

Ser Thr His Ser Ala Asn Thr Thr Ile Pro Phe Ser Phe Pro Ala Thr
            405                 410                 415

Val His Val Gly Pro Asp Leu Ser Val Val Asp His Pro Trp Asp Ser
            420                 425                 430

Thr Pro Thr Ser Val Met Pro Gln Gly Asn Phe Val Met Val Ser Gly
            435                 440                 445

Trp Asp Phe Ile Leu His Pro Ser Tyr Phe Trp Arg Arg Arg Lys
450                 455                 460

Pro Val Pro Tyr Phe Phe Ala Asp Val Arg Val Ala Ala
465                 470                 475
```

<210> SEQ ID NO 44
<211> LENGTH: 463
<212> TYPE: PRT
<213> ORGANISM: Human papillomavirus type 43

<400> SEQUENCE: 44

```
Met Val Ser His Thr His Lys Arg Arg Lys Arg Ala Ser Ala Thr Gln
1               5                   10                  15

Leu Tyr Gln Thr Cys Lys Ala Ala Gly Thr Cys Pro Ser Asp Val Ile
            20                  25                  30

Asn Lys Val Glu His Thr Thr Ile Ala Asp Gln Ile Leu Lys Trp Ala
            35                  40                  45

Ser Met Gly Val Tyr Phe Gly Gly Leu Gly Ile Gly Thr Gly Ser Gly
    50                  55                  60

Thr Gly Gly Arg Thr Gly Tyr Val Pro Leu Thr Thr Gly Arg Thr Gly
65                  70                  75                  80

Ile Val Pro Lys Val Thr Ala Glu Pro Gly Val Val Ser Arg Pro Pro
                85                  90                  95

Ile Val Val Glu Ser Val Ala Pro Thr Asp Pro Ser Ile Val Ser Leu
            100                 105                 110

Ile Glu Glu Ser Ser Ile Ile Gln Ser Gly Ala Pro Ile Thr Asn Ile
            115                 120                 125

Pro Ser His Gly Gly Phe Glu Val Thr Ser Ser Gly Ser Glu Val Pro
            130                 135                 140

Ala Ile Leu Asp Val Ser Pro Ser Thr Ser Val His Ile Thr Thr Ser
145                 150                 155                 160

Thr His Leu Asn Pro Ala Phe Thr Asp Pro Thr Ile Val Gln Pro Thr
                165                 170                 175

Pro Pro Val Glu Ala Gly Gly Arg Ile Ile Ile Ser His Ser Thr Val
            180                 185                 190

Thr Ala Asp Ser Ala Glu Gln Ile Pro Met Asp Thr Phe Val Ile His
            195                 200                 205

Ser Asp Pro Thr Thr Ser Thr Pro Ile Pro Gly Thr Ala Pro Arg Pro
```

```
                     210                 215                 220
Arg Leu Gly Leu Tyr Ser Lys Ala Leu Gln Gln Val Glu Ile Val Asp
225                 230                 235                 240

Pro Thr Phe Leu Ser Ser Pro Gln Arg Leu Ile Thr Tyr Asp Asn Pro
                245                 250                 255

Val Phe Glu Asp Pro Asn Ala Thr Leu Thr Phe Glu Gln Pro Thr Val
                260                 265                 270

His Glu Ala Pro Asp Ser Arg Phe Met Asp Ile Val Thr Leu His Arg
                275                 280                 285

Pro Ala Leu Thr Ser Arg Arg Gly Ile Val Arg Phe Ser Arg Val Gly
                290                 295                 300

Ala Arg Gly Thr Met Tyr Thr Arg Ser Gly Ile Arg Ile Gly Gly Arg
305                 310                 315                 320

Val His Phe Phe Thr Asp Ile Ser Ser Ile Pro Thr Glu Glu Ser Ile
                325                 330                 335

Glu Leu Gln Pro Leu Gly Arg Ser Gln Ser Phe Pro Thr Val Ser Asp
                340                 345                 350

Thr Ser Asp Leu Tyr Asp Ile Tyr Ala Asp Glu Asn Leu Leu Asn Asn
                355                 360                 365

Asp Ile Ser Phe Thr Asp Thr His Val Ser Leu Gln Asn Ser Thr Lys
                370                 375                 380

Val Val Asn Thr Ala Val Pro Leu Ala Thr Val Pro Asp Ile Tyr Ala
385                 390                 395                 400

Gln Thr Gly Pro Asp Ile Ser Phe Pro Thr Ile Pro Ile His Ile Pro
                405                 410                 415

Tyr Ile Pro Val Ser Pro Ser Ile Ser Pro Gln Ser Val Ser Ile His
                420                 425                 430

Gly Thr Asp Phe Tyr Leu His Pro Ser Leu Trp His Leu Gly Lys Arg
                435                 440                 445

Arg Lys Arg Phe Ser Tyr Phe Phe Thr Asp Asn Tyr Val Ala Ala
                450                 455                 460

<210> SEQ ID NO 45
<211> LENGTH: 460
<212> TYPE: PRT
<213> ORGANISM: Human papillomavirus type 44

<400> SEQUENCE: 45

Met Ala His Ser Arg Ala Arg Arg Lys Arg Ala Ser Ala Thr Gln
1               5                   10                  15

Leu Tyr Gln Thr Cys Lys Ala Ala Gly Thr Cys Pro Ser Asp Ile Ile
                20                  25                  30

Pro Lys Val Glu His Asn Thr Ile Ala Asp Gln Ile Leu Lys Trp Gly
                35                  40                  45

Ser Leu Gly Val Phe Phe Gly Gly Leu Gly Ile Gly Thr Gly Ser Gly
                50                  55                  60

Thr Gly Gly Arg Thr Gly Tyr Ile Pro Leu Gln Ser Thr Pro Arg Pro
65                  70                  75                  80

Asp Ile Pro Ser Val Pro Thr Ala Arg Pro Pro Ile Leu Val Asp Thr
                85                  90                  95

Val Ala Pro Gly Asp Pro Ser Ile Val Ser Leu Val Glu Glu Ser Ala
                100                 105                 110

Ile Ile Asn Ser Gly Ala Pro Glu Leu Val Pro Ser His Ala Gly
                115                 120                 125
```

```
Phe Glu Ile Thr Thr Ser Glu Ser Thr Thr Pro Ala Ile Leu Asp Val
    130                 135                 140

Ser Val Thr Thr His Thr Thr Ser Thr Val Phe Lys Asn Pro Ser
145                 150                 155                 160

Phe Ala Asp Pro Ser Val Val Gln Ser Gln Pro Ala Val Glu Ala Gly
                165                 170                 175

Gly His Ile Leu Ile Ser Thr Ser Ile Ser Ser His Pro Val Glu
            180                 185                 190

Glu Ile Pro Leu Asp Thr Phe Ile Val Ser Ser Asp Ser Asn Pro
        195                 200                 205

Ala Ser Ser Thr Pro Ile Pro Ala Ser Gly Ala Arg Pro Arg Ile Gly
    210                 215                 220

Leu Tyr Ser Lys Ala Leu His Gln Val Gln Val Thr Asp Pro Ala Phe
225                 230                 235                 240

Leu Ser Ser Pro Gln Arg Leu Ile Thr Phe Asp Asn Pro Ala Tyr Glu
                245                 250                 255

Gly Glu Asp Val Thr Leu His Phe Ala His Asn Thr Ile His Glu Pro
            260                 265                 270

Pro Asp Asp Ala Phe Met Asp Ile Ile Arg Leu His Arg Pro Ala Ile
        275                 280                 285

Gln Ser Arg Arg Gly Arg Val Arg Phe Ser Arg Ile Gly Gln Arg Gly
    290                 295                 300

Ser Met Tyr Thr Arg Ser Gly Lys His Ile Gly Gly Arg Ile His Phe
305                 310                 315                 320

Tyr Gln Asp Ile Ser Pro Ile Ser Ala Ala Glu Glu Ile Glu Leu
                325                 330                 335

His Pro Leu Val Ala Thr Ala Gln Asp Ser Gly Leu Phe Asp Ile Tyr
            340                 345                 350

Ala Glu Pro Asp Pro Asp Val Thr Glu Glu Pro Val Ser Leu Ser Phe
        355                 360                 365

Ser Thr Ser Thr Pro Phe Gln Arg Ser Ser Val Ser Ala Thr Pro Trp
    370                 375                 380

Gly Asn Thr Thr Val Pro Leu Ser Leu Pro Ala Asp Met Phe Val Gln
385                 390                 395                 400

Pro Gly Pro Asp Ile Ile Phe Pro Thr Ala Ser Thr Thr Pro Tyr
                405                 410                 415

Ser Pro Val Thr Pro Ala Leu Pro Thr Gly Pro Val Phe Ile Ser Gly
            420                 425                 430

Ala Ala Phe Tyr Leu Tyr Pro Thr Trp Tyr Phe Ala Arg Lys Arg Arg
        435                 440                 445

Lys Arg Val Ser Leu Phe Phe Ala Asp Val Ala Ala
    450                 455                 460

<210> SEQ ID NO 46
<211> LENGTH: 518
<212> TYPE: PRT
<213> ORGANISM: Human papillomavirus type 47

<400> SEQUENCE: 46

Met Ala Arg Ala Arg Arg Val Lys Arg Asp Ser Val Thr His Ile Tyr
1               5                   10                  15

Gln Thr Cys Lys Gln Ala Gly Thr Cys Pro Ser Asp Val Val Asn Lys
                20                  25                  30

Val Glu Gln Thr Thr Val Ala Asp Asn Ile Leu Lys Tyr Gly Ser Ala
            35                  40                  45
```

-continued

```
Gly Val Phe Gly Gly Leu Gly Ile Gly Thr Gly Arg Gly Thr Gly
    50                  55                  60
Gly Ala Thr Gly Tyr Val Pro Leu Gly Glu Gly Pro Gly Val Arg Val
65                  70                  75                  80
Gly Gly Thr Pro Thr Val Val Arg Pro Ser Leu Val Pro Glu Ala Ile
                85                  90                  95
Gly Pro Val Asp Ile Leu Pro Ile Asp Thr Ile Ala Pro Val Glu Pro
            100                 105                 110
Thr Ala Ser Ser Leu Val Pro Leu Thr Glu Ser Ser Gly Ala Asp Leu
        115                 120                 125
Leu Pro Gly Glu Val Glu Thr Ile Ala Glu Ile His Pro Ile Pro Glu
    130                 135                 140
Gly Pro Thr Ile Asp Ser Pro Val Val Thr Thr Thr Gly Ser Ser
145                 150                 155                 160
Ala Val Leu Glu Val Ala Pro Glu Pro Val Pro Pro Thr Arg Val Arg
                165                 170                 175
Ile Ala Arg Thr Gln Tyr His Asn Pro Ser Phe Gln Ile Leu Thr Glu
            180                 185                 190
Ser Thr Pro Ala Gln Gly Glu Ser Ser Leu Ala Asp His Ile Leu Val
        195                 200                 205
Thr Ser Gly Ser Gly Gly Gln Arg Ile Gly Gly Asp Ile Thr Asp Glu
    210                 215                 220
Ile Glu Leu Thr Glu Phe Pro Ser Arg Tyr Thr Phe Glu Ile Glu Glu
225                 230                 235                 240
Pro Thr Pro Pro Arg Lys Ser Ser Thr Pro Leu Gln Thr Val Ala Ser
                245                 250                 255
Ala Val Arg Arg Arg Gly Phe Ser Leu Thr Asn Arg Arg Leu Val Gln
            260                 265                 270
Gln Val Ala Val Asp Asn Pro Leu Phe Leu Ser Gln Pro Ser Lys Met
        275                 280                 285
Val Arg Phe Ser Phe Asp Asn Pro Ala Phe Glu Glu Glu Val Thr Asn
    290                 295                 300
Ile Phe Glu Gln Asp Val Asn Ser Phe Glu Glu Pro Pro Asp Arg Asp
305                 310                 315                 320
Phe Leu Asp Ile Lys Gln Leu Gly Arg Pro Gln Tyr Ser Thr Thr Pro
                325                 330                 335
Ala Gly Tyr Ile Arg Val Ser Arg Leu Gly Thr Arg Gly Thr Ile Arg
            340                 345                 350
Thr Arg Ser Gly Ala Gln Ile Gly Ser Gln Val His Phe Tyr Arg Asp
        355                 360                 365
Leu Ser Ser Ile Asn Thr Glu Asp Pro Ile Glu Leu Gln Leu Leu Gly
    370                 375                 380
Gln His Ser Gly Asp Ala Thr Ile Val Gln Gly Pro Val Glu Ser Thr
385                 390                 395                 400
Phe Ile Asp Met Asp Ile Ala Glu Asn Pro Leu Ser Glu Thr Ile Asp
                405                 410                 415
Ala Ser Ser Asn Asp Leu Leu Leu Asp Glu Thr Val Glu Asp Phe Ser
            420                 425                 430
Gly Ser Gln Leu Val Ile Gly Asn Arg Arg Ser Thr Thr Ser Tyr Thr
        435                 440                 445
Val Pro Arg Phe Glu Thr Thr Arg Ser Ser Ser Tyr Tyr Val Gln Asp
    450                 455                 460
```

Thr Asp Gly Tyr Tyr Val Ala Tyr Pro Glu Ser Arg Asp Thr Ile Asp
465                 470                 475                 480

Ile Ile Tyr Pro Thr Pro Glu Leu Pro Val Val Ile His Thr His
            485                 490                 495

Asp Asn Ser Gly Asp Phe Tyr Leu His Pro Ser Leu Arg Arg Lys
            500                 505                 510

Arg Lys Arg Lys Tyr Leu
        515

<210> SEQ ID NO 47
<211> LENGTH: 502
<212> TYPE: PRT
<213> ORGANISM: Human papillomavirus type 48

<400> SEQUENCE: 47

Met Ser Leu Arg Arg Lys Arg Ala Ser Pro Thr Asp Leu Tyr Lys
1               5                   10                  15

Thr Cys Leu Gln Gly Gly Asp Cys Ile Pro Asp Val Lys Asn Lys Phe
            20                  25                  30

Glu Asn Ser Thr Ile Ala Asp Trp Leu Leu Lys Ile Phe Gly Ser Leu
            35                  40                  45

Val Tyr Phe Gly Asn Leu Gly Ile Gly Ser Gly Lys Gly Ser Gly Gly
        50                  55                  60

Ser Phe Gly Tyr Arg Pro Leu Gly Ser Ala Gly Ser Gly Arg Pro Ala
65              70                  75                  80

Thr Asp Leu Pro Val Thr Arg Pro Asn Val Val Ile Glu Pro Ile Gly
                85                  90                  95

Pro Gln Ser Ile Val Pro Ile Asp Pro Gly Ala Ser Ser Ile Val Pro
            100                 105                 110

Leu Val Glu Gly Gly Pro Asp Ile Ser Phe Ile Ala Pro Asp Ala Gly
            115                 120                 125

Pro Gly Ile Gly Gly Glu Asp Ile Glu Leu Phe Thr Phe Arg Asp Pro
        130                 135                 140

Ala Thr Asp Val Gly Gly Val Ser Gly Gly Pro Thr Thr Ile Ser Thr
145             150                 155                 160

Glu Glu Ser Glu Thr Ala Ile Ile Asp Ala Leu Pro Ser Ala Thr Thr
                165                 170                 175

Pro Lys Gln Leu Phe Tyr Asp Ser Tyr Thr Gln Thr Ile Leu Gln Thr
            180                 185                 190

Gln Val Asn Pro Phe Leu Asn Asn Ala Ile Ser Asp Thr Asn Val Phe
        195                 200                 205

Val Asp Pro Leu Phe Ala Gly Glu Thr Ile Gly Asp Asn Ile Phe Glu
        210                 215                 220

Glu Ile Pro Leu Gln Asn Leu Asn Phe Ser Phe Pro Arg Glu Ser Thr
225             230                 235                 240

Pro Val Lys Pro Gly Arg Gly Leu Arg Thr Pro Ala Gln Arg Ser Tyr
                245                 250                 255

Ser Arg Phe Met Glu Gln Tyr Pro Ile Gln Ala Pro Glu Phe Leu Ser
            260                 265                 270

Gln Pro Ser Arg Leu Val Gln Phe Glu Phe Glu Asn Pro Ala Phe Asp
        275                 280                 285

Pro Asp Ile Ser Ile Gln Phe Gln Arg Asp Val Asn Ser Leu Glu Ala
        290                 295                 300

Ala Pro Asn Pro Ala Phe Ala Asp Ile Ala Tyr Leu Ser Arg Pro His
305             310                 315                 320

```
Met Ser Ala Thr Ser Glu Gly Leu Val Arg Val Ser Arg Ile Gly Ser
                325                 330                 335

Arg Ala Val Leu Gln Thr Arg Ser Gly Leu Thr Ile Gly Pro Lys Val
                340                 345                 350

His Tyr Tyr Met Asp Leu Ser Ala Ile Ser Thr Glu Ala Ile Glu Leu
                355                 360                 365

Gln Thr Phe Ala Asp Ser Gly His Val His Thr Ile Val Asp Asp Phe
            370                 375                 380

Leu Ser Val Thr Ala Leu Asp Asp Pro Ala Asn Ile Ala Asp Ile Asn
385                 390                 395                 400

Tyr Thr Glu Asp Asp Leu Leu Pro Leu Leu Glu Asn Phe Asn Asn
                405                 410                 415

Ser His Ile Thr Val Gln Gly Val Asp Glu Glu Gly Glu Thr Val Ala
                420                 425                 430

Leu Pro Ile Pro Ser Ile Thr Asn Ser Ser Lys Thr Phe Val Thr Asp
                435                 440                 445

Ile Ala Glu Asn Gly Leu Phe Ala Asn Asp Thr Asp Ser Leu Leu Thr
                450                 455                 460

Pro Ala Ser Thr Ile Val Pro Ala Ile Asn Trp Phe Pro Leu Phe Asp
465                 470                 475                 480

Ser Tyr Ser Asp Phe Ala Leu Asp Pro Phe Phe Ile Pro Arg Lys Lys
                485                 490                 495

Arg Arg Leu Asp Ile Leu
                500

<210> SEQ ID NO 48
<211> LENGTH: 521
<212> TYPE: PRT
<213> ORGANISM: Human papillomavirus type 49

<400> SEQUENCE: 48

Met Val Arg Ala Arg Arg Thr Lys Arg Asp Ser Val Thr Asn Ile Tyr
1               5                   10                  15

Arg Thr Cys Lys Gln Ala Gly Asn Cys Pro Pro Asp Val Val Asn Lys
                20                  25                  30

Val Glu Gln Thr Thr Ile Ala Asp Gln Ile Leu Lys Phe Gly Ser Thr
                35                  40                  45

Gly Val Phe Phe Gly Gly Leu Gly Ile Gly Thr Gly Arg Gly Thr Gly
            50                  55                  60

Gly Ser Thr Gly Tyr Val Pro Ile Gly Glu Gly Pro Ala Ile Arg Val
65                  70                  75                  80

Gly Gly Thr Pro Ser Val Val Arg Pro Gly Ile Leu Pro Glu Ala Ile
                85                  90                  95

Gly Pro Ala Asp Ile Ile Pro Ile Asp Thr Val Asn Pro Ile Asp Pro
                100                 105                 110

Asn Ala Ser Ser Val Val Pro Leu Thr Asp Thr Gly Pro Asp Leu Leu
                115                 120                 125

Pro Gly Thr Ile Glu Thr Ile Ala Glu Val Asn Pro Ala Pro Asp Ile
            130                 135                 140

Pro Arg Val Asp Thr Ser Val Val Thr Thr Ser Arg Gly Ser Ser Ala
145                 150                 155                 160

Val Leu Glu Val Ala Ser Glu Pro Thr Pro Pro Thr Arg Thr Arg Ile
                165                 170                 175

Ser Arg Thr Gln Tyr His Asn Pro Ser Phe Gln Ile Leu Thr Glu Ser
```

```
                180             185              190
Thr Pro Ser Leu Gly Glu Ser Ala Leu Thr Asp His Val Val Thr
            195                 200             205

Ser Gly Ser Gly Gly Gln Pro Ile Gly Gly Val Thr Pro Val Glu Ile
        210                 215             220

Glu Leu Gln Glu Leu Pro Ser Arg Tyr Thr Phe Glu Ile Glu Glu Pro
225                 230                 235                 240

Thr Pro Pro Arg Arg Ser Ser Thr Pro Leu Arg Asn Ile Thr Gln Ala
                245                 250                 255

Val Gly Asn Leu Arg Arg Ser Leu Tyr Asn Arg Arg Leu Thr Gln Gln
            260                 265                 270

Val Asn Val Gln Asp Pro Leu Phe Leu Gln Gln Pro Ser Arg Leu Val
        275                 280                 285

Arg Phe Ala Phe Asp Asn Pro Val Phe Glu Glu Val Thr Gln Ile
            290                 295                 300

Phe Glu Arg Asp Val Ala Ala Val Glu Glu Pro Pro Asp Arg Asp Phe
305                 310                 315                 320

Leu Asp Ile Ala Lys Leu Ser Arg Pro Leu Tyr Ser Glu Thr Pro Gln
                325                 330                 335

Gly Tyr Val Arg Val Ser Arg Leu Gly Asn Arg Ala Ser Ile Arg Thr
            340                 345                 350

Arg Ser Gly Ala Thr Val Gly Ala Gln Val His Phe Tyr Thr Asp Leu
        355                 360                 365

Ser Thr Ile Asp Ala Glu Glu Ser Ile Glu Leu Ser Leu Leu Gly Glu
    370                 375                 380

His Ser Gly Asp Ala Thr Ile Val Gln Gly Pro Val Glu Ser Ser Phe
385                 390                 395                 400

Val Asp Leu Asn Val Gln Glu Leu Pro Gln Val Ile Glu Val Asp Pro
                405                 410                 415

Glu Pro Thr Phe His Ser Asp Asp Leu Leu Leu Asp Gly Gln Asn Glu
            420                 425                 430

Asp Phe Ser Gly Ser Gln Leu Val Tyr Gly Ser Gly Arg Arg Ser Thr
        435                 440                 445

Thr Phe Thr Val Pro Arg Phe Ser Thr Pro Arg Ser Asp Thr Phe Tyr
    450                 455                 460

Val Gln Asp Leu Glu Gly Tyr Ala Val Ser Tyr Pro Glu Arg Arg Asn
465                 470                 475                 480

Tyr Pro Glu Ile Ile Tyr Pro Gln Pro Asp Leu Pro Thr Val Ile Ile
                485                 490                 495

His Thr Ala Asp Thr Ser Gly Asp Phe Tyr Leu His Pro Ser Leu Arg
            500                 505                 510

Arg Arg Lys Arg Lys Arg Thr Tyr Leu
            515                 520

<210> SEQ ID NO 49
<211> LENGTH: 506
<212> TYPE: PRT
<213> ORGANISM: Human papillomavirus type 50

<400> SEQUENCE: 49

Met Leu Arg Arg Arg Lys Arg Ala Ser Pro Thr Asp Leu Tyr Arg Ser
1               5                   10                  15

Cys Leu Gln Gly Gly Asp Cys Ile Pro Asp Val Gln Asn Lys Phe Glu
            20                  25                  30
```

```
Gly Asn Thr Ile Ala Asp Trp Leu Lys Ile Phe Gly Leu Val
         35                  40                  45

Tyr Phe Gly Asn Leu Gly Ile Gly Thr Gly Arg Gly Thr Gly Gly Thr
 50                  55                  60

Phe Gly Tyr Arg Pro Phe Gly Ala Pro Gly Ser Gly Arg Pro Thr Gln
 65                  70                  75                  80

Glu Leu Pro Ile Ala Arg Pro Asn Val Val Ile Asp Pro Leu Gly Pro
                 85                  90                  95

Ala Pro Ile Val Pro Val Asp Pro Ser Ala Ala Ser Ile Val Pro Leu
            100                 105                 110

Val Glu Gly Ala Pro Asp Val Gly Phe Ala Ala Pro Asp Ala Gly Pro
            115                 120                 125

Ala Ala Gly Gly Thr Asp Ile Glu Leu Tyr Thr Ile Thr Asn Ser Thr
        130                 135                 140

Thr Asp Val Gly Ala Val Gly Gly Pro Thr Val Thr Ser Asn Glu
145                 150                 155                 160

Glu Phe Glu Val Ala Val Ile Asp Ala Gln Pro Ile Ala Pro Tyr Pro
                165                 170                 175

Lys Gln Leu Leu Tyr Asp Ser Thr Ile Ala Ala Thr Phe Glu Thr Gln
            180                 185                 190

Ile Asn Pro Phe Ile Asn Pro Asp Ile Asn Asn Val Asn Val Leu Val
            195                 200                 205

Asp Pro Ser Phe Ala Gly Asp Thr Val Gly Asp Tyr Phe Tyr Glu Glu
            210                 215                 220

Ile Pro Leu Glu Arg Leu Asp Ile Gln Thr Phe Asp Ile Leu Glu Pro
225                 230                 235                 240

Pro Thr Glu Ser Thr Pro Thr Gln Leu Gly Asn Arg Phe Val Ser Arg
                245                 250                 255

Ala Arg Asp Leu Tyr Ser Arg Phe Val Ala Gln Gln Pro Ile Ser Glu
            260                 265                 270

Pro Asp Phe Leu Ser Gln Pro Ser Arg Leu Val Gln Phe Glu Tyr Arg
            275                 280                 285

Asn Pro Ala Phe Asp Pro Asp Val Ser Leu Tyr Phe Glu Arg Asp Leu
            290                 295                 300

Glu Gly Leu Arg Ala Ala Pro Leu Gln Glu Phe Ala Asp Val Val Tyr
305                 310                 315                 320

Leu Gly Arg Pro Arg Val Ser Ser Thr Ser Glu Gly Thr Ile Arg Val
                325                 330                 335

Ser Arg Leu Gly Thr Arg Ala Ala Leu Thr Thr Arg Ser Gly Leu Ser
            340                 345                 350

Val Gly Pro Gln Val His Phe Tyr Met Asp Leu Ser Asp Ile Pro Pro
            355                 360                 365

Glu Asp Ser Ile Glu Leu His Thr Leu Asn Val Thr Pro Gln Thr Ser
370                 375                 380

Thr Ile Val Asp Asp Ile Leu Ala Thr Thr Phe Asp Asp Pro Ala
385                 390                 395                 400

Asn Ser Leu Phe Thr Gln Phe Asn Glu Asp Val Leu Thr Asp Val
                405                 410                 415

Glu His Asn Phe Thr Glu Ser His Leu Val Ile Pro Ala Thr Asp Glu
            420                 425                 430

Glu Asn Asp Thr Ala Ile Asn Ile Ile Asn Leu Arg Asn Ile Pro Leu
            435                 440                 445

Thr Val Gly Met Asn Ser Gly Asp Ile Ser Thr Thr Leu Ser Asp Tyr
```

```
            450                 455                 460
Asn Ile Leu Asp Ala Ser Leu Ile Val Lys Ser Asn Val Ser Glu Gln
465                 470                 475                 480

Pro Leu Phe Val Leu Asp Tyr Ser Asp Tyr Asp Leu His Pro Gly Leu
                485                 490                 495

Leu Pro Lys Arg Arg Arg Ile Asp Tyr Phe
            500                 505

<210> SEQ ID NO 50
<211> LENGTH: 468
<212> TYPE: PRT
<213> ORGANISM: Human papillomavirus type 51

<400> SEQUENCE: 50

Met Val Ala Thr Arg Ala Arg Arg Lys Arg Ala Ser Val Thr Gln
1               5                   10                  15

Leu Tyr Ser Thr Cys Lys Ala Ala Gly Thr Cys Pro Pro Asp Val Val
                20                  25                  30

Asn Lys Val Glu Gly Thr Thr Leu Ala Asp Lys Ile Leu Gln Trp Ser
                35                  40                  45

Gly Leu Gly Ile Phe Leu Gly Gly Leu Gly Ile Gly Thr Gly Ser Gly
            50                  55                  60

Ser Gly Gly Arg Thr Gly Tyr Ile Pro Leu Gly Gly Gly Arg Pro
65                  70                  75                  80

Gly Val Val Asp Ile Ala Pro Ala Arg Pro Pro Ile Ile Asp Leu
                85                  90                  95

Trp His His Thr Glu Pro Ser Ile Val Asn Leu Val Glu Asp Ser Ser
                100                 105                 110

Ile Ile Gln Ser Gly Ser Pro Ile Pro Thr Phe Thr Gly Thr Asp Gly
            115                 120                 125

Phe Glu Ile Thr Ser Ser Ser Thr Thr Thr Pro Ala Val Leu Asp Ile
130                 135                 140

Thr Pro Ser Ala Gly Thr Val His Val Ser Ser Thr Asn Ile Glu Asn
145                 150                 155                 160

Pro Leu Tyr Ile Glu Pro Pro Ser Ile Glu Ala Pro Gln Ser Gly Glu
                165                 170                 175

Val Ser Asp Ile Tyr Leu Leu Val His Tyr Ser Gly Thr His Gly Tyr
                180                 185                 190

Glu Glu Ile Pro Met Glu Val Phe Ala Ser Asn Val Ser Thr Gly Thr
            195                 200                 205

Glu Pro Ile Ser Ser Thr Pro Thr Pro Gly Val Ser Arg Ile Ala Ala
210                 215                 220

Pro Arg Leu Tyr Ser Lys Ser Tyr Thr Gln Val Lys Val Thr Asn Pro
225                 230                 235                 240

Asp Phe Ile Ser Lys Pro Ser Thr Phe Val Thr Phe Asn Asn Pro Ala
                245                 250                 255

Phe Glu Pro Ile Asp Thr Ser Ile Thr Phe Glu Pro Asp Ala Val
                260                 265                 270

Ala Pro Asp Pro Asp Phe Leu Asp Ile Ile Thr Leu His Arg Pro Ala
            275                 280                 285

Leu Thr Ser Arg Arg Gly Thr Val Arg Phe Ser Arg Leu Gly Gln Lys
290                 295                 300

Ala Thr Met Arg Thr Arg Ser Gly Lys Gln Ile Gly Ala Arg Val His
305                 310                 315                 320
```

```
Tyr Tyr His Asp Ile Ser Arg Ile Ala Pro Ala Asp Glu Leu Glu Met
            325                 330                 335

Gln Pro Leu Leu Ser Pro Ser Asn Asn Tyr Ser Tyr Asp Ile Tyr Ala
        340                 345                 350

Asp Leu Asp Glu Ala Glu Thr Gly Phe Ile Gln Pro Thr His Thr Thr
        355                 360                 365

Pro Met Ser His Ser Ser Leu Ser Arg Gln Leu Pro Ser Leu Ser Ser
    370                 375                 380

Ser Met Ser Ser Ser Tyr Ala Asn Val Thr Ile Pro Phe Ser Thr Thr
385                 390                 395                 400

Tyr Ser Val Pro Ile His Thr Gly Pro Asp Val Val Leu Pro Thr Ser
                405                 410                 415

Pro Thr Val Trp Pro Tyr Val Pro His Thr Ser Ile Asp Thr Lys His
                420                 425                 430

Ser Ile Val Ile Leu Gly Gly Asp Tyr Tyr Leu Trp Pro Tyr Thr His
            435                 440                 445

Leu Leu Arg Lys Arg Arg Lys Arg Ile Pro Tyr Phe Phe Thr Asp Gly
    450                 455                 460

Ile Val Ala His
465

<210> SEQ ID NO 51
<211> LENGTH: 466
<212> TYPE: PRT
<213> ORGANISM: Human papillomavirus type 52

<400> SEQUENCE: 51

Met Arg Tyr Arg Arg Ser Thr Arg His Lys Arg Ala Ser Ala Thr Gln
1               5                   10                  15

Leu Tyr Gln Thr Cys Lys Ala Ser Gly Thr Cys Pro Pro Asp Val Ile
            20                  25                  30

Pro Lys Val Glu Gly Thr Thr Ile Ala Asp Gln Leu Leu Lys Tyr Gly
        35                  40                  45

Ser Leu Gly Val Phe Phe Gly Gly Leu Gly Ile Gly Thr Gly Ala Gly
    50                  55                  60

Ser Gly Gly Arg Ala Gly Tyr Val Pro Leu Ser Thr Arg Pro Pro Thr
65                  70                  75                  80

Ser Ser Ile Thr Thr Ser Thr Ile Arg Pro Pro Val Thr Val Glu Pro
                85                  90                  95

Ile Gly Pro Leu Glu Pro Ser Ile Val Ser Met Ile Glu Glu Thr Thr
            100                 105                 110

Phe Ile Glu Ser Gly Ala Pro Ala Pro Ser Ile Pro Ser Ala Thr Gly
        115                 120                 125

Phe Asp Val Thr Thr Ser Ala Asn Asn Thr Pro Ala Ile Ile Asn Val
    130                 135                 140

Thr Ser Ile Gly Glu Ser Ser Val Gln Ser Val Ser Thr His Leu Asn
145                 150                 155                 160

Pro Thr Phe Thr Glu Pro Ser Ile Ile Gln Pro Pro Ala Pro Ala Glu
                165                 170                 175

Ala Ser Gly His Val Leu Phe Ser Pro Thr Ile Ser Thr His Thr
            180                 185                 190

Tyr Glu Glu Ile Pro Met Asp Thr Phe Val Thr Ser Thr Asp Ser Ser
        195                 200                 205

Ser Val Thr Ser Ser Thr Pro Ile Pro Gly Ser Arg Pro Thr Thr Arg
    210                 215                 220
```

```
Leu Gly Leu Tyr Ser Arg Ala Thr Gln Gln Val Lys Val Asp Pro
225                 230                 235                 240

Ala Phe Met Ser Ser Pro Gln Lys Leu Val Thr Tyr Asn Asn Pro Val
                245                 250                 255

Phe Glu Gly Val Asp Thr Asp Glu Thr Ile Ile Phe Arg Ser Gln
            260                 265                 270

Leu Leu Pro Ala Pro Asp Pro Phe Leu Asp Ile Ile Ala Leu His
            275                 280                 285

Arg Pro Ala Leu Thr Ser Arg Arg Gly Thr Val Arg Phe Ser Arg Leu
    290                 295                 300

Gly Asn Lys Ala Thr Leu Arg Thr Arg Ser Gly Lys Gln Ile Gly Ala
305                 310                 315                 320

Arg Val His Tyr Tyr His Asp Ile Ser Pro Ile Gln Pro Ala Glu Val
                325                 330                 335

Gln Glu Asp Ile Glu Leu Gln Pro Leu Leu Pro Gln Ser Val Ser Pro
                340                 345                 350

Tyr Thr Ile Asn Asp Gly Leu Tyr Asp Val Tyr Ala Asp Ser Leu Gln
                355                 360                 365

Gln Pro Thr Phe His Leu Pro Ser Thr Leu Ser Thr His Asn Asn Thr
    370                 375                 380

Phe Thr Val Pro Ile Asn Ser Gly Ile Asp Phe Val Tyr Gln Pro Thr
385                 390                 395                 400

Met Ser Ile Glu Ser Gly Pro Asp Ile Pro Leu Pro Ser Leu Pro Thr
                405                 410                 415

His Thr Pro Phe Val Pro Ile Ala Pro Thr Ala Pro Ser Thr Ser Ile
                420                 425                 430

Ile Val Asp Gly Thr Asp Phe Ile Leu His Pro Ser Tyr Phe Leu Leu
    435                 440                 445

Arg Arg Arg Arg Lys Arg Phe Pro Tyr Phe Phe Thr Asp Val Arg Val
    450                 455                 460

Ala Ala
465

<210> SEQ ID NO 52
<211> LENGTH: 463
<212> TYPE: PRT
<213> ORGANISM: Human papillomavirus type 53

<400> SEQUENCE: 52

Met Val Ala His Arg Ala Arg Arg Lys Arg Ala Ser Ala Thr Gln
1               5                   10                  15

Leu Tyr Gln Thr Cys Lys Gln Ser Gly Thr Cys Pro Glu Asp Val Ile
                20                  25                  30

Asn Lys Ile Glu Gln Lys Thr Trp Ala Asp Lys Ile Leu Gln Trp Gly
            35                  40                  45

Ser Leu Phe Thr Phe Phe Gly Gly Leu Gly Ile Gly Thr Gly Ser Gly
    50                  55                  60

Thr Gly Gly Arg Thr Gly Tyr Ile Pro Leu Gly Thr Arg Pro Ser Thr
65                  70                  75                  80

Val Val Asp Val Thr Pro Ala Arg Pro Ile Val Val Glu Ser Val
                85                  90                  95

Gly Pro Thr Asp Pro Ser Ile Val Thr Leu Val Glu Glu Ser Ser Val
            100                 105                 110

Ile Glu Ser Gly Ala Ser Phe Pro Asn Phe Thr Gly Thr Ala Gly Phe
```

```
                    115                 120                 125
Glu Val Thr Ser Ser Thr Thr Thr Pro Ala Val Leu Asp Ile Thr
    130                 135                 140

Pro Thr Ser Thr Ser Val His Val Ser Ser Thr Thr Tyr Ser Asn Pro
145                 150                 155                 160

Thr Phe Val Asp Pro Val Ile Glu Val Pro Gln Thr Gly Glu Val
                165                 170                 175

Ser Gly Asn Ile Leu Ile Ser Thr Pro Thr Ser Gly Val His Ser Tyr
            180                 185                 190

Glu Glu Ile Pro Met Gln Thr Phe Ala Val Gln Gly Thr Gly Asn Glu
                195                 200                 205

Pro Ile Ser Ser Thr Pro Ile Pro Gly Leu Arg Arg Ile Ala Ala Pro
    210                 215                 220

Arg Leu Tyr Lys Lys Ala Phe Gln Gln Val Lys Val Thr Asp Pro Ala
225                 230                 235                 240

Phe Leu His Lys Pro Glu Thr Leu Ile Asn Val Asp Asn Pro Ile Phe
                245                 250                 255

Glu Thr Ala Asp Thr Thr Leu Thr Phe Ser Pro Ser Gly Val Ala Pro
            260                 265                 270

Asp Pro Asp Phe Leu Asp Ile Val Ala Leu His Arg Pro Ala Phe Thr
        275                 280                 285

Thr Arg Arg Gly Gly Val Arg Phe Ser Arg Leu Gly Thr Lys Ala Thr
    290                 295                 300

Met Arg Thr Arg Ser Gly Lys Gln Ile Gly Ala Arg Val His Tyr Tyr
305                 310                 315                 320

Tyr Asp Val Ser Pro Ile Thr Gln Thr Glu Glu Ile Glu Met Gln Pro
                325                 330                 335

Leu Leu Ser Thr Asp Asn Thr Phe Asp Gly Leu Tyr Asp Ile Tyr Ala
            340                 345                 350

Asn Ile Asp Asp Glu Ala Pro Val Ser Ser Arg Phe Ser Ile Ala Thr
        355                 360                 365

Pro Ser Arg Leu Pro Thr Asn Thr Val Pro Leu Ser Phe Ser Gly Ser
    370                 375                 380

Thr Ser Asn Val Thr Ile Pro Phe Gly Thr Ser Trp Asp Val Pro Ile
385                 390                 395                 400

Tyr Ser Gly Pro Asp Val Val Leu Pro Thr Gly Pro Thr Trp Pro
                405                 410                 415

Tyr Ala Pro Gln Ser Pro Phe Asp Thr Thr His Asp Val Val Ile Gln
            420                 425                 430

Gly Ser Thr Phe Ala Leu Trp Pro Val Tyr Phe Leu Lys Arg Arg Arg
        435                 440                 445

Arg Lys Arg Ile Pro Tyr Phe Leu Ala Asp Gly Val Ala Ala
    450                 455                 460

<210> SEQ ID NO 53
<211> LENGTH: 470
<212> TYPE: PRT
<213> ORGANISM: Human papillomavirus type 54

<400> SEQUENCE: 53

Met Ala Lys Ala Arg Ala Pro Arg Arg Lys Arg Ala Ser Ala Thr Gln
1               5                   10                  15

Leu Tyr Gln Thr Cys Lys Ala Ser Gly Thr Cys Pro Ser Asp Val Ile
            20                  25                  30
```

```
Pro Lys Val Glu Gly Thr Thr Ile Ala Asp Gln Ile Leu Arg Trp Gly
         35                  40                  45
Ser Met Gly Val Phe Phe Gly Gly Leu Gly Ile Gly Thr Gly Ser Gly
 50                  55                  60
Thr Gly Gly Arg Thr Gly Tyr Ile Pro Leu Gly Arg Pro Ser Thr Thr
 65                  70                  75                  80
Leu Glu Pro Gly Pro Val Val Arg Pro Ala Gly Ala Val Glu Thr Val
                 85                  90                  95
Ala Pro Ser Asp Pro Ser Ile Val Ser Leu Val Glu Glu Ser Ser Val
                100                 105                 110
Val Asp Val Gly Ala Pro Thr Pro Thr Ile Pro Thr His Gly Gly Phe
            115                 120                 125
Glu Ile Thr Thr Ser Ser Asp Ala Thr Pro Ala Ile Leu Asp Val Thr
    130                 135                 140
Ser Thr Thr Thr Pro Ile Arg Val Ser Val Thr Ser His Thr Asn Pro
145                 150                 155                 160
Ile Tyr Thr Glu Pro Ser Leu Leu Asp Pro Pro Pro Val Gln Met
                165                 170                 175
Asp Gly Arg Val Leu Val Ser Thr Ser Thr Leu Pro Ser Ser Thr Ala
            180                 185                 190
Glu His Ile Pro Met Asp Thr Phe Ile Ile Met Gln Asp His Ile Gly
            195                 200                 205
Thr Thr Thr Ser Thr Pro Val Pro Arg Pro Ala Arg Pro Arg Leu
    210                 215                 220
Gly Leu Tyr Ser Arg Ala Leu Gln Gln Val Pro Val His Asp Pro Ala
225                 230                 235                 240
Phe Leu Gln Gln Pro Ser Ser Leu Ile Thr Tyr Asp Asn Pro Val Tyr
                245                 250                 255
Glu Gly Asn Pro Asp Val Thr Leu His Phe Glu Gln Pro Thr Ile His
                260                 265                 270
Asn Ala Pro Asp Pro Ala Phe Met Asp Ile Phe Ala Leu His Arg Pro
            275                 280                 285
Ala Leu Thr Thr Arg Arg Gly Val Val Arg Tyr Ser Arg Val Gly Glu
    290                 295                 300
Arg Ala Thr Val His Thr Arg Ser Gly Leu Gln Leu Lys Pro Arg Val
305                 310                 315                 320
His Tyr Phe Gln Asp Leu Ser Pro Ile Ala His Val Pro Glu Glu Ile
                325                 330                 335
Glu Leu His Pro Leu Ile Ser Ala Asn Asn Thr Ser Ile Asn Asn Gly
            340                 345                 350
Leu Tyr Ser Asp Ile Tyr Asp Val Tyr Ala Asp Thr Asp Phe Ala Asp
            355                 360                 365
Thr Gly Gly Val Ser Thr Ser Thr Val Ser Arg Ser Ser Val His Thr
    370                 375                 380
Thr Leu Gln Thr Thr Ser Ile Pro Ser Gln Tyr Gly Asn Thr Thr Val
385                 390                 395                 400
Pro Leu Thr Ala Ser Ser Pro Tyr Thr Pro Ile Pro Thr Ser Phe Arg
                405                 410                 415
Pro Ser Ser Gly Gln Ala Pro Phe Ile Pro Ala Arg Pro Ile Phe Pro
            420                 425                 430
Gln Thr Pro Ile Ala Val Asn Gly Gly Asp Phe Tyr Leu His Pro Ser
    435                 440                 445
Tyr Thr Ser Leu Arg Lys Arg Arg Lys Arg Leu Pro Tyr Phe Leu Ala
```

Asp Gly Tyr Val Ala Ala
465                 470

<210> SEQ ID NO 54
<211> LENGTH: 460
<212> TYPE: PRT
<213> ORGANISM: Human papillomavirus type 55

<400> SEQUENCE: 54

Met Ala His Ser Arg Ala Arg Arg Lys Arg Ala Ser Ala Thr Gln
1               5                   10                  15

Leu Tyr Gln Thr Cys Lys Ala Ala Gly Thr Cys Pro Ser Asp Ile Ile
            20                  25                  30

Pro Lys Val Glu His Asn Thr Ile Ala Asp Gln Ile Leu Lys Trp Gly
        35                  40                  45

Ser Leu Gly Val Phe Phe Gly Gly Leu Gly Ile Gly Thr Gly Ser Gly
    50                  55                  60

Thr Gly Gly Arg Thr Gly Tyr Ile Pro Leu Gln Ser Thr Pro Arg Pro
65                  70                  75                  80

Glu Ile Pro Ser Gly Pro Thr Thr Arg Pro Pro Ile Leu Val Asp Thr
                85                  90                  95

Val Ala Pro Gly Asp Pro Ser Ile Val Ser Leu Val Glu Glu Ser Ala
            100                 105                 110

Ile Ile Asn Ser Gly Ala Pro Glu Leu Val Pro Pro Ser His Gly Gly
        115                 120                 125

Phe Glu Ile Thr Thr Ser Glu Ser Thr Thr Pro Ala Ile Leu Asp Val
    130                 135                 140

Ser Val Thr Thr His Thr Thr Ser Thr Ser Val Phe Arg Asn Pro Ser
145                 150                 155                 160

Phe Ala Asp Pro Ser Val Val Gln Ser Gln Pro Ala Val Glu Ala Gly
                165                 170                 175

Gly His Ile Leu Ile Ser Thr Ser Thr Ile Ser Ser His Pro Val Glu
            180                 185                 190

Glu Ile Pro Leu Asp Thr Phe Ile Val Ser Ser Ser Asp Ser Asn Pro
        195                 200                 205

Ala Ser Ser Thr Pro Ile Pro Ala Ser Gly Ala Arg Pro Arg Ile Gly
    210                 215                 220

Leu Tyr Ser Lys Ala Leu His Gln Val Gln Val Thr Asp Pro Ala Phe
225                 230                 235                 240

Leu Ser Ser Pro Gln Arg Leu Ile Thr Phe Asp Asn Pro Ala Tyr Glu
                245                 250                 255

Gly Glu Asp Val Ser Leu Glu Phe Ala His Asn Thr Ile His Gln Pro
            260                 265                 270

Pro Asp Asp Ala Phe Met Asp Ile Ile Arg Leu His Arg Pro Ala Ile
        275                 280                 285

Gln Ser Arg Arg Gly Arg Val Arg Phe Ser Arg Ile Gly Gln Arg Gly
    290                 295                 300

Ser Met Tyr Thr Arg Ser Gly Lys His Ile Gly Gly Arg Ile His Phe
305                 310                 315                 320

Tyr Gln Asp Ile Ser Pro Ile Ser Ala Ala Ala Glu Glu Ile Glu Leu
                325                 330                 335

His Pro Leu Val Ala Thr Ala His Asp Thr Ser Leu Phe Asp Ile Tyr
            340                 345                 350

```
Ala Glu Pro Asp Pro Asp Phe Thr Glu Pro Val Pro Leu Ser Phe
            355                 360                 365

Ser Thr Ser Thr Pro Phe Gln Arg Ser Ser Val Ser Ala Thr Pro Trp
    370                 375                 380

Gly Asn Thr Thr Val Pro Leu Ser Leu Pro Gly Asp Met Phe Val Gln
385                 390                 395                 400

Pro Gly Pro Asp Ile Ile Phe Pro Thr Ala Ser Thr Thr Thr Pro Tyr
                405                 410                 415

Ser Pro Val Thr Pro Ala Leu Pro Thr Gly Pro Val Phe Ile Ser Gly
            420                 425                 430

Ala Thr Phe Tyr Leu Tyr Pro Ala Trp Tyr Phe Ala Arg Lys Arg Arg
        435                 440                 445

Lys Arg Val Ser Leu Phe Phe Ala Asp Val Ala Ala
    450                 455                 460

<210> SEQ ID NO 55
<211> LENGTH: 464
<212> TYPE: PRT
<213> ORGANISM: Human papillomavirus type 56

<400> SEQUENCE: 55

Met Val Ala His Arg Ala Thr Arg Arg Lys Arg Ala Ser Ala Thr Gln
1               5                   10                  15

Leu Tyr Lys Thr Cys Lys Leu Ser Gly Thr Cys Pro Glu Asp Val Val
            20                  25                  30

Asn Lys Ile Glu Gln Lys Thr Trp Ala Asp Lys Ile Leu Gln Trp Gly
        35                  40                  45

Ser Leu Phe Thr Tyr Phe Gly Gly Leu Gly Ile Gly Thr Gly Thr Gly
    50                  55                  60

Ser Gly Gly Arg Ala Gly Tyr Val Pro Leu Gly Ser Arg Pro Ser Thr
65                  70                  75                  80

Ile Val Asp Val Thr Pro Ala Arg Pro Pro Ile Val Val Glu Ser Val
                85                  90                  95

Gly Pro Thr Asp Pro Ser Ile Val Thr Leu Val Glu Glu Ser Ser Val
            100                 105                 110

Ile Glu Ser Gly Ala Gly Ile Pro Asn Phe Thr Gly Ser Gly Gly Phe
        115                 120                 125

Glu Ile Thr Ser Ser Ser Thr Thr Thr Pro Ala Val Leu Asp Ile Thr
    130                 135                 140

Pro Thr Ser Ser Thr Val His Val Ser Ser Thr His Ile Thr Asn Pro
145                 150                 155                 160

Leu Phe Ile Asp Pro Pro Val Ile Glu Ala Pro Gln Thr Gly Glu Val
                165                 170                 175

Ser Gly Asn Ile Leu Ile Ser Thr Pro Thr Ser Gly Ile His Ser Tyr
            180                 185                 190

Glu Glu Ile Pro Met Gln Thr Phe Ala Val His Gly Ser Gly Thr Glu
        195                 200                 205

Pro Ile Ser Ser Thr Pro Ile Pro Gly Phe Arg Arg Ile Ala Ala Pro
    210                 215                 220

Arg Leu Tyr Arg Lys Ala Phe Gln Gln Val Lys Val Thr Asp Pro Thr
225                 230                 235                 240

Phe Leu Asp Arg Pro Ala Thr Leu Val Ser Ala Asp Asn Pro Leu Phe
                245                 250                 255

Glu Gly Thr Asp Thr Ser Leu Ala Phe Ser Pro Ser Gly Val Ala Pro
            260                 265                 270
```

-continued

```
Asp Pro Asp Phe Met Asn Ile Val Ala Leu His Arg Pro Ala Phe Thr
            275                 280                 285

Thr Arg Arg Gly Gly Val Arg Phe Ser Arg Leu Gly Arg Lys Ala Thr
290                 295                 300

Ile Gln Thr Arg Arg Gly Thr Gln Ile Gly Ala Arg Val His Tyr Tyr
305                 310                 315                 320

Tyr Asp Ile Ser Pro Ile Ala Gln Ala Glu Glu Ile Glu Met Gln Pro
                325                 330                 335

Leu Leu Ser Ala Asn Asn Ser Phe Asp Gly Leu Tyr Asp Ile Tyr Ala
            340                 345                 350

Asn Ile Asp Asp Glu Ala Pro Gly Leu Ser Ser Gln Ser Val Ala Thr
        355                 360                 365

Pro Ser Ala His Leu Pro Ile Lys Pro Ser Thr Leu Ser Phe Ala Ser
370                 375                 380

Asn Thr Thr Asn Val Thr Ala Pro Leu Gly Asn Val Trp Glu Thr Pro
385                 390                 395                 400

Phe Tyr Ser Gly Pro Asp Met Val Leu Pro Thr Gly Pro Ser Thr Trp
                405                 410                 415

Pro Phe Val Pro Gln Ser Pro Tyr Asp Val Thr His Asp Val Tyr Ile
            420                 425                 430

Gln Gly Ser Ser Phe Ala Leu Trp Pro Val Tyr Phe Phe Arg Arg Arg
        435                 440                 445

Arg Arg Lys Arg Ile Pro Tyr Phe Phe Ala Asp Gly Asp Val Ala Ala
450                 455                 460
```

<210> SEQ ID NO 56
<211> LENGTH: 465
<212> TYPE: PRT
<213> ORGANISM: Human papillomavirus type 57

<400> SEQUENCE: 56

```
Met Ser Pro Arg Ala Lys Arg Val Arg Ala Ser Pro Thr Asp Leu
1               5                   10                  15

Tyr Arg Thr Cys Lys Gln Ala Gly Thr Cys Pro Pro Asp Ile Ile Pro
                20                  25                  30

Arg Val Glu Gln Asp Thr Leu Ala Asp Arg Ile Leu Lys Trp Gly Ser
            35                  40                  45

Leu Gly Val Phe Phe Gly Gly Leu Gly Ile Gly Thr Gly Ser Gly Thr
        50                  55                  60

Gly Gly Arg Thr Gly Tyr Ile Pro Val Gly Thr Arg Pro Thr Thr Val
65                  70                  75                  80

Val Asp Val Gly Leu Ala Pro Arg Pro Pro Val Val Ile Glu Pro Val
                85                  90                  95

Gly Ala Ser Glu Pro Ser Ile Val Asn Leu Val Glu Asp Ser Ser Ile
            100                 105                 110

Ile Asn Ala Gly Ser Ser His Pro Thr Phe Thr Gly Thr Gly Gly Phe
        115                 120                 125

Glu Val Thr Thr Ser Thr Val Thr Asp Pro Ala Val Leu Asp Ile Thr
130                 135                 140

Pro Ser Gly Asn Gly Val Gln Val Ser Ser Ser Ser Phe Val Asn Pro
145                 150                 155                 160

Leu Phe Thr Asp Pro Ala Ile Ile Glu Ala Pro Gln Ala Gly Glu Val
                165                 170                 175

Thr Gly His Val Leu Val Ser Thr Ala Thr Ser Gly Ser His Gly Phe
```

```
                180                 185                 190
Glu Glu Ile Pro Met Gln Thr Phe Ala Thr Ser Gly Gly Asp Gly Gly
            195                 200                 205
Glu Pro Ile Ser Ser Thr Pro Val Pro Gly Val Arg Arg Val Ala Gly
        210                 215                 220
Pro Arg Leu Tyr Ser Arg Ala Asn Gln Gln Val Arg Val Arg Asp Pro
225                 230                 235                 240
Ala Phe Ile Asp Arg Pro Ala Asp Leu Val Thr Phe Asp Asn Pro Val
                245                 250                 255
Tyr Asp Pro Glu Glu Thr Ile Ile Phe Gln His Pro Gly Leu His Glu
            260                 265                 270
Pro Pro Asp Pro Asp Phe Leu Asp Ile Val Ser Leu His Arg Pro Ala
        275                 280                 285
Leu Thr Ser Thr Arg Gln Gly Thr Val Arg Phe Ser Arg Leu Gly Arg
    290                 295                 300
Arg Ala Thr Leu Arg Thr Arg Ser Gly Lys Gln Ile Gly Ala Arg Val
305                 310                 315                 320
His Phe Tyr His Asp Ile Ser Pro Val Ala Pro Glu Glu Leu Glu Met
                325                 330                 335
Glu Pro Leu Leu Pro Pro Thr Ser Glu Pro Leu Tyr Asp Ile Tyr Ala
            340                 345                 350
Glu Ser Asp Phe Leu Gln Pro Leu Asp Ser Asp Val Pro Ala Ala Pro
        355                 360                 365
Arg Gly Thr Leu Ser Leu Ala Asp Thr Ala Val Ser Ala Ser Thr Ala
    370                 375                 380
Ser Thr Leu Arg Gly Ala Thr Thr Val Pro Leu Ser Gly Gly Val Asp
385                 390                 395                 400
Val Pro Val Tyr Thr Gly Pro Asp Ile Asp Pro Ser Val Gly Pro Gly
                405                 410                 415
Met Gly Pro Leu Val Pro Val Ile Pro Ala Ile Pro Ser Ser Val Tyr
            420                 425                 430
Ile Val Gly Gly Asp Tyr Tyr Leu Leu Pro Ser Tyr Val Leu Trp Pro
        435                 440                 445
Lys Arg Arg Lys Arg Val His Tyr Phe Phe Ala Asp Gly Tyr Val Ala
    450                 455                 460
Ala
465

<210> SEQ ID NO 57
<211> LENGTH: 472
<212> TYPE: PRT
<213> ORGANISM: Human papillomavirus type 58

<400> SEQUENCE: 57

Met Arg His Lys Arg Ser Thr Arg Arg Lys Arg Ala Ser Ala Thr Gln
1               5                   10                  15
Leu Tyr Gln Thr Cys Lys Ala Ser Gly Thr Cys Pro Pro Asp Val Ile
                20                  25                  30
Pro Lys Val Glu Gly Thr Thr Ile Ala Asp Gln Ile Leu Arg Tyr Gly
            35                  40                  45
Ser Leu Gly Val Phe Phe Gly Gly Leu Gly Ile Gly Thr Gly Ser Gly
        50                  55                  60
Thr Gly Gly Arg Thr Gly Tyr Val Pro Leu Gly Ser Thr Pro Pro Ser
65                  70                  75                  80
```

-continued

Glu Ala Ile Pro Leu Gln Pro Ile Arg Pro Pro Val Thr Val Asp Thr
                85                  90                  95

Val Gly Pro Leu Asp Ser Ser Ile Val Ser Leu Ile Glu Glu Ser Ser
            100                 105                 110

Phe Ile Asp Ala Gly Ala Pro Ala Pro Ser Ile Pro Thr Pro Ser Gly
            115                 120                 125

Phe Asp Ile Thr Thr Ser Ala Asp Thr Thr Pro Ala Ile Leu Asn Val
            130                 135                 140

Ser Ser Ile Gly Glu Ser Ser Ile Gln Thr Val Ser Thr His Leu Asn
145                 150                 155                 160

Pro Ser Phe Thr Glu Pro Ser Val Leu Arg Pro Pro Ala Pro Ala Glu
                165                 170                 175

Ala Ser Gly His Leu Ile Phe Ser Ser Pro Thr Val Ser Thr His Ser
            180                 185                 190

Tyr Glu Asn Ile Pro Met Asp Thr Phe Val Ile Ser Thr Asp Ser Gly
            195                 200                 205

Asn Val Thr Ser Ser Thr Pro Ile Pro Gly Ser Arg Pro Val Ala Arg
210                 215                 220

Leu Gly Leu Tyr Ser Arg Asn Thr Gln Gln Val Lys Val Val Asp Pro
225                 230                 235                 240

Ala Phe Leu Thr Ser Pro His Arg Leu Val Thr Tyr Asp Asn Pro Ala
                245                 250                 255

Phe Glu Gly Phe Asn Pro Glu Asp Thr Leu Gln Phe Gln His Ser Asp
            260                 265                 270

Ile Ser Pro Ala Pro Asp Pro Asp Phe Leu Asp Ile Val Ala Leu His
            275                 280                 285

Arg Pro Ala Leu Thr Ser Arg Arg Gly Thr Val Arg Tyr Ser Arg Val
290                 295                 300

Gly Gln Lys Ala Thr Leu Arg Thr Arg Ser Gly Lys Gln Ile Gly Ala
305                 310                 315                 320

Lys Val His Tyr Tyr Gln Asp Leu Ser Pro Ile Gln Pro Val Gln Glu
                325                 330                 335

Gln Val Gln Gln Gln Gln Gln Phe Glu Leu Gln Ser Leu Asn Thr Ser
            340                 345                 350

Val Ser Pro Tyr Ser Ile Asn Asp Gly Leu Tyr Asp Ile Tyr Ala Asp
            355                 360                 365

Asp Ala Asp Thr Ile His Asp Phe Gln Ser Pro Leu His Ser His Thr
370                 375                 380

Ser Phe Ala Thr Thr Arg Thr Ser Asn Val Ser Ile Pro Leu Asn Thr
385                 390                 395                 400

Gly Phe Asp Thr Pro Leu Val Ser Leu Glu Pro Gly Pro Asp Ile Ala
                405                 410                 415

Ser Ser Val Thr Ser Met Ser Ser Pro Phe Ile Pro Ile Ser Pro Leu
            420                 425                 430

Thr Pro Phe Asn Thr Ile Ile Val Asp Gly Ala Asp Phe Met Leu His
            435                 440                 445

Pro Ser Tyr Phe Ile Leu Arg Arg Arg Lys Arg Phe Pro Tyr Phe
            450                 455                 460

Phe Ala Asp Val Arg Val Ala Ala
465                 470

<210> SEQ ID NO 58
<211> LENGTH: 464
<212> TYPE: PRT

<213> ORGANISM: Human papillomavirus type 59

<400> SEQUENCE: 58

```
Met Val Ser His Arg Ala Ala Arg Arg Lys Arg Ala Ser Ala Thr Asp
1               5                   10                  15

Leu Tyr Lys Thr Cys Lys Gln Ala Gly Thr Cys Pro Ser Asp Val Ile
            20                  25                  30

Asn Lys Val Glu Gly Thr Thr Leu Ala Asp Lys Ile Leu Gln Trp Thr
        35                  40                  45

Ser Leu Gly Ile Phe Leu Gly Leu Gly Ile Gly Thr Gly Ser Gly
    50                  55                  60

Thr Gly Gly Arg Thr Gly Tyr Ile Pro Leu Gly Gly Arg Thr Asn Thr
65                  70                  75                  80

Ile Val Asp Val Ser Pro Ala Lys Pro Val Val Ile Glu Pro Val
                85                  90                  95

Gly Pro Thr Asp Pro Ser Ile Val Thr Leu Val Glu Asp Ser Ser Val
            100                 105                 110

Ile Thr Ser Gly Ala Pro Ala Pro Thr Phe Thr Gly Thr Ser Gly Phe
        115                 120                 125

Glu Ile Ser Thr Ser Ser Thr Thr Thr Pro Ala Val Leu Asp Ile Thr
130                 135                 140

Pro Thr Ser Ser Val Gln Ile Ser Ser Ser Phe Ile Asn Pro Ala
145                 150                 155                 160

Phe Thr Asp Pro Ser Val Ile Glu Val Pro Gln Thr Gly Glu Ile Ser
                165                 170                 175

Gly Asn Ile Leu Ile Ser Thr Pro Thr Ser Gly Ala His Gly Tyr Glu
            180                 185                 190

Glu Ile Pro Met Gln Thr Phe Ala Thr Glu Gly Thr Gly Leu Glu Pro
        195                 200                 205

Ile Ser Ser Thr Pro Asn Pro Thr Val Arg Arg Val Ala Gly Pro Arg
210                 215                 220

Leu Tyr Ser Arg Ala Asn Gln Gln Val Arg Val Ser Asn Ala Asp Phe
225                 230                 235                 240

Leu Thr Arg Pro Ser Thr Phe Val Thr Tyr Asp Asn Pro Ala Tyr Asp
                245                 250                 255

Pro Ile Asp Thr Thr Leu Thr Phe Asp Pro Ser Ser Glu Val Pro Asp
            260                 265                 270

Pro Asp Phe Met Asp Ile Val Arg Leu His Arg Pro Ala Leu Thr Ser
        275                 280                 285

Arg Arg Ser Thr Val Arg Phe Ser Arg Leu Gly Gln Arg Ala Thr Met
290                 295                 300

Phe Thr Arg Ser Gly Lys Gln Ile Gly Ala Arg Val His Phe Tyr His
305                 310                 315                 320

Asp Ile Ser Pro Ile Pro His Ala Glu Asp Ile Glu Leu Gln Pro Leu
                325                 330                 335

Val Ser Ser Gln Ala Ala Thr Asp Ile Tyr Asp Ile Tyr Ala Asp
            340                 345                 350

Ile Thr Asp Glu Ala Pro Thr Ser Thr Ala Asn Thr Ala Phe Thr Ile
        355                 360                 365

Pro Lys Ser Ser Phe Gln Ser Leu Ser Leu Thr Arg Ser Ala Ser Ser
370                 375                 380

Thr Phe Ser Asn Val Thr Val Pro Leu Ala Thr Ala Trp Asp Val Pro
385                 390                 395                 400
```

```
Val Asn Thr Gly Pro Asp Ile Val Leu Pro Asn Thr Asn Ile Val Glu
            405                 410                 415

Pro Thr Tyr Ser Thr Thr Pro Phe Thr Thr Ile Gln Ser Ile Asn Ile
            420                 425                 430

Glu Gly Thr Asn Tyr Phe Leu Trp Pro Ile Tyr Tyr Phe Leu Pro Arg
            435                 440                 445

Lys Arg Lys Arg Val Pro Tyr Phe Phe Thr Asp Gly Ser Met Ala Phe
450                 455                 460

<210> SEQ ID NO 59
<211> LENGTH: 525
<212> TYPE: PRT
<213> ORGANISM: Human papillomavirus type 60

<400> SEQUENCE: 59

Met Tyr Ala Arg Val Lys Arg Val Lys Arg Asp Ser Val Glu Asn Leu
1               5                   10                  15

Tyr Lys Gln Cys Gln Leu Gly Ala Asp Cys Pro Pro Asp Val Arg Asn
            20                  25                  30

Lys Val Glu Gly Thr Thr Leu Ala Asp Arg Leu Leu Gln Ile Phe Gly
            35                  40                  45

Ser Ile Leu Tyr Leu Gly Asn Leu Gly Ile Gly Thr Gly Lys Gly Ser
    50                  55                  60

Gly Gly Ala Thr Gly Tyr Thr Pro Leu Gly Thr Ala Arg Val Pro Ala
65                  70                  75                  80

Ser Thr Pro Gly Thr Val Ile Lys Pro Thr Arg Pro Phe Ser Val Pro
                85                  90                  95

Leu Asp Pro Ile Gly Ser Gly Ile Pro Ser Gln Pro Val Gly Gly Arg
            100                 105                 110

Leu Pro Val Asp Ile Ile Asp Ala Ser Ala Ser Ser Ile Ile Pro Leu
            115                 120                 125

Gln Glu Val Leu Pro Glu Thr Thr Ile Ile Val Gly Gly Asp Ser Gly
    130                 135                 140

Pro Gly Leu Gly Ala Ser Glu Ile Asp Ile Val Ser Glu Pro Arg Pro
145                 150                 155                 160

Asp Val Val Gly Val Asp Thr Gln Pro Thr Val Tyr Thr Ser Ile Asp
                165                 170                 175

Asn Thr Val Ala Thr Leu Asp Ile Thr Pro Ala Thr Pro Pro Val Lys
            180                 185                 190

Lys Ile Ile Leu Asp Pro Ile Ser Ser Gly Ser Glu Gly Ala Ala Ala
            195                 200                 205

Ile Thr Phe Ser Asp Ile Ser Ala Ala Asp Leu Asn Val Phe Val Asp
    210                 215                 220

Pro Gln Gly Ala Gly Asp Arg Ile Ser Phe Gly Glu Glu Ile Glu Leu
225                 230                 235                 240

Gly Pro Ile Asn Gln Pro Ala Gln Phe Glu Ile Glu Glu Pro Pro Arg
                245                 250                 255

Thr Ser Thr Pro Gly Glu Gly Phe Gln Arg Val Thr Thr Arg Ala Arg
            260                 265                 270

Glu Leu Tyr Asn Arg Phe Val Gln Gln Pro Thr Gln Asn Ile Asp
            275                 280                 285

Phe Leu Gly Arg Pro Ser Arg Ala Val Gln Phe Glu Phe Glu Asn Pro
    290                 295                 300

Ala Phe Phe Asn Asp Glu Val Thr Met Gln Phe Glu Gln Asp Leu Gln
305                 310                 315                 320
```

```
Glu Val Ala Ala Ala Pro Asp Gln Asp Phe Ala Asp Val Arg Glu Leu
                325                 330                 335

Gly Arg Ala Arg Phe Ser Glu Thr Ser Ala Gly Thr Ile Arg Val Ser
                340                 345                 350

Arg Leu Gly Thr Lys Gly Thr Met Lys Thr Arg Ser Gly Leu Thr Ile
            355                 360                 365

Gly Gln Lys Val His Phe Tyr Phe Asp Ile Ser Asp Ile Pro Ala Ala
        370                 375                 380

Glu Thr Ile Gln Leu Arg Thr Leu Gly Glu Ser Ser His Asp Phe Ser
385                 390                 395                 400

Ala Val Asp Asn Ile Thr Glu Ser Thr Tyr Ile Asn Leu Thr Glu Thr
                405                 410                 415

Thr Asn Glu Gly Leu Ile Pro Asp Asn Ile Leu Glu Asp Glu Phe Thr
                420                 425                 430

Glu Asn Phe Asn Asn Ala Gln Leu Ile Phe Ala Thr Ile Asp Glu Gly
            435                 440                 445

Glu Ser Met Ile Met Pro Thr Ile Pro Pro Gly Val Ala Leu Lys Leu
        450                 455                 460

Phe Ile Pro Glu Ile Ala Ala Ser Val Leu Asn Val Val His Pro Ser
465                 470                 475                 480

Ser Glu Trp Thr Ile Leu Ile Pro Asn Val Pro Asp Glu Ile Ile Gln
                485                 490                 495

Pro Ala Met Ala Val Asp Val Tyr Asp Phe Tyr Leu His Pro His
                500                 505                 510

Leu Leu Arg Arg Arg Lys Arg Lys Arg Leu Asp Phe Phe
            515                 520                 525

<210> SEQ ID NO 60
<211> LENGTH: 459
<212> TYPE: PRT
<213> ORGANISM: Human papillomavirus type 61

<400> SEQUENCE: 60

Met Ala Leu Lys Arg Arg Lys Arg Ala Ser Ala Thr Asp Leu Tyr Arg
1               5                   10                  15

Thr Cys Lys Gln Ser Gly Thr Cys Pro Pro Asp Val Val Pro Lys Val
                20                  25                  30

Glu Gly Asp Thr Leu Ala Asp Arg Ile Leu Lys Trp Ala Ser Leu Gly
            35                  40                  45

Val Phe Phe Gly Gly Leu Gly Ile Gly Thr Ser Gly Thr Gly Gly
        50                  55                  60

Arg Thr Gly Tyr Val Pro Ile Gly Thr Arg Pro Pro Thr Val Val Asp
65                  70                  75                  80

Ile Gly Pro Val Ser Arg Pro Pro Val Val Ile Asp Pro Val Gly Ala
                85                  90                  95

Ala Asp Pro Ser Ile Val Thr Leu Val Glu Glu Ser Ser Val Ile Glu
                100                 105                 110

Ala Gly Ala Thr Val Pro Thr Phe Ser Gly Ser Gly Gly Phe Asn Val
            115                 120                 125

Thr Ser Ser Ser Thr Thr Thr Pro Ala Val Leu Asp Ile Thr Pro Ser
        130                 135                 140

Gly Gly Ser Val Gln Val Ser Ser Thr Ser Phe Ile Asn Pro Leu Phe
145                 150                 155                 160

Thr Glu Pro Ser Ile Ile Glu Pro Pro Gln Ala Gly Asp Leu Ala Gly
```

-continued

```
                165                 170                 175
His Val Ile Ser Ser Thr Pro Thr Ala Gly Ser His Ser Phe Glu Glu
            180                 185                 190

Ile Pro Met His Thr Phe Ala Thr Ser Glu Gly Pro Gly Ser Ser Thr
        195                 200                 205

Pro Leu Pro Gly Ile Arg Arg Leu Ala Arg Pro Arg Leu Asn Leu Tyr
    210                 215                 220

Ser Lys Ala Asn Gln Gln Ile Lys Val Ala Asn Pro Thr Phe Met Ser
225                 230                 235                 240

Asp Pro Ala Ser Leu Ile Thr Tyr Asp Asn Pro Ile Phe Asp Pro Glu
            245                 250                 255

Glu Thr Ile Ile Phe Glu His Pro Ser Ile Tyr Thr Pro Pro Asp Pro
        260                 265                 270

Asp Phe Leu Asp Ile Val Ser Leu His Arg Pro Ala Leu Thr Ser Arg
    275                 280                 285

Gln Gly Thr Val Arg Phe Ser Arg Leu Gly Gln Arg Ala Thr Leu Arg
    290                 295                 300

Thr Arg Ser Gly Arg Arg Ile Gly Ala Arg Val His Phe Tyr His Asp
305                 310                 315                 320

Ile Ser Pro Ile Pro Ser Asp Ala Val Glu Leu Gln Pro Leu Val Pro
            325                 330                 335

Ser Ser Ser Pro Ser Ile Thr Tyr Asp Ile Tyr Ala Asp Pro Glu Val
        340                 345                 350

Leu Asp Leu Pro Ala Gln His Thr Gln Pro Thr Leu Thr Val Gln Gly
    355                 360                 365

Pro Ser Leu Ser Ala Ala Ser Ala Ser Thr Lys Val His Asn Val Thr
370                 375                 380

Val Pro Leu Ala Thr Gly Leu Asp Thr Pro Val Thr Ser Gly Pro Asp
385                 390                 395                 400

Val Asp Phe Ala His Ala Pro Ala Pro Val Pro Ala Val Pro Tyr Val
            405                 410                 415

Pro Ala Thr His Pro His Ser Ile Tyr Ile Gln Gly Ser Asp Phe Tyr
        420                 425                 430

Leu Leu Pro Ala Tyr Val Phe Phe Pro Lys Arg Arg Lys Arg Val Pro
    435                 440                 445

Tyr Ser Phe Ser Asp Gly Phe Val Ala Ala Trp
    450                 455
```

<210> SEQ ID NO 61
<211> LENGTH: 475
<212> TYPE: PRT
<213> ORGANISM: Human papillomavirus type 62

<400> SEQUENCE: 61

```
Met Pro Lys Val Leu His Arg Arg Lys Arg Ala Ser Ala Thr Asp Leu
1               5                   10                  15

Tyr Arg Thr Cys Lys Val Ser Gly Thr Cys Pro Ser Asp Val Ile Pro
            20                  25                  30

Lys Val Glu Gly Asn Thr Leu Ala Asp Lys Ile Leu Lys Trp Ala Ser
        35                  40                  45

Leu Gly Val Phe Phe Gly Gly Leu Gly Ile Gly Thr Ala Ser Gly Thr
    50                  55                  60

Gly Gly Arg Thr Gly Tyr Ile Pro Ile Gly Gly Arg Pro Pro Ser Val
65                  70                  75                  80
```

-continued

Val Asp Ile Gly Pro Val Ser Arg Pro Pro Val Ile Glu Pro Val
                85                  90                  95

Gly Ala Thr Asp Pro Ser Ile Val Thr Leu Val Glu Ser Ser Ile
            100                 105                 110

Ile Glu Ala Gly Ala Val His Pro Asn Phe Thr Gly Ser Gly Phe
            115                 120                 125

Glu Val Thr Thr Ser Ser Thr Ala Thr Pro Ala Val Leu Asp Ile Ser
            130                 135                 140

Pro Thr Gly Thr Thr Val Gln Val Ser Ser Thr Asn Phe Leu Asn Pro
145                 150                 155                 160

Ala Tyr Thr Glu Pro Ser Ile Ile Asp Pro Pro Gln Thr Gly Glu Leu
                165                 170                 175

Ser Gly His Val Leu Thr Ser Thr Pro Thr Ala Gly Ser His Ser Tyr
            180                 185                 190

Glu Glu Ile Pro Met Val Thr Phe Ala Ser Asn Ala Gly Thr Gly Ser
            195                 200                 205

Glu Pro Ile Ser Ser Thr Pro Leu Pro Gly Val Arg Arg Val Ala Gly
            210                 215                 220

Pro Arg Leu Gly Leu Tyr Thr Lys Ala Thr Gln Gln Val Pro Val Ala
225                 230                 235                 240

Asp Pro Ala Phe Val Ser Arg Pro Ala Ser Phe Ala Thr Phe Asp Asn
                245                 250                 255

Pro Ile Tyr Asp Pro Glu Thr Ile Ile Phe Glu His Pro Ser Ile
            260                 265                 270

Tyr Thr Pro Pro Asp Pro Asp Phe Leu Asp Ile Val Thr Leu His Arg
                275                 280                 285

Pro Ala Leu Thr Ser Arg Gln Gly Thr Val Arg Leu Ser Arg Val Gly
290                 295                 300

Gln Arg Ala Ser Leu Arg Thr Arg Ser Gly Lys Arg Ile Gly Ala Arg
305                 310                 315                 320

Val His Phe Tyr His Asp Ile Ser Pro Ile Pro Ser Thr Thr Thr Gly
                325                 330                 335

Asp Ile Glu Leu Gln Pro Leu Leu Pro Ser Gly Ser Ser Ser Ala Asp
            340                 345                 350

Thr Leu Tyr Asp Val Tyr Ala Asp Asp Gln His Leu Asp Ala Val Leu
            355                 360                 365

Gln Ser Val Pro Ser Met Ser Ser Arg Pro Leu Val Pro Ser Asn Ala
370                 375                 380

Thr Ile Ser Ala Thr Ser Val Ala Ser Ser His Thr Asn Val Thr Val
385                 390                 395                 400

Pro Leu Ser Thr Gly Leu Ser Val Pro Ala Ser Thr Gly Pro Asp Val
                405                 410                 415

Glu Leu Pro Gln Phe Ser Val Pro Val Ser Val Leu Thr Pro Ser Phe
            420                 425                 430

Pro Ala Thr Thr Pro Tyr Ser Ile Tyr Ile Val Gly Ser Asp Tyr Tyr
                435                 440                 445

Leu Phe Pro Ser Tyr Ile Phe Phe Pro Lys Lys His Lys Arg Leu His
    450                 455                 460

Tyr Phe Phe Thr Asp Gly Tyr Val Ala Ala Trp
465                 470                 475

<210> SEQ ID NO 62
<211> LENGTH: 504
<212> TYPE: PRT

<213> ORGANISM: Human papillomavirus type 63

<400> SEQUENCE: 62

```
Met Leu Arg Val Arg Lys Arg Ala Ala Pro Gln Asp Ile Tyr Pro
1               5                   10                  15

Ala Cys Lys Val Ala Asn Asn Cys Pro Pro Asp Ile Gln Asn Lys Ile
            20                  25                  30

Glu Gln Thr Thr Val Ala Asp Lys Ile Leu Gln Tyr Gly Ser Leu Gly
                35                  40                  45

Ile Phe Leu Gly Gly Leu Gly Ile Gly Thr Gly Lys Gly Gly Gly Gly
            50                  55                  60

Arg Tyr Gly Tyr Thr Pro Leu Gly Asp Ser Gly Ala Val Arg Val Gly
65                  70                  75                  80

Gly Arg Ser Thr Pro Val Arg Pro Thr Val Pro Val Glu Thr Val Gly
                85                  90                  95

Pro Arg Asp Ile Leu Pro Ile Asp Ser Leu Asp Pro Leu Gly Pro Ser
            100                 105                 110

Val Ile Glu Leu Glu Asp Ile Pro Ala Thr Thr Val Glu Val Val Ala
                115                 120                 125

Glu Val His Pro Ile Ser Asp Thr Pro Gln Ile Pro Ala Pro Thr Thr
            130                 135                 140

Asp Glu Ser Ser Ser Ala Val Leu His Ile Pro Gln Glu Ser Pro Ala
145                 150                 155                 160

Ala Arg Thr Ile Thr Arg Ser Gln Tyr Asn Asn Pro Leu Phe Arg Ile
                165                 170                 175

Thr Ala Ser Ala Asp Ile Ala Ser Gly Glu Ala Ser Ala Ser Asp Asn
            180                 185                 190

Ile Phe Ile Asp Val Asp Thr Pro Gly Gln Ile Val Gly Gln Glu Ile
        195                 200                 205

Pro Leu Val Asn Phe Asp Met Gly Pro Ile Ser Thr Glu Gly Glu Leu
    210                 215                 220

Glu Thr Glu Phe Thr Thr Ser Thr Pro Arg Thr Thr Gln Val Gln Glu
225                 230                 235                 240

Arg Pro Thr Arg Phe Tyr Asn Arg Arg Tyr Glu Gln Val Pro Val
                245                 250                 255

Thr Ala Pro Glu Phe Ile Thr Arg Pro Ala Ser Leu Val Thr Phe Glu
            260                 265                 270

Asn Pro Ala Phe Glu Arg Ser Val Ser Leu Ile Phe Glu Gln Asp Leu
        275                 280                 285

Glu Asp Ile Leu Asn Ala Pro Asp Gln Asp Phe Arg Asp Ile Val Tyr
    290                 295                 300

Leu Ser Arg Pro Thr Tyr Ser Arg Ala Pro Asp Gly Arg Met Arg Leu
305                 310                 315                 320

Ser Arg Leu Gly Arg Arg Ala Thr Ile Ser Thr Arg Ser Gly Val Thr
                325                 330                 335

Ile Gly Ala Gln Ser His Phe Tyr Met Asp Ile Ser Ser Ile Ser Ser
            340                 345                 350

Asn Asp Gly Ile Glu Leu Gln Thr Leu Gly Glu Ala Ser Gly Glu Thr
        355                 360                 365

Val Val Gln Ser Ser Leu Ala Ala Ser Asp Pro Ile Glu Ala Glu His
    370                 375                 380

Ser Phe Ile Glu Pro Ala Pro Ser Ile Asp Ser Tyr Asp Ile Val Ser
385                 390                 395                 400
```

```
Leu Gln Ser Glu Thr Tyr Ser Asp Glu His Leu Leu Asp Met Tyr Glu
                405                 410                 415

Pro Val Gly Ser Ser Leu Gln Leu Gln Ile Ser Asp Val Arg Gly Arg
            420                 425                 430

Pro Thr Val Ile Asp Ile Pro Phe Arg Pro Arg Pro Pro Leu Gly
        435                 440                 445

Pro Ile Asn Ala Gly Val Asp Ile Tyr Ser Pro Thr Ala Ser Val Gly
        450                 455                 460

Ser Pro Thr Ile Asn Pro Thr Asp Leu Asp Ile Pro Leu Ile Ile Ile
465                 470                 475                 480

His Leu Asp Asn Ser Thr Gly Asp Tyr Asp Leu His Pro Ser Leu Arg
                485                 490                 495

Lys Arg Arg Lys Leu Val His Ile
            500

<210> SEQ ID NO 63
<211> LENGTH: 518
<212> TYPE: PRT
<213> ORGANISM: Human papillomavirus type 65

<400> SEQUENCE: 63

Met Gln Ala Ser Arg Arg Thr Lys Arg Asp Ser Ile Pro Asn Leu Tyr
1               5                   10                  15

Ala Lys Cys Gln Leu Ser Gly Asn Cys Leu Pro Asp Val Lys Asn Lys
            20                  25                  30

Val Glu Ala Asp Thr Leu Ala Asp Arg Leu Leu Arg Trp Leu Gly Ser
        35                  40                  45

Val Ile Tyr Leu Gly Gly Leu Gly Ile Gly Thr Gly Arg Gly Ser Gly
    50                  55                  60

Gly Ser Ser Gly Tyr Asn Pro Leu Gly Ala Pro Ser Arg Val Thr Pro
65                  70                  75                  80

Ser Gly Thr Val Ile Arg Pro Thr Val Pro Val Glu Gly Leu Gly Pro
                85                  90                  95

Ser Glu Ile Ile Pro Val Asp Val Val Asn Pro Gly Ser Ser Ser Val
            100                 105                 110

Val Pro Leu Glu Asp Leu Thr Val Pro Glu Val Thr Ile Asp Ser Gly
        115                 120                 125

Glu Val Gly Gly Gly Leu His Pro Ser Glu Ile Asp Val Val Thr
    130                 135                 140

Ser Ser Asp Pro Ile Ser Asp Val Thr Gly Thr Ser Ser His Pro Thr
145                 150                 155                 160

Ile Ile Ser Gly Glu Asp Asn Ala Ile Ala Val Leu Asp Val Ser Pro
                165                 170                 175

Thr Glu Pro Pro Thr Lys Arg Ile Ala Leu Gly Thr Arg Gly Ala Thr
            180                 185                 190

Ser Thr Pro His Ile Ser Val Ile Ser Gly Thr Thr Glu Phe Gly Gln
        195                 200                 205

Ser Ser Asp Leu Asn Val Phe Val Asn Ala Thr Phe Ser Gly Asp Ser
    210                 215                 220

Ile Gly Tyr Thr Glu Glu Ile Pro Leu Glu Glu Leu Asn Thr Ile Gln
225                 230                 235                 240

Gln Phe Glu Ile Glu Thr Pro Pro Lys Thr Ser Thr Pro Arg Glu Thr
                245                 250                 255

Ile Gly Arg Ala Leu Glu Arg Ala Arg Asp Leu Tyr Asn Arg Arg Val
            260                 265                 270
```

```
Gln Gln Ile Ala Thr Arg Asn Pro Ala Met Leu Gly Gln Pro Ser Arg
            275                 280                 285

Ala Ile Val Phe Gly Phe Glu Asn Pro Ala Phe Asp Ala Asp Ile Thr
290                 295                 300

Gln Val Phe Glu Arg Asp Leu Glu Gln Val Ala Ala Pro Asp Ala
305                 310                 315                 320

Asp Phe Ala Asp Ile Val Arg Ile Gly Arg Pro Arg Phe Ser Gln Thr
                325                 330                 335

Asp Thr Gly Gln Ile Arg Ile Ser Arg Leu Gly Arg Arg Gly Thr Ile
            340                 345                 350

Lys Thr Arg Ser Gly Leu Gln Ile Gly Gln Ala Val His Phe Tyr Tyr
            355                 360                 365

Asp Leu Ser Thr Ile Asp Thr Ala Asp Ala Ile Glu Leu Ser Thr Leu
        370                 375                 380

Gly Gln His Ser Gly Glu Gln Ser Ile Val Asp Ala Met Ile Glu Ser
385                 390                 395                 400

Ser Phe Val Asp Pro Phe Glu Thr Pro Asp Pro Thr Tyr Thr Glu Glu
                405                 410                 415

Gln Gln Leu Leu Asp Pro Leu Thr Glu Asp Phe Ser Asn Ser His Leu
            420                 425                 430

Val Leu Thr Ser Ser Arg Arg Gly Ser Ser Phe Ser Ile Pro Thr Ile
            435                 440                 445

Pro Pro Gly Leu Gly Leu Arg Ile Tyr Val Asp Asp Val Gly Ser Asp
        450                 455                 460

Leu Phe Val Ser Tyr Pro Glu Thr Arg Val Ile Pro Ala Gly Gly Leu
465                 470                 475                 480

Pro Thr Glu Pro Phe Thr Pro Leu Glu Pro Pro Phe Phe Ser Glu Phe
                485                 490                 495

Tyr Ser Ser Asp Phe Val Tyr Arg Pro Ser Leu Tyr Arg Lys Lys Arg
                500                 505                 510

Lys Arg Ser Asp Ile Phe
        515

<210> SEQ ID NO 64
<211> LENGTH: 464
<212> TYPE: PRT
<213> ORGANISM: Human papillomavirus type 66

<400> SEQUENCE: 64

Met Val Ala His Arg Ala Thr Arg Arg Lys Arg Ala Ser Ala Thr Gln
1               5                   10                  15

Leu Tyr Lys Thr Cys Lys Leu Ser Gly Thr Cys Pro Glu Asp Val Ile
                20                  25                  30

Asn Lys Val Glu Gln Lys Thr Trp Ala Asp Arg Ile Leu Gln Trp Gly
            35                  40                  45

Ser Leu Phe Thr Tyr Phe Gly Gly Leu Gly Ile Gly Thr Gly Ser Gly
        50                  55                  60

Ser Gly Gly Arg Ala Gly Tyr Val Pro Leu Gly Ser Arg Pro Ser Thr
65                  70                  75                  80

Ile Val Asp Val Thr Pro Ala Arg Pro Pro Ile Val Val Glu Ser Val
                85                  90                  95

Gly Pro Thr Asp Pro Ser Ile Val Thr Leu Val Glu Glu Ser Ser Val
                100                 105                 110

Ile Asn Ser Gly Ala Gly Val Pro Asn Phe Thr Gly Ser Gly Gly Phe
```

115                 120                 125
Glu Val Thr Ser Ser Thr Thr Thr Pro Ala Val Leu Asp Ile Thr
130                 135                 140

Pro Thr Ser Ser Thr Val His Val Ser Ser Thr Thr Ile Thr Asn Pro
145                 150                 155                 160

Leu Tyr Ile Asp Pro Val Ile Glu Ala Pro Gln Thr Gly Glu Val
                165                 170                 175

Ser Gly Asn Ile Leu Ile Ser Thr Pro Thr Ser Gly Ile His Ser Tyr
            180                 185                 190

Glu Glu Ile Pro Met Gln Thr Phe Ala Ile His Gly Thr Gly Asn Glu
            195                 200                 205

Pro Ile Ser Ser Thr Pro Ile Pro Gly Phe Arg Arg Leu Ala Ala Pro
210                 215                 220

Arg Leu Tyr Ser Arg Ala Phe Gln Gln Val Arg Val Thr Asp Pro Ala
225                 230                 235                 240

Phe Leu Asp Asn Pro Thr Thr Leu Ile Thr Ala Asp Asn Pro Val Phe
                245                 250                 255

Glu Gly Ala Asp Thr Thr Leu Thr Phe Ser Pro Ser Gly Val Ala Pro
            260                 265                 270

Asp Pro Asp Phe Met Asp Ile Val Ala Leu His Arg Pro Ala Phe Thr
            275                 280                 285

Thr Arg Arg Thr Gly Val Arg Phe Ser Arg Leu Gly Lys Lys Ala Thr
290                 295                 300

Met Gln Thr Arg Arg Gly Thr Gln Ile Gly Ala Arg Val His Tyr Tyr
305                 310                 315                 320

Tyr Asp Ile Ser Pro Ile Ala Gln Ala Asp Glu Ile Glu Met Gln Pro
                325                 330                 335

Leu Leu Ser Thr Asp Asn Ser Phe Asp Gly Leu Tyr Asp Ile Tyr Ala
            340                 345                 350

Asn Ile Asp Asp Glu Ala Pro Ile Ser Phe Arg Gln Ser Gly Ala Thr
            355                 360                 365

Pro Ser Ala Gln Leu Pro Ile Lys Pro Ser Thr Leu Ser Phe Ala Ser
370                 375                 380

Asn Thr Thr Asn Val Thr Ala Pro Leu Gly Asn Val Trp Glu Thr Pro
385                 390                 395                 400

Leu Tyr Ser Gly Pro Asp Ile Val Leu Pro Thr Gly Pro Ser Thr Trp
                405                 410                 415

Pro Phe Val Pro Gln Ser Pro Tyr Asp Val Thr His Asp Val Tyr Ile
            420                 425                 430

Gln Gly Ala Thr Phe Ala Leu Trp Pro Val Tyr Phe Phe Lys Arg Arg
            435                 440                 445

Arg Arg Lys Arg Ile Pro Tyr Phe Phe Ala Asp Gly Asp Val Ala Ala
450                 455                 460

<210> SEQ ID NO 65
<211> LENGTH: 465
<212> TYPE: PRT
<213> ORGANISM: Human papillomavirus type 67

<400> SEQUENCE: 65

Met Arg His Lys Arg Ser Thr Arg Arg Lys Arg Ala Ser Ala Thr Gln
1               5                   10                  15

Leu Tyr Gln Thr Cys Lys Ala Ala Gly Thr Cys Pro Pro Asp Val Ile
            20                  25                  30

-continued

```
Pro Lys Val Glu Arg Thr Thr Ile Ala Asp Gln Ile Leu Lys Phe Gly
         35                  40                  45

Ser Leu Gly Val Phe Gly Gly Leu Gly Ile Gly Thr Gly Ser Gly
 50                  55                  60

Thr Gly Gly Arg Thr Gly Tyr Val Pro Leu Ser Thr Arg Pro Pro Thr
 65                  70                  75                  80

Ala Ser Ala Pro Thr Ser Thr Ile Arg Pro Pro Val Ser Val Asp Thr
                 85                  90                  95

Val Gly Pro Leu Asp Ser Ser Ile Val Ser Met Ile Glu Glu Thr Ser
                100                 105                 110

Phe Ile Glu Ser Gly Ala Pro Ala Pro Ser Ile Pro Thr Ala Ser Gly
        115                 120                 125

Phe Asp Val Ala Thr Ser Ala Asp Asn Thr Pro Ala Ile Ile Asn Val
        130                 135                 140

Ser Ser Ile Gly Glu Ser Ser Val Gln Ser Val Thr Thr His Leu Asn
145                 150                 155                 160

Pro Thr Phe Thr Glu Pro Ser Val Leu Arg Pro Phe Ser Ser Glu
                165                 170                 175

Ala Ser Gly His Leu Ile Phe Ser Thr Pro Thr Ile Ser Thr His Ser
                180                 185                 190

Tyr Glu Asp Ile Pro Met Asp Thr Phe Ile Val Ser Thr Ser Asp
        195                 200                 205

Asn Val Thr Ser Ser Thr Pro Ile Pro Arg Pro Arg Pro Thr Ala Arg
        210                 215                 220

Leu Gly Leu Tyr Ser Lys Gly Thr Gln Gln Val Lys Val Val Asp Pro
225                 230                 235                 240

Ala Phe Leu Thr Ser Pro Arg Arg Leu Ile Thr Phe Asp Asn Pro Ala
                245                 250                 255

Phe Gln Pro Thr Glu Pro Asp Glu Thr Leu Tyr Phe Gln His Gln Asp
        260                 265                 270

Ile Ser Pro Ala Pro Asp Pro Asp Phe Leu Asp Ile Val Ala Leu His
        275                 280                 285

Arg Pro Ala Leu Thr Ser Arg Lys Gly Thr Ile Arg Phe Ser Arg Leu
        290                 295                 300

Gly Ser Lys Ala Thr Met Lys Thr Arg Ser Gly Lys Gln Ile Gly Ala
305                 310                 315                 320

Arg Val His Tyr Tyr Gln Asp Leu Ser Pro Ile Val Pro Ala Asp Ser
                325                 330                 335

Ile Glu Leu Gln Pro Leu Ser Arg Pro Val Ser Ser Ala Ser His Ser
        340                 345                 350

Ile Asn Asp Gly Leu Tyr Asp Val Tyr Met Asp Pro Asp Thr Pro Phe
        355                 360                 365

Pro Gln Pro Ser Ile Ser Tyr Ser Leu His Ser Pro Gln Thr Thr Asn
        370                 375                 380

Val Thr Val Pro Leu Ser Ser Gly Phe Asp Phe Pro Phe Ser Ser Thr
385                 390                 395                 400

Val Pro Leu Gln Pro Gly Pro Asp Ile Val Ser Pro Val Ala Pro Thr
                405                 410                 415

Tyr Thr Pro Phe Val Pro Val Ile Pro Thr Ser Pro Phe Asn Asn Val
        420                 425                 430

Leu Val Tyr Gly Ser Asp Phe Ile Leu His Pro Ser Tyr Phe Leu Arg
        435                 440                 445

Arg Arg Arg Lys Arg Phe Pro Tyr Phe Phe Ala Asp Val Arg Val Ala
```

Ala
465

<210> SEQ ID NO 66
<211> LENGTH: 469
<212> TYPE: PRT
<213> ORGANISM: Human papillomavirus type 68

<400> SEQUENCE: 66

```
Met Val Ser His Arg Ala Ala Arg Arg Lys Arg Ala Ser Ala Thr Asp
1               5                   10                  15

Leu Tyr Lys Thr Cys Lys Gln Ser Gly Thr Cys Pro Ser Asp Val Ile
            20                  25                  30

Asn Lys Val Glu Gly Thr Thr Leu Ala Asp Lys Ile Leu Gln Trp Thr
        35                  40                  45

Ser Leu Gly Ile Phe Leu Gly Gly Leu Gly Ile Gly Thr Gly Ser Gly
    50                  55                  60

Thr Gly Gly Arg Ala Gly Tyr Ile Pro Leu Gly Gly Lys Pro Asn Thr
65                  70                  75                  80

Val Val Asp Val Ser Pro Ala Arg Pro Pro Val Val Ile Glu Pro Val
                85                  90                  95

Gly Pro Thr Glu Pro Ser Ile Val Gln Leu Val Glu Asp Ser Ser Val
            100                 105                 110

Ile Thr Ser Gly Thr Pro Val Pro Thr Phe Thr Gly Thr Ser Gly Phe
        115                 120                 125

Glu Ile Thr Ser Ser Ser Thr Thr Pro Ala Val Leu Asp Ile Thr
    130                 135                 140

Pro Ser Ser Gly Ser Val Gln Val Ser Ser Thr Ser Phe Thr Asn Pro
145                 150                 155                 160

Ala Phe Thr Asp Pro Thr Ile Ile Glu Val Pro Gln Thr Gly Glu Val
                165                 170                 175

Ser Gly Asn Val Phe Val Ser Thr Pro Thr Ser Gly Thr His Gly Tyr
            180                 185                 190

Glu Glu Ile Pro Met Gln Val Phe Ala Thr His Gly Thr Gly Thr Glu
        195                 200                 205

Pro Ile Ser Ser Thr Pro Ile Pro Gly Val Ser Arg Val Ala Gly Pro
    210                 215                 220

Arg Leu Tyr Ser Arg Ala His Gln Gln Val Arg Val Ser Asn Phe Asp
225                 230                 235                 240

Phe Val Thr His Pro Ser Ser Phe Val Thr Phe Asp Asn Pro Ala Phe
                245                 250                 255

Glu Pro Val Asp Thr Thr Leu Thr Tyr Glu Pro Ala Asp Ile Ala Pro
            260                 265                 270

Asp Pro Asp Phe Leu Asp Ile Val Arg Leu His Arg Pro Ala Leu Thr
        275                 280                 285

Ser Arg Arg Gly Thr Val Arg Phe Ser Arg Val Gly Lys Lys Ala Thr
    290                 295                 300

Met Phe Thr Arg Arg Gly Thr Gln Ile Gly Ala Gln Val His Tyr Tyr
305                 310                 315                 320

His Asp Ile Ser Asn Ile Thr Pro Ala Asp Ser Ile Glu Leu Gln Pro
                325                 330                 335

Leu Val Ala Pro Glu Gln Ala Asp Pro Met Asp Asn Leu Tyr Asp Ile
            340                 345                 350
```

```
Tyr Ala Pro Asp Thr Asp Asn Thr Val Leu Asp Thr Ala Phe His
            355                 360                 365

Asn Ala Thr Phe Thr Thr Arg Ser His Ile Ser Val Pro Ser Leu Ala
370                 375                 380

Ser Ala Ala Ser Thr Thr Tyr Thr Asn Thr Thr Ile Pro Leu Gly Thr
385                 390                 395                 400

Ala Trp Asn Thr Pro Val Asn Thr Gly Pro Asp Val Val Leu Pro Ser
                405                 410                 415

Thr Thr Pro Gln Leu Pro Leu Thr Pro Ser Thr Pro Ile Asp Thr Thr
            420                 425                 430

Phe Ala Ile Thr Ile Tyr Gly Ser Asn Tyr Tyr Leu Leu Pro Leu Leu
            435                 440                 445

Phe Phe Leu Leu Lys Lys Arg Lys His Leu Pro Tyr Phe Phe Thr Asp
450                 455                 460

Gly Ile Val Ala Ser
465

<210> SEQ ID NO 67
<211> LENGTH: 467
<212> TYPE: PRT
<213> ORGANISM: Human papillomavirus type 69

<400> SEQUENCE: 67

Met Val Val Arg Ala Ser Arg Lys Arg Ala Ser Ala Thr Asp
1               5                   10                  15

Leu Tyr Lys Thr Cys Lys Ala Ala Gly Thr Cys Pro Pro Asp Val Ile
                20                  25                  30

Pro Lys Ile Glu Gly Ser Thr Leu Ala Asp Lys Ile Leu Gln Trp Ser
            35                  40                  45

Gly Leu Gly Ile Phe Leu Gly Gly Leu Gly Ile Gly Thr Gly Thr Gly
50                  55                  60

Thr Gly Gly Arg Thr Gly Tyr Ile Pro Leu Gly Gly Gly Gly Arg Pro
65                  70                  75                  80

Ser Val Val Asp Ile Gly Pro Thr Arg Pro Pro Ile Ile Ile Glu Pro
                85                  90                  95

Val Gly Pro Thr Glu Pro Ser Ile Val Thr Leu Val Glu Glu Ser Ser
            100                 105                 110

Ile Ile Gln Ser Gly Ser Pro Phe Pro Asn Phe Ser Gly Gly Asp Gly
        115                 120                 125

Phe Glu Val Thr Thr Ser Ser Thr Thr Thr Pro Ala Val Leu Asp Ile
130                 135                 140

Thr Pro Ser Pro Gly Thr Val His Val Thr Ser Thr Asn Ile Gln Asn
145                 150                 155                 160

Pro Leu Tyr Ile Glu Pro Pro Val Asp Ile Pro Gln Ser Gly Glu Ala
                165                 170                 175

Leu Gly His Ile Phe Thr Ser Thr Ser Thr Ala Gly Thr His Ser Tyr
            180                 185                 190

Glu Glu Ile Pro Met Glu Val Phe Ala Ser Asn Thr Ser Ser Gly Ser
        195                 200                 205

Lys Pro Ile Ser Ser Thr Pro Ile Pro Gly Ile Arg Arg Val Ala Ala
210                 215                 220

Pro Arg Leu Tyr Ser Lys Ala Tyr Gln Gln Val Lys Val Thr Asp Pro
225                 230                 235                 240

Asn Phe Ile Ser Lys Pro Ser Thr Phe Ile Thr Phe Asp Asn Pro Ala
                245                 250                 255
```

Tyr Glu Pro Met Asp Thr Thr Leu Thr Phe Ser Ala Asp Ser His Val
        260                 265                 270

Ala Pro Asp Pro Asp Phe Leu Asp Ile Ile Ala Leu His Arg Pro Ala
        275                 280                 285

Leu Thr Ser Arg Arg Gly Thr Val Arg Phe Ser Arg Leu Gly Gln Lys
        290                 295                 300

Ala Thr Leu Lys Thr Arg Ser Gly Lys Gln Ile Gly Ala Lys Val His
305                 310                 315                 320

Tyr Tyr His Asp Ile Ser Pro Ile His Ala Thr Glu Glu Ala Ile Glu
                325                 330                 335

Leu Gln Pro Leu Ile Thr Ser Glu Gln His Ser Thr Pro Leu Phe Asp
        340                 345                 350

Val Tyr Ala Asp Ala Asp Pro Ala Pro Thr Phe Thr Phe Pro Ser Thr
        355                 360                 365

Thr Pro Thr Thr Ile Pro Arg Phe Ser Ser Thr Ile Phe Ser Thr Thr
        370                 375                 380

Ser Ser Ala Pro Leu Asn Val Thr Ile Pro Leu Ser Thr Ser Phe Asp
385                 390                 395                 400

Ile Pro Ile Tyr Asn Gly Pro Asp Ile Tyr Ala Pro Val Pro Ser Ser
                405                 410                 415

Thr Trp Pro Tyr Ile Pro Pro Pro Thr Thr Met Ser His Ser Val
        420                 425                 430

Val Ala Gln Gly Gly Asn Tyr Tyr Leu Trp Pro Tyr Ile Tyr Leu Ile
        435                 440                 445

His Lys Arg Arg Arg Lys Arg Val Pro Cys Phe Phe Ser Asp Gly Leu
450                 455                 460

Ala Ala Tyr
465

<210> SEQ ID NO 68
<211> LENGTH: 466
<212> TYPE: PRT
<213> ORGANISM: Human papillomavirus type 70

<400> SEQUENCE: 68

Met Val Ser Ser Arg Ala Ser Arg Arg Lys Arg Ala Ser Ala Thr Asp
1               5                   10                  15

Ile Tyr Lys Thr Cys Lys Gln Ser Gly Thr Cys Pro Pro Asp Val Val
                20                  25                  30

Asn Lys Val Glu Gly Thr Thr Leu Ala Asp Arg Phe Leu Gln Trp Ala
            35                  40                  45

Ser Leu Gly Ile Phe Leu Gly Gly Leu Gly Ile Gly Thr Gly Thr Gly
        50                  55                  60

Thr Gly Gly Arg Thr Gly Tyr Ile Pro Leu Gly Gly Arg Pro Ser Thr
65                  70                  75                  80

Val Val Asp Val Thr Pro Ala Arg Pro Pro Val Val Ile Glu Pro Val
                85                  90                  95

Gly Pro Thr Glu Pro Ser Ile Val Gln Leu Val Glu Glu Ser Ser Val
            100                 105                 110

Val Ser Ser Gly Thr Pro Ile Pro Thr Phe Thr Gly Ser Ser Gly Phe
        115                 120                 125

Glu Ile Thr Ser Ser Ala Thr Thr Thr Pro Ala Val Leu Asp Ile Thr
    130                 135                 140

Pro Ala Ser Gly Ser Val Gln Ile Ser Thr Thr Ser Tyr Thr Asn Pro

-continued

```
                145                 150                 155                 160
        Ala Phe Ala Asp Pro Ser Leu Ile Glu Val Pro Gln Thr Gly Glu Val
                        165                 170                 175

Ser Gly Asn Ile Phe Val Thr Pro Thr Ser Gly Thr His Gly Tyr
                    180                 185                 190

Glu Glu Ile Pro Met Gln Val Phe Ala Ser His Gly Thr Gly Thr Glu
                        195                 200                 205

Pro Ile Ser Ser Thr Pro Val Pro Gly Val Ser Arg Val Ala Gly Pro
                    210                 215                 220

Arg Leu Tyr Ser Arg Ala Tyr His Gln Val Arg Val Asn Asn Phe Asp
        225                 230                 235                 240

Phe Val Thr Arg Pro Ser Ser Phe Val Thr Phe Asp Asn Pro Ala Phe
                        245                 250                 255

Glu Pro Gly Asp Thr Ser Leu Thr Phe Glu Pro Ala Asp Thr Ala Pro
                    260                 265                 270

Asp Pro Asp Phe Leu Asp Ile Val Arg Leu His Arg Pro Ala Leu Thr
                    275                 280                 285

Ser Arg Arg Gly Thr Val Arg Phe Ser Arg Leu Gly Lys Lys Ala Thr
                290                 295                 300

Met Phe Thr Arg Arg Gly Thr Gln Ile Gly Ala Gln Val His Tyr Tyr
        305                 310                 315                 320

His Asp Ile Ser Asn Ile Thr Ala Thr Glu Asp Ile Glu Met Gln Pro
                        325                 330                 335

Leu Leu Thr Ser Glu Ser Thr Asp Gly Leu Tyr Asp Ile Tyr Ala Asp
                    340                 345                 350

Ala Asp Ile Asp Asn Ala Met Leu His Thr Thr Ser His Thr Gly Ser
                    355                 360                 365

Thr Gly Pro Arg Ser His Leu Ser Phe Pro Ser Ile Pro Ser Thr Val
                370                 375                 380

Ser Thr Lys Tyr Ser Asn Thr Thr Ile Pro Phe Thr Thr Ser Trp Asp
        385                 390                 395                 400

Ile Pro Val Thr Thr Gly Pro Asp Ile Val Leu Pro Thr Ala Ser Pro
                        405                 410                 415

Asn Leu Pro Phe Val Pro Pro Thr Ser Ile Asp Thr Thr Val Ala Ile
                    420                 425                 430

Ala Ile Gln Gly Ser Asn Tyr Tyr Leu Leu Pro Leu Leu Tyr Tyr Phe
                    435                 440                 445

Leu Lys Lys Arg Lys Arg Ile Pro Tyr Phe Phe Thr Asp Gly Phe Val
                450                 455                 460

Ala Val
        465

<210> SEQ ID NO 69
<211> LENGTH: 475
<212> TYPE: PRT
<213> ORGANISM: Human papillomavirus type 73

<400> SEQUENCE: 69

Met Arg Arg Lys Arg Asp Thr His Ile Arg Lys Lys Arg Ala Ser Ala
        1               5                   10                  15

Thr Gln Leu Tyr Lys Thr Cys Lys Gln Ala Gly Thr Cys Pro Pro Asp
                        20                  25                  30

Val Ile Pro Lys Val Glu Gly Ser Thr Ile Ala Asp Asn Ile Leu Lys
                    35                  40                  45
```

-continued

Tyr Gly Ser Ile Gly Val Phe Phe Gly Gly Leu Gly Ile Gly Ser Gly
    50                  55                  60

Ser Gly Ser Gly Gly Arg Thr Gly Tyr Val Pro Leu Ser Thr Gly Thr
65              70                  75                  80

Pro Ser Lys Pro Val Glu Ile Pro Leu Gln Pro Ile Arg Pro Ser Val
                85                  90                  95

Val Thr Ser Val Gly Pro Ser Asp Ser Ser Ile Val Ser Leu Val Glu
            100                 105                 110

Glu Ser Ser Phe Ile Glu Ser Gly Ile Pro Gly Pro Thr Ser Ile Val
            115                 120                 125

Pro Ser Thr Ser Gly Phe Asp Ile Thr Thr Ser Val Asn Ser Thr Pro
    130                 135                 140

Ala Ile Ile Asp Val Ser Ala Ile Ser Asp Thr Thr Gln Ile Ser Val
145                 150                 155                 160

Thr Thr Phe Lys Asn Pro Thr Phe Thr Asp Pro Ser Val Leu Gln Pro
                165                 170                 175

Pro Pro Pro Leu Glu Ala Ser Gly Arg Leu Leu Phe Ser Asn Asp Thr
            180                 185                 190

Val Thr Thr His Ser Tyr Glu Asn Ile Pro Leu Asp Thr Phe Val Val
            195                 200                 205

Thr Thr Asp His Asn Ser Ile Val Ser Ser Thr Pro Ile Pro Gly Arg
210                 215                 220

Gln Pro Ala Ala Arg Leu Gly Leu Tyr Gly Arg Ala Ile Gln Gln Val
225                 230                 235                 240

Lys Val Val Asp Pro Ala Phe Leu Thr Thr Pro Thr Arg Leu Val Thr
                245                 250                 255

Tyr Asp Asn Pro Ala Phe Glu Gly Leu Gln Asp Thr Thr Leu Glu Phe
            260                 265                 270

Gln His Ser Asp Leu His Asn Ala Pro Asp Ser Asp Phe Leu Asp Ile
            275                 280                 285

Val Lys Leu His Arg Pro Ala Leu Thr Ser Arg Lys Thr Gly Ile Arg
290                 295                 300

Val Ser Arg Leu Gly Gln Arg Ala Thr Leu Ser Thr Arg Ser Gly Lys
305                 310                 315                 320

Arg Ile Gly Ala Lys Val His Phe Tyr His Asp Ile Ser Pro Ile Pro
                325                 330                 335

Thr Asn Asp Ile Glu Met Gln Pro Leu Val Thr Pro Gln Thr Pro Ser
            340                 345                 350

Ile Val Thr Gly Ser Ser Ile Asn Asp Gly Leu Tyr Asp Val Phe Leu
            355                 360                 365

Asp Asn Asp Val Glu Glu Thr Val Leu Gln Gln Thr Tyr Thr Pro Thr
370                 375                 380

Ser Ile His Ser Asn Ser Leu Val Ser Ser Asp Ile Ser Thr Ala Thr
385                 390                 395                 400

Ala Asn Thr Thr Ile Pro Phe Ser Thr Gly Leu Asp Thr His Pro Gly
                405                 410                 415

Pro Asp Ile Ala Leu Pro Leu Pro Ser Thr Glu Thr Ile Phe Thr Pro
            420                 425                 430

Ile Val Pro Leu Gln Pro Ala Gly Pro Ile Tyr Ile Tyr Gly Ser Gly
            435                 440                 445

Phe Ile Leu His Pro Ser Tyr Tyr Leu Leu Lys Arg Lys Arg Lys Arg
450                 455                 460

Leu Ser Tyr Ser Phe Thr Asp Val Ala Thr Tyr

<210> SEQ ID NO 70
<211> LENGTH: 473
<212> TYPE: PRT
<213> ORGANISM: Human papillomavirus type 82

<400> SEQUENCE: 70

```
Met Val Ala Ala Arg Ala Arg Arg Lys Arg Ala Ser Val Thr Gln
1               5                   10                  15

Leu Tyr Ser Thr Cys Lys Ala Ala Gly Thr Cys Pro Ala Asp Val Ile
            20                  25                  30

Pro Lys Val Glu Gly Thr Thr Leu Ala Asp Lys Ile Leu Gln Trp Ser
                35                  40                  45

Gly Leu Gly Ile Phe Leu Gly Gly Leu Gly Ile Gly Thr Gly Ser Gly
        50                  55                  60

Thr Gly Gly Arg Thr Gly Tyr Ile Pro Leu Gly Gly Gly Arg Pro
65                  70                  75                  80

Gly Val Val Asp Ile Ala Pro Ala Arg Pro Pro Ile Ile Ile Glu Pro
                85                  90                  95

Val Ala Pro Thr Glu Pro Ser Ile Val Asn Leu Val Glu Asp Ser Ser
                100                 105                 110

Ile Ile Asn Ser Gly Ser Thr Ile Pro Thr Phe Thr Gly Thr Asp Gly
            115                 120                 125

Phe Glu Ile Thr Ser Ser Ser Thr Thr Thr Pro Ala Val Leu Asp Ile
130                 135                 140

Thr Pro Ser Thr Gly Thr Val Arg Val Thr Ser Thr Asn Ile Glu Asn
145                 150                 155                 160

Pro Leu Tyr Ile Glu Pro Pro Phe Ile Glu Ala Pro Gln Ser Gly Glu
                165                 170                 175

Val Ser Gly His Ile Phe Thr Ser Thr Pro Thr Ser Gly Thr His Gly
            180                 185                 190

Tyr Glu Glu Ile Pro Met Glu Val Phe Ala Ser Asn Val Ser Thr Gly
        195                 200                 205

Glu Gln Pro Ile Ser Ser Thr Pro Thr Pro Gly Val Arg Arg Ile Ala
210                 215                 220

Ala Pro Arg Leu Tyr Ser Lys Ala Phe Thr Gln Val Lys Val Thr Asn
225                 230                 235                 240

Pro Asp Phe Ile Ser Arg Pro Ser Ser Phe Val Thr Phe Asp Asn Pro
                245                 250                 255

Ala Phe Glu Pro Ile Asp Ala Ser Leu Ser Phe Gly Glu Pro Thr Thr
            260                 265                 270

Val Ala Pro Asp Pro Asp Phe Leu Asp Ile Ile Lys Leu His Arg Pro
        275                 280                 285

Ala Leu Thr Ser Arg Arg Gly Thr Val Arg Phe Ser Arg Leu Gly Gln
290                 295                 300

Lys Ala Thr Ile Arg Thr Arg Ser Gly Lys Gln Ile Gly Ala Arg Val
305                 310                 315                 320

His Tyr Tyr His Asp Ile Ser Asn Ile Thr Pro Thr Glu Glu Leu Glu
                325                 330                 335

Met Gln Pro Leu Leu Ser Pro Ser Thr Asn Asn Tyr Ser Tyr Asp Ile
            340                 345                 350

Tyr Ala Asp Leu Asp Glu Ala Glu Thr Gly Phe Ile Gln Pro Thr His
        355                 360                 365
```

-continued

```
Thr Thr Pro Met Leu Arg Ser Ser Tyr Ser Pro Leu Ser Thr Gln Leu
        370                 375                 380

Pro Ser Leu Ser Ser Val Ser Ser Tyr Ala Asn Val Thr Ile
385                 390                 395                 400

Pro Phe Ser Thr Thr Tyr His Val Pro Ile His Thr Gly Pro Asp Val
                    405                 410                 415

Val Leu Pro Thr Ser Pro Thr Val Trp Pro Phe Ile Pro His Thr Ser
                420                 425                 430

Ile Asp Thr Gln His Ala Ile Val Ile Gln Gly Gly Asp Tyr Tyr Leu
                435                 440                 445

Trp Pro Tyr Thr Tyr Leu Leu Arg Lys Arg Arg Lys Arg Ile Pro Tyr
450                 455                 460

Phe Phe Ala Asp Gly Phe Val Ala Tyr
465                 470

<210> SEQ ID NO 71
<211> LENGTH: 20
<212> TYPE: PRT
<213> ORGANISM: Human papillomavirus type 16

<400> SEQUENCE: 71

Gln Leu Tyr Lys Thr Cys Lys Gln Ala Gly Thr Cys Pro Pro Asp Ile
1               5                   10                  15

Ile Pro Lys Val
            20

<210> SEQ ID NO 72
<211> LENGTH: 20
<212> TYPE: PRT
<213> ORGANISM: Human papillomavirus type 1a

<400> SEQUENCE: 72

Asp Ile Tyr Pro Ser Cys Lys Ile Ser Asn Thr Cys Pro Pro Asp Ile
1               5                   10                  15

Gln Asn Lys Ile
            20

<210> SEQ ID NO 73
<211> LENGTH: 20
<212> TYPE: PRT
<213> ORGANISM: Human papillomavirus type 2

<400> SEQUENCE: 73

Asp Leu Tyr Arg Thr Cys Lys Gln Ala Gly Thr Cys Pro Pro Asp Ile
1               5                   10                  15

Ile Pro Arg Val
            20

<210> SEQ ID NO 74
<211> LENGTH: 20
<212> TYPE: PRT
<213> ORGANISM: Human papillomavirus type 63

<400> SEQUENCE: 74

Asp Ile Tyr Pro Ala Cys Lys Val Ala Asn Cys Pro Asp Ile
1               5                   10                  15

Gln Asn Lys Ile
            20

<210> SEQ ID NO 75
```

```
<211> LENGTH: 20
<212> TYPE: PRT
<213> ORGANISM: Human papillomavirus type 5

<400> SEQUENCE: 75

His Ile Tyr Gln Thr Cys Lys Gln Ala Gly Thr Cys Pro Pro Asp Val
1               5                   10                  15

Ile Asn Lys Val
            20

<210> SEQ ID NO 76
<211> LENGTH: 20
<212> TYPE: PRT
<213> ORGANISM: Human papillomavirus type 8

<400> SEQUENCE: 76

His Ile Tyr Gln Thr Cys Lys Gln Ala Gly Thr Cys Pro Pro Asp Val
1               5                   10                  15

Ile Asn Lys Val
            20

<210> SEQ ID NO 77
<211> LENGTH: 20
<212> TYPE: PRT
<213> ORGANISM: Human papillomavirus type 6

<400> SEQUENCE: 77

Gln Leu Tyr Gln Thr Cys Lys Leu Thr Gly Thr Cys Pro Pro Asp Val
1               5                   10                  15

Ile Pro Lys Val
            20

<210> SEQ ID NO 78
<211> LENGTH: 20
<212> TYPE: PRT
<213> ORGANISM: Human papillomavirus type 11

<400> SEQUENCE: 78

Gln Leu Tyr Gln Thr Cys Lys Ala Thr Gly Thr Cys Pro Pro Asp Val
1               5                   10                  15

Ile Pro Lys Val
            20

<210> SEQ ID NO 79
<211> LENGTH: 20
<212> TYPE: PRT
<213> ORGANISM: Human papillomavirus type 18

<400> SEQUENCE: 79

Asp Leu Tyr Lys Thr Cys Lys Gln Ser Gly Thr Cys Pro Pro Asp Val
1               5                   10                  15

Val Pro Lys Val
            20

<210> SEQ ID NO 80
<211> LENGTH: 20
<212> TYPE: PRT
<213> ORGANISM: Human papillomavirus type 31

<400> SEQUENCE: 80

Gln Leu Tyr Gln Thr Cys Lys Ala Ala Gly Thr Cys Pro Ser Asp Val
1               5                   10                  15
```

```
Ile Pro Lys Ile
            20

<210> SEQ ID NO 81
<211> LENGTH: 20
<212> TYPE: PRT
<213> ORGANISM: Human papillomavirus type 33

<400> SEQUENCE: 81

Gln Leu Tyr Gln Thr Cys Lys Ala Thr Gly Thr Cys Pro Pro Asp Val
1               5                   10                  15

Ile Pro Lys Val
            20

<210> SEQ ID NO 82
<211> LENGTH: 20
<212> TYPE: PRT
<213> ORGANISM: Human papillomavirus type 35

<400> SEQUENCE: 82

Gln Leu Tyr Arg Thr Cys Lys Ala Ala Gly Thr Cys Pro Pro Asp Val
1               5                   10                  15

Ile Pro Lys Val
            20

<210> SEQ ID NO 83
<211> LENGTH: 20
<212> TYPE: PRT
<213> ORGANISM: Human papillomavirus type 39

<400> SEQUENCE: 83

Asp Leu Tyr Arg Thr Cys Lys Gln Ser Gly Thr Cys Pro Pro Asp Val
1               5                   10                  15

Val Asp Lys Val
            20

<210> SEQ ID NO 84
<211> LENGTH: 20
<212> TYPE: PRT
<213> ORGANISM: Human papillomavirus type 45

<400> SEQUENCE: 84

Asp Leu Tyr Arg Thr Cys Lys Gln Ser Gly Thr Cys Pro Pro Asp Val
1               5                   10                  15

Ile Asn Lys Val
            20

<210> SEQ ID NO 85
<211> LENGTH: 20
<212> TYPE: PRT
<213> ORGANISM: Human papillomavirus type 51

<400> SEQUENCE: 85

Gln Leu Tyr Ser Thr Cys Lys Ala Ala Gly Thr Cys Pro Pro Asp Val
1               5                   10                  15

Val Asn Lys Val
            20

<210> SEQ ID NO 86
<211> LENGTH: 20
<212> TYPE: PRT
<213> ORGANISM: Human papillomavirus type 52
```

-continued

```
<400> SEQUENCE: 86

Gln Leu Tyr Gln Thr Cys Lys Ala Ser Gly Thr Cys Pro Pro Asp Val
1               5                   10                  15

Ile Pro Lys Val
            20

<210> SEQ ID NO 87
<211> LENGTH: 20
<212> TYPE: PRT
<213> ORGANISM: Human papillomavirus type 56

<400> SEQUENCE: 87

Gln Leu Tyr Lys Thr Cys Lys Leu Ser Gly Thr Cys Pro Glu Asp Val
1               5                   10                  15

Val Asn Lys Ile
            20

<210> SEQ ID NO 88
<211> LENGTH: 20
<212> TYPE: PRT
<213> ORGANISM: Human papillomavirus type 58

<400> SEQUENCE: 88

Gln Leu Tyr Gln Thr Cys Lys Ala Ser Gly Thr Cys Pro Pro Asp Val
1               5                   10                  15

Ile Pro Lys Val
            20

<210> SEQ ID NO 89
<211> LENGTH: 20
<212> TYPE: PRT
<213> ORGANISM: Human papillomavirus type 59

<400> SEQUENCE: 89

Asp Leu Tyr Lys Thr Cys Lys Gln Ala Gly Thr Cys Pro Ser Asp Val
1               5                   10                  15

Ile Asn Lys Val
            20

<210> SEQ ID NO 90
<211> LENGTH: 20
<212> TYPE: PRT
<213> ORGANISM: Human papillomavirus type 68

<400> SEQUENCE: 90

Asp Leu Tyr Lys Thr Cys Lys Gln Ser Gly Thr Cys Pro Ser Asp Val
1               5                   10                  15

Ile Asn Lys Val
            20

<210> SEQ ID NO 91
<211> LENGTH: 20
<212> TYPE: PRT
<213> ORGANISM: Human papillomavirus type 73

<400> SEQUENCE: 91

Gln Leu Tyr Lys Thr Cys Lys Gln Ala Gly Thr Cys Pro Pro Asp Val
1               5                   10                  15

Ile Pro Lys Val
            20
```

```
<210> SEQ ID NO 92
<211> LENGTH: 20
<212> TYPE: PRT
<213> ORGANISM: Human papillomavirus type 82

<400> SEQUENCE: 92

Gln Leu Tyr Ser Thr Cys Lys Ala Ala Gly Thr Cys Pro Pro Asp Val
1               5                   10                  15

Ile Pro Lys Val
            20

<210> SEQ ID NO 93
<211> LENGTH: 440
<212> TYPE: PRT
<213> ORGANISM: Human papillomavirus

<400> SEQUENCE: 93

Asp Ile Tyr Pro Ser Cys Lys Ile Ser Asn Thr Cys Pro Pro Asp Ile
1               5                   10                  15

Gln Asn Lys Ile Asp Leu Tyr Arg Thr Cys Lys Gln Ala Gly Thr Cys
            20                  25                  30

Pro Pro Asp Ile Ile Pro Arg Val Asp Ile Tyr Pro Ala Cys Lys Val
        35                  40                  45

Ala Asn Asn Cys Pro Pro Asp Ile Gln Asn Lys Ile His Ile Tyr Gln
    50                  55                  60

Thr Cys Lys Gln Ala Gly Thr Cys Pro Pro Asp Val Ile Asn Lys Val
65                  70                  75                  80

His Ile Tyr Gln Thr Cys Lys Gln Ala Gly Thr Cys Pro Pro Asp Val
                85                  90                  95

Ile Asn Lys Val Gln Leu Tyr Gln Thr Cys Lys Leu Thr Gly Thr Cys
            100                 105                 110

Pro Pro Asp Val Ile Pro Lys Val Gln Leu Tyr Gln Thr Cys Lys Ala
        115                 120                 125

Thr Gly Thr Cys Pro Pro Asp Val Ile Pro Lys Val Gln Leu Tyr Lys
    130                 135                 140

Thr Cys Lys Gln Ala Gly Thr Cys Pro Pro Asp Ile Ile Pro Lys Val
145                 150                 155                 160

Asp Leu Tyr Lys Thr Cys Lys Gln Ser Gly Thr Cys Pro Pro Asp Val
                165                 170                 175

Val Pro Lys Val Gln Leu Tyr Gln Thr Cys Lys Ala Ala Gly Thr Cys
            180                 185                 190

Pro Ser Asp Val Ile Pro Lys Ile Gln Leu Tyr Gln Thr Cys Lys Ala
        195                 200                 205

Thr Gly Thr Cys Pro Pro Asp Val Ile Pro Lys Val Gln Leu Tyr Arg
    210                 215                 220

Thr Cys Lys Ala Ala Gly Thr Cys Pro Pro Asp Val Ile Pro Lys Val
225                 230                 235                 240

Asp Leu Tyr Arg Thr Cys Lys Gln Ser Gly Thr Cys Pro Pro Asp Val
                245                 250                 255

Val Asp Lys Val Asp Leu Tyr Arg Thr Cys Lys Gln Ser Gly Thr Cys
            260                 265                 270

Pro Pro Asp Val Ile Asn Lys Val Gln Leu Tyr Ser Thr Cys Lys Ala
        275                 280                 285

Ala Gly Thr Cys Pro Pro Asp Val Val Asn Lys Val Gln Leu Tyr Gln
    290                 295                 300

Thr Cys Lys Ala Ser Gly Thr Cys Pro Pro Asp Val Ile Pro Lys Val
```

```
                305                 310                 315                 320
Gln Leu Tyr Lys Thr Cys Lys Leu Ser Gly Thr Cys Pro Glu Asp Val
                325                 330                 335

Val Asn Lys Ile Gln Leu Tyr Gln Thr Cys Lys Ala Ser Gly Thr Cys
                340                 345                 350

Pro Pro Asp Val Ile Pro Lys Val Asp Leu Tyr Lys Thr Cys Lys Gln
                355                 360                 365

Ala Gly Thr Cys Pro Ser Asp Val Ile Asn Lys Val Asp Leu Tyr Lys
                370                 375                 380

Thr Cys Lys Gln Ser Gly Thr Cys Pro Ser Asp Val Ile Asn Lys Val
385                 390                 395                 400

Gln Leu Tyr Lys Thr Cys Lys Gln Ala Gly Thr Cys Pro Pro Asp Val
                405                 410                 415

Ile Pro Lys Val Gln Leu Tyr Ser Thr Cys Lys Ala Ala Gly Thr Cys
                420                 425                 430

Pro Pro Asp Val Ile Pro Lys Val
                435                 440

<210> SEQ ID NO 94
<211> LENGTH: 78
<212> TYPE: PRT
<213> ORGANISM: Human papillomavirus type 1a

<400> SEQUENCE: 94

Lys Arg Ala Ser Ala Thr Gln Leu Tyr Lys Thr Cys Lys Gln Ala Gly
1               5                   10                  15

Thr Cys Pro Pro Asp Ile Ile Pro Lys Val Glu Gly Lys Thr Ile Ala
                20                  25                  30

Asp Gln Ile Leu Gln Tyr Gly Ser Met Gly Val Phe Phe Gly Gly Leu
                35                  40                  45

Gly Ile Gly Thr Gly Ser Gly Thr Gly Gly Arg Thr Gly Tyr Ile Pro
        50                  55                  60

Leu Gly Thr Arg Pro Pro Thr Ala Thr Asp Thr Leu Ala Pro
65                  70                  75

<210> SEQ ID NO 95
<211> LENGTH: 78
<212> TYPE: PRT
<213> ORGANISM: Human papillomavirus type 5

<400> SEQUENCE: 95

Lys Arg Ala Ser Val Thr Asp Leu Tyr Lys Thr Cys Lys Gln Ser Gly
1               5                   10                  15

Thr Cys Pro Pro Asp Val Val Pro Lys Val Glu Gly Thr Thr Leu Ala
                20                  25                  30

Asp Lys Ile Leu Gln Trp Ser Ser Leu Gly Ile Phe Leu Gly Gly Leu
                35                  40                  45

Gly Ile Gly Thr Gly Ser Gly Thr Gly Gly Arg Thr Gly Tyr Ile Pro
        50                  55                  60

Leu Gly Gly Arg Ser Asn Thr Val Val Asp Val Gly Pro Thr
65                  70                  75

<210> SEQ ID NO 96
<211> LENGTH: 78
<212> TYPE: PRT
<213> ORGANISM: Human papillomavirus type 6

<400> SEQUENCE: 96
```

```
Lys Arg Ala Ala Pro Lys Asp Ile Tyr Pro Ser Cys Lys Ile Ser Asn
1               5                   10                  15

Thr Cys Pro Pro Asp Ile Gln Asn Lys Ile Glu His Thr Thr Ile Ala
            20                  25                  30

Asp Lys Ile Leu Gln Tyr Gly Ser Leu Gly Val Phe Leu Gly Gly Leu
                35                  40                  45

Gly Ile Gly Thr Ala Arg Gly Ser Gly Gly Arg Ile Gly Tyr Thr Pro
            50                  55                  60

Leu Gly Glu Gly Gly Gly Val Arg Val Ala Thr Arg Pro Thr
65                  70                  75
```

<210> SEQ ID NO 97
<211> LENGTH: 78
<212> TYPE: PRT
<213> ORGANISM: Human papillomavirus type 16

<400> SEQUENCE: 97

```
Lys Arg Asp Ser Val Thr His Ile Tyr Gln Thr Cys Lys Gln Ala Gly
1               5                   10                  15

Thr Cys Pro Pro Asp Val Ile Asn Lys Val Glu Gln Thr Thr Val Ala
            20                  25                  30

Asp Asn Ile Leu Lys Tyr Gly Ser Ala Gly Val Phe Phe Gly Gly Leu
                35                  40                  45

Gly Ile Ser Thr Gly Arg Gly Thr Gly Gly Ala Thr Gly Tyr Val Pro
            50                  55                  60

Leu Gly Glu Gly Pro Gly Val Arg Val Gly Gly Thr Pro Thr
65                  70                  75
```

<210> SEQ ID NO 98
<211> LENGTH: 78
<212> TYPE: PRT
<213> ORGANISM: Human papillomavirus type 18

<400> SEQUENCE: 98

```
Lys Arg Ala Ser Ala Thr Gln Leu Tyr Gln Thr Cys Lys Leu Thr Gly
1               5                   10                  15

Thr Cys Pro Pro Asp Val Ile Pro Lys Val Glu His Asn Thr Ile Ala
            20                  25                  30

Asp Gln Ile Leu Lys Trp Gly Ser Leu Gly Val Phe Phe Gly Gly Leu
                35                  40                  45

Gly Ile Gly Thr Gly Ser Gly Thr Gly Gly Arg Thr Gly Tyr Val Pro
            50                  55                  60

Leu Gly Thr Ser Ala Lys Pro Ser Ile Thr Ser Gly Pro Met
65                  70                  75
```

<210> SEQ ID NO 99
<211> LENGTH: 79
<212> TYPE: PRT
<213> ORGANISM: Human papillomavirus type 6

<400> SEQUENCE: 99

```
Ser Ala Thr Gln Leu Tyr Gln Thr Cys Lys Leu Thr Gly Thr Cys Pro
1               5                   10                  15

Pro Asp Val Ile Pro Lys Val Glu His Asn Thr Ile Ala Asp Gln Ile
            20                  25                  30

Leu Lys Trp Gly Ser Leu Gly Val Phe Phe Gly Gly Leu Gly Ile Gly
                35                  40                  45
```

```
Thr Gly Ser Gly Thr Gly Gly Arg Thr Gly Tyr Val Pro Leu Gln Thr
         50                  55                  60

Ser Ala Lys Pro Ser Ile Thr Ser Gly Pro Met Ala Lys Arg Ala
 65                  70                  75

<210> SEQ ID NO 100
<211> LENGTH: 77
<212> TYPE: PRT
<213> ORGANISM: Human papillomavirus type 16

<400> SEQUENCE: 100

Ser Ala Thr Gln Leu Tyr Lys Thr Cys Lys Gln Ala Gly Thr Cys Pro
 1               5                  10                  15

Pro Asp Ile Ile Pro Lys Val Glu Gly Lys Thr Ile Ala Asp Gln Ile
                 20                  25                  30

Leu Gln Tyr Gly Ser Met Gly Val Phe Phe Gly Gly Leu Gly Ile Gly
             35                  40                  45

Thr Gly Ser Gly Thr Gly Gly Arg Thr Gly Tyr Ile Pro Leu Gly Thr
         50                  55                  60

Arg Pro Pro Thr Ala Thr Asp Thr Leu Ala Pro Arg Ala
 65                  70                  75

<210> SEQ ID NO 101
<211> LENGTH: 79
<212> TYPE: PRT
<213> ORGANISM: Human papillomavirus type 18

<400> SEQUENCE: 101

Ser Val Thr Asp Leu Tyr Lys Thr Cys Lys Gln Ser Gly Thr Cys Pro
 1               5                  10                  15

Pro Asp Val Val Pro Lys Val Glu Gly Thr Thr Leu Ala Asp Lys Ile
                 20                  25                  30

Leu Gln Trp Ser Ser Leu Gly Ile Phe Leu Gly Gly Leu Gly Ile Gly
             35                  40                  45

Thr Gly Ser Gly Thr Gly Gly Arg Thr Gly Tyr Ile Pro Leu Gly Gly
         50                  55                  60

Arg Ser Asn Thr Val Val Asp Val Gly Pro Thr Arg Lys Arg Ala
 65                  70                  75

<210> SEQ ID NO 102
<211> LENGTH: 77
<212> TYPE: PRT
<213> ORGANISM: Human papillomavirus type 31

<400> SEQUENCE: 102

Ser Ala Thr Gln Leu Tyr Gln Thr Cys Lys Ala Ala Gly Thr Cys Pro
 1               5                  10                  15

Ser Asp Val Ile Pro Lys Ile Glu His Thr Thr Ile Ala Asp Gln Ile
                 20                  25                  30

Leu Arg Tyr Gly Ser Met Gly Val Phe Phe Gly Gly Leu Gly Ile Gly
             35                  40                  45

Ser Gly Ser Gly Thr Gly Gly Arg Thr Gly Tyr Val Pro Leu Ser Thr
         50                  55                  60

Arg Pro Ser Thr Val Ser Glu Ala Ser Ile Pro Arg Ala
 65                  70                  75

<210> SEQ ID NO 103
<211> LENGTH: 78
<212> TYPE: PRT
```

<213> ORGANISM: Human papillomavirus type 39

<400> SEQUENCE: 103

Ser Ala Thr Asp Leu Tyr Arg Thr Cys Lys Gln Ser Gly Thr Cys Pro
1               5                   10                  15

Pro Asp Val Val Asp Lys Val Glu Gly Thr Thr Leu Ala Asp Lys Ile
            20                  25                  30

Leu Gln Trp Thr Ser Leu Gly Ile Phe Leu Gly Gly Leu Gly Ile Gly
        35                  40                  45

Thr Gly Thr Gly Thr Gly Gly Arg Thr Gly Tyr Ile Pro Leu Gly Gly
    50                  55                  60

Arg Pro Asn Thr Val Val Asp Val Ser Pro Ala Arg Arg Ala
65                  70                  75

<210> SEQ ID NO 104
<211> LENGTH: 78
<212> TYPE: PRT
<213> ORGANISM: Human papillomavirus type 51

<400> SEQUENCE: 104

Ser Val Thr Gln Leu Tyr Ser Thr Cys Lys Ala Ala Gly Thr Cys Pro
1               5                   10                  15

Pro Asp Val Val Asn Lys Val Glu Gly Thr Thr Leu Ala Asp Lys Ile
            20                  25                  30

Leu Gln Trp Ser Gly Leu Gly Ile Phe Leu Gly Gly Leu Gly Ile Gly
        35                  40                  45

Thr Gly Ser Gly Ser Gly Gly Arg Thr Gly Tyr Ile Pro Leu Gly Gly
    50                  55                  60

Gly Gly Arg Pro Gly Val Val Asp Ile Ala Pro Ala Arg Ala
65                  70                  75

<210> SEQ ID NO 105
<211> LENGTH: 80
<212> TYPE: PRT
<213> ORGANISM: Human papillomavirus type 56

<400> SEQUENCE: 105

Ser Ala Thr Gln Leu Tyr Lys Thr Cys Lys Leu Ser Gly Thr Cys Pro
1               5                   10                  15

Glu Asp Val Val Asn Lys Ile Glu Gln Lys Thr Trp Ala Asp Lys Ile
            20                  25                  30

Leu Gln Trp Gly Ser Leu Phe Thr Tyr Phe Gly Gly Leu Gly Ile Gly
        35                  40                  45

Thr Gly Thr Gly Ser Gly Gly Arg Ala Gly Tyr Val Pro Leu Gly Ser
    50                  55                  60

Arg Pro Ser Thr Ile Val Asp Val Thr Pro Ala Arg Lys Lys Arg Ala
65                  70                  75                  80

<210> SEQ ID NO 106
<211> LENGTH: 74
<212> TYPE: PRT
<213> ORGANISM: Human papillomavirus type 73

<400> SEQUENCE: 106

Ser Ala Thr Gln Leu Tyr Lys Thr Cys Lys Gln Ala Gly Thr Cys Pro
1               5                   10                  15

Pro Asp Val Ile Pro Lys Val Glu Gly Ser Thr Ile Ala Asp Asn Ile
            20                  25                  30

Leu Lys Tyr Gly Ser Ile Gly Val Phe Phe Gly Leu Gly Ile Gly
                 35                  40                  45

Ser Gly Ser Gly Ser Gly Gly Arg Thr Gly Tyr Val Pro Leu Ser Thr
 50                  55                  60

Gly Thr Pro Ser Lys Pro Val Glu Ile Pro
 65                  70

<210> SEQ ID NO 107
<211> LENGTH: 388
<212> TYPE: PRT
<213> ORGANISM: Human papillomavirus

<400> SEQUENCE: 107

Lys Arg Ala Ser Ala Thr Gln Leu Tyr Lys Thr Cys Lys Gln Ala Gly
 1               5                  10                  15

Thr Cys Pro Pro Asp Ile Ile Pro Lys Val Glu Gly Lys Thr Ile Ala
                 20                  25                  30

Asp Gln Ile Leu Gln Tyr Gly Ser Met Gly Val Phe Phe Gly Gly Leu
                 35                  40                  45

Gly Ile Gly Thr Gly Ser Gly Thr Gly Gly Arg Thr Gly Tyr Ile Pro
 50                  55                  60

Leu Gly Thr Arg Pro Pro Thr Ala Thr Asp Thr Leu Ala Pro Lys Arg
 65                  70                  75                  80

Ala Ser Val Thr Asp Leu Tyr Lys Thr Cys Lys Gln Ser Gly Thr Cys
                 85                  90                  95

Pro Pro Asp Val Val Pro Lys Val Glu Gly Thr Thr Leu Ala Asp Lys
                100                 105                 110

Ile Leu Gln Trp Ser Ser Leu Gly Phe Leu Gly Leu Gly Ile Gly
                115                 120                 125

Thr Gly Ser Gly Thr Gly Gly Arg Thr Gly Tyr Ile Pro Leu Gly Gly
                130                 135                 140

Arg Ser Asn Thr Val Val Asp Val Gly Pro Thr Lys Arg Ala Ala Pro
145                 150                 155                 160

Lys Asp Ile Tyr Pro Ser Cys Lys Ile Ser Asn Thr Cys Pro Pro Asp
                165                 170                 175

Ile Gln Asn Lys Ile Glu His Thr Thr Ile Ala Asp Lys Ile Leu Gln
                180                 185                 190

Tyr Gly Ser Leu Gly Val Phe Leu Gly Gly Leu Gly Ile Gly Thr Ala
                195                 200                 205

Arg Gly Ser Gly Gly Arg Ile Gly Tyr Thr Pro Leu Gly Glu Gly Gly
                210                 215                 220

Gly Val Arg Val Ala Thr Arg Pro Thr Lys Arg Asp Ser Val Thr His
225                 230                 235                 240

Ile Tyr Gln Thr Cys Lys Gln Ala Gly Thr Cys Pro Pro Asp Val Ile
                245                 250                 255

Asn Lys Val Glu Gln Thr Thr Val Ala Asp Asn Ile Leu Lys Tyr Gly
                260                 265                 270

Ser Ala Gly Val Phe Phe Gly Gly Leu Gly Ile Ser Thr Gly Arg Gly
                275                 280                 285

Thr Gly Gly Ala Thr Gly Tyr Val Pro Leu Gly Glu Gly Pro Gly Val
                290                 295                 300

Arg Val Gly Gly Thr Pro Thr Lys Arg Ala Ser Ala Thr Gln Leu Tyr
305                 310                 315                 320

Gln Thr Cys Lys Leu Thr Gly Thr Cys Pro Pro Asp Val Ile Pro Lys
                325                 330                 335

Val Glu His Asn Thr Ile Ala Asp Gln Ile Leu Lys Trp Gly Ser Leu
                340                 345                 350

Gly Val Phe Phe Gly Gly Leu Gly Ile Gly Thr Gly Ser Gly Thr Gly
            355                 360                 365

Gly Arg Thr Gly Val Pro Leu Gly Thr Ser Ala Lys Pro Ser Ile Thr
370                 375                 380

Ser Gly Pro Met
385

<210> SEQ ID NO 108
<211> LENGTH: 622
<212> TYPE: PRT
<213> ORGANISM: Human papillomavirus

<400> SEQUENCE: 108

Ser Ala Thr Gln Leu Tyr Gln Thr Cys Lys Leu Thr Gly Thr Cys Pro
1               5                   10                  15

Pro Asp Val Ile Pro Lys Val Glu His Asn Thr Ile Ala Asp Gln Ile
            20                  25                  30

Leu Lys Trp Gly Ser Leu Gly Val Phe Phe Gly Gly Leu Gly Ile Gly
        35                  40                  45

Thr Gly Ser Gly Thr Gly Gly Arg Thr Gly Tyr Val Pro Leu Gln Thr
    50                  55                  60

Ser Ala Lys Pro Ser Ile Thr Ser Gly Pro Met Ala Lys Arg Ala Ser
65                  70                  75                  80

Ala Thr Gln Leu Tyr Lys Thr Cys Lys Gln Ala Gly Thr Cys Pro Pro
                85                  90                  95

Asp Ile Ile Pro Lys Val Glu Gly Lys Thr Ile Ala Asp Gln Ile Leu
            100                 105                 110

Gln Tyr Gly Ser Met Gly Val Phe Phe Gly Gly Leu Gly Ile Gly Thr
        115                 120                 125

Gly Ser Gly Thr Gly Gly Arg Thr Gly Tyr Ile Pro Leu Gly Thr Arg
    130                 135                 140

Pro Pro Thr Ala Thr Asp Thr Leu Ala Pro Arg Ala Ser Val Thr Asp
145                 150                 155                 160

Leu Tyr Lys Thr Cys Lys Gln Ser Gly Thr Cys Pro Pro Asp Val Val
                165                 170                 175

Pro Lys Val Glu Gly Thr Thr Leu Ala Asp Lys Ile Leu Gln Trp Ser
            180                 185                 190

Ser Leu Gly Ile Phe Leu Gly Gly Leu Gly Ile Gly Thr Gly Ser Gly
        195                 200                 205

Thr Gly Gly Arg Thr Gly Tyr Ile Pro Leu Gly Gly Arg Ser Asn Thr
    210                 215                 220

Val Val Asp Val Gly Pro Thr Arg Lys Arg Ala Ser Ala Thr Gln Leu
225                 230                 235                 240

Tyr Gln Thr Cys Lys Ala Ala Gly Thr Cys Pro Ser Asp Val Ile Pro
                245                 250                 255

Lys Ile Glu His Thr Thr Ile Ala Asp Gln Ile Leu Arg Tyr Gly Ser
            260                 265                 270

Met Gly Val Phe Phe Gly Gly Leu Gly Ile Gly Ser Gly Ser Gly Thr
        275                 280                 285

Gly Gly Arg Thr Gly Tyr Val Pro Leu Ser Thr Arg Pro Ser Thr Val
    290                 295                 300

Ser Glu Ala Ser Ile Pro Arg Ala Ser Ala Thr Asp Leu Tyr Arg Thr

Cys Lys Gln Ser Gly Thr Cys Pro Pro Asp Val Val Asp Lys Val Glu
305                 310                 315                 320

Gly Thr Thr Leu Ala Asp Lys Ile Leu Gln Trp Thr Ser Leu Gly Ile
            325                 330                 335

Phe Leu Gly Leu Gly Ile Gly Thr Gly Thr Gly Gly Arg
            340                 345                 350

Thr Gly Tyr Ile Pro Leu Gly Gly Arg Pro Asn Thr Val Val Asp Val
        355                 360                 365

Ser Pro Ala Arg Arg Ala Ser Val Thr Gln Leu Tyr Ser Thr Cys Lys
370                 375                 380

Ala Ala Gly Thr Cys Pro Pro Asp Val Val Asn Lys Val Glu Gly Thr
385                 390                 395                 400

Thr Leu Ala Asp Lys Ile Leu Gln Trp Ser Gly Leu Gly Ile Phe Leu
            405                 410                 415

Gly Gly Leu Gly Ile Gly Thr Gly Ser Gly Ser Gly Gly Arg Thr Gly
        420                 425                 430

Tyr Ile Pro Leu Gly Gly Gly Arg Pro Gly Val Val Asp Ile Ala
            435                 440                 445

Pro Ala Arg Ala Ser Ala Thr Gln Leu Tyr Lys Thr Cys Lys Leu Ser
450                 455                 460

Gly Thr Cys Pro Glu Asp Val Val Asn Lys Ile Glu Gln Lys Thr Trp
465                 470                 475                 480

Ala Asp Lys Ile Leu Gln Trp Gly Ser Leu Phe Thr Tyr Phe Gly Gly
            485                 490                 495

Leu Gly Ile Gly Thr Gly Thr Gly Ser Gly Gly Arg Ala Gly Tyr Val
        500                 505                 510

Pro Leu Gly Ser Arg Pro Ser Thr Ile Val Asp Val Thr Pro Ala Arg
515                 520                 525

Lys Lys Arg Ala Ser Ala Thr Gln Leu Tyr Lys Thr Cys Lys Gln Ala
530                 535                 540

Gly Thr Cys Pro Pro Asp Val Ile Pro Lys Val Glu Gly Ser Thr Ile
545                 550                 555                 560

Ala Asp Asn Ile Leu Lys Tyr Gly Ser Ile Gly Val Phe Phe Gly Gly
            565                 570                 575

Leu Gly Ile Gly Ser Gly Ser Gly Ser Gly Gly Arg Thr Gly Tyr Val
        580                 585                 590

Pro Leu Ser Thr Gly Thr Pro Ser Lys Pro Val Glu Ile Pro
610                 615                 620

<210> SEQ ID NO 109
<211> LENGTH: 624
<212> TYPE: PRT
<213> ORGANISM: Human papillomavirus

<400> SEQUENCE: 109

Met Ala Ser Ala Thr Gln Leu Tyr Gln Thr Cys Lys Leu Thr Gly Thr
1               5                   10                  15

Cys Pro Pro Asp Val Ile Pro Lys Val Glu His Asn Thr Ile Ala Asp
            20                  25                  30

Gln Ile Leu Lys Trp Gly Ser Leu Gly Val Phe Phe Gly Gly Leu Gly
        35                  40                  45

Ile Gly Thr Gly Ser Gly Thr Gly Gly Arg Thr Gly Tyr Val Pro Leu
    50                  55                  60

```
Gln Thr Ser Ala Lys Pro Ser Ile Thr Ser Gly Pro Met Ala Lys Arg
 65                  70                  75                  80

Ala Ser Ala Thr Gln Leu Tyr Lys Thr Cys Lys Gln Ala Gly Thr Cys
                 85                  90                  95

Pro Pro Asp Ile Ile Pro Lys Val Glu Gly Lys Thr Ile Ala Asp Gln
            100                 105                 110

Ile Leu Gln Tyr Gly Ser Met Gly Val Phe Phe Gly Leu Gly Ile
            115                 120                 125

Gly Thr Gly Ser Gly Thr Gly Arg Thr Gly Tyr Ile Pro Leu Gly
    130                 135                 140

Thr Arg Pro Pro Thr Ala Thr Asp Thr Leu Ala Pro Arg Ala Ser Val
145                 150                 155                 160

Thr Asp Leu Tyr Lys Thr Cys Lys Gln Ser Gly Thr Cys Pro Pro Asp
                165                 170                 175

Val Val Pro Lys Val Glu Gly Thr Thr Leu Ala Asp Lys Ile Leu Gln
            180                 185                 190

Trp Ser Ser Leu Gly Ile Phe Leu Gly Leu Gly Ile Gly Thr Gly
            195                 200                 205

Ser Gly Thr Gly Gly Arg Thr Gly Tyr Ile Pro Leu Gly Gly Arg Ser
    210                 215                 220

Asn Thr Val Val Asp Val Gly Pro Thr Arg Lys Arg Ala Ser Ala Thr
225                 230                 235                 240

Gln Leu Tyr Gln Thr Cys Lys Ala Ala Gly Thr Cys Pro Ser Asp Val
                245                 250                 255

Ile Pro Lys Ile Glu His Thr Thr Ile Ala Asp Gln Ile Leu Arg Tyr
            260                 265                 270

Gly Ser Met Gly Val Phe Phe Gly Leu Gly Ile Gly Ser Gly Ser
            275                 280                 285

Gly Thr Gly Gly Arg Thr Gly Tyr Val Pro Leu Ser Thr Arg Pro Ser
    290                 295                 300

Thr Val Ser Glu Ala Ser Ile Pro Arg Ala Ser Ala Thr Asp Leu Tyr
305                 310                 315                 320

Arg Thr Cys Lys Gln Ser Gly Thr Cys Pro Pro Asp Val Val Asp Lys
                325                 330                 335

Val Glu Gly Thr Thr Leu Ala Asp Lys Ile Leu Gln Trp Thr Ser Leu
            340                 345                 350

Gly Ile Phe Leu Gly Gly Leu Gly Ile Gly Thr Gly Thr Gly Thr Gly
            355                 360                 365

Gly Arg Thr Gly Tyr Ile Pro Leu Gly Gly Arg Pro Asn Thr Val Val
    370                 375                 380

Asp Val Ser Pro Ala Arg Arg Ala Ser Val Thr Gln Leu Tyr Ser Thr
385                 390                 395                 400

Cys Lys Ala Ala Gly Thr Cys Pro Pro Asp Val Val Asn Lys Val Glu
                405                 410                 415

Gly Thr Thr Leu Ala Asp Lys Ile Leu Gln Trp Ser Gly Leu Gly Ile
            420                 425                 430

Phe Leu Gly Gly Leu Gly Ile Gly Thr Gly Ser Gly Ser Gly Gly Arg
            435                 440                 445

Thr Gly Tyr Ile Pro Leu Gly Gly Gly Arg Pro Gly Val Val Asp
    450                 455                 460

Ile Ala Pro Ala Arg Ala Ser Ala Thr Gln Leu Tyr Lys Thr Cys Lys
465                 470                 475                 480

Leu Ser Gly Thr Cys Pro Glu Asp Val Val Asn Lys Ile Glu Gln Lys
```

```
                    485                 490                 495
Thr Trp Ala Asp Lys Ile Leu Gln Trp Gly Ser Leu Phe Thr Tyr Phe
                500                 505                 510

Gly Gly Leu Gly Ile Gly Thr Gly Thr Gly Ser Gly Gly Arg Ala Gly
                515                 520                 525

Tyr Val Pro Leu Gly Ser Arg Pro Ser Thr Ile Val Asp Val Thr Pro
            530                 535                 540

Ala Arg Lys Lys Arg Ala Ser Ala Thr Gln Leu Tyr Lys Thr Cys Lys
545                 550                 555                 560

Gln Ala Gly Thr Cys Pro Pro Asp Val Ile Pro Lys Val Glu Gly Ser
                565                 570                 575

Thr Ile Ala Asp Asn Ile Leu Lys Tyr Gly Ser Ile Gly Val Phe Phe
            580                 585                 590

Gly Gly Leu Gly Ile Gly Ser Gly Ser Gly Ser Gly Arg Thr Gly
                595                 600                 605

Tyr Val Pro Leu Ser Thr Gly Thr Pro Ser Lys Pro Val Glu Ile Pro
            610                 615                 620
```

<210> SEQ ID NO 110
<211> LENGTH: 192
<212> TYPE: PRT
<213> ORGANISM: Human papillomavirus

<400> SEQUENCE: 110

```
Lys Arg Ala Ser Ala Thr Gln Leu Tyr Gln Thr Cys Lys Ala Ser Gly
1               5                   10                  15

Thr Cys Pro Pro Asp Ile Ile Ala Lys Val Glu Gln Asn Thr Leu Ala
                20                  25                  30

Asp Lys Ile Leu Lys Trp Gly Ser Leu Gly Val Phe Phe Gly Gly Leu
            35                  40                  45

Gly Ile Gly Thr Gly Ser Gly Thr Gly Gly Arg Thr Gly Tyr Val Pro
        50                  55                  60

Val Gln Thr Ala Pro Arg Pro Ala Ile Pro Phe Gly Pro Thr Ala Arg
65                  70                  75                  80

Pro Pro Ile Ile Val Asp Thr Val Gly Pro Ser Asp Ser Ser Ile Val
                85                  90                  95

Ser Leu Val Glu Asp Ser Thr Ile Ile Asn Ser Ala Ala Ser Asp Phe
                100                 105                 110

Val Pro Pro Ile Arg Glu Gly Phe Glu Ile Ser Thr Ser Glu Thr Thr
            115                 120                 125

Thr Pro Ala Ile Leu Asp Val Ser Val Thr Thr His Asn Thr Thr Ser
130                 135                 140

Thr Ser Ile Phe Lys Asn Pro Ala Phe Ala Glu Pro Ser Ile Val Gln
145                 150                 155                 160

Ser Gln Pro Ser Val Glu Ala Ser Gly His Val Leu Thr Ser Thr Tyr
                165                 170                 175

Thr Ser Thr Ile Ser Ser His Ser Val Glu Asp Ile Pro Leu Asp Thr
            180                 185                 190
```

<210> SEQ ID NO 111
<211> LENGTH: 191
<212> TYPE: PRT
<213> ORGANISM: Human papillomavirus

<400> SEQUENCE: 111

Lys Arg Ala Ser Ala Thr Gln Leu Tyr Lys Thr Cys Lys Gln Ala Gly

```
            1               5                  10                  15
         Thr Cys Pro Pro Asp Ile Ile Pro Lys Val Glu Gly Lys Thr Ile Ala
                         20                  25                  30

Asp Gln Ile Leu Gln Tyr Gly Ser Met Gly Val Phe Phe Gly Gly Leu
                         35                  40                  45

Gly Ile Gly Thr Gly Ser Gly Thr Gly Gly Arg Thr Gly Tyr Ile Pro
          50                  55                  60

Leu Gly Thr Arg Pro Pro Thr Ala Thr Asp Thr Leu Ala Pro Val Arg
          65                  70                  75                  80

Pro Pro Leu Thr Val Asp Pro Val Gly Pro Ser Asp Pro Ser Ile Val
                         85                  90                  95

Ser Leu Val Glu Glu Thr Ser Phe Ile Asp Ala Gly Ala Pro Thr Pro
                         100                 105                 110

Val Pro Ser Ile Pro Pro Asp Val Ser Gly Phe Ser Ile Thr Thr Ser
                         115                 120                 125

Thr Asp Thr Thr Pro Ala Ile Leu Asp Ile Asn Asn Thr Val Phe Thr
                         130                 135                 140

Thr Val Thr Thr His Asn Asn Pro Thr Phe Thr Asp Pro Ser Val Leu
          145                 150                 155                 160

Gln Pro Pro Thr Pro Ala Glu Thr Gly Gly His Phe Thr Leu Ser Ser
                         165                 170                 175

Ser Thr Ile Ser Thr His Asn Tyr Glu Glu Ile Pro Met Asp Thr
                         180                 185                 190

<210> SEQ ID NO 112
<211> LENGTH: 191
<212> TYPE: PRT
<213> ORGANISM: Human papillomavirus

<400> SEQUENCE: 112

Lys Arg Ala Ser Val Thr Asp Leu Tyr Lys Thr Cys Lys Gln Ser Gly
          1               5                  10                  15

Thr Cys Pro Pro Asp Val Val Pro Lys Val Glu Gly Thr Thr Leu Ala
                         20                  25                  30

Asp Lys Ile Leu Gln Trp Ser Ser Leu Gly Ile Phe Leu Gly Gly Leu
                         35                  40                  45

Gly Ile Gly Thr Gly Ser Gly Thr Gly Gly Arg Thr Gly Tyr Ile Pro
          50                  55                  60

Leu Gly Gly Arg Ser Asn Thr Val Val Asp Val Gly Pro Thr Arg Pro
          65                  70                  75                  80

Pro Val Val Ile Glu Pro Val Gly Pro Thr Asp Pro Ser Ile Val Thr
                         85                  90                  95

Leu Ile Glu Asp Ser Ser Val Val Thr Ser Gly Ala Pro Arg Pro Thr
                         100                 105                 110

Phe Thr Gly Thr Ser Gly Phe Ile Asp Ile Thr Ser Ala Gly Thr Thr
                         115                 120                 125

Thr Pro Ala Val Leu Asp Ile Thr Pro Ser Ser Thr Ser Val Ser Ile
          130                 135                 140

Ser Thr Thr Asn Phe Thr Asn Pro Ala Phe Ser Asp Pro Ser Ile Ile
          145                 150                 155                 160

Glu Val Pro Gln Thr Gly Glu Val Ala Gly Asn Val Phe Val Gly Thr
                         165                 170                 175

Pro Thr Ser Gly Thr His Gly Tyr Glu Glu Ile Pro Leu Gln Thr
                         180                 185                 190
```

<210> SEQ ID NO 113
<211> LENGTH: 568
<212> TYPE: PRT
<213> ORGANISM: Human papillomavirus

<400> SEQUENCE: 113

Lys Arg Ala Ser Ala Thr Gln Leu Tyr Gln Thr Cys Lys Ala Ser Gly
1               5                   10                  15

Thr Cys Pro Pro Asp Ile Ile Ala Lys Val Glu Gln Asn Thr Leu Ala
            20                  25                  30

Asp Lys Ile Leu Lys Trp Gly Ser Leu Gly Val Phe Phe Gly Gly Leu
        35                  40                  45

Gly Ile Gly Thr Gly Ser Gly Thr Gly Gly Arg Thr Gly Tyr Val Pro
    50                  55                  60

Val Gln Thr Ala Pro Arg Pro Ala Ile Pro Phe Gly Pro Thr Ala Arg
65                  70                  75                  80

Pro Pro Ile Ile Val Asp Thr Val Gly Pro Ser Asp Ser Ser Ile Val
                85                  90                  95

Ser Leu Val Glu Asp Ser Thr Ile Ile Asn Ser Ala Ala Ser Asp Phe
            100                 105                 110

Val Pro Pro Ile Arg Glu Gly Phe Glu Ile Ser Thr Ser Glu Thr Thr
        115                 120                 125

Thr Pro Ala Ile Leu Asp Val Ser Val Thr Thr His Asn Thr Thr Ser
    130                 135                 140

Thr Ser Ile Phe Lys Asn Pro Ala Phe Ala Glu Pro Ser Ile Val Gln
145                 150                 155                 160

Ser Gln Pro Ser Val Glu Ala Ser Gly His Val Leu Thr Ser Thr Tyr
                165                 170                 175

Thr Ser Thr Ile Ser Ser His Ser Val Glu Asp Ile Pro Leu Asp Thr
            180                 185                 190

Lys Met Ser Ala Thr Gln Leu Tyr Lys Thr Cys Lys Gln Ala Gly Thr
        195                 200                 205

Cys Pro Pro Asp Ile Ile Pro Lys Val Glu Gly Ile Ala Asp Gln Ile
    210                 215                 220

Leu Gln Tyr Gly Ser Met Gly Val Phe Phe Gly Gly Leu Gly Ile Gly
225                 230                 235                 240

Thr Gly Ser Gly Thr Gly Gly Arg Thr Gly Tyr Ile Pro Leu Gly Thr
                245                 250                 255

Arg Pro Pro Thr Ala Thr Asp Thr Leu Ala Pro Val Arg Pro Pro Leu
            260                 265                 270

Thr Val Asp Pro Val Gly Pro Ser Asp Pro Ser Ile Val Ser Leu Val
        275                 280                 285

Glu Glu Thr Ser Phe Ile Asp Ala Gly Ala Pro Thr Pro Val Pro Ser
    290                 295                 300

Ile Pro Pro Asp Val Ser Gly Phe Ser Ile Thr Thr Ser Thr Asp Thr
305                 310                 315                 320

Thr Pro Ala Ile Leu Asp Ile Asn Asn Thr Val Thr Thr Val Thr Thr
                325                 330                 335

His Asn Asn Pro Thr Phe Thr Asp Pro Ser Val Leu Gln Pro Pro Thr
            340                 345                 350

Pro Ala Glu Thr Gly Gly His Phe Thr Leu Ser Ser Ser Thr Ile Ser
        355                 360                 365

Thr His Asn Tyr Glu Glu Ile Pro Met Asp Thr Lys Arg Ala Ser Val
    370                 375                 380

Thr Asp Leu Tyr Lys Thr Cys Lys Gln Ser Gly Thr Cys Pro Pro Asp
385                 390                 395                 400

Val Val Pro Lys Val Glu Gly Thr Leu Ala Asp Lys Ile Leu Gln Trp
                405                 410                 415

Ser Ser Leu Gly Ile Phe Leu Gly Gly Leu Gly Ile Gly Thr Gly Ser
            420                 425                 430

Gly Thr Gly Gly Arg Thr Gly Tyr Ile Pro Leu Gly Gly Arg Ser Asn
        435                 440                 445

Thr Val Val Asp Val Gly Pro Thr Arg Pro Pro Val Val Ile Glu Pro
450                 455                 460

Val Gly Pro Thr Asp Pro Ser Ile Val Thr Leu Ile Glu Asp Ser Ser
465                 470                 475                 480

Val Val Thr Ser Gly Ala Pro Arg Pro Thr Phe Thr Gly Thr Ser Gly
            485                 490                 495

Phe Asp Ile Thr Ser Ala Gly Thr Thr Thr Pro Ala Val Leu Asp Ile
            500                 505                 510

Thr Pro Ser Ser Thr Ser Val Ser Ile Ser Thr Thr Asn Phe Thr Asn
            515                 520                 525

Pro Ala Phe Ser Asp Pro Ser Ile Ile Glu Val Pro Gln Thr Gly Glu
            530                 535                 540

Val Ala Gly Asn Val Phe Val Gly Thr Pro Thr Ser Gly Thr His Gly
545                 550                 555                 560

Tyr Glu Glu Ile Pro Leu Gln Thr
                565

<210> SEQ ID NO 114
<211> LENGTH: 526
<212> TYPE: PRT
<213> ORGANISM: Human papillomavirus

<400> SEQUENCE: 114

Met Ala Ser Ala Thr Gln Leu Tyr Gln Thr Cys Lys Leu Thr Gly Thr
1               5                   10                  15

Cys Pro Pro Asp Val Ile Pro Lys Val Glu His Asn Thr Ile Ala Asp
                20                  25                  30

Gln Ile Leu Lys Ala Ser Ala Thr Gln Leu Tyr Gln Thr Cys Lys Ala
            35                  40                  45

Thr Gly Thr Cys Pro Pro Asp Val Ile Pro Lys Val Glu His Thr Thr
        50                  55                  60

Ile Ala Asp Gln Ile Leu Lys Ala Ser Ala Thr Gln Leu Tyr Lys Thr
65                  70                  75                  80

Cys Lys Gln Ala Gly Thr Cys Pro Pro Asp Ile Ile Pro Lys Val Glu
                85                  90                  95

Gly Lys Thr Ile Ala Asp Gln Ile Leu Gln Ala Ser Val Thr Asp Leu
            100                 105                 110

Tyr Lys Thr Cys Lys Gln Ser Gly Thr Cys Pro Pro Asp Val Val Pro
        115                 120                 125

Lys Val Glu Gly Thr Thr Leu Ala Asp Lys Ile Leu Gln Ala Ser Ala
130                 135                 140

Thr Gln Leu Tyr Gln Thr Cys Lys Ala Ala Gly Thr Cys Pro Ser Asp
145                 150                 155                 160

Val Ile Pro Lys Ile Glu His Thr Thr Ile Ala Asp Gln Ile Leu Arg
            165                 170                 175

Ala Ser Ala Thr Gln Leu Tyr Gln Thr Cys Lys Ala Thr Gly Thr Cys

```
            180                 185                 190
Pro Pro Asp Val Ile Pro Lys Val Glu Gly Ser Thr Ile Ala Asp Gln
            195                 200                 205
Ile Leu Lys Ala Ser Ala Thr Gln Leu Tyr Arg Thr Cys Lys Ala Ala
            210                 215                 220
Gly Thr Cys Pro Pro Asp Val Ile Pro Lys Val Glu Gly Asn Thr Val
225                 230                 235                 240
Ala Asp Gln Ile Leu Lys Ala Ser Ala Thr Asp Leu Tyr Arg Thr Cys
                245                 250                 255
Lys Gln Ser Gly Thr Cys Pro Pro Asp Val Val Asp Lys Val Glu Gly
                260                 265                 270
Thr Thr Leu Ala Asp Lys Ile Leu Gln Ala Ser Ala Thr Asp Leu Tyr
                275                 280                 285
Arg Thr Cys Lys Gln Ser Gly Thr Cys Pro Pro Asp Val Ile Asn Lys
                290                 295                 300
Val Glu Gly Thr Thr Leu Ala Asp Lys Ile Leu Gln Ala Ser Val Thr
305                 310                 315                 320
Gln Leu Tyr Ser Thr Cys Lys Ala Ala Gly Thr Cys Pro Pro Asp Val
                325                 330                 335
Val Asn Lys Val Glu Gly Thr Thr Leu Ala Asp Lys Ile Leu Gln Ala
                340                 345                 350
Ser Ala Thr Gln Leu Tyr Gln Thr Cys Lys Ala Ser Gly Thr Cys Pro
                355                 360                 365
Pro Asp Val Ile Pro Lys Val Glu Gly Thr Thr Ile Ala Asp Gln Leu
                370                 375                 380
Leu Lys Ala Ser Ala Thr Gln Leu Tyr Lys Thr Cys Lys Leu Ser Gly
385                 390                 395                 400
Thr Cys Pro Glu Asp Val Val Asn Lys Ile Glu Gln Lys Thr Trp Ala
                405                 410                 415
Asp Lys Ile Leu Gln Ala Ser Ala Thr Gln Leu Tyr Gln Thr Cys Lys
                420                 425                 430
Ala Ser Gly Thr Cys Pro Pro Asp Val Ile Pro Lys Val Glu Gly Thr
                435                 440                 445
Thr Ile Ala Asp Gln Ile Leu Arg Ala Ser Ala Thr Asp Leu Tyr Lys
                450                 455                 460
Thr Cys Lys Gln Ala Gly Thr Cys Pro Ser Asp Val Ile Asn Lys Val
465                 470                 475                 480
Glu Gly Thr Thr Leu Ala Asp Lys Ile Leu Gln Ala Ser Ala Thr Gln
                485                 490                 495
Leu Tyr Lys Thr Cys Lys Gln Ala Gly Thr Cys Pro Pro Asp Val Ile
                500                 505                 510
Pro Lys Val Glu Gly Ser Thr Ile Ala Asp Asn Ile Leu Lys
                515                 520                 525

<210> SEQ ID NO 115
<211> LENGTH: 44
<212> TYPE: PRT
<213> ORGANISM: Human papillomavirus

<400> SEQUENCE: 115

Asp Gln His Leu Ile Tyr Lys Pro Arg Gln Ser Thr Ser Ala Cys Lys
1               5                   10                  15

Gln Ile Val Leu Ala Ala Ser Thr Gly Asn Thr Asn Cys Pro Pro Asp
            20                  25                  30
```

```
Ile Val Ile Val Gln Pro Asn Asp Lys Arg Val Ile
            35                  40
```

<210> SEQ ID NO 116
<211> LENGTH: 20
<212> TYPE: PRT
<213> ORGANISM: Human papillomavirus
<220> FEATURE:
<221> NAME/KEY: MISC_FEATURE
<223> OTHER INFORMATION: x = j
<220> FEATURE:
<221> NAME/KEY: misc_feature
<222> LOCATION: (17)..(17)
<223> OTHER INFORMATION: Xaa can be any naturally occurring amino acid

<400> SEQUENCE: 116

```
Ala Asx Tyr Cys Asp Cys Lys Glu Phe Gly His Cys Pro Pro Asp Ile
1               5                   10                  15

Xaa Lys Leu Met
            20
```

<210> SEQ ID NO 117
<211> LENGTH: 17
<212> TYPE: PRT
<213> ORGANISM: Human papillomavirus

<400> SEQUENCE: 117

```
Lys Leu Ile Pro Asn Ala Ser Leu Ile Glu Asn Cys Thr Lys Ala Glu
1               5                   10                  15

Leu
```

<210> SEQ ID NO 118
<211> LENGTH: 13
<212> TYPE: PRT
<213> ORGANISM: Human papillomavirus

<400> SEQUENCE: 118

```
Lys Leu Phe Ala Val Trp Lys Ile Thr Tyr Lys Asp Thr
1               5                   10
```

<210> SEQ ID NO 119
<211> LENGTH: 13
<212> TYPE: PRT
<213> ORGANISM: Human papillomavirus

<400> SEQUENCE: 119

```
Asn Lys Leu Ile Ala Tyr Pro Ala Val Glu Ala Leu Ser
1               5                   10
```

<210> SEQ ID NO 120
<211> LENGTH: 15
<212> TYPE: PRT
<213> ORGANISM: Human papillomavirus

<400> SEQUENCE: 120

```
Gln Tyr Ile Lys Ala Asn Ser Lys Phe Ile Gly Ile Thr Glu Leu
1               5                   10                  15
```

<210> SEQ ID NO 121
<211> LENGTH: 12
<212> TYPE: PRT
<213> ORGANISM: Human papillomavirus
<220> FEATURE:
<221> NAME/KEY: MISC_FEATURE
<222> LOCATION: (1)..(12)
<223> OTHER INFORMATION: a = D-Ala

```
<220> FEATURE:
<221> NAME/KEY: MISC_FEATURE
<222> LOCATION: (3)..(3)
<223> OTHER INFORMATION: x = L-cyclohexyl-Ala)

<400> SEQUENCE: 121

Ala Lys Xaa Val Met Trp Thr Leu Lys Ala Ala Ala
1               5                   10

<210> SEQ ID NO 122
<211> LENGTH: 10
<212> TYPE: PRT
<213> ORGANISM: Human papillomavirus

<400> SEQUENCE: 122

Thr Asp Leu Tyr Cys Tyr Glu Gln Leu Asn
1               5                   10

<210> SEQ ID NO 123
<211> LENGTH: 10
<212> TYPE: PRT
<213> ORGANISM: Human papillomavirus

<400> SEQUENCE: 123

Ala Glu Pro Asp Arg Ala His Tyr Asn Ile
1               5                   10

<210> SEQ ID NO 124
<211> LENGTH: 19
<212> TYPE: PRT
<213> ORGANISM: Human papillomavirus

<400> SEQUENCE: 124

Lys Cys Asp Ser Thr Leu Arg Leu Cys Val Gln Ser Thr His Val Ile
1               5                   10                  15

Arg Thr Leu

<210> SEQ ID NO 125
<211> LENGTH: 10
<212> TYPE: PRT
<213> ORGANISM: Human papillomavirus

<400> SEQUENCE: 125

Gly Thr Leu Gly Ile Val Gly Pro Ile Cys
1               5                   10

<210> SEQ ID NO 126
<211> LENGTH: 13
<212> TYPE: PRT
<213> ORGANISM: Human papillomavirus

<400> SEQUENCE: 126

Lys Leu Val Val Val Gly Ala Arg Gly Val Gly Lys Ser
1               5                   10

<210> SEQ ID NO 127
<211> LENGTH: 15
<212> TYPE: PRT
<213> ORGANISM: Human papillomavirus

<400> SEQUENCE: 127

His Leu Asp Met Leu Arg His Leu Tyr Gln Gly Gly Gln Val Val
1               5                   10                  15
```

```
<210> SEQ ID NO 128
<211> LENGTH: 15
<212> TYPE: PRT
<213> ORGANISM: Human papillomavirus

<400> SEQUENCE: 128

Ser Arg Leu Leu Gly Ile Cys Leu Thr Ser Thr Val Gln Leu Val
1               5                   10                  15

<210> SEQ ID NO 129
<211> LENGTH: 14
<212> TYPE: PRT
<213> ORGANISM: Human papillomavirus

<400> SEQUENCE: 129

Leu Leu Lys Tyr Arg Ala Arg Glu Pro Val Thr Lys Ala Glu
1               5                   10
```

MULTITYPE HPV PEPTIDE COMPOSITIONS AND METHODS FOR TREATMENT OR PREVENTION OF HUMAN PAPILLOMAVIRUS INFECTION

This application is a §371 of PCT Application No. PCT/US2008/082290, filed Nov. 3, 2008, which is a Non-Provisional of Application No. 61/001,630, filed Nov. 2, 2007, which is a Non-Provisional of Application No. 61/001,629, filed Nov. 2, 2007 the entire contents of which are hereby incorporated by reference.

This application claims priority to U.S. Provisional Patent Applications Ser. Nos. 61/001,630 and 61/001,629 filed Nov. 2, 2007, which is incorporated herein by reference in its entirety.

This invention was made with government support under grant number P50 CA098252 awarded by the National Institutes of Health (NIH). The government has certain rights in the invention.

BACKGROUND OF THE INVENTION

I. Field of the Invention

Embodiments of this invention are directed generally to biology and medicine. In certain embodiments the invention is directed to compositions and method of using multitype HPV polypeptides.

II. BACKGROUND

Genital-tropic human papillomavirus (HPV) infections are considered the most common sexually transmitted infection in the United States (CDC Report to Congress, Prevention of Genital Human Papillomavirus Infection, January 2004). The major manifestations of anogenital HPV include genital warts (condyloma acuminatum) and intraepithelial neoplasia of the vulva, cervix, anus, or penis. A small fraction of persistent high-risk HPV infections, if left untreated, progresses to cancer. (e.g., cervical cancer, on occasion head and neck cancer, and some types of non-melanoma skin cancer). The presence of HPV DNA has been reported in 99.7% of cervical carcinomas worldwide, suggesting that HPV infection is a necessary cause of this cancer and that this disease can be prevented by prophylactic HPV vaccination (Walboomers et al., 1999).

In addition to genital warts, HPV infection can result in common warts, plantar warts, or planar warts. Warts may exist in different forms depending on the HPV type responsible and the epithelium involved. Common warts (verruca vulgaris) usually occur on the hands, as flesh-colored to brown, exophytic, and hyperkeratotic papules. Plantar warts (verruca plantaris) occur on the soles of the feet and can be quite painful. They can be differentiated from calluses by removing the surface layer to reveal thrombosed capillaries. Flat or planar warts (verruca plana) are most common among children and can occur on the face, neck, chest and flexor surfaces of the forearms and legs.

Approximately 35 of the more than 100 subtypes of HPV are specific for the anogenital epithelium and have varying potentials for malignant transformation (Munoz et al., 2003). Of the 15 oncogenic genital HPV types, HPV16 is the most common, followed by HPV 18 and HPV45 (contributing ~50%, ~20% and ~10% of cervical cancer cases, respectively). Despite the successes of public health efforts to reduce the incidence and mortality of cervical cancer with the implementation of cervical cytology screening programs, women who do not undergo regular screening account for most of the patients with invasive cancers (Hoffman and Cavanagh, 1995) and cervical cancer remains the second most common cause of cancer death in women worldwide and the most prevalent cancer in women of sub-Saharan Africa, Central America, south-central Asia and Melanesia (a subregion of Oceania extending from the western side of the West Pacific to the Arafura Sea, north and northeast of Australia; the term was first used to denote an ethnic and geographical grouping of islands distinct from Polynesia and Micronesia) (Parkin, 2001). Approximately 471,000 cases of invasive cervical carcinoma are diagnosed annually (Parkin, 2001).

The HPV genome is surrounded by a 60-nm, non-enveloped icosahedral capsid (Baker et al., 1991) which contains the two genetically-unrelated major capsid protein L1 and the minor capsid protein L2. Recombinant L1 self-assembles into virus-like particles (VLPs) which are morphologically and immunologically similar to native virions (Kirnbauer et al., 1992). L1 VLP-based vaccines are highly protective against infection corresponding to the papillomavirus type used to derive the immunogen (homologous vaccine), but are ineffective against all but the most closely related HPV types (Roden et al., 2000). Licensed HPV vaccines have circumvented this obstacle by designing multivalent vaccine preparations; CERVARIX™ contains L1 VLP derived from HPV16 and HPV18, while GARDASIL™ also contains HPV6 and HPV11 L1 VLPs for prevention of benign genital warts. Unfortunately, the expense and the need for refrigeration of these L1 VLP vaccines currently renders them impractical for use in low resource and remote areas where they are most needed. Furthermore, because these vaccines are ineffective against a significant fraction of oncogenic HPV types, costly cytologic screening programs remain necessary. To realize the full potential of HPV prevention globally, the vaccine should be safe and effective, stable at ambient temperature to facilitate delivery in remote locations, inexpensive to manufacture, and administered without needles, preferably available in a single dose formulation. The disease burden resulting from the plethora of HPV types suggest that a broadly protective vaccine is necessary. Thus, there is a need for additional cross-neutralizing HPV vaccines.

SUMMARY OF THE INVENTION

Embodiments of the present invention are directed to multitype peptide compositions. Other embodiments of the invention are directed to the use of these multitype peptide compositions as immunogens or vaccines. A multitype peptide composition of the invention includes two or more peptides (immunogenic peptides, i.e., peptides that induce an immune response in a subject) representing isotypes or types of a pathogenic organism(s) or distinct immunogenic peptides of an organism. The organisms can be types or variants of a target organism, a genus of organisms, or a family of organisms. In other aspects the peptides can be from distinct pathogenic organisms (e.g., HPV and HSV). In some aspects the distinct pathogenic organisms are related by methods of transmission (e.g., sexually transmitted diseases (STDs)), or organ or organ system infected (e.g., reproductive system, skin or the like). In one aspect, the multitype peptide composition can be comprised of a number of peptides derived from various variants or types of an organism, conferring a broad cross-neutralizing immune response. Cross-neutralization of HPV types would be an example of such a cross-neutralizing multitype peptide composition. In other aspects, a multitype peptide composition can include peptides derived from various pathogens, such as sexually transmitted viruses, bacteria, or fungi, including but not limited to papillomavirus (PV), HPV, cytomegalovirus (CMV), herpes virus, Hepatitis B, Human Immunodeficiency Virus (HIV/AIDS), Kaposi's sarcoma-associated herpesvirus (KSHV/HHV8), chancroid (*Haemophilus ducreyi*), donovanosis (*Granuloma inguinale* or *Calymmatobacterium granulomatis*), Gonorrhea (*Neisseria gonorrhoeae*), Lymphogranuloma venereum (LGV) (*Chlamydia trachomatis*), Non-gonococcal urethritis (NGU) (*Ureaplasma urealyticum* or *Mycoplasma hominis*), *Staphylococcus aureus*, Syphilis (*Treponema pallidum*) and the like.

HPV is one example of an organism that may be targeted by using a multitype peptide composition described herein. HPV infection causes 5% of human cancers worldwide. Cytologic (Pap) screening identifies the precursor lesions of cervical cancer that can be ablated. Prevention of HPV infection will eliminate HPV associated cancers and their precursors, as has been described for the licensed vaccines GARDASIL™ (Merck) and CERVARIX™ (GSK). However, the licensed vaccines are derived from L1 capsid protein and only target a subset of the oncogenic HPV types (therefore Pap screening programs are still needed). The inventors describe compositions and methods to broadly prevent benign and oncogenic HPV infections and their sequelae based upon administration of a multitype HPV L2 peptide composition. The multitype HPV L2 peptide composition will comprise a plurality of polypeptide segments derived from two or more HPV types. The segments or peptides can be from corresponding regions of homologous polypeptides (i.e., a polypeptide from another type or variant organism that is the functional equivalent of a first polypeptide) or may be from a different segment of a homologous polypeptide or can be from a different polypeptide from a different type. The polypeptide segments (or peptides) are configured as a multitype peptide composition by conjugation or production as a fusion protein, liposome, nanoparticle, polymer, or peptide dendrimer (branched polypeptide).

In certain embodiments an isolated polypeptide composition comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, or more immunogenic peptides of corresponding or homologous polypeptides from at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, or more distinct isolates or types or infectious organisms, wherein a first immunogenic peptide comprising an amino acid sequence of a first peptide of a first polypeptide is operably coupled to a second corresponding or homologous immunogenic peptide from a second polypeptide. "Operatively coupled" refers to the attachment of a peptide directly or indirectly with a second peptide. For example, it is possible for a functional group to be directly attached to a first peptide or a surface by a portion of the functional group that is also attached to a second polypeptide (e.g., a peptide bond). Alternatively, it is possible that the functional group is attached to the peptide or surface via an intermediate component that couples the functional group with the peptide or surface. Such intermediate components are often referred to as linkers. Linkers are bi-functional molecules that can have one moiety that chemically attaches to a first peptide and a second moiety that chemically attaches to a functional group. Any number of intermediate components are encompassed by the present invention, and are known to those skilled in the art.

In one embodiment, the inventors described a multitype PV peptide composition for prevention of infection by various PV types. In certain aspects, a multitype PV peptide composition is a non-naturally occurring polypeptide comprising two or more PV protein segments or immunogenic peptides from different PV types configured as a linear (concatamer) or branched polypeptide structure, a multitype PV L2 polypeptide. The PV L2 peptide can comprise all or part of the amino acid sequence of a L2 protein of a virus in the family papovavirus; polyomavirus; papillomavirus; and/or a papillomavirus within the α0 genus, or the genera β, γ, δ, ε, ζ, η, θ, ι, κ, λ, μ, ν, ξ, o, π (See de Villiers et al., Classification of papillomaviruses. Virology. 2004 Jun. 20; 324(1):17-27); and/or human papillomaviruses: HPV1, HPV2, HPV3, HPV4, HPV5, HPV6, HPV7, HPV8, HPV9, HPV10, HPV11, HPV12, HPV13, HPV14, HPV15, HPV16, HPV17, HPV18, HPV19, HPV20, HPV21, HPV22, HPV23, HPV24, HPV25, HPV26, HPV27, HPV28, HPV29, HPV30, HPV31, HPV32, HPV33, HPV34, HPV35, HPV36, HPV37, HPV38, HPV39, HPV40, HPV41, HPV42, HPV43, HPV44, HPV45, HPV46, HPV47, HPV48, HPV49, HPV50, HPV51, HPV52, HPV53, HPV54, HPV55, HPV56, HPV57, HPV58, HPV59, HPV60, HPV61, HPV62, HPV63, HPV64, HPV65, HPV66, HPV67, HPV68, HPV69, HPV70, HPV71, HPV72, HPV73, HPV74, HPV75, HPV76, HPV77, HPV78, HPV79, HPV80, HPV81, HPV82, HPV83, HPV84, HPV85, HPV86, HPV87, HPV88, HPV89, HPV90, HPV91, HPV92, HPV93, HPV94, HPV95, HPV96, HPV97, HPV98, HPV99, HPV100, HPV101, HPV102, HPV103, HPV104, HPV105, HPV106, HPV107, HPV108, HPV109, HPV110, HPV111; and/or animal papillomaviruses: bovine papillomavirus type 1 (BPV1), bovine papillomavirus type 2 (BPV2), bovine papillomavirus type 4 (BPV4), cottontail rabbit papillomavirus (CRPV), deer papillomavirus (DPV), European elk papillomavirus (EEPV), canine oral papillomavirus (COPV), Rhesus monkey papillomavirus (RhPV) and rabbit oral papillomavirus (ROPV).

An PV antigen or epitope or peptide or polypeptide segment of the invention can comprise 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 200, 250, 300, 350, 400, 450, 500 contiguous amino acids, including all values and ranges there between, of a papillomavirus L2 polypeptide (e.g., SEQ ID NOs: 1-70).

In a further aspect a polypeptide segment can comprise at most, at least, or about amino acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 189, 180, 181, 182, 183, 184, 185, 186, 187, 188, 189, 190, 191, 192, 193, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 289, 280, 281, 282, 283, 284, 285, 286, 287, 288, 289, 290, 291, 292, 293, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 389, 380, 381, 382, 383, 384, 385, 386, 387, 388, 389, 390, 391, 392, 393, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 489, 480, 481, 482, 483, 484, 485, 486, 487, 488, 489, 490 or more to amino acid position 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 89, 80, 81, 82, 83, 84, 85, 86, 87, 88, 89, 90, 91, 92, 93, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 189, 180, 181, 182, 183, 184, 185, 186, 187, 188, 189, 190, 191, 192, 193, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 289, 280, 281, 282, 283, 284, 285, 286, 287, 288, 289, 290, 291, 292, 293, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 389, 380, 381, 382, 383, 384, 385, 386, 387, 388, 389, 390, 391, 392, 393, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 489, 480, 481, 482, 483, 484, 485, 486, 487, 488, 489, 490, 491, 492, 493, 494, 495, 496, 497, 498, 499, 500 or more of an L2 polypeptide (e.g., SEQ ID NOs:1-70).

In still a further aspect an L2 peptide includes a polypeptide segment that includes at most, at least, or about amino acids 17-36, 13-45, 11-88, or 11-200 of an L2 polypeptide disclosed in SEQ ID NO:1 herein or the corresponding region of SEQ ID NO:2-70, or a consensus sequence thereof. Each of the positions can be approximate amino acid positions and may vary ±1, 2, 3, 4, 5, 6, 7, 8, 9, 10 or more amino acid positions. The amino acid positions identified are based on the numbering of the HPV16 L2 protein (SEQ ID NO:1). Amino acid positions from L2 proteins of other HPV types may vary, but one of skill in the art would be capable of aligning any L2 amino acid sequence with HPV16 and identifying the peptide sequence that corresponds with the amino acid positions of HPV16 L2.

In certain embodiments, the L2 peptide is a segment of a HPV16 L2 protein (SEQ ID NO:1), an HPV18 L2 protein (SEQ ID NO:2), an HPV45 L2 protein (SEQ ID NO:3), an HPV6 L2 protein (SEQ ID NO:9), an HPV1 L2 protein (SEQ ID NO:4), an HPV2 L2 protein (SEQ ID NO:5), an HPV63 L2 protein (SEQ ID NO:62), an HPV5 L2 protein (SEQ ID NO:8), an HPV8 L2 protein (SEQ ID NO:11), an HPV11 L2 protein (SEQ ID NO:14), an HPV31 L2 protein (SEQ ID NO:32), an HPV33 L2 protein (SEQ ID NO:34), an HPV35 L2 protein (SEQ ID NO:36), an HPV39 L2 protein (SEQ ID NO:40), an HPV51 L2 protein (SEQ ID NO:50), an HPV52 L2 protein (SEQ ID NO:51), an HPV56 L2 protein (SEQ ID NO:55), an HPV58 L2 protein (SEQ ID NO:57), an HPV59 L2 protein (SEQ ID NO:58), an HPV68 L2 protein (SEQ ID NO:66), an HPV73 L2 protein (SEQ ID NO:69), and/or an HPV82 L2 protein (SEQ ID NO:70).

In certain aspects a multitype polypeptide has a general formula of:

[epitope X(a)-L-epitope X+1(b)-L-epitope X+n(c)](d), wherein a and/or b and/or c and/or d are independently 1, 2, 3, 4, 5, 6, 7, 8, 9, 10, 11, 12, 13, 14, 15, 16, 17, 18, 19, 20, 21, 22, 23, 24, 25; and n is independently 1 to 98; and peptide X, peptide X+1, peptide X+n, are distinct immunogenic epitopes selected from one or more sexually transmitted organism; and (L) can represent a linker, a chemical coupling, a peptide bond. The peptides of the formula can be derived from the same protein or a different protein from the same organism or pathogen, or these peptides can be derived from a homologous or a heterologous protein from a different pathogenic organism. In one embodiment peptide X is an HPV polypeptide; and peptide X+1 is a different HPV peptide or a peptide from another pathogenic organism, and peptide X+n is one or more other distinct peptide from any HPV type or other pathogenic organism. The "-L-" represents a linker, a chemical linker, a peptide linker, a chemical coupling, or a peptide bond in the case of a polypeptide fusion, or other ways of coupling or connecting peptides to peptides or peptides to substrates that are know in the art.

Embodiments of the invention include at most, at least, or about 2, 3, 4, 5, 6, 7, 8, 9, 10, 11, 12, 13, 14, 15, 16, 17, 18, 19, 20, 21, 22, 23, 24, 25, 50, 100, 150, 200, 250, 500 or more of two or more peptide sequences of SEQ ID NO:71-92, 94-106, and/or 110-112. In other aspects the peptides of the invention include corresponding sequences of SEQ ID NO:1-70 and other HPV L2 polypeptides. In certain aspects, L2 polypeptide segment is at least or more than 50%, 55%, 60%, 65%, 70%, 75%, 80%, 85%, 90%, 91%, 92%, 93%, 94%, 95%, 96%, 97%, 98%, 99%, or 100% identical to SEQ ID NO:71-92, 94-106, 110-112, and/or corresponding sequences of SEQ ID NO:1-70, and/or segments of SEQ ID NO:1-70, and/or other PV L2 polypeptides or segments thereof.

One or more of the polypeptides can be useful as a vaccine composition for the prophylaxis, treatment, or prevention of papillomavirus infection. In certain aspects the composition can be combined with a pharmaceutical carrier. The vaccine composition is administered to an individual prior to papillomavirus exposure to minimize or prevent papillomavirus infection, or is administered after a patient has been infected to reduce the severity of infection and retard/halt progression of the disease, or to prevent transmission of a papillomavirus from the infected host to another individual who does not have a papillomavirus infection.

As used herein, the term "antigen" or "immunogenic peptide" is a molecule capable of being bound by an antibody or T-cell receptor. An antigen is additionally capable of inducing a humoral immune response and/or cellular immune response leading to the production of B- and/or T-lymphocytes. The structural aspect of an antigen that gives rise to a biological response is referred to herein as an "antigenic determinant." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. Typically, an antigen will be a peptide derived from a protein expressed by a pathogenic organism (e.g., HPV). An antigenic determinant need not be a contiguous sequence or segment of protein and may include various sequences that are not immediately adjacent to one another. In certain aspects an antigenic determinant is an PV polypeptide segment, PV peptide.

With regard to a particular amino acid sequence, an "epitope" is a set of amino acid residues which is involved in recognition by a particular immunoglobulin, or in the context of T-cells, those residues necessary for recognition by T-cell receptor proteins and/or Major Histocompatibility Complex (MHC) receptors. The amino acid residues of an epitope need not be contiguous. In an immune system setting, in vivo or in vitro, an epitope is the collective features of a molecule, such as primary, secondary and tertiary peptide structure, and charge, that together form a site recognized by an immunoglobulin, T-cell receptor, or HLA molecule. Throughout this disclosure, "epitope" and "peptide" are often used interchangeably.

As used herein, "B-cell epitope" or "target epitope" refers to a feature of a peptide or protein that is recognized by a B-cell receptor in the immunogenic response to the peptide comprising that antigen (e.g., an HPV L2 segment or sub region thereof).

As used herein, "HPV" and "human papillomavirus" refer to the members of the genus Papillomavirus (PV) that are capable of infecting humans. There are two major groups of HPVs (genital and cutaneous groups), each of which contains multiple virus "types" or "strains" (e.g., HPV 16, HPV 18, HPV 31, HPV 32, etc.). Of particular interest in the present invention are the HPV types that are associated with genital infection and malignancy.

The term "vaccine" refers to a formulation which contains 1, 2, 3, 4, 5, 6, 7, 8, 9, 10 or more multitype HPV peptide compositions of the present invention. The multitype HPV peptide compositions typically will be in a form that is capable of being administered to a subject and induces a protective or therapeutic immune response sufficient to induce immunity to prevent and/or ameliorate an infection and/or to reduce at least one symptom of an infection and/or to enhance the efficacy of another anti-HPV therapy and/or to attenuate HPV infection and/or attenuate transmissibility of HPV. Typically, the vaccine comprises a conventional saline or buffered aqueous solution medium in which the composition of the present invention is suspended or dissolved. In other aspects the vaccine can be a solid (e.g., powdered or lyophilized formulation). The composition of the present invention can be used conveniently to prevent, ameliorate, or otherwise treat an infection. Upon introduction into a host, the composition is able to provoke an immune response including, but not limited to, the production of antibodies and/or cytokines and/or the activation of cytotoxic T cells, antigen presenting cells, helper T cells, dendritic cells and/or other cellular responses.

As used herein, "prophylactic" and "preventive" vaccines or compositions are compositions designed and administered to prevent infection, disease, and/or any related sequelae caused by or associated with a pathogenic organism, particularly HPV.

As used herein, "therapeutic" vaccines or compositions are compositions designed and administered to patients already infected with a pathogenic organism such as at least one HPV strain. Therapeutic vaccines (e.g., therapeutic HPV vaccines) are used to prevent and/or treat the development of benign or malignant tumors in these infected individuals.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

It is contemplated that one or more members of a list provided herein may be specifically excluded from or included in a claimed invention.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention. Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
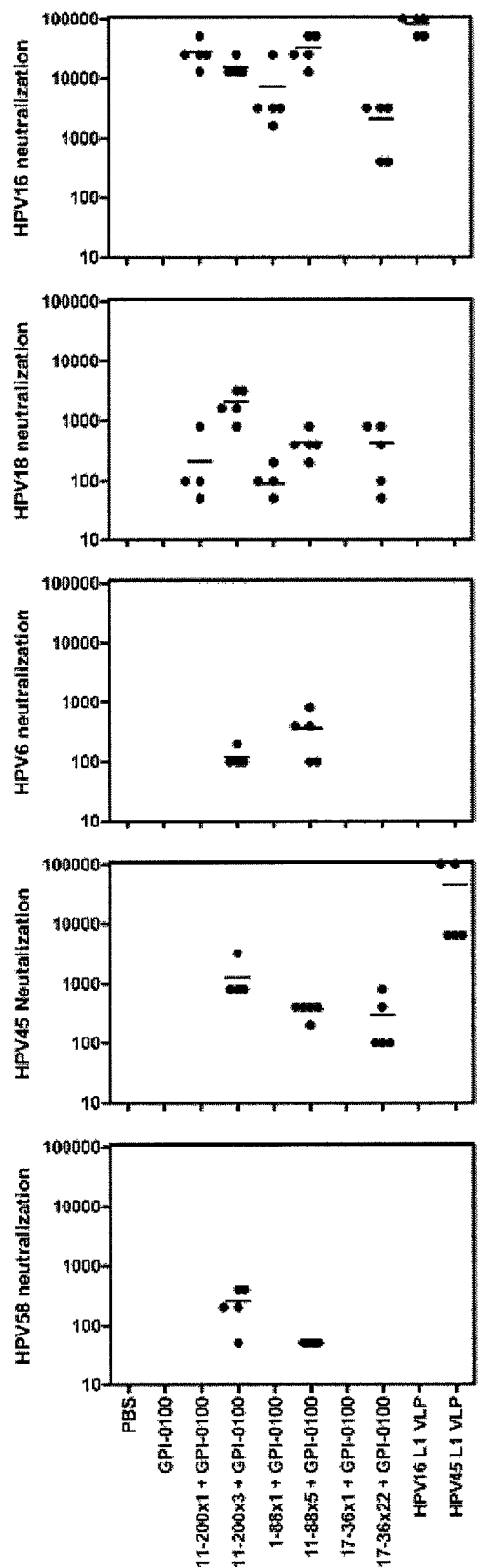
FIG. 1. Vaccination of mice with multi-type L2 vaccines induces more broadly cross-neutralizing antibodies than monomeric L2 vaccines or L1 VLP. BALB/c mice were vaccinated s.c. on days 0, 15, 30 with PBS or 25 µg of different L2 monomeric and multi-type constructs in GPI-0100 (50 µg) adjuvant or either HPV16 L1 VLP or HPV45 L1 VLP without an adjuvant. In vitro neutralization assays were performed using HPV pseudovirus for the genotypes indicated on two fold dilutions of the antisera collected from the mice two weeks after the final immunization. End point titers achieving 50% neutralization are plotted.

The high cost and type-restricted protection by first generation HPV L1 virus-like particle vaccines necessitates the development of additional broadly protective second generation compositions and vaccines. Minor capsid protein L2 protects animals from papillomavirus challenge by the induction of neutralizing antibodies. While L2 induces antibodies that cross-neutralize diverse papillomavirus types, the inventors observe that L2-specific antibodies typically neutralize related types more effectively than less evolutionarily related types. To enhance cross-protection L2 fusion proteins were designed consisting of known cross-neutralizing epitopes of divergent HPV types. Vaccination with HPV16 L2 polypeptides comprising residues 17-36, 1-88 or 11-200, was compared with three multitype L2 fusion proteins; 11-200x3 (SEQ ID NO:113) types (HPV6, 16, 18), 1 1-88x5 (SEQ ID NO:108) types (HPV 1, 5, 6, 16, 18), 17-36x22 types (5 cutaneous, 2 mucosal low risk and 15 oncogenic types). Mice were vaccinated three times subcutaneously with 25 µg of antigen in GPI-0100 adjuvant. Among all the monotype polypeptides, 11-200 generated the highest HPV16 neutralization titer. However, 11-200x3 induced the highest neutralization titer against HPV45 and HPV58 as well as with HPV16, HPV18, HPV6 as compared to other multitype and monotype fusion proteins. Immunized mice were challenged with HPV16 pseudovirus expressing luciferase. Vaccination with 11-200x3 (SEQ ID NO:113) protected mice against HPV16 challenge as well as HPV16 L1 VLP. Induction of HPV neutralizing antibodies upon vaccination with 25 µg of 11-200x3 (SEQ ID NO:113) protein alone or with alum or 50 µg or 200 µg of GPI-0100, or 50 µg GPI-0100 with Tween-40 was compared. The presence of an adjuvant significantly boosted the humoral response to 11-200x3, but there was no significant difference among adjuvants. The inventors conclude that vaccination with a single fusion protein comprising HPV6 L2 11-200 (SEQ ID NO:96), HPV16 L2 11-200 (SEQ ID NO:100), and HPV18 L2 11-200 (SEQ ID NO:101) produced in *E. coli* and formulated with an adjuvant is protective and induces broadly cross-neutralizing antibodies.

It is also contemplated that such multitype HPV compositions can be used in conjunction with or as a model for other pathogenic organisms, particularly those associate with diseases communicated in the same manner as HPV, e.g., sexually transmitted diseases. Thus, the teachings of this application in regard to HPV can be extended to other pathogenic organism either alone or in conjunction with multitype HPV L2 peptides.

I. THERAPEUTIC AND PROPHYLACTIC COMPOSITIONS

Embodiments of the invention include HPV peptide compositions comprising a two or more HPV polypeptide segments from two or more HPV types. In certain aspects, the HPV types include all or some of the HPV types that are pathogenic to a particular organism or animal or human subject being administered the composition. In certain embodiments, the HPV polypeptide comprises at least two L2 epitopes or peptides. In still a further aspect, the HPV polypeptide comprises a L2 epitope from at least two HPV types. HPV polypeptide segments are described in detail herein.

The methods of the present invention include treatment for a disease or condition caused by or related to papillomavirus infection (e.g., HPV infection). An immunogenic multitype HPV peptide compositions and/or antibodies that bind the same, can be given to induce or provide a therapeutic response in a person infected with, or suspected of having been exposed to, or at risk of being infected with or exposed to HPV. Methods may be employed with respect to individuals who have tested positive for exposure to HPV or other sexually transmitted diseases, or who are deemed to be at risk for infection based on possible exposure or future exposure. In particular, the invention encompasses methods of treatment for HPV infection.

In some embodiments, the treatment is administered in the presence of adjuvants or carriers or other antigens, either HPV antigens or antigens from other pathogens that have an exposure risk that is related or coincident with HPV exposure risk. Furthermore, in some examples, treatment comprises administration of other agents commonly used against viral infection, such as one or more anti-virals.

In certain aspects of the invention, peptides of the invention are configured so that multiple peptides are presented to components of the immune system in close proximity to each other. Each peptide may stimulate multiple components of the immune system (two or more effector cells) or a single component of the immune system (an effector cell with a propensity to recognize multiple types or variants of a peptide). The peptides can be configured as a linear concatamer, as a branched concatamer (dendrimer), as projections from a support or base (e.g., nanoparticle, liposome, polymer, etc.). The number of recognition sites or peptides presented an entity and their spacing will determine the degree of oligomerization of the peptides. For example, a tetravalent entity such as streptavidin will result in a tetramer. Much higher valences are however possible. Preferably the number of peptides will be in the range of 2, 3, 4, 5, 6, 7, 8, 9, 10 to 10, 20, 25, 50 or more including all ranges there between.

In certain embodiments a multitype peptide composition is a natural polymer or a derivative thereof such as a protein, a branched polypeptide (dendrimer), a multimeric protein, or a nucleic acid encoding the same. A plurality of peptides can be attached to a polysaccharide, such as dextran, starch, cellulose, hyaluronic acid, chitin, or alginic acid or a derivative of these polysaccharides; a synthetic polymer such as polypropyleneglycol, polyethyleneglycol (PEG); a phospholipid membrane, such as a vesicle or a liposome, and an inorganic particle such as polystyrene or acrylic beads or magnetic beads.

In certain aspects a multitype polypeptide is a dendrimer. These dendrimers may, for example, be made according to the protocol as disclosed in "Chemoselective and orthogonal ligation techniques" in chapter 11 of Weng and Peter, White Eds., "Fmoc solid phase peptide synthesis, A Practical Approach" Oxford University Press (2000), and U.S. Patent publication 20080207485, which is incorporated herein by reference. Several other methods for synthesizing branched polypeptides will be well known to the practitioner skilled in the art. A branched polypeptide has peptides incorporated at predetermined sites in two or more of its branches. Each branch of the peptide may have a desired length. Preferably each branch is less than 24 amino acids long. Branching of the peptide may be effected by branching the peptide during synthesis on Lys residues by known methods. In this manner the peptide is branched on a first Lysine residue into two branches and further branched on further lysine residues to form a tetravalent entity thereafter. Other valencies, such as octamers, may be effected by including more or less branching steps. Odd valencies are also achievable by only partially branching the synthetic peptide.

In certain embodiments one or more termni of the polypeptide is attached to a support or base, e.g., in one aspect forming polypeptide loops extending from a support. Peptides of the invention can be comprised in various delivery vehicles or forms, such as virus-like particles (VLPs) or liposomes, or on the surface of biodegradable particle, or on the surface of beads or microparticles or nanoparticles.

A. Infectious Agents

An "infection" or "infectious disease", as used herein, refers to a disorder arising from the invasion of a host, superficially, locally, or systemically, by an infectious organism. Infectious organisms include bacteria, viruses, parasites, fungi, and protozoa.

Bacteria include gram-negative and gram-positive bacteria. Examples of gram-positive bacteria include, but are not limited to *Pasteurella* species, *Staphylococcus* species including *Staphylococcus aureus*; *Streptococcus* species including *Streptococcus pyogenes* group A, *Streptococcus viridans* group, *Streptococcus agalactiae* group B, *Streptococcus bovis*, *Streptococcus anaerobic* species, *Streptococcus pneumoniae*, and *Streptococcus faecalis*; *Bacillus* species including *Bacillus anthracis*; *Corynebacterium* species including *Corynebacterium diphtheriae*, aerobic *Corynebacterium* species, and anaerobic *Corynebacterium* species; *Diphtheroids* species; *Listeria* species including *Listeria monocytogenes*; *Erysipelothrix* species including *Erysipelothrix rhusiopathiae*; *Clostridium* species including *Clostridium perfringens, Clostridium tetani*, and *Clostridium difficile*.

Gram-negative bacteria include, but are not limited to *Neisseria* species including *Neisseria gonorrhoeae* and *Neisseria meningitidis*; *Branhamella* species including *Branhamella catarrhalis*; *Escherichia* species including *Escherichia coli*; *Enterobacter* species; *Proteus* species including *Proteus mirabilis*; *Pseudomonas* species including *Pseudomonas aeruginosa*, *Pseudomonas mallei*, and *Pseudomonas pseudomallei*; *Klebsiella* species including *Klebsiella pneumoniae*; *Salmonella* species; *Shigella* species; *Serratia* species; *Acinetobacter* species; *Haemophilus* species including *Haemophilus influenzae* and *Haemophilus ducreyi*; *Brucella* species; *Yersinia* species including *Yersinia pestis* and *Yersinia enterocolitica*; *Francisella* species including *Francisella tularensis*; *Pasturella* species including *Pasteurella multocida*; *Vibrio cholerae*; *Flavobacterium* species; meningosepticum; *Campylobacter* species including *Campylobacter jejuni*; *Bacteroides* species (oral, pharyngeal) including *Bacteroides fragilis*; *Fusobacterium* species including *Fusobacterium nucleatum*; *Calymmatobacterium granulomatis*; *Streptobacillus* species including *Streptobacillus moniliformis*; *Legionella* species including *Legionella pneumophila*.

Other types of bacteria include acid-fast bacilli, spirochetes, and actinomycetes. Examples of acid-fast bacilli include *Mycobacterium* species including *Mycobacterium tuberculosis* and *Mycobacterium leprae*. Examples of spirochetes include *Treponema* species including *Treponema pallidum, Treponema pertenue, Borrelia* species including *Borrelia burgdorferi* (Lyme disease), and *Borrelia recurrentis*, and *Leptospira* species. Examples of actinomycetes include: *Actinomyces* species including *Actinomyces israelii*, and *Nocardia* species including *Nocardia asteroides*.

Examples of viruses include, but are not limited to: Retroviruses, human immunodeficiency viruses including HIV-1, HDTV-III, LAVE, HTLV-III/LAV, HIV-III, HIV-LP, Cytomegaloviruses (CMV), Picornaviruses, polio viruses, hepatitis A virus, enteroviruses, human Coxsackie viruses, rhinoviruses, echoviruses, Caliciviruses, Togaviruses, equine encephalitis viruses, rubella viruses, Flaviruses, dengue viruses, encephalitis viruses, yellow fever viruses, Coronaviruses, Rhabdoviruses, vesicular stomatitis viruses, rabies viruses, Filoviruses, ebola virus, Paramyxoviruses, parainfluenza viruses, mumps virus, measles virus, respiratory syncytial virus (RSV), Orthomyxoviruses, influenza viruses, Bungaviruses, Hantaan viruses, phleboviruses and Nairo viruses, Arena viruses, hemorrhagic fever viruses, reoviruses, orbiviruses, rotaviruses, Bimaviruses, Hepadnaviruses, Hepatitis B virus, parvoviruses, Papovaviridae, papilloma viruses, polyoma viruses, Adenoviruses, Herpesviruses including herpes simplex virus 1 and 2, varicella zoster virus, Poxviruses, variola viruses, vaccinia viruses, Irido viruses, African swine fever virus, delta hepatitis virus, non-A, non-B hepatitis virus, Hepatitis C, Norwalk viruses, astroviruses, and unclassified viruses.

Examples of fungi include, but are not limited to: *Cryptococcus* species including *Crytococcus neoformans*; *Histoplasma* species including *Histoplasma capsulatum*; *Coccidioides* species including *Coccidiodes immitis*; *Paracoccidioides* species including *Paracoccidioides brasiliensis*; *Blastomyces* species including *Blastomyces dermatitidis*; *Chlamydia* species including *Chlamydia trachomatis*; *Candida* species including *Candida albicans*; *Sporothrix* species including *Sporothrix schenckii*; *Aspergillus* species, and fungi of mucormycosis.

Other infectious organisms include parasites. Parasites include *Plasmodium* species, such as *Plasmodium* species including *Plasmodium falciparum, Plasmodium malariae, Plasmodium ovale,* and *Plasmodium vivax* and *Toxoplasma gondii*. Blood-borne and/or tissues parasites include *Plasmodium* species, *Babesia* species including *Babesia microti* and *Babesia divergens, Leishmania* species including *Leishmania tropica, Leishmania braziliensis, Leishmania donovani*; *Trypanosoma* species including *Trypanosoma gambiense, Trypanosoma rhodesiense* (African sleeping sickness), and *Trypanosoma cruzi* (Chagas' disease).

Other medically relevant microorganisms have been described extensively in the literature, e.g., See Thomas, Medical Microbiology, Bailliere Tindall, Great Britain 1983 and Murray, Medical Microbiology (ISBN 0323033032), 2005, the entire contents of which is hereby incorporated by reference.

B. HPV Vaccines

The present invention includes compositions for preventing or ameliorating HPV infections. As such, the invention contemplates vaccines for use in both active and passive immunization embodiments. Immunogenic compositions, proposed to be suitable for use as a vaccine, may be prepared from multitype HPV polypeptide(s) comprising segments of HPV L2 protein. In other embodiments, multitype HPV L2 polypeptides can be used in combination with other HPV proteins or segments thereof, such as E1, E2, E3, E4, E5, E6, E7, E8, and/or L1 protein. See for example U.S. Pat. Nos. 7,425,438, 7,416,846, 7,416,732, 7,407,807, 7,374,767, 7,201,908, 7,189,513, and 7,288,258, each of which is incorporated herein by reference in its entirety.

Typically, vaccines are administered in a manner compatible with a vaccine formulation, and in such amount as will be therapeutically effective and/or immunogenic. The quantity to be administered depends on the subject to be treated, including the capacity of the individual's immune system to synthesize antibodies and the degree of protection desired. Precise amounts of active ingredient required to be administered depend on the judgment of the practitioner. Typically, 0.1, 1, 5, 10, 20, 30, 40, 50, 60, 70, 80, 90, to 100 ng, µg, or mg may be administered per vaccination or administration. Suitable regimes for initial administration and booster shots are also variable, but are typified by an initial administration followed by subsequent inoculations or other administrations.

1. HPV Polypeptides and Polypeptide Segments

In certain aspects of the invention various segments of HPV polypeptides are used as a HPV peptide component of a multitype HPV polypeptide vaccine. In certain aspects, the HPV polypeptide is an L2 polypeptide. In a further aspect the L2 polypeptide is a HPV1, HPV2, HPV3, HPV4, HPV5, HPV6, HPV7, HPV8, HPV9, HPV10, HPV11, HPV12, HPV13, HPV14, HPV15, HPV16, HPV17, HPV18, HPV19, HPV20, HPV21, HPV22, HPV23, HPV24, HPV25, HPV26, HPV27, HPV28, HPV29, HPV30, HPV31, HPV32, HPV33, HPV34, HPV35, HPV36, HPV37, HPV38, HPV39, HPV40, HPV41, HPV42, HPV43, HPV44, HPV45, HPV46, HPV47, HPV48, HPV49, HPV50, HPV51, HPV52, HPV53, HPV54, HPV55, HPV56, HPV57, HPV58, HPV59, HPV60, HPV61, HPV62, HPV63, HPV64, HPV65, HPV66, HPV67, HPV68, HPV69, HPV70, HPV71, HPV72, HPV73, HPV74, HPV75, HPV76, HPV77, HPV78, HPV79, HPV80, HPV81, HPV82, HPV83, HPV84, HPV85, HPV86, HPV87, HPV88, HPV89, HPV90, HPV91, HPV92, HPV93, HPV94, HPV95, HPV96, HPV97, HPV98, HPV99, HPV100 or more (See SEQ ID NO:1-70); and animal papillomaviruses: bovine papillomavirus type 1 (BPV1), bovine papillomavirus type 2 (BPV2), bovine papillomavirus type 4 (BPV4), cottontail rabbit papillomavirus (CRPV), deer papillomavirus (DPV), European elk papillomavirus (EEPV), canine oral papillomavirus (COPV), Rhesus monkey papillomavirus (RhPV) or rabbit oral papillomavirus (ROPV) L2 peptide epitope. The Human Papillomaviruses Compendium On Line compiles and publishes relevant molecular data concerning the human papillomaviruses (HPV) and related animal papillomaviruses. The compendium is accessed on the interne at (hpv-web.lanl.gov/stdgen/viras/hpv/compendium/htdocs/HTML_FILES/HPVcompintro4.html), which is incorporated by reference as of the priority date and filing date of this application.

Examples of L2 polypeptides can be found in publicly available protein databases such as GenBank (gb), SwissPro (sp), EMBL, and the like. Representative database entries, listed by HPV type with accession number in parenthesis, include, but are not limited to: HPV2 (gb/AAY86489, gb/ABN49461, gb/ABN49469, gb/ABO14925, gb/NP_077121); HPV3 (sp/P36744); HPV7 (gb/NP_041858.1); HPV10 (gb/NP_041745); HPV16 (gb/AAO85414, gb/AA015703, gb/AA015711, gb/AAQ10726, gb/AAV91650); HPV18 (gb/AAF14009, gb/ABP99710, gb/ABP99718, gb/ABP99726, gb/ABP99742, gb/ABP99766, gb/ABP99774, gb/ABP99782, gb/ABP99790, gb/ABP99798, gb/ABP99806, gb/NP_040316); HPV26 (gb/NP_041786.1); HPV27 (dbj/BAE16268, sp/P36755); HPV28 (sp/P50799); HPV29 (sp/P50800); HPV30 (sp/P36756); HPV33 (sp/P06418); HPV39 (gb/AAA47055); HPV40 (sp/P36760); HPV43 (sp/Q705H5); HPV45 (gb/AAY86493); HPV45 (gb/ABP99814, gb/ABP99854, gb/ABP99862, gb/ABP99870, gb/ABP99878, gb/ABP99894, gb/ABP99902, sp/P36761); HPV51 (sp/P26539); HPV52 (sp/P36763); HPV53 (gb/ABU54103, gb/ABU54117, gb/ABU54131, gb/ABU54152, gb/ABU54159, gb/ABU54173, gb/NP_041847); HPV56 (gb/AB076808, gb/AB076815, gb/AB076822, gb/AB076829, sp/P36765); HPV57 (dbj/BAF80485, sp/P22164); HPV58 (sp/P26538); HPV59 (emb/CAA54855); HPV61 (ref/NP_043449); HPV62 (sp/Q676U7); HPV66 (gb/AB076836, gb/AB076843, gb/AB076857, gb/AB076864, gb/AB076885, gb/AB076892, gb/AB076899, sp/Q80960); HPV68a (gb/AAZ39497); HPV69 (sp/Q9JH45); HPV70 (gb/AAC54856); HPV71 (gb/AAQ95182, gb/AAQ95189, gb/AAQ95203, ref/NP_597937); HPV72 (emb/CAA63878); HPV77 (emb/CAA75467); HPV81 (emb/CAF05697); HPV82 (gb/AAK28455, sp/Q91R53); HPV83 (gb/AAD38973); HPV84 (gb/AAK09276); HPV85 (gb/AAD24187); HPV86 (gb/AAL06740); HPV87 (emb/CAC17717); HPV89 (gb/AAM92156); HPV90 (ref/NP_671508); HPV91 (gb/AAM89135); HPV94 (dbj/BAD89178, emb/CAF05714); HPV97 (gb/AAZ39505, gb/AB027082); HPV102 (gb/AAZ39525); or HPV106 (gb/AAZ39518). Each amino acid sequence represented by the accession number is incorporated herein by reference as of the filing date of this application. In certain aspects at least 2, 3, 4, 5, 6, 7, 8, 9, 10, or more L2 peptides from at least 2, 3, 4, 5, 6, 7, 8, 9, 10, 11, 12, 13, 14, 15, 16, 17, 18, 19, 20, 21, 22 or more HPV types are coupled together to form a multitype HPV polypeptide (See SEQ ID NO:94, 108, 109, and 113). Coupling of the segments can be by expression or synthesis of a fusion protein, or by chemical conjugation of the peptides to each other or chemical conjugation of the peptides to a common substrate or polymer.

A peptide of the invention can include 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320 330, 340, 350, 360, 370, 380, 390, 400, 410, 420, 43, 440, 450, 460, 470, 480, or 490 consecutive amino acids, including all values and ranges there between, starting from amino acid 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320 330, 340, 350, 360, 370, 380, 390, 400, 410, 420, 43, 440, 450, 460, 470, 480, or 490, including all values there between, of a HPV L2 polypeptide. In certain embodiments an HPV L2 polypeptide includes, but is not limited to SEQ ID NO:1 to SEQ ID NO:70.

In certain aspects the multitype HPV polypeptide comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, 70, 80, 90, 100, 200, or more of 2, 3, 4, 5, 6, 7, 8, 9, 10, 11, 12, 13, 14, 15, 16, 17, 18, 19, 20, 21, 22, 23, 24, 25 or more of the peptides selected from HPV L2 17-36—DIYPSCKISNTCPP-DIQNKI (SEQ ID NO:72), HPV L2 17-36—DLYRTCK-QAGTCPPDIIPRV (SEQ ID NO:73), HPV L2 17-36-DIY-PACKVANNCPPDIQNKI (SEQ ID NO:74), HPV L2 17-36-HIYQTCKQAGTCPPDVINKV (SEQ ID NO:75), HPV L2 17-36-HIYQTCKQAGTCPPDVINKV (SEQ ID NO:76), HPV L2 17-36-QLYQTCKLTGTCPPDVIPKV (SEQ ID NO:77), HPV L2 17-36-QLYQTCKATGTCPPDVIPKV (SEQ ID NO:78), HPV L2 17-36-QLYKTCKQAGTCPPDI-IPKV (SEQ ID NO:71), HPV L2 17-36-DLYKTCKQS-GTCPPDVVPKV (SEQ ID NO:79), HPV L2 17-36-QLYQTCKAAGTCPSDVIPKI (SEQ ID NO:80), HPV L2 17-36-QLYQTCKATGTCPPDVIPKV (SEQ ID NO:81), HPV L2 17-36-QLYRTCKAAGTCPPDVIPKV (SEQ ID NO:82), HPV L2 17-36-DLYRTCKQSGTCPPDVVDKV (SEQ ID NO:83), HPV L2 17-36-DLYRTCKQSGTCPPD-VINKV (SEQ ID NO:84), HPV L2 17-36-QLYSTCK-AAGTCPPDVVNKV (SEQ ID NO:85), HPV L2 17-36-QLYQTCKASGTCPPDVIPKV (SEQ ID NO:86), HPV L2 17-36-QLYKTCKLSGTCPEDVVNKI (SEQ ID NO:87), HPV L2 17-36-QLYQTCKASGTCPPDVIPKV (SEQ ID NO:88), HPV L2 17-36-DLYKTCKQAGTCPSDVINKV (SEQ ID NO:89), HPV L2 17-36-DLYKTCKQSGTCPSD-VINKV (SEQ ID NO:90), HPV L2 17-36-QLYKTCK-QAGTCPPDVIPKV (SEQ ID NO:91), and/or QLYSTCK-AAGTCPPDVIPKV (SEQ ID NO:92).

In a still a further aspect the multitype HPV polypeptide comprises an amino sequence of HPV L2 17-36x22—DIYP-SCKISNTCPPDIQNKIDLYRTCK-QAGTCPPDIIPRVDIYPACKVANNCPPDIQNKIHIY QTCKQAGTCPPDVINKVHIYQTCK-QAGTCPPDVINKVQLYQTCKLTGTCPPDVIPKVQL YQTCKATGTCPPDVIPKVQLYKTCK-QAGTCPPDIIPKVDLYKTCKQSGTCPPDVVPKVQ LYQTCKAAGTCP SDVIPKIQLYQTCKATGTCPPDVIP-KVQLYRTCKAAGTCPPDVIPKVD LYRTCKQSGTCPP-DVVDKVDLYRTCKQSGTCPPD-VINKVQLYSTCKAAGTCPPDVVNK VQLYQTCKASGTCPPDVIPKVQLYK-
TCKLSGTCPEDVVNKIQLYQTCKASGTCPPDVIPK VDLYKTCKQAGTCPSDVINKVDLYKTCK-QSGTCPSDVINKVQLYKTCKQAGTCPPDVIP KVQLYSTCKAAGTCPPDVIPKV (SEQ ID NO:93)

In yet another aspect the multitype HPV polypeptide comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, 70, 80, 90, 100, 200, or more of 1, 2, 3, 4, 5, 6, 7 8, 9, 10, 11, 12, 13, 14, 15, 16, 17, 18, 19, 20, 21, 22, 23, 24, 25 or more of the peptides selected from HPV L2 11-88-KRASATQLYKTCK-QAGTCPPDIIPKVEGKTIAD-QILQYGSMGVFFGGLGIGTGSGTGGRT GYIPLGTR-PPTATDTLAP (SEQ ID NO:94), HPV L2 11-88—KRASVTDLYKTCKQSGTCPPDVVPKVEGTTLADKIL QWSSLGIFLGGLGIGTGSGTGGRT GYIPLGGRSNTV-VDVGPT (SEQ ID NO:95), HPV L2 11-88—KRAAP-KDIYPSCKISNTCPPDIQNKIEHTTIAD-KILQYGSLGVFLGGLGIGTARGSGGRIGY TPLGEGGGVRVATRPT (SEQ ID NO:96), HPV L2 11-88—KRDSVTHIYQTCKQAGTCPPD-VINKVEQTTVADNILKYGSAGVFFG-GLGISTGRGTGGA TGYVPLGEGPGVRVGGTPT (SEQ ID NO:97), HPV L2 11-88—KRASATQLYQTCKLTGTCP-PDVIPKVEHNTIADQILKWGSLGVFFG-GLGIGTGSGTGGRT GYVPLGTSAKPSITSGPM (SEQ ID NO:98) HPV L2 11-88 SATQLYQTCKLTGTCPPDVIP-KVEHNTIADQILKWGSLGVFFGGL-GIGTGSGTGGRTGYV PLQTSAKPSITSGPMAKRA (SEQ ID NO:99), HPV L2 11-88 SATQLYKTCKQAGTCP-PDIIPKVEGKTIADQILQYGSMGVFFG-GLGIGTGSGTGGRTGYIP LGTRPPTATDTLAPRA (SEQ ID NO:100), HPV L2 11-88 SVTDLYKTCKQSGTCPPDV-VPKVEGTTLADKILQWS SLGIFLGGLGIGTGSGTG-GRTGYI PLGGRSNTVVDVGPTRKRA (SEQ ID NO:101), HPV L2 11-88 SATQLYQTCKAAGTCPSDVIP-KIEHTTIADQILRYGSMGVFFGGL-GIGSGSGTGGRTGYV PLSTRPSTVSEASIPRA (SEQ ID NO:102), HPV L2 11-88 SATDLYRTCKQ SGTCPPDVVD-KVEGTTLADKILQWTSLGIFLGGLGIGT-GTGTGGRTGYI PLGGRPNTVVDVSPARRA (SEQ ID NO:103), HPV L2 11-88 SVTQLYSTCKAAGTCPPDV-VNKVEGTTLADKILQWSGLGIFLGGL-GIGTGSGSGGRTGYI PLGGGGRPGVVDIAPARA (SEQ ID NO:104), HPV L2 11-88 SATQLYKTCKLS GTCPEDV-VNKIEQKTWADKILQWGSLFTYFGGL-GIGTGTGSGGRAGY VPLGSRPSTIVDVTPARKKRA (SEQ ID NO:105), and/or HPV L2 11-88 SATQLYKTCK-QAGTCPPDVIPKVEGS TIADNILKYGSIGVFFGGL-GIGSGSGSGGRTGYVP LSTGTPSKPVEIP (SEQ ID NO:106).

In certain embodiments a multitype HPV polypeptide comprises an amino acid of HPV L2 11-88x5 —KRASATQ-LYKTCKQAGTCPPDIIPKVEGKTIAD-QILQYGSMGVFFGGLGIGTGSGTGGRT GYIPLGTR-PPTATDTLAPKRASVTDLYKTCKQSGTCPPDVVPKV EGTTLADKILQWSSLG FLGGLGIGTGSGTGGRTGYI-PLGGRSNTVVDV GPTKRAAPKDIYPSCKISNTCPP-DIQNKI EHTTIADKILQYGSLGVFLGGLGIG-TARGSGGRIGYTPLGEGGGVRVATRPTKRDSVTHI YQTCKQAGTCPPDVINKVEQTTVAD-NILKYGSAGVFFGGLGISTGRGTGGATGYVPLGE GPGVRVGGTPTKRASATQLYQTCKLT-GTCPPDVIPKVEHNTIADQILKWGSLGVFFGGL GIGTGSGTGGRTGVPLGTSAKPSITSGPM (SEQ ID NO:107).

In still a further embodiment a multitype HPV polypeptide comprises an amino acid of HPV L2 11-88x8 SATQ- LYQTCKLTGTCPPDVIPKVEHNTIAD-
QILKWGSLGVFFGGLGIGTGSGTGGRTGYV PLQT-
SAKPSITSGPMAKRASATQLYKTCKQAGTCPPDIIPK
VEGKTIADQILQYGSMGVF FGGLGIGTGSGTGGRT-
GYIPLGTRPPTATDTLAPRASVTDLYK-
TCKQSGTCPPDVVPKVE GTTLADKILQWSSLGIFLG-
GLGIGTGSGTGGRTGYIPLGGRSNTVVDVGPTRKRA
SATQL YQTCKAAGTCPSDVIPKIEHTTIADQIL-
RYGSMGVFFGGLGIGSGSGTGGRTGYVPLSTRP
STVSEASIPRASATDLYRTCKQSGTCPP-
DVVDKVEGTTLADKILQWTSLGIFLGGLGIGT
GTGTGGRTGYIPLGGRPNTVVDVSPAR-
RASVTQLYSTCKAAGTCPPDVVNKVEGTTLA
DKILQWSGLGIFLGGLGIGTGSGSGGRT-
GYIPLGGGGRPGVVDIAPARASATQLYKTCKL
SGTCPEDVVNKIEQKTWAD-
KILQWGSLFTYFGGLGIGTGTGSG-
GRAGYVPLGSRPSTIV DVTPARKKRASATQLYKTCK-
QAGTCPPDVIPKVEGSTIADNILKYGSIGVFFGGLGIGSG
SGSGGRTGYVPLSTGTPSKPVEIP (SEQ ID NO:108).

In still a further embodiment a multitype HPV polypeptide comprises homologous regions from L2s of HPV6b, HPV16, HPV18, HPV31, HPV39, HPV51, HPV56 and HPV73. The amino acid of HPV L2 11-88x8 is MASATQLYQTCKLT-
GTCPPDVIPKVEHNTIADQILK-
WGSLGVFFGGLGIGTGSGTGGRT GYVPLQTSAKP-
SITSGPMAKRASATQLYKTCKQAGTCPPDIIPKVEGK
TIADQILQYGSM GVFFGGLGIGTGSGTGGRTGYI-
PLGTRPPTATDTLAPRASVTDLYKTCK-
QSGTCPPDVVP KVEGTTLADKILQWSSLGIFLGGL-
GIGTGSGTGGRTGYIPLGGRSNTVVDVGPTRKRASA
TQLYQTCKAAGTCPSDVIPKIEHTTIAD-
QILRYGSMGVFFGGLGIGSGSGTGGRTGYVPL STRP-
STVSEASIPRASATDLYRTCKQSGTCPP-
DVVDKVEGTTLADKILQWTSLGIFLGGL
GIGTGTGTGGRTGYIPLGGRPNTVVDVS-
PARRASVTQLYSTCKAAGTCPPDVVNKVEGT TLAD-
KILQWSGLGIFLGGLGIGTGSGSGGRT-
GYIPLGGGGRPGVVDIAPARASATQLYKT
CKLSGTCPEDVVNKIEQKTWAD-
KILQWGSLFTYFGGLGIGTGTGSGGRAGYVPLGSRPS
TIVDVTPARKKRASATQLYKTCK-
QAGTCPPDVIPKVEGSTIADNILKYGSIGVFFGGLGIG
SGSGSGGRTGYVPLSTGTPSKPVEIP (SEQ ID NO:109).

In yet still a further embodiment a multitype HPV polypeptide comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, 70, 80, 90, 100, 200, or more of 1, 2, 3, 4, 5, 6, 7 8, 9, 10 or more of the peptides selected from HPV L2-200 KRASATQ-
LYQTCKASGTCPPDIIAKVEQNTLAD-
KILKWGSLGVFFGGLGIGTGSGTGGRT GYVPVQTAP-
RPAIPFGPTARPPIIVDTVGPSDSSIVSLVEDSTIINSAA
SDFVPPIREGFEIST SETTTPAILDVS-
VTTHNTTSTSIFKNPAFAEPSIVQSQPS-
VEASGHVLTSTYTSTISSHSVED IPLDT (SEQ ID NO:110), HPV L2 11-200-KRASATQLYKTCKQAGTCPP-
DIIPKVEGKTIADQILQYGSMGVFFGGL-
GIGTGSGTGGRT GYIPLGTRPPTATDTLAPVRP-
PLTVDPVGPSDSIVSLVEETSFIDAGAPTPVPSIPPDV
SGF SITTSTDTTPAILDINNTVFT-
TVTTHNNPTFTDPSVLQPPTPAETGGH-
FTSSSTISTHNYEE IPMDT (SEQ ID NO:111), and/or HPV L2 11-200-KRASVTDLYKTCKQSSLGIFLGGL-
GIGTGSGTGGRT GYIPLGGRSNTVVDVGPTRPPV-
VIEPVGPTDPSIVTLIEDSSVVTS-
GAPRPTFTGTSGFIDIT
SAGTTTPAVLDITPSSTSVSISTTNFT-
NPAFSDPSIIEVPQTGEVAGNVFVGTPTSGTHGYE
EIPLQT (SEQ ID NO:112). In certain embodiments a multitype HPV polypeptide comprises the amino acid sequence HPV L2 11-200x3 KRASATQLYQTCKASGTCPPDI-
IAKVEQNTLADKILKWGSLGVFFGGL-
GIGTGSGTGGRT GYVPVQTAPRPAIPFGPTARPPI-
IVDTVGPSDSSIV
SLVEDSTIINSAASDFVPPIREGFEIST SETTTPAILDVS-
VTTHNTTSTSIFKNPAFAEPSIVQSQPS-
VEASGHVLTSTYTSTISSHSVED IPLDTKMSATQLYK-
TCKQAGTCPPDIIPKVEGIADQILQYGSMGVFFGGLG
IGTGSGTGG RTGYIPLGTRPPTATDTLAPVRPPLTVD-
PVGPSDPSIVSLVEETSFIDAGAPTPVPSIPPDVS
GFSITTSTDTTPAILDINNTVTTVTTHNNPTFTDP
SVLQPPTPAETGGHFTLSS STISTHNYE EIPMDT-
KRASVTDLYKTCKQSGTCPPDVVPKVEG-
TLADKILQWSSLGIFLGGLGIGTGSG TGGRTGYIPLG-
GRSNTVVDVGPTRPPVVIEPVGPTDPSIVTLIEDSSV
VTSGAPRPTFTGTS GFDITSAGTTTPAVLDITPSSTSV-
SISTTNFTNPASDPSIIEVPQTGEVAGNVFVGTPTSGT
HGYEEIPLQT (SEQ ID NO:113).

In certain embodiments a multitype polypeptide, "FurinD-KILKx15" comprises L2 protein sequences from HPV6b, HPV11, HPV16, HPV18, HPV31, HPV33, HPV35, HPV39, HPV45, HPV51, HPV52, HPV56, HPV58, HPV59 and HPV73. The amino acid sequence of FurinDKILKx 15 is MASATQLYQTCKLTGTCPPDVIPKVE-
HNTIADQILKASATQLYQTCKATGTCPPDVIPKV EHT-
TIADQILKASATQLYKTCKQAGTCPPDI-
IPKVEGKTIADQILQASVTDLYKTCKQSGT
CPPDVVPKVEGTTLADKILQASATQ-
LYQTCKAAGTCPSDVIPKIEHTTIADQILRASATQL
YQTCKATGTCPPDVIPKVEGSTIADQIL-
KASATQLYRTCKAAGTCPPDVIPKVEGNTVAD
QILKASATDLYRTCKQSGTCPPDVVD-
KVEGTTLADKILQASATDLYRTCKQSGTCPPDVI
NKVEGTTLADKILQASVTQLYSTCK-
AAGTCPPDVVNKVEGTTLADKILQASATQLYQTC
KASGTCPPDVIPKVEGTTIADQLLKA-
SATQLYKTCKLSGTCPEDVVNKIEQKTWADKILQ
ASATQLYTCKASGTCPPDVIPKVEGT-
TIADQILRASATDLYKTCKQAGTCPSDVINKVE
GTTLADKILQASATQLYKTCKQAGTCPP-
DVIPKVEGSTIADNILK (SEQ ID NO:114).

Peptides of the invention are typically synthesized using methods of peptide synthesis known to those skilled in the art and/or are coupled using peptide chemistry known to those of skill in the art. In other aspects, peptides and polypeptides of the invention can be expressed and purified using recombinant techniques known to those skilled in the art.

2. Linker

Encompassed by the invention are oligomers or fusion proteins that contain a number of peptides. Such oligomers may be in the form of covalently-linked or non-covalently-linked multimers, including dimers, trimers, or higher oligomers. In one aspect of the invention, the oligomers maintain the ability to stimulate an immune response. One embodiment of the invention is directed to oligomers comprising multiple peptides joined via covalent or non-covalent linkers between peptides. Such linkers may be peptide linkers (spacers), or peptides that have the property of promoting oligomerization. Leucine zippers and certain polypeptides derived from antibodies are among the peptides that can promote oligomerization of the peptides attached thereto. Among the suitable peptide linkers are those described in U.S. Pat. Nos. 4,751,180 and 4,935,233, which are hereby incorporated by reference. In certain embodiments peptides of the invention are linked by peptide bonds with no discernable linker between the peptides.

3. Delivery Vehicles

Known formulations for vaccines have employed a variety of delivery vehicles for presenting such antigens to the mammalian immune system, so as to invoke a protective or therapeutic immune response against a pathogen. Such "delivery vehicles" have included as a vaccine agent heat or chemically-inactivated whole virus, protein particles of the whole virus, virus vectors, such as adenovirus and vaccinia, among others, and DNA-based vectors or plasmids.

Virus Like Particles Virus like particles (VLPs) have been investigated as vaccine agents. In general, encapsidated viruses include a protein coat or "capsid" that is assembled to contain the viral nucleic acid. Many viruses have capsids that can be "self-assembled" from the individually expressed capsid proteins to form VLPs, both within the cell the capsid is expressed in ("in vivo assembly") and outside of the cell after isolation and purification ("in vitro assembly").

Virus like particles mimic the overall structure of a virus particle without the requirement of containing infectious material. VLPs can lack a viral DNA or RNA genome, but retain the three-dimensional structure of an authentic virus. VLPs have the ability to stimulate B-cell mediated responses, CD4 proliferative responses and cytotoxic T lymphocytes responses. See, Schirmbeck et al. (1996) Intervirology 39, 111-119; Paliard et al. (2000) AIDS Res. Hum. Retroviruses 16, 273-282; Murata et al. (2000) PNAS USA 100, 6753-6758. also see U.S. Patent publication 20070041999, which is incorporated by reference in its entirety.

VLPs have been produced for more than 30 different viruses that infect humans and other animals, including Norwalk, Hepatitis B and C, Papillomavirus, Parvovirus, and Influenza A.

Virus like particles can also be manipulated to act as carrier molecules for the delivery of epitopes from other pathogenic agents. See, Noad et al. (2003) Trends in Microbiology 11(9), 438-444; Sadeyen et al. (2003) Virology 309:32-40; PCT publication WO 2005/005614; U.S. Patent Publications 2004/0033585 and 2005/0048082; U.S. Pat. Nos. 6,448,070; 6,110,466; 6,171,591; Brinkman et al. (2004) Lett. Drug Des. & Disc. 1:137-147. A capsid protein can be modified to contain an antigenic peptide, generating a recombinant viral capsid protein-antigenic peptide fusion. This fusion capsid protein-antigenic peptide product can then be expressed in a host cell, assembled in vivo or in vitro to form recombinant viral or virus-like particles, and administered to a host in order to illicit an immune response.

Nanoparticles—In one aspect, peptide can be coupled to non-protein materials such as, for example, nanoparticles and other substrates. Nanoparticles are typically about 1 nm to 200 nm in diameter may be used to provide for delivery of immunogenic peptides to a subject. A one or more peptide can be attached to a nanoparticle by a covalent or noncovalent chemical interactions. Noncovalent chemical interactions can include affinity (e.g., avidin/biotin, antigen/antibody, receptor/ligand), ionic interaction, and/or hydrophobic interaction. Methods for attaching peptides to solid supports such as nanoparticles are described, for example, in U.S. Patent Publication 2004/0258698. Nanoparticles having a diameter of from about 50 nm to about 200 nm may be delivered systemically. As used herein, the term "nanoparticle" means a polymer sphere or spheroid that can be formulated to have a regular arrayed surface of defined, tethered molecules in the nanometer size range (about 1 nm to 500 nm). Preferably, self-assembling monomers are utilized to form the nanoparticles. Moreover, the term nanoparticle encompasses the use of both polymerized and unpolymerized liposomes, bicelles and micelles, as well as viral capsid structures. Although nanoparticles are preferred for the compositions and methods of the present invention, other frameworks, scaffolds and other "presenters" such as dendrimers may be used as would be well known to persons skilled in the art as being appropriate to present ligands according to the present invention. Polyvalent nanoparticles U.S. Publication 20030223938.

Peptides of the invention can be administered in a liposomal composition. The liposome of the present invention can be multilamellar vesicle (MLV). The liposome comprises liposome-forming lipids having a hydrophilic tail portion and a polar or chemically reactive portion which in turn comprises an acid, alcohol, aldehyde, amine or ester. The liposomes may be further characterized by hydrocarbon chains or steroid tail group and a polar head group. The liposome-forming lipids comprise a phospholipid. Examples of suitable phospholipids include, but are not limited to phosphatidic acid, phosphatidyl choline, phosphatidyl ethanolamine, phosphatidyl glycerol, phosphatidylinositol and sphingomyelin.

Substances that can be encapsulated in or coupled to the liposomes of the present invention include proteins and peptides. In some embodiments, the substance comprises more than one compound. Peptides of the invention can comprise or be conjugated to a lipophilic moiety that localizes the peptides to the surface of the lipid. Multitype peptides can be localized to the liposome surface. See U.S. Patent publication 20060035853.

C. Adjuvants and Other Immunostimulatory or Enhancing Components

The immunogenicity of polypeptide or peptide or multitype HPV peptide compositions can be enhanced by the use of additional non-specific stimulators of the immune response, known as adjuvants. Suitable adjuvants include all acceptable immunostimulatory compounds, such as cytokines, toxins, or synthetic compositions.

A number of adjuvants can be used to enhance an antibody response against a multitype HPV polypeptide or any other composition described herein. Adjuvants can be used to (1) trap the antigen in the body to cause a slow release; (2) attract cells involved in the immune response to the site of administration; (3) induce proliferation or activation of immune system cells; or (4) improve the spread of the antigen throughout the subject's body.

Adjuvant formulations include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum salts, such as aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion, CpG1018, and/or GPI-0100, including various combinations thereof. In certain aspects, an adjuvant is a CpG1018 or GPI-0100 combined with one or more of TWEEN™ or alum or combinations thereof MHC antigens may even be used. Others adjuvants or methods are exemplified in U.S. Pat. Nos. 6,814,971, 5,084,269, 6,656, 462, each of which is incorporated herein by reference.

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (CARBOPOL®) used as an about 0.25% solution, aggregation of a protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide mono-oleate (Aracel A)); or emulsion with a 20% solution of a perfluorocarbon (FLUO-SOL-DA®) used as a block substitute may also be employed to produce an adjuvant effect. A typical adjuvant is complete Freund's adjuvant (containing killed *Mycobacterium tuberculosis*), incomplete Freund's adjuvants, and aluminum hydroxide.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, Pa.); or low-dose Cyclophosphamide (CYP; 300 mg/m$^2$) (Johnson/Mead, N.J.) and cytokines such as γ-interferon, IL-2, or IL-12 or genes encoding proteins involved in immune helper functions, such as B-7.

T helper epitopes—Two types of major T lymphocytes have been described, CD8+ cytotoxic lymphocytes (CTLs) and CD4 helper cells (Th cells). CD8+T cells are effector cells that, via the T cell receptor (TCR), recognize foreign antigens presented by class I MHC molecules on, for instance, virally or bacterially infected cells. Upon recognition of foreign antigens, CD8+ cells undergo an activation, maturation and proliferation process. This differentiation process results in CTL clones which have the capacity of destroying the target cells displaying foreign antigens. T helper cells on the other hand are involved in both humoral and cell-mediated forms of effector immune responses. With respect to the humoral, or antibody immune response, antibodies are produced by B lymphocytes through interactions with Th cells. Specifically, extracellular antigens, such as circulating microbes, are taken up by specialized antigen presenting cells (APCs), processed, and presented in association with class II major histocompatibility complex (MHC) molecules to CD4+Th cells. These Th cells in turn activate B lymphocytes, resulting in antibody production. The cell-mediated, or cellular immune response, in contrast, functions to neutralize microbes which inhabit intracellular locations, such as after successful infection of a target cell. Foreign antigens, such as for example, microbial antigens, are synthesized within infected cells and presented on the surfaces of such cells in association with Class I MHC molecules. Presentation of such epitopes leads to the above described stimulation of CD8+CTLs, a process which in turn is also stimulated by CD4+Th cells. Th cells are composed of at least two distinct subpopulations, termed Th1 and Th2 cells. The Th1 and Th2 subtypes represent polarized populations of Th cells which differentiate from common precursors after exposure to antigen.

In some aspects, a multitype HPV polypeptide may also comprise a preferential inducer of either a Th1 or a Th2 type of response. High levels of Th1-type cytokines tend to favor the induction of cell mediated immune responses to a given antigen, while high levels of Th2-type cytokines tend to favor the induction of humoral immune responses to the antigen.

The distinction between Th1 and Th2-type immune response is not absolute. In reality an individual will support an immune response which is described as being predominantly Th1 or predominantly Th2. However, it is often convenient to consider the families of cytokines in terms of that described in murine CD4+T cell clones by Mosmann and Coffman (Mosmann and Coffman, 1989). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10.

In certain aspects, Th epitopes include, but are not limited to T-cell epitopes derived from bacterial proteins and toxins, such as Tetanus and Diphtheria toxins. For example, the P2 and P30 epitopes from Tetanus toxin, Hepatitis B core antigen, tuberculosis, *Mycobacterium tuberculosis* RA12 (a subsequence (amino acids 192 to 323) of MTB32A (Skeiky et al. 1999)), p25 protein of morbillivirus/canine distemper virus: KLIPNASLIENCTKAEL (SEQ ID NO:117) PV (poliovirus) sequence 103-115: KLFAVWKITYKDT (SEQ ID NO:118) M5: NKLIAYPAVEALS (SEQ ID NO:119), TT (tetanus toxin) 830-844: QYIKANSKFIGITEL (SEQ ID NO:120), PADRE: aKXVMWTLKAAa (a=D-Ala, X=L-cyclohexyl-Ala) (SEQ ID NO:121), E7 p20-29 TDLYCYEQLN (SEQ ID NO:122), E7 p45-54: AEPDRAHYNI (SEQ ID NO:123), E7 p60-79: KCDSTLRLCVQSTHVIRTL (SEQ ID NO:124), E7 p85-94: GTLGIVGPIC (SEQ ID NO:125), ras p5-17: KLVVVGARGVGKS (SEQ ID NO:126), neu p42-56: HLD-MLRHLYQGGQVV (SEQ ID NO:127), neu p783-797, SRLLGICLTSTVQLV (SEQ ID NO:128), and MAGE-3$_{121-134}$: LLKYRAREPVTKAE (SEQ ID NO:129)).

Toll-Like Receptor agonist—It is now widely recognized that the generation of protective immunity depends not only on exposure to antigen, but also the context in which the antigen is encountered. Numerous examples exist in which introduction of a novel antigen into a host in an inflammatory context generates immunological tolerance rather than long-term immunity whereas exposure to antigen in the presence of an inflammatory agent (adjuvant) induces immunity. (Mondino et al., 1996; Pulendran et al., 1998; Jenkins et al., 1994; and Keamey et al., Immunity 1:327, 1994). Since it can mean the difference between tolerance and immunity, much effort has gone into discovering the "adjuvants" present within infectious agents that stimulate the molecular pathways involved in creating the appropriate immunogenic context of antigen presentation. It is now known that a good deal of the adjuvant activity is due to interactions of microbial and viral products with different members of the Toll Like Receptors (TLRs) expressed on immune cells (Beutler et al., 2004; Kaisho, 2002; Akira et al., 2003; and Takeda and Akira, 2004). The TLRs are named for their homology to a molecule in the *Drosophila*, called Toll, which functions in the development thereof and is involved in anti-microbial immunity (Lemaitre et al., 1996; and Hashimoto et al., 1988).

Early work showed the mammalian homologues to Toll and Toll pathway molecules were critical to the ability of cells of the innate immune system to respond to microbial challenges and microbial byproducts (Medzhitov et al., 1997; Medzhitov et al., 1998; Medzhitov et al., 2000; Medzhitov et al., 2000; and Janeway et al., 2002). Since the identification of LPS as a TLR4 agonist (Poltorok et al., 1998) numerous other TLR agonists have been described such as tri-acyl multitype HPV polypeptides (TLR1), peptidoglycan, lipoteichoic acid and Pam$_3$Cys (TLR2), dsRNA (TLM), flagellin (TLRS), diacyl multitype HPV polypeptides such as Malp-2 (TLR6), imidazoquinolines and single stranded RNA (TLR7,8), bacterial DNA, unmethylated CpG DNA sequences, and even human genomic DNA antibody complexes (TLR9). Takeuchi et al., 2001; Edwards et al., 2002; Hayashi et al., 2003; Nagase et al., 2003).

In certain aspects, TLR2 ligands include, but are not limited to lipoteichoic acid, mannuronic acids, peptidoglycans, atypical LPS, MALP-2 and MALP-404 (lipoproteins), OspA, Porin, LcrV, lipomannan, GPI anchor, lysophosphatidylserine, lipophosphoglycan (LPG), glycophosphatidylinositol (GPI), zymosan, hemagglutinin, and analogs or derivatives thereof. In a further aspect, TLR2 agonist include bacterial lipopeptide from *M. tuberculosis, B. burgdorferi, T. pallidum*; peptidoglycans from species including *Staphylococcus aureus*; Neisseria porins, bacterial fimbriae, Yersina virulence factors, CMV virions, measles haemagglutinin, and zymosan from yeast.

In certain aspects, the TLR agonist is a lipid moiety. Lipid moieties include, but are not limited to fatty acids such as palmitoyl, myristoyl, stearoyl and decanoyl groups or, more generally, any C2 to C30 saturated, monounsaturated, or polyunsaturated fatty acyl group. In certain aspects the lipid moiety is a $Pam_2Cys$ [S-[2,3-bis(palmitoyloxy)propyl]cysteine] or $Pam_3Cys$ [N-palmitoyl-S-[2,3-bis(palmitoyloxy) propyl]cysteine] moiety. $Pam_3Cys$ or $Pam_3Cys$-OH (Wiesmuller et al., 1983), is a synthetic version of the N-terminal moiety of Braun's lipoprotein that spans the inner and outer membranes of Gram negative bacteria (U.S. Pat. No. 5,700,910 for example, which is incorporated herein by reference in its entirety). Additional TLR agonist are described in U.S. Patent Publication 20080145375, which is incorporated herein by reference in its entirety.

D. Lipid Components and Moieties

In certain embodiments, the present invention concerns compositions comprising one or more lipids non-covalently associated with a multitype HPV peptide. A lipid is a substance that is insoluble in water and extractable with an organic solvent. Compounds other than those specifically described herein are understood by one of skill in the art as lipids, and are encompassed by the compositions and methods of the present invention.

A lipid may be a naturally occurring lipid or a synthetic lipid. However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A multitype HPV peptide associated with a lipid may be dispersed in a solution containing a lipid, dissolved with a lipid, emulsified with a lipid, mixed with a lipid, combined with a lipid, contained as a suspension in a lipid or otherwise associated with a lipid. A lipid-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL) or Superfect (Qiagen) complex is also contemplated.

In certain embodiments, a composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% weight percent lipid, or any range or value there between, of a particular lipid, lipid type, or non-lipid component such as an adjuvant, sugar, nucleic acid or other material disclosed herein or as would be known to one of skill in the art. Thus, it is contemplated that compositions of the present invention may comprise any of the lipids, lipid types or other components in any combination or percentage range.

II. PRODUCTION OF POLYPEPTIDES AND FRAGMENTS THEREOF

A. Polypeptide Synthesis and/or Conjugation

In certain aspects the polypeptides can be synthesized using conventional methods as modified for the particular amino acid sequences. Such techniques include, but are not limited to methods well known to those skilled in the art of peptide synthesis, e.g., solution phase synthesis (see Finn and Hoffman, 1976), or solid phase synthesis (see Barany and Merrifield, 1979), or stepwise solid phase synthesis as reported by Merrifield (1963), the contents of each of which are incorporated herein by reference. Other references to peptide synthesis techniques include peptides synthesized by the Fmoc-polyamide mode of solid-phase peptide synthesis as disclosed by Lu et al. (1981), peptides synthesized using an Fmoc/tBu procedure (Atherton and Sheppard, 1989). Fmoc amino acids can be obtained from various vendors, e.g., Chem-Impex International (Wood Dale, Ill., USA), Merck Biosciences (Nottingham, UK), and Bachem UK Ltd. (St. Helens, UK).

After or during synthesis a peptide can be conjugated to a spacer, an amino acid, a polymer or a lipid. In certain aspects, the terminal side chain group of a lysine or a lysine analog (e.g., epsilon amino group of the internal lysine) is protected by one of a number of protecting groups. Blocking groups or protecting groups or masking groups are used to protect the amino group of the amino acid having an activated carboxyl group that is involved in the coupling reaction, or to protect the carboxyl group of the amino acid having an acylated amino group that is involved in the coupling reaction. For coupling to occur, a blocking group must be removed without disrupting a peptide bond, or any protecting group attached to another part of the peptide. Peptides can be lipidated by methods well known in the art. Standard condensation, addition, substitution or oxidation (e.g., disulfide bridge formation or amide bond formation between a terminal amino group on the internal lysine or lysine analog with the carboxy terminal group of an incoming amino acid or peptide or lipoamino acid) reactions result in the addition of lipid to the peptide.

B. Expression Systems

Expression, isolation and purification of the polypeptides and fragments of the invention may be accomplished by any suitable technique.

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell. Polypeptides of the invention can include various leader sequences that direct trafficking or assist in purification.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. (1985). Cell-free translation systems could also be employed to produce polypeptides using RNAs derived from DNA constructs disclosed herein.

1. Prokaryotic Systems

Prokaryotes include gram-negative or gram-positive organisms. Suitable prokaryotic host cells for transformation include, for example, *E. coli, Bacillus subtilis, Salmonella typhimurium*, and various other species within the genera Pseudomonas, Streptomyces, and Staphylococcus. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., 1978; and Goeddel et al., 1979), tryptophan (trp) promoter system (Goeddel et al., 1980; and EP-A-36776) and tac promoter (Maniatis, 1982). A particularly useful prokaryotic host cell expression system employs a phage $\lambda P_L$ promoter and a c1857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

2. Yeast Systems

Alternatively, the polypeptides may be expressed in yeast host cells, preferably from the Saccharomyces genus (e.g., *S. cerevisiae*). Other genera of yeast, such as *Pichia* or Kluyveromyces, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., 1980) or other glycolytic enzymes (Hess et al., 1968; and Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in European patent application 73,657. Another alternative is the glucose-repressible ADH2 promoter described by Russell et al. (1982) and Beier et al. (1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., Kurjan et al., 1982 and Bitter et al., 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

3. Mammalian or Insect Systems

Mammalian or insect host cell culture systems also may be employed to express recombinant polypeptides. Baculovirus systems for production of heterologous proteins in insect cells are reviewed by Luckow and Summers, Bio/Technology 6:47 (1988). Established cell lines of mammalian origin also may be employed. Examples of suitable mammalian host cell lines include the COS-7 line of monkey kidney cells (ATCC CRL 1651) (Gluzman et al., 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (1991).

Established methods for introducing DNA into mammalian cells have been described (Kaufman, 1990). Additional protocols using commercially available reagents, such as Lipofectamine lipid reagent (Gibco/BRL) or Lipofectamine-Plus lipid reagent, can be used to transfect cells (Feigner et al., 1987). In addition, electroporation can be used to transfect mammalian cells using conventional procedures, such as those in Sambrook et al. (1989). Selection of stable transformants can be performed using methods known in the art, such as, for example, resistance to cytotoxic drugs. Kaufman et al., 1990, describes several selection schemes, such as dihydrofolate reductase (DHFR) resistance. A suitable host strain for DHFR selection can be CHO strain DX-B11, which is deficient in DHFR (Urlaub and Chasin, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., 1978; Kaufman, 1990).

Additional control sequences shown to improve expression of heterologous genes from mammalian expression vectors include such elements as the expression augmenting sequence element (EASE) derived from CHO cells (Morris et al., Animal Cell Technology, 1997, pp. 529-534 and PCT Application WO 97/25420) and the tripartite leader (TPL) and VA gene RNAs from Adenovirus 2 (Gingeras et al., J. Biol. Chem. 257:13475-13491, 1982). The internal ribosome entry site (IRES) sequences of viral origin allows bi-cistronic mRNAs to be translated efficiently (Oh and Sarnow, 1993; Ramesh et al., 1996). Expression of a heterologous cDNA as part of a bi-cistronic mRNA followed by the gene for a selectable marker (e.g. DHFR) has been shown to improve transfectability of the host and expression of the heterologous cDNA (Kaufman, 1990). Exemplary expression vectors that employ bi-cistronic mRNAs are pTR-DC/GFP described by Mosser et al. (1997), and p2A5I described by Morris et al. (1997).

A useful high expression vector, pCAVNOT, has been described by Mosley et al. (1989). Other expression vectors for use in mammalian host cells can be constructed as disclosed by Okayama and Berg (1983). A useful system for stable high level expression of mammalian cDNAs in C127 murine mammary epithelial cells can be constructed substantially as described by Cosman et al. (1986). A useful high expression vector, PMLSV N1/N4, described by Cosman et al. (1984), has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1 kD), hydrophilic, FLAG® marker peptide to the N-terminus of a recombinant protein expressed by pFLAG® expression vectors. pDC311 is another specialized vector used for expressing proteins in CHO cells. pDC311 is characterized by a bi-cistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Regarding signal peptides that may be employed, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., Nature 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

C. Isolation and Purification

The invention also includes methods of isolating and purifying the polypeptides and fragments thereof.

In one embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above as well as Fc moieties.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means. Methods of releasing positively selected cells from the solid phase are known in the art and encompass, for example, the use of enzymes. Such enzymes are preferably non-toxic and non-injurious to the cells and are preferably directed to cleaving the cell-surface binding region.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

III. FORMULATION AND ADMINISTRATION

The manner of administration of the compositions described herein may vary. Any of the conventional methods for administration of a vaccine are applicable. These are believed to include oral application on a solid physiologically acceptable base or in a physiologically acceptable dispersion, parenterally by injection, inhalation of a powder, via transcutaneous patch, via vaginal instillation and the like. The dosage of the vaccine will depend on the route of administration and will vary according to the size and health of the subject.

The preparation of vaccines that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be administered by inhalation. In certain embodiments a vaccine can be administered as an aerosol. As used herein the term "aerosol" or "aerosolized composition" refers to a suspension of solid or liquid particles in a gas. The terms may be used generally to refer to a composition that has been vaporized, nebulized, or otherwise converted from a solid or liquid form to an inhalable form including suspended solid or liquid drug particles. Such aerosols can be used to deliver a vaccine via the respiratory system. As used herein, "respiratory system" refers to the system of organs in the body responsible for the intake of oxygen and the expiration of carbon dioxide. The system generally includes all the air passages from the nose to the pulmonary alveoli. In mammals it is generally considered to include the lungs, bronchi, bronchioles, trachea, nasal passages, and diaphragm. For purposes of the present disclosure, delivery of a vaccine to the respiratory system indicates that a drug is delivered to one or more of the air passages of the respiratory system, in particular to the lungs.

Additional formulations which are suitable for other modes of administration include suppositories (for anal or vaginal application) and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The polypeptide, peptide, and lipopeptide compositions may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In many instances, it will be desirable to have multiple administrations of the vaccine, usually at most, at least, or not exceeding 1, 2, 3, 4, 5, 6, 7, 8, 9, 10, 11, 12, 13, 14, 15, or more vaccinations including all ranges there between. The vaccinations will normally be at 1, 2, 3, 4, 5, 6, to 5, 6, 7, 8, 9, 10, 11, to 12 week/month/year intervals, including all values and ranges there between, more usually from three to five week intervals. Typically, periodic boosters at intervals of 1-15 years, usually ten years, will be desirable to maintain protective levels of the antibodies. The course of the immunization may be followed by assays for antibodies against the antigens, as described supra, U.S. Pat. Nos. 3,791,932; 4,174,384 and 3,949,064, which are illustrative of these types of assays.

A. Combination Therapy

The compositions and related methods of the present invention, particularly administration of an HPV epitope, including a polypeptide or peptide of an HPV L2 protein to a patient/subject, may also be used in combination with the administration of traditional HPV screening and/or other vaccines, including, but not limited to, antibodies or antibody fragments, Pap smears, PCR, Southern blotting, administering CERVARIX™, GARDASIL™, vaccines for HPV or other infectious agents, ablative therapy of HPV lesions, or the like.

In one aspect, it is contemplated that a HPV peptide composition and/or therapy is used in conjunction with HPV screening and/or other treatment. Alternatively, the therapy may precede or follow the other treatment by intervals ranging from minutes to weeks. In embodiments where the other agents are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several months (1, 2, 3, 4, 5, 6, 7, 8, 9, 10, 11, 12), or years (2, 3, 4, 5, 6, 7, 8, 9, 10, 11, 12) lapse between the respective administrations.

Various combinations may be employed, for example a multitype HPV peptide therapy is "A" and another vaccine or antibody or treatment given as a therapy, is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of the immunogenic compositions of the present invention to a patient/subject will follow general protocols for the administration of such compounds, taking into account the toxicity, if any, of the multitype HPV polypeptide composition, or composition of any other antigen or antigen combination described herein. It is expected that the treatment cycles would be repeated as necessary. It also is contemplated that various standard therapies, such as hydration, may be applied in combination with the described therapy.

B. Preventive and/or Therapeutic Methods

In some embodiments, pharmaceutical compositions are administered to a subject. Different aspects of the present invention involve administering an effective amount of a composition to a subject. In some embodiments of the present invention, multitype HPV peptide compositions are administered to the patient to protect against or treat infection by at least one or more HPV pathogens. Such compositions will generally be dissolved or dispersed in a pharmaceutically acceptable carrier or aqueous medium.

As used herein, the term "pharmaceutically acceptable" or "pharmacologically acceptable" refer to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent. Pharmaceutically acceptable carrier includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The active compounds of the present invention can be formulated for parenteral administration, e.g., formulated for injection via the intravenous, intramuscular, sub-cutaneous, or even intraperitoneal routes. In addition to the compounds formulated for aerosol or parenteral administration, such as those for intravenous or intramuscular injection, other pharmaceutically acceptable forms include, e.g., tablets or other solids for oral administration; time release capsules.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The multitype HPV polypeptide compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, anal suppository, intra-vaginal, respiratory, or intravenous administration. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

1. In Vitro, Ex Vivo, or In Vivo Administration

As used herein, the term in vitro administration refers to manipulations performed on cells removed from or outside of an animal, including, but not limited to cells in culture. The term ex vivo administration refers to cells which have been manipulated in vitro, and are subsequently administered to a living animal. The term in vivo administration includes all manipulations performed within an animal.

In certain aspects of the present invention, the compositions may be administered either in vitro, ex vivo, or in vivo. In certain in vitro embodiments, autologous B-lymphocyte cell lines or dendritic cells are incubated with a multitype HPV composition. The activated cells can then be used for in vitro analysis, or alternatively for ex vivo administration.

2. Antibodies And Passive Immunization

Another aspect of the invention is a method of preparing an immunoglobulin for use in prevention or treatment of HPV infection comprising the steps of immunizing a recipient with a vaccine of the invention and isolating immunoglobulin or antibodies from the recipient, and/or recombinantly producing such immunoglobulins or fragments thereof. An immunoglobulin prepared by this method is a further aspect of the invention. A pharmaceutical composition comprising the immunoglobulin of the invention and a pharmaceutically acceptable carrier is a further aspect of the invention which could be used in the manufacture of a medicament for the treatment or prevention of HPV infection. A method for treatment or prevention of HPV infection comprising a step of administering to a patient an effective amount of the pharmaceutical preparation of the invention is a further aspect of the invention.

Inocula for polyclonal antibody production are typically prepared by dispersing the antigenic composition in a physiologically tolerable diluent such as saline or other adjuvants suitable for human use to form an aqueous composition. An immunostimulatory amount of inoculum is administered to a mammal, e.g., a human, and the inoculated subject is then maintained for a time sufficient for the antigenic composition to induce protective antibodies. The antibodies can be isolated to the extent desired by well known techniques such as affinity chromatography (Harlow and Lane, Antibodies: A Laboratory Manual 1988).

Antibodies can include antiserum preparations from a variety of commonly used animals, e.g., goats, primates, donkeys, swine, horses, guinea pigs, rats, or man. The animals are bled and serum recovered.

An immunoglobulin produced in accordance with the present invention can include whole antibodies, antibody fragments or subfragments. Antibodies can be whole immunoglobulins of any class, e.g., IgG, IgM, IgA, IgD or IgE, chimeric antibodies or hybrid antibodies with dual specificity to two or more antigens of the invention. They may also be fragments, e.g., F(ab')$_2$, Fab', Fab, Fv and the like including hybrid fragments. An immunoglobulin can also include natural, synthetic, or genetically engineered proteins that act like an antibody by binding to specific antigens to form a complex.

An HPV composition or vaccine of the present invention can be administered to a recipient who then acts as a source of immunoglobulin, produced in response to challenge from the HPV composition. A subject thus treated would donate plasma from which hyperimmune globulin would be obtained via conventional plasma fractionation methodology. The hyperimmune globulin would be administered to another subject in order to impart resistance against or treat HPV infection. Hyperimmune globulins of the invention are particularly useful for treatment or prevention of HPV infection in infants, immune compromised individuals or where treatment is required and there is no time for the individual to produce antibodies in response to vaccination.

An additional aspect of the invention is a pharmaceutical composition comprising one or more monoclonal antibodies (or fragments thereof; preferably human or humanized) reactive against constituents of the immunogenic composition of the invention, which could be used to treat or prevent infection by multiple HPV types.

Methods of making monoclonal antibodies are well known in the art and can include the fusion of splenocytes with myeloma cells (Kohler and Milstein, 1975; Harlow and Lane, 1988). Alternatively, monoclonal Fv fragments can be obtained by screening a suitable phage display library (Vaughan et al., 1998). Monoclonal antibodies may be human, humanized, or partly humanized by known methods.

IV. Kits

Another aspect of the invention is a kit for vaccination or treatment according to the present invention. In one embodiment, the kit comprises a vial and optionally a package insert with administration instructions, the vial comprises a multitype HPV polypeptide composition or vaccine for administration according to the methods of the present invention.

Any of the compositions described herein may be comprised in a kit. In a non-limiting example, reagents for preparing a multitype HPV polypeptide, formulating a multitype HPV polypeptide, and/or administering a multitype HPV polypeptide can be included in a kit. The kit may further include reagents for assessing the activity of the lipopetide both in vitro and in vivo. The kits will thus comprise, in suitable container means, a multitype HPV polypeptide composition. In certain aspects, the kit can include reagents and/or devices for administration, e.g., inhaler or nebulizer. It may also include one or more buffers, compounds, or devices for preparing the composition for administration.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

In other aspects, a kit or device can include polyclonal or monoclonal antibodies directed to polypeptides of the invention. Such a kit or device can be used to detect or identify or purify virus in a variety of samples and or patients.

A kit will also include instructions for employing the kit components as well the use of any other reagent not included in the kit. Instructions may include variations that can be implemented.

It is contemplated that such reagents are embodiments of kits of the invention. Such kits, however, are not limited to the particular items identified above and may include any reagent used for the preparation and/or administration of a multitype HPV polypeptide vaccine.

V. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

A. Results

L2 vaccines comprising residues 11-200 and 1-88 used in earlier studies were selected based upon convenient restriction sites rather than immunogenicity considerations (Campo and Jarrett, 1994; Roden et al., 1994). Therefore they may not contain all of the relevant neutralizing epitopes, or have optimal immunogenicity and stability. Nevertheless, these studies indicate that the presence of neutralizing L2-specific antibodies is sufficient for protective immunity (Embers et al., 2002; Gambhira et al., 2007). Indeed vaccination with L2 11-200 induces cross-neutralizing antibodies and protection in the BPV4, CRPV and ROPV challenge models (Gambhira et al., 2007; Campo and Jarrett, 1994). Vaccination with the L2 1-88 peptide was also protective, but there was some suggestion that the cross-neutralization and cross-protection might not be as effective in comparison to animals vaccinated with L2 11-200 (Gambhira et al., 2007). Consistent with this notion, vaccination with L2 peptides from 94-112 and 107-122 were both protective against homologous challenge (Embers et al., 2002). Therefore to assess the benefits of including these regions within an L2 vaccine, we generated N-terminal L2 polypeptides terminating at 88, 107 or 200 for vaccine studies (Table 1).

TABLE 1

Antibody responses of rabbits vaccinated with momeric or multimeric L2 polypeptides of different sizes.

| Antigen | Rb | 16L2 ELISA | HPV16 ELISA | HPV16 IVN | HPV18 IVN | HPV31 IVN | HPV45 IVN | HPV58 IVN | HPV6 IVN | HPV5 IVN |
|---|---|---|---|---|---|---|---|---|---|---|
| A. | | | | | | | | | | |
| HPV16 L2 1-88 | a | 409600 | 204800 | 409600 | 200 | 3200 | 3200 | 12800 | 1600 | 800 |
| HPV16 L2 13-88# | a | 51200 | 6400 | 3200 | None | None | None | 200 | — | 200 |
| HPV16 L2 1-107 | a | 204800 | 102400 | 409600 | 6400 | 12800 | 6400 | 102400 | 400 | 25600 |
| | b | 409600 | 102400 | 102400 | 800 | 3200 | 400 | 6400 | — | 12800 |

TABLE 1-continued

Antibody responses of rabbits vaccinated with momeric or multimeric L2 polypeptides of different sizes.

| Antigen | Rb | 16L2 ELISA | HPV16 ELISA | HPV16 IVN | HPV18 IVN | HPV31 IVN | HPV45 IVN | HPV58 IVN | HPV6 IVN | HPV5 IVN |
|---|---|---|---|---|---|---|---|---|---|---|
| HPV16 L2 13-107 | a | 409600 | 102400 | 204800 | 1600 | 3200 | 200 | 6400 | — | 6400 |
| HPV16 L2 11-200 | a | 102400 | 102400 | 409600 | 200 | 400 | 400 | 800 | 800 | 800 |
| HPV16 L2 13-200 | a | 819200 | 102400 | 102400 | 800 | 1600 | 3200 | 6400 | — | 12800 |
| HPV16 L2 89-200# | a | None | None | None | None | None | None | None | None | None |
|  | b | 204800 | 12800 | 3200 | None | None | None | None | — | None |

B.

| 17-36x22 | a | 409600 | 102400 | 204800 | 12800 | 800 | 12800 | 25600 | 800 | 3200 |
|---|---|---|---|---|---|---|---|---|---|---|
|  | b | 409600 | 102400 | 12800 | 6400 | None | 3200 | 3200 | — | 400 |
| 11-88x5 | a | 819200 | 819200 | 819200 | 204800 | 51200 | 102400 | 409600 | 102400 | >102400 |
|  | b | 1638400 | 819200 | 819200 | 102400 | 102400 | 102400 | 409600 | — | >102400 |
| 11-200x3 | a | 409600 | 102400 | 204800 | 25600 | 1600 | 12800 | 25600 | 6400 | 1600 |
|  | b | 409600 | 102400 | 51200 | 6400 | 1600 | 3200 | 12800 | — | 800 |

Rabbits were vaccinated four times with 300 μg of the HPV16 L2 polypeptides (A) or polymeric L2 constructs (B) using CFA/IFA as an adjuvant. Hyper-immune sera were collected at one month after the final immunization and tested for L2-specific antibody by enzyme-linked imunosorbant assay (ELISA) with microtiter plates coated with full length HPV16 L2 (16L2 ELISA) or HPV16 L2/L2 pseudovirions (HPV16 ELISA). The sera were also tested for in vitro neutralization (IVN) titers for the HPV pseudovirion types indicated. Neutralization titers were not detected in the pre-immune sera.
protein exhibited significant degradation in E. coli.
"Rb" individual rabbit.
"None" corresponds to less than 50% neutralization at the lowest dilution tested of 1:50.
"—" not tested.

L2 is necessary for infection (Roden et al., 2001), and may have multiple distinct functions (Richards et al., 2006; Bossis et al., 2005; Kamper et al., 2006). During infection, L2 must be cleaved by furin to remove residues 1-13 (Richards et al., 2006) and this renders a conserved neutralizing epitope (between residues 17-36) more accessible to monoclonal antibody RG-1 (Day et al., 2008). Further, antisera to L2 1-88 or 11-200 polypeptides cross-neutralizes cutaneous as well as mucosal papillomavirus types (Pastrana et al., 2005). Therefore, we generated N-terminal L2 polypeptides initiating at residues 1, 11, 13 or 89 for vaccine studies (Table 1).

Responses in rabbits vaccinated with monomeric and multitype L2 polypeptides:

To map cross-neutralizing epitopes, seven HPV16 L2 polypeptides (Table 1) were expressed in E. coli with 6-His tags and affinity purified for vaccination studies. While all the polypeptides were readily purified, HPV16 L2 13-88 and 89-200, were unstable during storage. Rabbits were immunized five times with 300 μg of each polypeptide, initially in CFA, and in IFA for the booster immunizations. The success of each immunization was first verified by testing the hyper-immune sera in an HPV16 L2 full length ELISA and an HPV16 L1/L2 pseudovirion ELISA. High titers of serum antibodies were raised to each HPV16 L2 polypeptide, although the titers against HPV16 pseudovirions were lower for the antisera to the two unstable antigens, L2 13-88 and 89-200. HPV16 neutralization titers and HPV6, HPV18, HPV31, HPV45 and HPV58 cross-neutralizing titers were then determined for each rabbit antiserum induced by the L2 polypeptides. Consistent with earlier studies (Gambhira et al., 2007), the HPV16 L2 11-200 and 1-88 peptides induced robust titers of HPV16 neutralizing antibodies. Similarly robust HPV16 neutralizing antibody titers were observed for the antisera to HPV16 L2 13-200, 1-107, 13-107. Vaccination with HPV16 L2 89-200 produced considerably weaker neutralizing responses, although it did induce antibodies with high L2 ELISA titers in one of two rabbits. The L2-specific antisera induced by the various HPV16 L2 peptides neutralized not only HPV16 but also the diverse range of heterologous papillomavirus types, including the oncogenic types HPV18, HPV31, HPV45 and HPV58, which were tested (Table 2). However, neutralizing antibody titers against HPV16 were significantly higher than against other types, although there was no clear relationship between titers and evolutionary distance from HPV16.

TABLE 2

A summary of the multitype L2 constructs

| L2 residues x number of HPV types* | Molecular Weight | Types of HPV (in order from N to C terminus) |
|---|---|---|
| 1-88 x 1 | 16 kDa | 16 |
| 11-200 x 1 | 26 kDa | 16 |
| 11-200 x 3 | 63 kDa | 6, 16, 18 |
| 11-88 x 5 | 43 kDa | 1, 5, 6, 16, 18 |
| 17-36 x 22 | 49 kDa | 1, 2, 63, 5, 8 (Cutaneous) |
|  |  | 6, 11 (Mucosal Low Risk) |
|  |  | 16, 18, 31, 33, 35, 39, 45, |
|  |  | 51, 52, 56, 58, 59, 68, 73, |
|  |  | 82 (Mucosal High risk) |
| 11-88 x 8 | 69 kDa | 6, 16, 18, 31, 39, 51, 56, 73 |

*residue designations are based on HPV16 amino acid numbering, actual residue numbering for homologous peptides may vary, but can be determined by sequence alignment with HPV16 peptides Because none of the alternative HPV16 L2 peptides substantially increased neutralizing titers to heterologous viruses, we examined concatenated fusion proteins, consisting of several homologous L2 peptides derived from different medically-significant HPV genotypes. Based upon the results of this and prior studies, L2 polypeptides corresponding to HPV16 L2 17-36, 11-88 and 11-200 were chosen for fusion constructs. Since larger size recombinant proteins are often less efficiently produced in bacteria, we tested multitype constructs comprising 3 copies of 11-200 (termed 11-200x3), 5 copies of 11-88 (termed 11-88x5) and 22 copies of 17-36 (termed 17-36x22) and, as shown in Table 2, each being derived from medically-relevant and diverse HPV genotypes (de Villiers et al., 2004). The proteins were expressed in E. coli, affinity purified under denaturing conditions, and used to immunize rabbits as described for the HPV16 L2 polypeptides. Vaccination of rabbits with each of the multitype L2 fusion proteins (11-200x3, 11-88x5 and 17-36x22) in CFA/IFA adjuvant induced more robust cross-neutralization titers (Table 1B) as compared to monotype L2 peptides (Table 1A)

without compromising HPV16 neutralization titers. In particular, the 11-88x5 induced remarkably high titers of neutralizing antibodies to all the test HPV types, including three (HPV31, 45, and 58) that were not used to derive this fusion protein.

Responses in rabbits vaccinated with GARDASIL™: Vaccination with L1 VLPs can induce antibodies that cross-neutralize very closely related papillomavirus types, e.g., HPV18 and HPV45 (Smith et al., 2007; Lin et al., 1992; Richards et al., 2006). Therefore we sought to compare the levels of cross-neutralizing antibodies generated by vaccination with GARDASIL™ (which is formulated in alum) using two different concentrations versus multitype L2 proteins formulated in CFA/IFA (Table 3). Vaccination with GARDASIL™ produced high titers of neutralizing antibody to the oncogenic HPV types included in the vaccine, HPV16 and HPV18. While higher HPV16 and HPV18 titers were generated with the L2 fusion protein, this occurred with a higher dose of antigen and using a more potent adjuvant. Sera from rabbits vaccinated with GARDASIL™ consistently contained significant levels of HPV45 neutralizing antibody, occasionally HPV31 neutralizing antibody, but no detectable HPV58 neutralizing antibody titers. Thus neutralizing antibody titers to HPV types not included in the vaccine are much lower or sporadic or undetectable after GARDASIL™ vaccination.

TABLE 3

Antibody responses of rabbits vaccinated with GARDASIL ™.

| Antigen (µg) | Rb | HPV16 IVN | HPV18 IVN | HPV31 IVN | HPV45 IVN | HPV58 IVN |
|---|---|---|---|---|---|---|
| GARDASIL ™ | a | 51200 | 51200 | 50 | 100 | None |
| (30 µg) | b | 25600 | 51200 | None | 100 | None |
| | c | 25600 | 25600 | None | 800 | None |
| | d | 51200 | 102400 | 50 | 800 | None |
| GARDASIL ™ | a | 12800 | 25600 | None | None | None |
| (12 µg) | b | 51200 | 25600 | 200 | 1600 | None |
| | c | 51200 | 25600 | None | 800 | None |
| | d | 102400 | 51200 | 50 | 400 | None |
| 11-88x5 (300 µg) | a | 819200 | 204800 | 51200 | 102400 | 409600 |

Rabbits were vaccinated three times with 300 µg of the polymeric L2 constructs 11-88x5 using CFA/IFA adjuvant or with either 30 µg or 12 µg of GARDASIL ™.
Hyper-immune sera were collected at one month after the final immunization and tested for in vitro neutralization (IVT) titers for the HPV pseudovirion types indicated. Neutralization titers were not detected in the pre-immune sera.
"Rb" individual rabbit.
"None" corresponds to less than 50% neutralization at the lowest dilution tested of 1:50.
"—" not tested.

Responses of mice vaccinated with monomeric and multitype L2 polypeptides: Mice can be challenged with HPV pseudovirions and infection quantified by delivery of a reporter such as luciferase (Gambhira et al., 2007; Roberts et al., 2007). Mice were vaccinated three times at two week intervals with HPV16 L2 polypeptides comprising residues 17-36, 1-88 or 11-200, or one of the three concatenated multitype L2 fusion proteins, 11-200x3, 11-88x5, or 17-36x22, using the saponin-based GPI-0100 adjuvant (Marciani et al., 2000). Two weeks later their serum was harvested and the in vitro neutralization titers were determined for HPV16, HPV18, HPV45, HPV58 (four common oncogenic HPV types) and HPV6 (the most common type found in benign genital warts). As observed in rabbits, vaccination with HPV16 L2 1-88 or HPV16 L2 11-200 induced significant titers of neutralizing antibodies against the homologous virus type, HPV16. However, vaccination with a synthetic peptide comprising residues HPV16 L2 17-36 did not induce neutralizing antibodies, or L2-specific antibodies (not shown), probably because it lacks an T helper epitope for this mouse strain (Alphs et al., 2008). The positive control, vaccination with HPV16 L1 VLPs in the absence of adjuvant, induced even higher titers than the HPV16 L2 constructs. In contrast, vaccination with HPV45 L1 VLPs failed to induce HPV16 neutralizing antibodies, consistent with the type-restricted response to L1 VLP vaccines (FIG. 1). The L2 11-88x5 constructs generated enhanced HPV16 neutralizing antibody titers as the HPV16 L2 1-88 peptide, but this was not seen for the 11-200x3 versus HPV16 L2 11-200. The 17-36x22 even was less effective (FIG. 1), possibly a result of weak T help (Alphs et al., 2008). Surprisingly, the cross-neutralizing antibody responses observed in mice vaccinated with HPV16 L2 polypeptide were less robust than those generated in rabbits receiving the same vaccines. However, when comparing the multitype L2 versus the HPV16 L2 11-200 and 1-88 constructs, immunization with 11-200x3 and 11*88x5 was far more effective in inducing neutralizing antibodies against HPV6, HPV18, HPV45, and HPV58 (FIG. 1). Notably the 11-200x3 and 11-88x5 polypeptides do not contain sequences from either HPV45 or HPV58 and yet significant cross-neutralization was observed.

Figure 2:
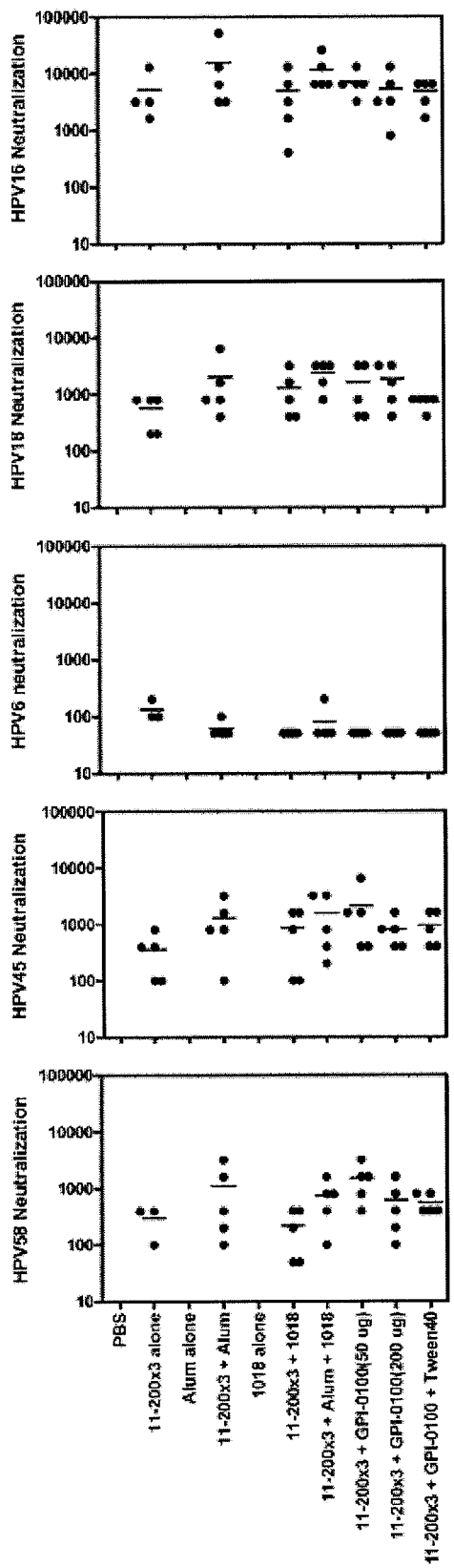
FIG. 2. Multi-type L2 protein alone is immunogenic and that no particular adjuvant is required for a broadly neutralizing antibody response. BALB/c mice were vaccinated on day 0, 15 and 30 s.c. with Alum alone (1.3 mg), or ISS1018 alone (10 µg/mouse), or PBS, or 25 µg 11-200x3 (SEQ ID NO:113) alone, or formulated with alum (1.3 mg), or with ISS1018 (10 µg/mouse), or with GPI-0100 (at either 50 µg/mouse or 200 µg/mouse), or with GPI-0100 (50 µg/mouse)+Tween 40 (1 mg/mouse), or with alum and ISS1018 (10 µg/mouse). In vitro neutralization titers were performed with two dilutions of the antisera of mice collected two weeks after final immunization using HPV pseudovirus for the genotypes indicated. End point titers for 50% neutralization are plotted.
Figure 3:
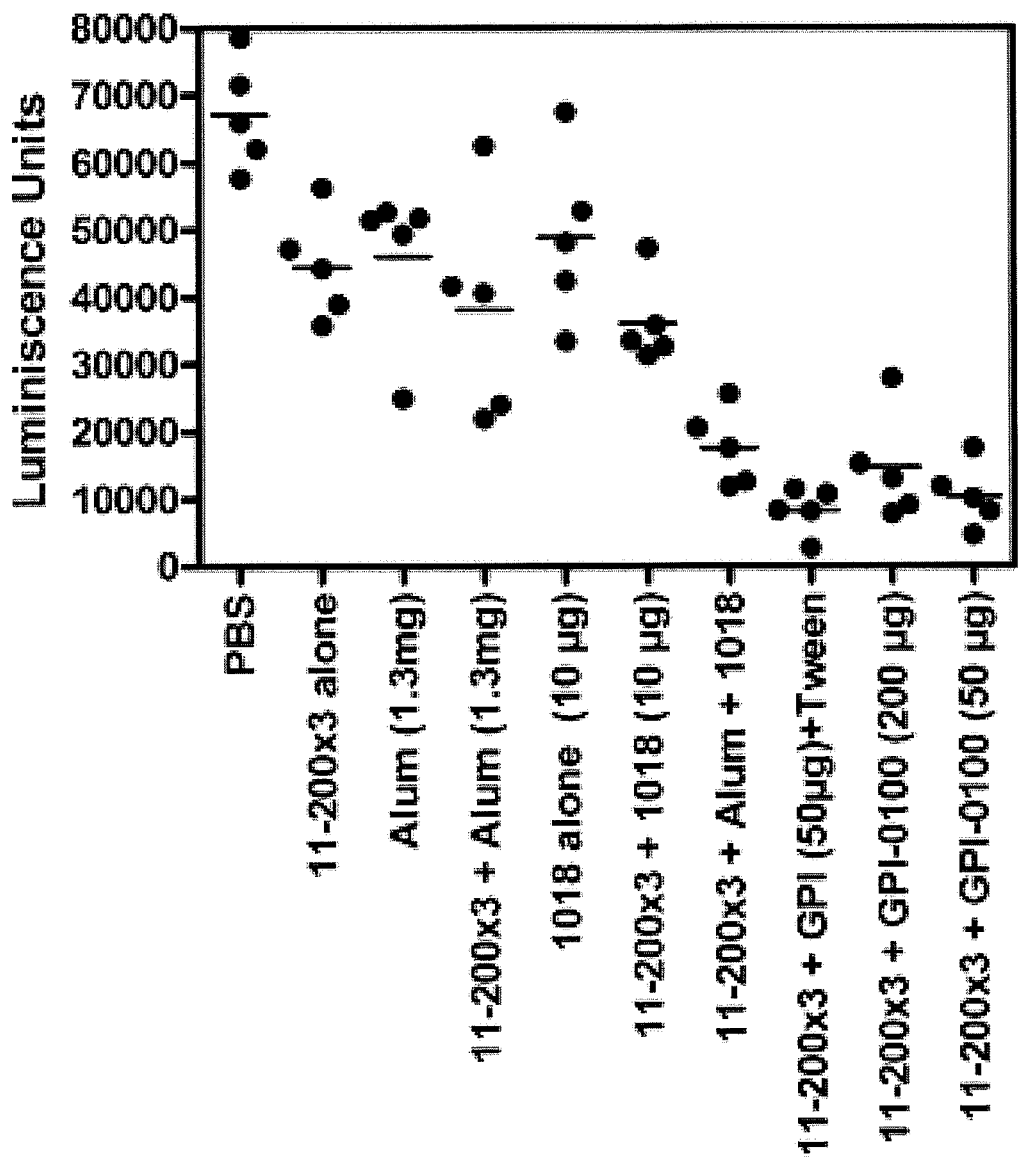
FIG. 3. In vivo HPV16 pseudovirus challenge of mice four months after vaccination with L2 11-200x3 (SEQ ID NO:113) in different adjuvant combinations. Mice were vaccinated three times at two week intervals with PBS or 25 µg of L2 11-200x3 (SEQ ID NO:113) in different adjuvants or adjuvant alone. Individual groups were as listed below from left to right: PBS alone, Alum alone (1.3 mg), ISS1018 alone (10 µg/mouse), 11-200x3 (SEQ ID NO:113) alone, 11-200x3 (SEQ ID NO:113)+ISS1018 (10 µg/mouse), 11-200x3 (SEQ ID NO:113)+Alum (1.3 mg), 11-200x3 (SEQ ID NO:113)+GPI-0100 (50 µg/mouse), 11-200x3 (SEQ ID NO:113)+GPI-0100 (200 µg/mouse), 11-200x3 (SEQ ID NO:113)+GPI-0100 (50 µg/mouse)+Tween 40 (1 mg/mouse), 11-200x3 (SEQ ID NO:113)+Alum+1018 (10 µg/mouse). Approximately 4 months after the immunization patch on the belly of each anesthetized BALB/c mouse was shaved with an electric razor without traumatizing the epithelium. Mice were then challenged with $3 \times 10^9$ HPV16 pseudovirions (100 ng) in 10 µl of 0.6% carboxymethylcellulose carrying a luciferase reporter construct. Three days later, the mice were anesthetized and injected with luciferin and images were acquired for 10 min with a Xenogen IVIS 200. Equally sized areas encompassing the site of inoculation were analyzed using Living Image 2.20 software and the relative luminescence units plotted relative to mice vaccinated with HPV16 µl prior to challenge.

Adjuvanted L2 multitype polypeptides: Several adjuvants that are potentially more effective than, or complementary to alum have shown promise in clinical vaccine trials, e.g., the immunostimulatory sequence (ISS) 1018, an oligonucleotide that activates toll-like receptor 9 (Halperin et al., 2005; Halperin et al., 2003), and the saponin-based adjuvant GPI-0100 (Marciani et al., 2003; Slovin et al., 2005). To address whether a particular adjuvant was more effective at inducing HPV neutralizing antibodies when formulated with a multitype L2 vaccine, we compared immune responses to 25 µg 11-200x3 formulated in a variety of adjuvants, and combinations thereof, head-to-head. Sera were obtained from mice two weeks after their third immunization and the titers for in vitro neutralization of HPV16, HPV18, HPV45 and HPV58 (FIG. 2) were measured. The in vitro neutralization titers were remarkably similar across each adjuvant group and none was notably superior to formulation of 11-200x3 in alum at this time point.

Figure 4:
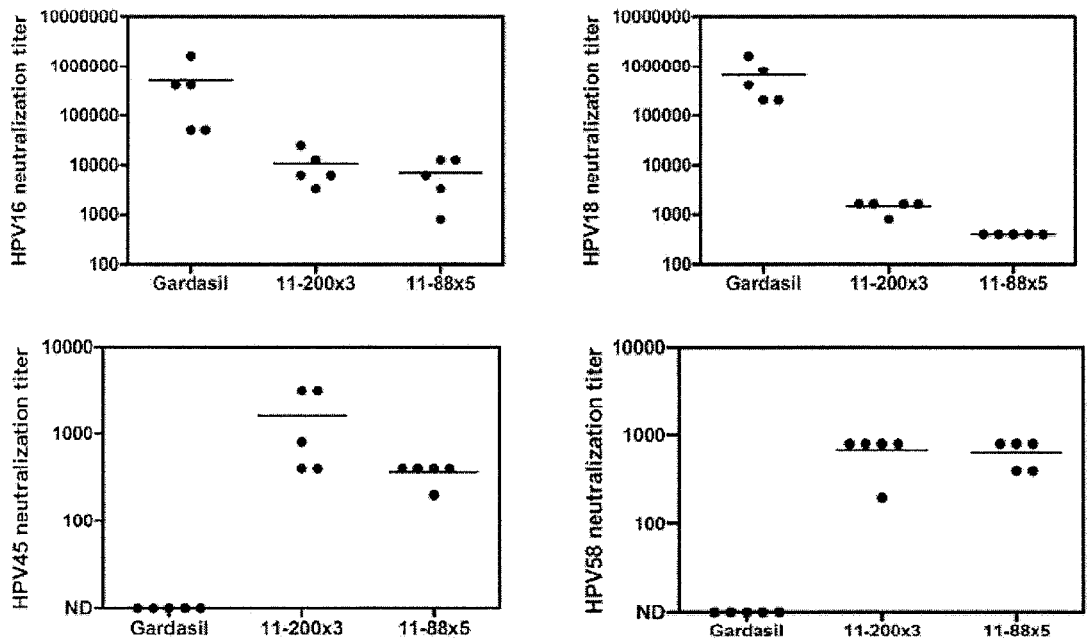
FIG. 4. Vaccination of mice with L2 11-200x3 (SEQ ID NO:113) or 11-88x5 (SEQ ID NO:108) induces lower but more broadly cross-neutralizing antibodies as compared with GARDASIL™. Mice were vaccinated three times on day 0, 15, and 30 with GARDASIL™ at one fifth of a human dose or with 25 µg of L2 11-200x3 (SEQ ID NO:113) or 11-88x5 (SEQ ID NO:108) in GPI-0100 (50 µg) adjuvant. In vitro neutralization assays were performed with a two fold dilution series of the antisera of mice collected two weeks after final immunization using pseudovirus of the HPV genotypes indicated. End point titers for 50% neutralization are plotted.

In addition to peak titers, adjuvants can increase the longevity of antibody responses. To assess the possibility that the differences between adjuvants would be more clear as the humoral responses wane, the mice were challenged with HPV16 pseudovirions at 4 months after vaccination. Cutaneous infection was detected as a bioluminescent signal 3 days after the administration of HPV16 pseudovirions carrying a luciferase reporter and injection of the challenged mice with its substrate, luciferin. One-way analysis of variance (ANOVA with Bonferroni comparisons) indicates that protection from HPV16 infection with 11-200x3 alone and PBS control immunizations were significantly different (P<0.05; FIG. 4). Vaccination with 11-200x3 in any of the adjuvants tested and PBS control immunizations were more significantly different (P<0.001; FIG. 4). In particular, the formulation of 11-200x3 with alum +ISS1018 was more effective than 11-200x3 alone (P<0.01). GPI-0100 formulations tested with 11-200x3 was more effective than 11-200x3 alone (P<0.001) or 11-200x3 in combination with alum (P<0.01). No statistically significant difference in protection was observed when using just alum or just ISS1018 with 11-200x3 as compared to the protein alone.

Vaccination with HPV16 L1 VLP alone, but not HPV45 L1 VLP, also gave a similar level of protection as vaccination with 11-200x3 with alum+ISS1018 or GPI-0100 (P<0.001; not shown). Therefore we sought to compare the in vitro neutralizing antibody titers induced by vaccination of mice with GARDASIL™ with those induced by vaccination of mice with either 11-200x3 or 11-88x5 in the adjuvant GPI- 0100. The in vitro neutralization titers generated against HPV16 and HPV18, for which L1 VLPs are included in GARDASIL™, were significantly higher in the sera of mice vaccinated with GARDASIL™ as compared to those vaccinated with either multi-type L2 construct. However, no HPV45 or HPV58 neutralizing antibody was detected in the sera of mice vaccinated with GARDASIL™ (FIG. 4). In contrast, robust titers of neutralizing antibodies were detected in the sera of mice vaccinated with either 11-200x3 or 11-88-5 even though neither construct contains L2 sequences derived from HPV45 or HPV58.

Several adjuvants have been tested in clinical trials and shown to be effective and safe, including alum, GPI-0100, alum and immunostimulatory sequence 1018 (a CpG oligonucleotide that activates toll-like receptor 9). To address whether polymeric L2 vaccines required a particular adjuvant, and the extent to which adjuvants boosted the neutralizing antibody response generated by polymeric L2 vaccines several adjuvants were compared head-to-head. Thus mice vaccinated with 2514 of L2 11-200x3 in different adjuvants or adjuvant alone. Individual groups were: (1) Alum alone (1.3 mg/mouse Aluminum hydroxide, Sigma A-8222), (2) CpG 1018 alone (10 μg/mouse), (3) PBS, (4) 11-200x3 alone, (5) 11-200x3+Alum (50% slurry), (6) 11-200x3+CpG1018 (10 μg/mouse, Dynavax, Berkley, Calif.), (7) 11-200x3+GPI-0100 (50 μg/mouse, Hawaii Biotech, Maui, Hi.), (8) 11-200x3+GPI-0100 (200 μg/mouse), (9) 11-200x3+GPI-0100 (50 μg/mouse)+Tween 40 (1 mg/mouse, Sigma P-1504), (10) 11-200x3+Alum+CpG1018 (10 μg/mouse). Sera were obtained two weeks after the final immunization and tested for in vitro neutralization of HPV6, HPV16, and HPV18. The in vitro neutralization titers were remarkably similar across each adjuvant group when compared to protein alone, suggesting that the polymeric L2 protein alone is immunogenic and that no particular adjuvant is required for a broadly neutralizing antibody response immediately after vaccination.

TABLE 4

ANOVA analysis of adjuvant groups.

| Bonferroni's Multiple Comparison Test | P |
|---|---|
| PBS vs Alum (1.3 mg) | P < 0.05 |
| PBS vs 1018 alone (10 μg/mouse) | P > 0.05 |
| PBS vs 11-200x3 alone | P < 0.05 |
| PBS vs 11-200x3 + CpG1018 (10 μg) | P < 0.001 |
| PBS vs 11-200x3 + Alum (1.3 mg) | P < 0.001 |
| PBS vs 11-200x3 + Alum + 1018 | P < 0.001 |
| PBS vs 11-200x3 + GPI (50 μg) + Tween | P < 0.001 |
| PBS vs 11-200x3 + GPI-0100 (200 μg) | P < 0.001 |
| PBS vs 11-200x3 + GPI-0100 (50 μg) | P < 0.001 |
| Alum (1.3 mg) vs 1018 alone (10 μg/mouse) | P > 0.05 |
| Alum (1.3 mg) vs 11-200x3 alone | P > 0.05 |
| Alum (1.3 mg) vs 11-200x3 + CpG1018 (10 μg) | P > 0.05 |
| Alum (1.3 mg) vs 11-200x3 + Alum (1.3 mg) | P > 0.05 |
| Alum (1.3 mg) vs 11-200x3 + Alum + 1018 | P < 0.001 |
| Alum (1.3 mg) vs 11-200x3 + GPI (50 μg) + Tween | P < 0.001 |
| Alum (1.3 mg) vs 11-200x3 + GPI-0100 (200 μg) | P < 0.001 |
| Alum (1.3 mg) vs 11-200x3 + GPI-0100 (50 μg) | P < 0.001 |
| 1018 alone (10 μg/mouse) vs 11-200x3 alone | P > 0.05 |
| 1018 alone (10 μg/mouse) vs 11-200x3 + CpG1018 (10 μg) | P > 0.05 |
| 1018 alone (10 μg/mouse) vs 11-200x3 + Alum (1.3 mg) | P > 0.05 |
| 1018 alone (10 μg/mouse) vs 11-200x3 + Alum + 1018 | P < 0.001 |
| 1018 alone (10 μg/mouse) vs 11-200x3 + GPI (50 μg) + Tween | P < 0.001 |
| 1018 alone (10 μg/mouse) vs 11-200x3 + GPI-0100 (200 μg) | P < 0.001 |
| 1018 alone (10 μg/mouse) vs 11-200x3 + GPI-0100 (50 μg) | P < 0.001 |
| 11-200x3 alone vs 11-200x3 + CpG1018 (10 μg) | P > 0.05 |
| 11-200x3 alone vs 11-200x3 + Alum (1.3 mg) | P > 0.05 |
| 11-200x3 alone vs 11-200x3 + Alum + 1018 | P < 0.01 |
| 11-200x3 alone vs 11-200x3 + GPI (50 μg) + Tween | P < 0.001 |
| 11-200x3 alone vs 11-200x3 + GPI-0100 (200 μg) | P < 0.001 |
| 11-200x3 alone vs 11-200x3 + GPI-0100 (50 μg) | P < 0.001 |
| 11-200x3 + CpG1018 (10 μg) vs 11-200x3 + Alum (1.3 mg) | P > 0.05 |
| 11-200x3 + CpG1018 (10 μg) vs 11-200x3 + Alum + 1018 | P > 0.05 |
| 11-200x3 + CpG1018 (10 μg) vs 11-200x3 + GPI (50 μg) + Tween | P < 0.01 |
| 11-200x3 + CpG1018 (10 μg) vs 11-200x3 + GPI-0100 (200 μg) | P < 0.05 |
| 11-200x3 + CpG1018 (10 μg) vs 11-200x3 + GPI-0100 (50 μg) | P < 0.01 |
| 11-200x3 + Alum (1.3 mg) vs 11-200x3 + Alum + 1018 | P > 0.05 |
| 11-200x3 + Alum (1.3 mg) vs 11-200x3 + GPI (50 μg) + Tween | P < 0.001 |
| 11-200x3 + Alum (1.3 mg) vs 11-200x3 + GPI-0100 (200 μg) | P < 0.05 |
| 11-200x3 + Alum (1.3 mg) vs 11-200x3 + GPI-0100 (50 μg) | P < 0.01 |
| 11-200x3 + Alum + 1018 vs 11-200x3 + GPI (50 μg) + Tween | P > 0.05 |
| 11-200x3 + Alum + 1018 vs 11-200x3 + GPI-0100 (200 μg) | P > 0.05 |
| 11-200x3 + Alum + 1018 vs 11-200x3 + GPI-0100 (50 μg) | P > 0.05 |
| 11-200x3 + GPI (50 μg) + Tween vs 11-200x3 + GPI-0100 (200 μg) | P > 0.05 |
| 11-200x3 + GPI (50 μg) + Tween vs 11-200x3 + GPI-0100 (50 μg) | P > 0.05 |
| 11-200x3 + GPI-0100 (200 μg) vs 11-200x3 + GPI-0100 (50 μg) | P > 0.05 |

B. Methods

Antigen preparation: HPV16 L2 polypeptide expression constructs were generated by PCR as described previously (Pastrana et al., 2005). The multi-type L2 constructs were codon optimized for E. coli expression by lowest free energy calculation and synthesized by Blue Heron Inc. with 5' BamHI and 3' XhoI sites to facilitate cloning. The L2 genes were subcloned into the pET28a vector (Novagen), and the resultant hexahistidine (6His)-tagged recombinant polypeptides expressed in E. coli BL21 (Rosetta cells, Novagen) (Pastrana et al., 2005). The recombinant L2 polypeptides were affinity purified by binding to a nickel-nitrilotriacetic acid (Ni-NTA) column (Qiagen) in 8M urea (using the QiaExpressionist standard purification protocol for denaturing conditions) and then dialyzed in cassettes (Pierce) against Dulbecco's phosphate buffered saline (PBS). Purity was monitored by SDS-PAGE and protein concentration determined by bicinchoninic acid test (Pierce) using a bovine serum albumin standard.

Enzyme-linked immunosorbent assays (ELISAs): Immobilon plates (Nunc) were coated overnight at 4° C. with 100 ng/well of 6His-HPV16 L2 prepared in E. coli or HPV16 L1/L2 pseudovirions produced in 293TT cells and diluted in PBS. Wells were then blocked with 1% bovine serum albumin (BSA)-PBS for 1 h at room temperature, and incubated with 2-fold dilutions of antisera for 1 h at room temperature. Following a wash step with PBS-0.01% (v/v) Tween 20, peroxidase-labeled goat anti-rabbit IgG (KPL Inc, Gaithersburg, Md.) diluted 1:5,000 in 1% BSA-PBS was added for 1 h. The plates were then washed again and developed with 2,2'-azino-bis(3-ethylbenzthiazoline-6-sulphonic acid solution (Roche) for 10 min (Viscidi et al., 2005). The absorbance was measured at 405 nm ($A_{405}$) in an ELISA plate reader (Bio-rad, Benchmark Plus).

Neutralization assays: The papillomavirus pseudovirion in vitro neutralization assays were performed as described earlier (Pastrana et al., 2004) and the secreted alkaline phosphatase activity in the clarified supernatant was determined using p-Nitrophenyl phosphate (Sigma, St. Louis, Mo.) dissolved in diethanolamine and absorbance measured at 405 nm. Constructs and detailed protocols for the preparation of the pseudovirions can be found on the internet at home.ccr-.cancer.gov/lco/. Titers were defined as the reciprocal of the highest dilution that caused a 50% reduction in $A_{405}$, and a titer <50 was not considered significant.

Animal Studies: Studies were performed in accordance with institutional policies and with the approval of the Johns Hopkins Animal Care and Use Committee and Institutional Animal Ethics Committee (IAEC, Inida). Balb/c mice (NCl Frederick) were vaccinated in groups of 5 animals three times at two week intervals s.c. with 25 µg of antigen (or HPV16 L2 17-36 peptide prepared by chemical synthesis (Sigma)) in the adjuvants indicated. Blood samples were obtained by tail vein bleeds two weeks after the final immunization. Rabbits were vaccinated at days 1, 28, 42, 60 and 76 with 300 µg L2 polypeptide in complete Freund's adjuvant initially and incomplete Freund's adjuvant thereafter. Vaccination with 12 or 30 µg of GARDASIL™ was done at days 1, 21, 35 and 56. Rabbits were bled one week after the final booster.

Cutaneous HPV challenge: A patch of skin on the ventral torso of anesthetized BALB/c mice was shaved with an electric razor, while taking care not to traumatize the epithelium. Challenge was performed by application of $3\times10^9$ pseudovirion particles (100 ng) containing pYLUC in 10 µl 0.6% carboxymethylcellulose (CMC, Sigma) to the patches of shaved skin. Three days later, mice were again anesthetized, injected with luciferin (100 µl at 7 mg/ml) and their image acquired for 10 min with an IVIS 200 bioluminescent imaging system (Xenogen, Cranbury, N.J.). Equal areas encompassing the site of virus inoculation were analyzed using Living Image 2.20 software (Xenogen), and background bioluminescence was determined by challenge with non-infectious HPV pseudovirions lacking L2.

Statistical methods: Comparison between groups for titers and levels of infection in the mouse model were made by one way ANOVA with Boneferroni comparisons (GraphPad Prism, version 4).

REFERENCES

The following references, to the extent that they provide exemplary procedural or other details supplementary to those set forth herein, are specifically incorporated herein by reference.

U.S. Pat. No. 3,791,932
U.S. Pat. No. 4,174,384
U.S. Pat. No. 3,949,064
U.S. Pat. No. 4,608,251
U.S. Pat. No. 4,601,903
U.S. Pat. No. 4,599,231
U.S. Pat. No. 4,599,230
U.S. Pat. No. 4,596,792
U.S. Pat. No. 4,578,770
U.S. Pat. No. 4,751,180
U.S. Pat. No. 4,935,233
U.S. Pat. No. 4,965,195
U.S. Pat. No. 4,968,607
U.S. Pat. No. 5,700,910
U.S. Pat. No. 6,448,070
U.S. Pat. No. 6,110,466
U.S. Pat. No. 6,171,591
U.S. Pat. No. 6,651,655
U.S. Pat. No. 6,814,971
U.S. Pat. No. 5,084,269
U.S. Pat. No. 6,656,462
U.S. Pat. No. 7,425,438
U.S. Pat. No. 7,416,846
U.S. Pat. No. 7,416,732
U.S. Pat. No. 7,407,807
U.S. Pat. No. 7,374,767
U.S. Pat. No. 7,201,908
U.S. Pat. No. 7,189,513
U.S. Pat. No. 7,288,258
U.S. Patent Publn. 2003/0223938
U.S. Patent Publn. 2004/0033585
U.S. Patent Publn. 2004/0258698
U.S. Patent Publn. 2005/0048082
U.S. Patent Publn. 2006/0035853
U.S. Patent Publn. 2007/0041999
U.S. Patent Publn. 2008/0145375
Alphs et al., Proc. Natl. Acad. Sci. USA, 105(15):5850-5, 2008.
Bachmann and Zinkernagel, Annu. Rev. Immunol., 15:235-70, 1997.
Baker et al., Biophys. J., 60:1445-1456, 1991.
Barr and Tamms, Clin. Infect. Dis., 45(5):609-7, 2007.
Beier et al., Nature. 300:724, 1982/Berg,
Berg. Mol. Cell. Biol., 3:280, 1983.
Bitter et al., Proc. Natl. Acad. Sci. USA, 81:5330, 1984.
Bossis et al., J. Virol., 79(11):6723-31, 2005.
Brinkman et al., Lett. Drug Des. & Disc. 1:137-147, 2004.
Brown, Group FIIS. Quadrivalent HPV (Type 6, 11, 16, 18) L1 VLP Vaccine: Second (FINAL) Analysis of Cross-Protection Against CIN/AIS Caused by Oncogenic HPV Types in Addition to 16/18. In: 24th International Papilloamvirus Conference; November 3-9, Beijing, China; 2007.
Buck et al., J. Virol., 78:751-757, 2004.
Buck et al., J. Virol. 79:2839-2846, 2005.
Buck et al., Methods Mol. Med., 119,445-462, 2005.
Campo and Jarrett, Ciba Found. Symp., 187:61-73, 1994.
Campo et al., Virology, 234(2):261-6, 1997.
Campo, Curr. Top. Microbiol. Immunol., 186:255-66, 1994.
Chackerian et al., J. Immunol. 169(11):6120-6, 2002.
Chandrachud et al., Virology, 211(1):204-8, 1995.
Chang et al., Nature, 275:615, 1978
Christensen et al., Virology, 181(2):572-9, 1991.
Christensen et al., Virology, 224(2):477-86, 1996.
Cosman et al., Mol. Immunol., 23:935, 1986.
Cosman et al., Nature, 312:768, 1984.
Day et al., J. Virol., 82(9):4638-46, 2008.

de Villiers et al., *Virology*, 324(1):17-27, 2004.
Dintzis et al., *Proc. Natl. Acad. Sci. USA*, 73(10):3671-5, 1976.
Dintzis et al., *Proc. Natl. Acad. Sci. USA*, 79(3):884-8, 1982.
Eisenbarth et al., *Nature*, 453(7198):1122-6, 2008.
Embers et al., *J. Virol.*, 76(19):9798-805, 2002.
Embers et al., *Vaccine*, 22:670-680, 2004.
EP 367,566;
EP 460,846
EP-A-0367566
EP-A-36776
EP 73,657
Felgner et al., *Proc. Natl. Acad. Sci. USA*, 84:7413-7417, 1987.
Fiers et al., *Nature*, 273:113, 1978
Flewy et al., *Archives of Virology*, 151:1511-1523, 2006.
Gambhira et al., *Cancer Res.*, 66(23):11120-4, 2006.
Gambhira et al., *J. Virol.*, 81:11585-11592, 2007.
Gambhira et al., *J. Virol.*, 81(21):13927-13931, 2007.
Gaukroger et al., *J. Gen. Virol.*, 77(Pt 7):1577-83, 1996.
Ghosh et al., *Immunology*, 104:58-66, 2001.
Gingeras et al., *J. Biol. Chem.*, 257:13475-13491, 1982.
Gluzman et al., *Cell*, 23:175, 1981.
Goeddel et al., *Nature*, 281:544, 1979.
Goeddel et al., *Nucl. Acids Res.*, 8:4057, 1980.
Gupta and Cooper, *Drugs R D*, 9(3):137-45, 2008.
Halperin et al., *Vaccine* 2005:in press.
Halperin et al., *Vaccine*, 21(19-20):2461-2467, 2003.
Harlow and Lane, *Antibodies: A Laboratory Manual* 1988.
Harper et al., *Lancet*, 364(9447):1757-65, 2004.
Harper et al., *Lancet*, 367(9518):1247-55, 2006.
Harro et al., *J. Natl. Cancer Inst.*, 93(4):284-92, 2001.
Hess et al., *J. Adv. Enzyme Reg.*, 7:149, 1968;
Hinnen et al., *Proc. Natl. Acad. Sci. USA*, 75:1929, 1978
Hitzeman et al., *J. Biol. Chem.*, 255:2073, 1980
Hoffman and Cavanagh, *Cancer Control*, 2:503-509, 1995.
Holland et al., *Biochem.*, 17:4900, 1978
Jackson et al., *Proc. Natl. Acad. Sci. USA*, 101, 15440-15445, 2004.
Kamper et al., *J. Virol.*, 80(2):759-68, 2006.
Kaufman et al., *Meth. Enzymology*, 185:487-511, 1990.
Kaufman, *Large Scale Mammalian Cell Culture*, 15-69, 1990.
Kawana et al., *J. Virol.*, 75:2331-2336, 2001.
Kawana et al., *J. Virol.*, 73(7):6188-90, 1999.
Kawana et al., *Vaccine*, 19(11-12):1496-502, 2001.
Kawana et al., *Vaccine*, 21(27-30):4256-60, 2003.
Kawana et al., *Virology*, 245(2):353-9, 1998.
Kirnbauer et al., *Proc. Natl. Acad. Sci. USA*, 89(24):12180-4, 1992.
Koutsky et al., *N. Engl. J. Med.*, 347(21):1645-51, 2002.
Kurjan et al., *Cell*, 30:933, 1982
Laniosz et al., *J. Virol.*, 81(14):7435-48, 2007.
Lin et al., *Virology*, 187(2):612-9, 1992.
Maniatis, Molecular Cloning: A Laboratory Manual, Cold Spring Harbor Laboratory, 412, 1982
Marciani et al., *Vaccine*, 18(27):3141-51, 2000.
Marciani et al., *Vaccine*, 21(25-26):3961-71, 2003.
McMahan et al., *EMBO J.*, 10:2821, 1991
Morris et al., *Animal Cell Technology*, 1 529-534, 1997.
Mosley et al., *Cell*, 59:335-348, 1989
Mosser et al., *Biotechniques*, 22:150-161, 1997
Muhlradt et al., *J. Exp. Med.*, 185:1951-1958, 1997.
Munoz et al., *Int. J. Cancer*, 111(2):278-85, 2004.
Munoz et al., *N. Engl. J. Med.*, 348(6):518-27, 2003.
Murata et al., *Proc. Natl. Acad. Sci. USA*, 100:6753-6758, 2000.
Murray, *Medical Microbiology* (ISBN 0323033032), 2005
Nardelli-Haefliger et al., *J. Virol.*, 73(11):9609-13, 1999.
Noad et al., *Trends in Microbiology*, 11(9):438-444, 2003.
Oh and Sarnow, *Curr. Opin. Genetics and Develop.*, 3:295-300, 1993.
Paavonen et al., *Lancet*, 369(9580):2161-70, 2007.
Paliard et al., *AIDS Res. Hum. Retroviruses*, 16:273-282, 2000.
Palmer et al., *Vaccine*, 24(26):5516-25, 2006.
Parkin and Bray, *Vaccine*, 24:Suppl 3:S11-25, 2006.
Parkin, *Int. J. Cancer*, 118(12):3030-44, 2006.
Parkin, *Lancet. Oncol.*, 2:533-543, 2001.
Pastrana et al., *Virology*, 279,361-369, 2001.
Pastrana et al., *Virology*, 321(2):205-16, 2004.
Pastrana et al., *Virology*, 337(2):365-72, 2005.
Ramesh et al., *Nucleic Acids Res.*, 24:2697-2700, 1996.
Remington's Pharmaceutical Sciences, 1990
Richards et al., *Proc. Natl. Acad. Sci. USA*, 103(5):1522-7, 2006.
Roberts et al., *Nature Med.*, 13(7):857-861, 2007.
Roden and Wu, *Nat. Rev. Cancer*, 6(10):753-63, 2006.
Roden et al., *J. Virol.*, 68(11):7570-4, 1994.
Roden et al., *J. Virol.*, 70(5):3298-301, 1996.
Roden et al., *J. Virol.*, 70(9):5875-83, 1996.
Roden et al., *J. Virol*; 75(21):10493-7, 2001.
Roden et al., *Virology*, 270:254-257, 2000.
Rose et al., *J. Gen. Virol.*, 75(Pt 9):2445-9, 1994.
Rose et al., *J. Virol.*, 67(4):1936-44, 1993.
Russell et al., *J. Biol. Chem.* 258:2674, 1982.
Sadeyen et al., *Virology*, 309:32-40, 2003.
Sambrook et al., Molecular Cloning: A Laboratory Manual, 2 ed. Vol. 1-3, Cold Spring Harbor Laboratory Press, 1989)
Schirmbeck et al., *Intervirology*, 39:111-119, 1996.
Slovin et al., *Vaccine*, 23(24):3114-22, 2005.
Smith et al., *Human vaccines*, 3(4):109-116, 2007.
Thomas, *Medical Microbiology*, Bailliere Tindall, Great Britain, 1983.
Urlaub and Chasin, *Proc. Natl. Acad. Sci. USA*, 77:4216-4220, 1980.
Villa et al., *Br. J. Cancer*, 95(11):1459-66, 2006.
Viscidi et al., *Cancer Epidemiol. Biomarkers Prev.*, 14(1): 283-8, 2005.
Walboomers et al., *J. Pathol.*, 189:12-19, 1999.
PCT Appln. WO 2005/005614
PCT Appln. WO 91/18982
PCT Appln. WO 97/25420)
Zeng et al., *J. Immunol.*, 169:4905-4912, 2002.

What is claimed is:

1. An isolated polypeptide composition comprising a fusion of residues from at least three homologous human papillomavirus L2 immunogenic peptides from at least three isolates of human papilloma virus wherein a first immunogenic peptide is coupled to a second homologous immunogenic peptide from a second isolate of human papilloma virus and the second immunogenic homologous peptide is coupled to a third homologous immunogenic peptide from a third isolate of human papilloma virus and wherein the immunogenic peptides are selected from one or more of:

L2 residues 11-200 from HPV6, HPV16 and HPV18; or

L2 residues 11-88 from HPV1, HPV5, HPV6, HPV16, HPV18; or

L2 residues 17-36 from HPV1, HPV2, HPV5, HPV6, HPV8, HPV11,
HPV16, HPV18, HPV31, HPV33, HPV35, HPV39, HPV45,
HPV51, HPV52, HPV56, HPV58, HPV59, HPV63, HPV68,
HPV73 and HPV82; or L2 residues 11-88 from HPV6, HPV16, HPV18, HPV31, HPV39, HPV51, HPV56 and HPV73.

2. The polypeptide composition of claim 1, wherein the immunogenic peptides are configured in a linear arrangement.

3. The polypeptide composition of claim 1, wherein the immunogenic peptides are coupled through a linker moiety.

4. The polypeptide composition of claim 1, wherein the polypeptide composition is a fusion protein.

5. The polypeptide composition of claim 4, wherein the fusion protein contains a peptide linker coupling the immunogenic peptides.

6. The polypeptide composition of claim 1, wherein the papillomavirus is a member of a papillomavirus genus selected from α, β, γ, δ, ε, ζ, η, θ, ι, κ, λ, μ, ν, ξ, o, o, or π papillomavirus.

7. The polypeptide composition of claim 1, wherein the HPV is a cutaneous HPV.

8. The polypeptide composition of claim 1, wherein the HPV is a mucosal high risk HPV.

9. The polypeptide composition of claim 1, wherein the immunogenic peptides are selected from one or more of HPV6, HPV16, HPV18, HPV31, HPV39, HPV51, HPV56, and/or HPV73 poly peptide.

10. The polypeptide composition of claim 1, wherein the immunogenic peptides are selected from HPV1, HPV5, HPV6, HPV16, and/or HPV18 polypeptide.

11. The polypeptide composition of claim 1, wherein the immunogenic peptides are selected from one or more of HPV6, HPV16, or HPV18 peptide.

12. The polypeptide composition of claim 1, wherein the HPV L2 peptide segments correspond to amino acid position 13-45, 17-36, 1-88, 11-88, or 11-200 of SEQ ID NO:1.

13. The polypeptide composition of claim 1, wherein at least one HPV L2 peptide is a HPV16 L2 peptide.

14. The polypeptide composition of claim 1, wherein at least one HPV L2 peptide is a HPV18 L2 peptide.

15. The polypeptide composition of claim 1, wherein at least one HPV L2 peptide is a HPV6 L2 peptide.

16. The polypeptide composition of claim 1, wherein at least one HPV L2 peptide is a HPV45 L2 peptide.

17. The polypeptide composition of claim 1, comprising at least 5, 6, 7, 8, 9, 10, 11, 12, 13, 14, 15, 16, 17, 18, 19, 20, 21, 22 or more immunogenic peptides.

18. The polypeptide composition of claim 1, comprising at least five immunogenic peptides.

19. The polypeptide composition of claim 1, comprising at least twenty immunogenic peptides.

20. The polypeptide composition of claim 1, wherein at least one HPV L2 peptide is a HPV16 L2 peptide.

21. The polypeptide composition of claim 1, wherein at least one HPV L2 peptide is a HPV18 L2 peptide.

22. The polypeptide composition of claim 1, wherein at least one HPV L2 peptide is a HPV6 L2 peptide.

23. The polypeptide composition of claim 1, wherein at least one HPV L2 peptide is a HPV45 L2 peptide.

24. The polypeptide composition of claim 1, wherein a first HPV L2 peptide is a HPV16 L2 peptide and a second HPV L2 peptide is a HPV18 L2 peptide.

25. The polypeptide composition of claim 1, wherein a first HPV L2 peptide is a HPV16 L2 peptide and a second HPV L2 peptide is a HPV6 L2 peptide.

26. The polypeptide composition of claim 1, wherein a first HPV L2 peptide is a HPV18 L2 peptide and a second HPV L2 peptide is a HPV6 L2 peptide.

27. The polypeptide composition of claim 1, wherein a first HPV L2 peptide is a HPV16 L2, a second HPV L2 peptide is a HPV18 L2 peptide and a third HPV L2 peptide is a HPV6 L2 peptide.

28. The polypeptide composition of claim 1, wherein the HPV L2 peptide has an amino acid sequence selected from SEQ ID NOs:71-92, and/or SEQ ID NOs:94-106 and/or SEQ ID NOs:110-112.

29. The polypeptide composition of claim 1, further comprising a non-HPV L2 peptide.

30. The polypeptide composition of claim 29, wherein the non-HPV L2 peptide is a HPV L1 peptide or HPV L1 protein.

31. The polypeptide composition of claim 29, wherein the non-HPV L2 peptide is a Th activating epitope, a carrier protein, or an adjuvant.

32. A kit comprising a polypeptide composition of claim 1.

33. An isolated polypeptide composition comprising at least two homologous papillomavirus L2 immunogenic peptides from at least two isolates of papilloma virus wherein a first immunogenic peptide from a first isolate of papilloma virus is coupled to a second homologous immunogenic peptide from a second isolate of papilloma virus, wherein the polypeptide is selected from the group consisting of SEQ ID NO:93 or SEQ ID NO:107 or SEQ ID NO:108 SEQ ID NO:109 SEQ ID NO:113 and SEQ ID NO:114.

\* \* \* \* \*